US008406859B2

(12) United States Patent
Zuzak et al.

(10) Patent No.: US 8,406,859 B2
(45) Date of Patent: Mar. 26, 2013

(54) DIGITAL LIGHT PROCESSING HYPERSPECTRAL IMAGING APPARATUS

(75) Inventors: Karel Zuzak, Arlington, TX (US); Jeffrey A. Cadeddu, Dallas, TX (US); Rafael Ufret-Vincenty, Dallas, TX (US); Robert P. Francis, Lewisville, TX (US); Edward Livingston, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 634 days.

(21) Appl. No.: 12/538,616

(22) Filed: Aug. 10, 2009

(65) Prior Publication Data
US 2010/0056928 A1 Mar. 4, 2010

Related U.S. Application Data

(60) Provisional application No. 61/087,714, filed on Aug. 10, 2008, provisional application No. 61/087,715, filed on Aug. 10, 2008, provisional application No. 61/168,347, filed on Apr. 10, 2009.

(51) Int. Cl.
*A61B 6/00* (2006.01)
(52) U.S. Cl. ........ 600/476; 600/473; 600/478; 257/440; 382/128; 356/326
(58) Field of Classification Search ............... 600/407, 600/476, 477, 478; 257/440, 59, 72, E31.001, 257/E27.132, E31.111; 438/73; 382/100, 382/103, 128; 356/326; 348/169, 269
See application file for complete search history.

(56) References Cited

U.S. PATENT DOCUMENTS

| 5,504,575 | A | 4/1996 | Stafford |
| 5,943,118 | A | 8/1999 | Koschmieder et al. |
| 6,504,943 | B1 * | 1/2003 | Sweatt et al. ................. 382/103 |
| 6,857,746 | B2 | 2/2005 | Dyner |
| 6,937,885 | B1 | 8/2005 | Lewis et al. |
| 6,992,775 | B2 | 1/2006 | Soliz et al. |
| 7,227,116 | B2 | 6/2007 | Gleckler |
| 7,281,796 | B2 | 10/2007 | Sumiya |
| 7,296,894 | B2 | 11/2007 | Liang et al. |
| 7,448,753 | B1 | 11/2008 | Chinnok |
| 7,652,765 | B1 | 1/2010 | Geshwind et al. |
| 7,692,784 | B2 | 4/2010 | MacKinnon et al. |
| 2003/0071970 | A1 | 4/2003 | Donnerhacke et al. |

(Continued)

OTHER PUBLICATIONS

Zuzak, K. et al "Characterization of a Near-Infrared Laparoscopic Hyperspectral Imaging System for Minimally Invasive Surgery", Anal. Chem., 79 (12), pp. 4709-4715 (2007).

(Continued)

*Primary Examiner* — Brian Casler
*Assistant Examiner* — Amanda Lauritzen
(74) *Attorney, Agent, or Firm* — Simpson & Simpson, PLLC

(57) ABSTRACT

A hyperspectral imaging system having an optical path. The system including an illumination source adapted to output a light beam, the light beam illuminating a target, a dispersing element arranged in the optical path and adapted to separate the light beam into a plurality of wavelengths, a digital micromirror array adapted to tune the plurality of wavelengths into a spectrum, an optical device having a detector and adapted to collect the spectrum reflected from the target and arranged in the optical path and a processor operatively connected to and adapted to control at least one of: the illumination source; the dispersing element; the digital micromirror array; the optical device; and, the detector, the processor further adapted to output a hyperspectral image of the target. The dispersing element is arranged between the illumination source and the digital micromirror array, the digital micromirror array is arranged to transmit the spectrum to the target and the optical device is arranged in the optical path after the target.

30 Claims, 56 Drawing Sheets

U.S. PATENT DOCUMENTS

| | | | |
|---|---|---|---|
| 2005/0234302 A1* | 10/2005 | MacKinnon et al. | 600/181 |
| 2005/0270528 A1 | 12/2005 | Geshwind et al. | |
| 2006/0134669 A1 | 6/2006 | Casasanta, III | |
| 2007/0038042 A1 | 2/2007 | Freeman et al. | |
| 2007/0249913 A1 | 10/2007 | Freeman et al. | |
| 2008/0007692 A1 | 1/2008 | Mihashi et al. | |
| 2008/0255457 A1 | 10/2008 | Khoobehi et al. | |
| 2009/0295910 A1* | 12/2009 | Mir et al. | 348/61 |
| 2010/0026957 A1 | 2/2010 | Tanguay, Jr. et al. | |
| 2011/0285995 A1* | 11/2011 | Tkaczyk et al. | 356/326 |

OTHER PUBLICATIONS

Zuzak, K., et al "Imaging hemoglobin oxygen saturation in sickle cell disease patients using noninvasive visible reflectance hyperspectral techniques: effects of nitric oxide", Am J Physiol Heart Circ Physicol, 285, pp. H1183-H1189 (2003).

Zuzak, K., et al "Intraoperative Bile Duct Visualization Using Near-Infrared Hyperspectral Video Imaging", Am J Sug, 195 (4), pp. 491-497 (2008).

Zuzak, K., et al "Noninvasive Determination of Spatially Resolved and Time-Resolved Tissue Perfusion . . . Inhalation of Use of a Visible-Reflectance Hyperspectral Imaging Technique", Clinical Investigation and Reports, 104 (24), pp. 2905-2920 (2001).

Zuzak K. et al "Visible and Infrared Hyperspectral Visualization of Normal and Ischemic Tissue", Engineering in Medicine and Biology, 21st Annual Conference (1999).

Zuzak K., et al "DLP Hyperspectral Imaging for Surgical and Clinical Utility", Proceedings of the SPIE,7210, pp. 721006-721006-9 (2009).

Zuzak K., et al "Hyperspectral Imaging Utilizing LCTF and DLP Technology for Surgical and Clinical Applications", Proceedings of the SPIE, 7170, pp. 71700C-71700C-9 (2009).

Naik, S. "Characterization of a Novel, In Vivo Laparoscopic Hyperspectral Imaging System for Minimally Invasive Surgery", The University of Texas at Arlington (2006).

Kothare, A. "A Visible Reflectance Hyperspectral Imaging System with Improved Capabilities for Translational Medicine Projects", The University of Texas at Arlington (2005).

Zinzuwadia N. "Characterization of a Hyperspectral Imager: A Diagnostic Tool for Monitoring Retinal Diseases", The University of Texas at Arlington (2007).

Shah, G. "Characterizatin of a Noninvasive, In Vivo, Microscopic Hyperspectral Imaging System for Micorvascular Visualization", The University of Texas at Arlington (2006).

Zuzak, K., et al "Intraoperative bile duckt visualiztion using near-infrared hyperspectral video imaging", The American Journal of Surgery, 195, pp. 491-497 (2008).

Zuzak, K. et al "DLP Hyperspectral Imaging Platform for Video Rate in vivo Chemical Imaging".

Chad, T, et al "Characterization of Renal Ischemia Using DLP Hyperspectral Imaging: A Comparison of Artery-Only Occlusion (AO) Versus Artery and Vein Occlusion (AV)", Journal of Endourology (2009).

Francis, R.P, "DLP Hyperspectral Imaging for Surgical and Clinical Utility", The University of Texas at Arlington (2009).

Fong, A. et al "Advanced phtononic tools for the hyperspectral imaging in the life sciences", SPIE Newsroom 10.117/2.1200803.1051 (2008).

International Search Report, International application No. PCT/US2009/053302, Published Feb. 23, 2010.

Visible spectroscopic imaging studies of normal and ischemic dermal tissue. Zuzak Krel J., Schaeberle Michael D., Lewis Neil E., Levin Ira W. SPIE 2000, 3918. (Proceedings).

* cited by examiner

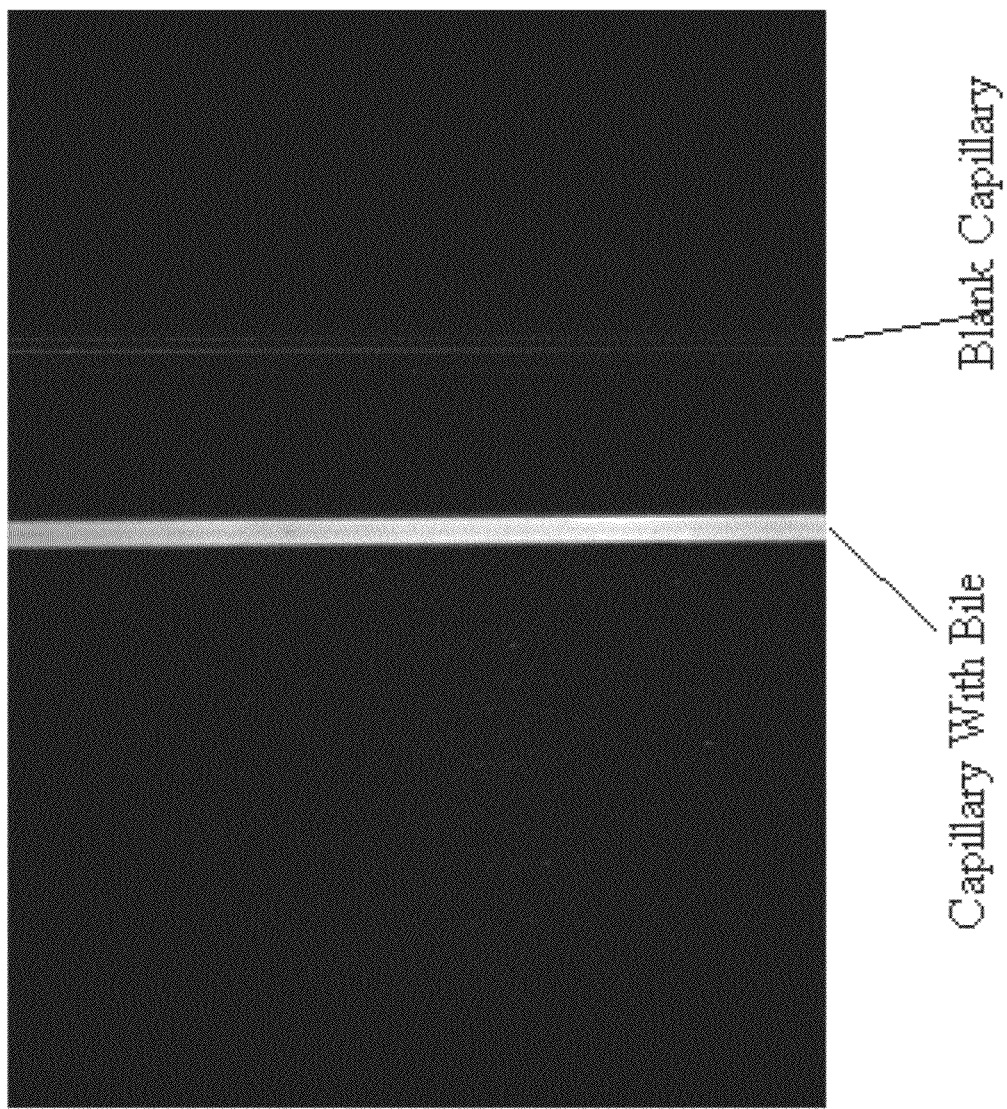

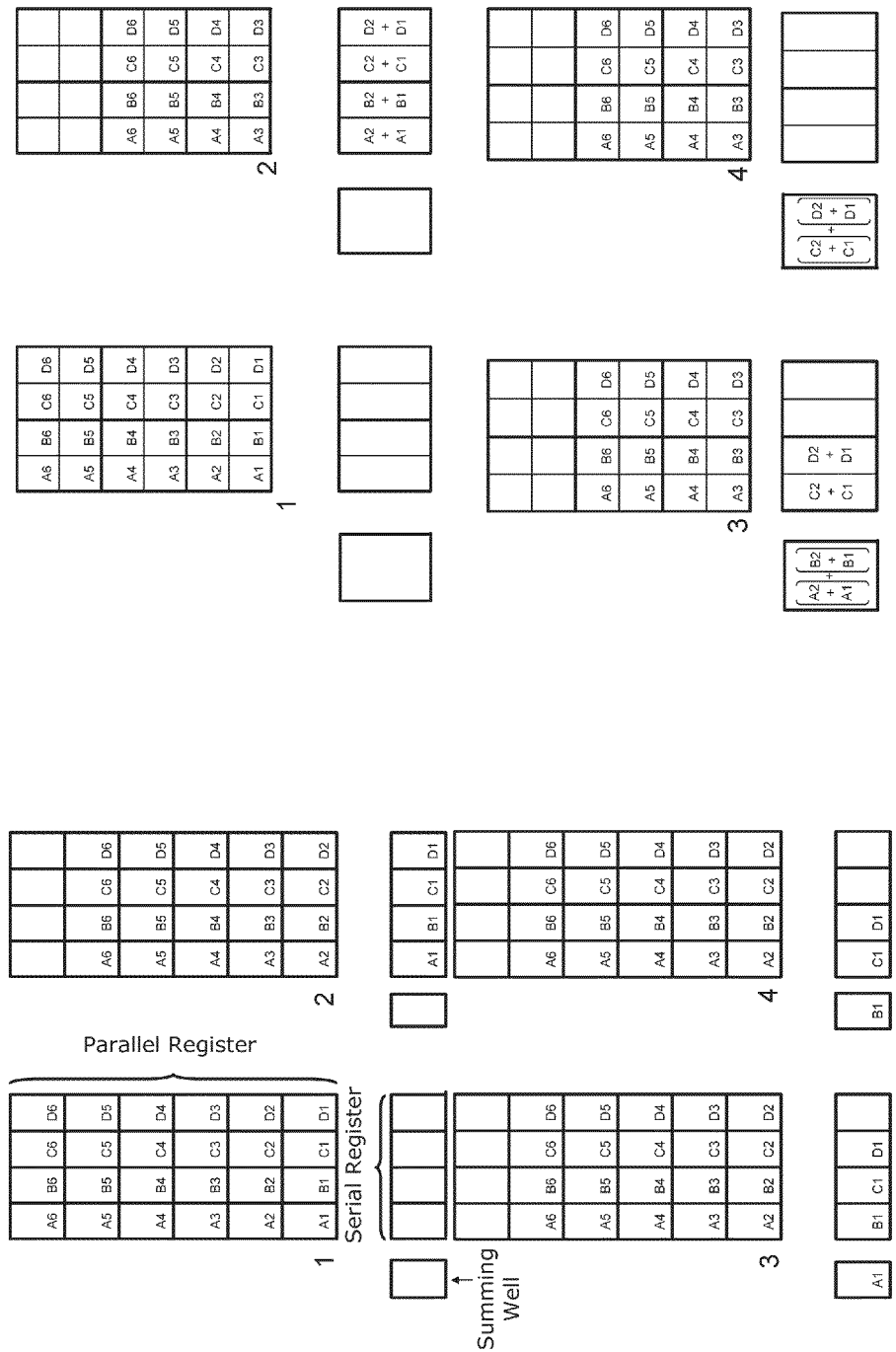

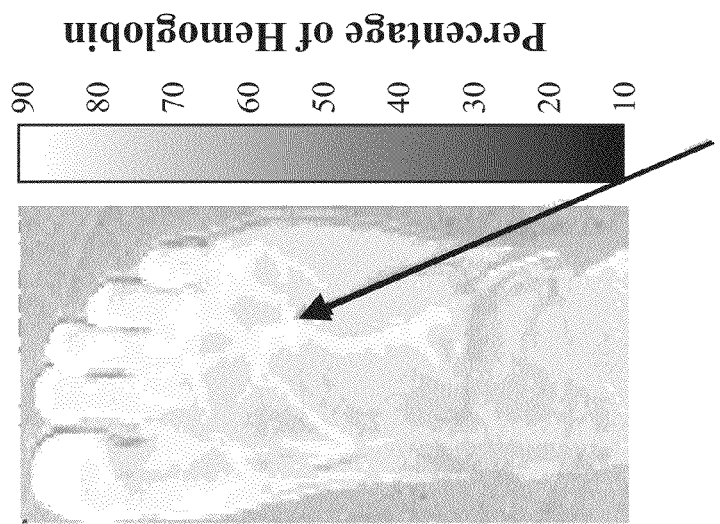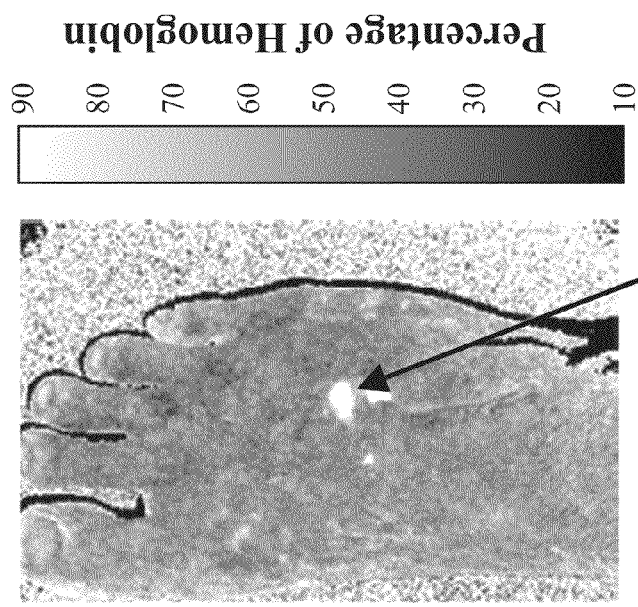
Fig. 47

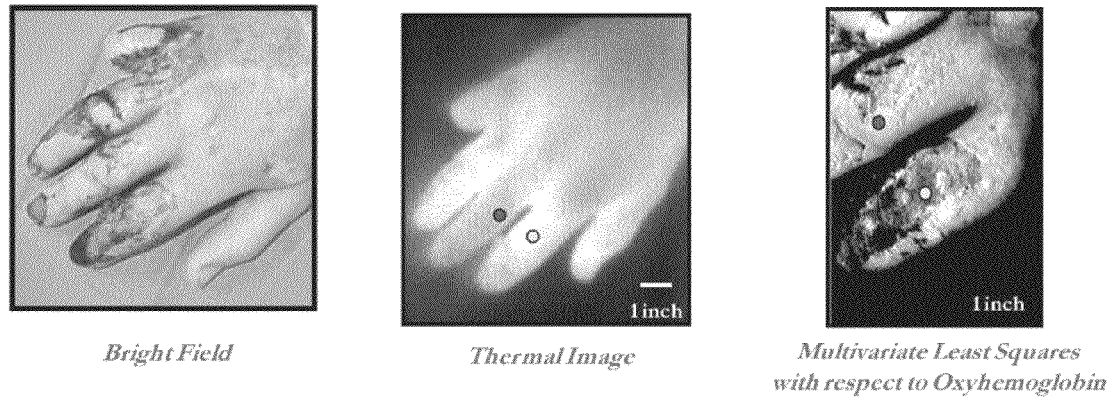
*Bright Field*  *Thermal Image*  *Multivariate Least Squares with respect to Oxyhemoglobin*
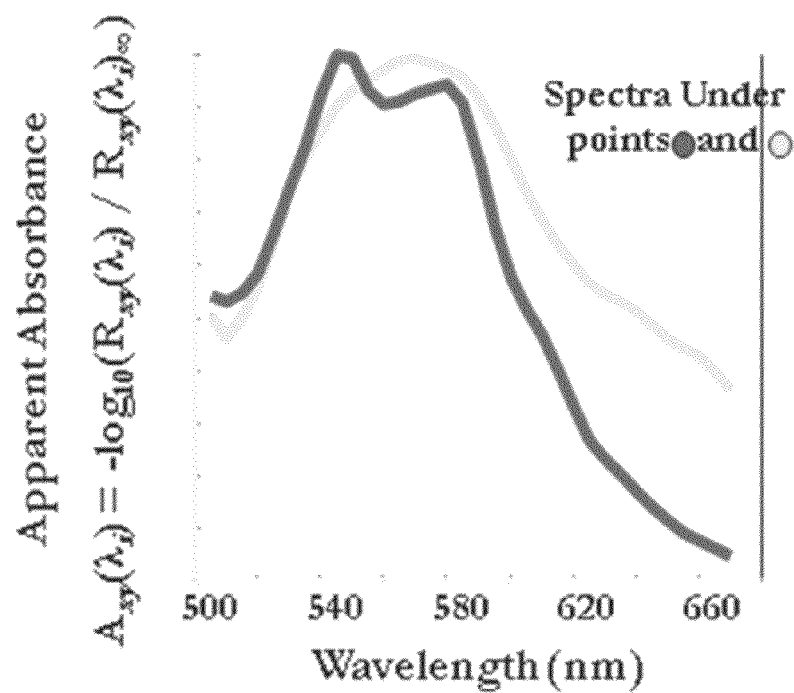
Fig. 48

Fig. 69

DIGITAL LIGHT PROCESSING HYPERSPECTRAL IMAGING APPARATUS

CROSS-REFERENCE TO RELATED APPLICATIONS

This patent application claims priority to U.S. Provisional Patent Application No. 61/087,714, filed Aug. 10, 2008, U.S. Provisional Patent Application No. 61/087,715, filed Aug. 10, 2008, and U.S. Provisional Patent Application No. 61/168,347, filed Apr. 10, 2009, which applications are incorporated herein by reference.

STATEMENT REGARDING FEDERALLY SPONSORED RESEARCH OR DEVELOPMENT

This invention was made with government support under Grant Number 5 U24 DK076169-02 awarded by the National Institutes of Health. The government has certain rights in the invention.

FIELD OF THE INVENTION

The present invention relates generally to the field of spectroscopic imaging that results in collecting/measuring spectroscopic image data and the associated algorithms that result in chemically encoded images of tissue, including devices, methods and systems for fluorescence imaging of tissues in real-time. Additionally, the present invention relates generally to the field of hyperspectral imaging of medical tissues. In particular, the invention is directed to new devices, tools and processes for the in vivo detection and evaluation of diseases and disorders. Moreover, the present invention describes, but is not limited to, a spectrally conformable illumination system and associated analytical algorithms, e.g., chemometrics, spectral and image digital signal processing, used to reduce the number of image frames required to generate a real-time processed image that is color-coded based on matching the reflectance of each pixel in an image to known reflectance spectra. Generally, the present invention is applicable to surgical and clinical applications, and is also applicable to a variety of other applications, including but not limited to microscopy, pathology, food safety/inspection and pharmacology.

BACKGROUND OF THE INVENTION

Without limiting the scope of the invention, its background is described in connection with laparoscopic procedures, such as cholecystectomy, in connection with a hyperspectral imaging system used for medical tissues and in connection with new devices, tools and processes for the in vivo detection and evaluation of diseases and disorders.

The gallbladder is a small pear-shaped organ that stores and concentrates bile. The gallbladder is connected to the liver by the hepatic duct. It is approximately 3 to 4 inches (7.6 to 10.2 cm) long and about 1 inch (2.5 cm) wide. The function of the gallbladder is to store bile and concentrate. The bile emulsifies fats and neutralizes acids in partly digested food. A muscular valve in the common bile duct opens, and the bile flows from the gallbladder into the cystic duct, along the common bile duct, and into the duodenum (part of the small intestine).

The following are disorders of the gall bladder. Cholelithiasis is a disorder of the extrahepatic biliary tract related to gallstones resulting in the presence of stones in the gall bladder. Gall stones are bodies formed within the body by accretion or concretion of normal or abnormal bile components. Gall stones of various shapes and sizes are formed within the gall bladder. Cholecsytitis is the inflammation of the gall bladder. Cholecystitis is often caused by Cholelithiasis, with choleliths most commonly blocking the cystic duct directly which causes the gallbladder's wall to become inflamed. Extreme cases may result in necrosis and rupture, and could cause further infection and pain resulting from such inflammation. Inflammation often spreads to its outer covering, irritating surrounding structures such as the diaphragm and bowel. Cholecystitis usually presents as a pain in the right upper quadrant. Gall bladder Cancer is a relatively uncommon cancer that occurs in the gall bladder. If detected early, this cancer can be cured by removing the gall bladder.

Gall bladder diseases are marked with some or all of the following symptoms: severe and constant pain in the upper right abdomen which can last for days; increasing pain when drawing a breath; and, radiating pain to the back or occurring under the shoulder blades. About a third of patients have fevers and chills. Nausea and vomiting may also occur. Complaints of gas, nausea, and abdominal discomfort after meals are the most common, but they may be vague and indistinguishable from similar complaints in people without gallbladder disease. Moreover, gall bladder diseases may result in jaundice (yellowish skin), dark urine, lighter stools, or combinations thereof.

As the majority of patients incur gallstones along with a gall bladder disease, the diagnosis can usually be confirmed thorough ultrasound imaging, a safe, painless and non-invasive technique that uses high frequency sound waves to create an image of gallbladder and gallstones. Other diagnosis methods like X-Ray and other scanning technology may be used.

Cholecystectomy is one of the most common operations performed in United States. It is frequently used for the treatment of symptomatic gallstones. Cholecystectomy is the surgical removal of gall bladder. The two procedures utilized to surgically remove the gall bladder are Open Cholecystectomy and Laparoscopic Cholecsytectomy. The laparoscopic method is utilized more frequently. The choice of the procedure is made on individual basis. A Cholecystectomy is performed to treat Cholelithiasis and Cholecystitis.

In conventional Cholecsytectomy, a surgeon makes an incision approximately 6 inches long. The incision is made either longitudinally in the upper portion of the abdomen or obliquely beneath the ribs on the right side. During the procedure, drains may be inserted into the abdomen, which are usually removed while the patient is still in the hospital. Following a normal cholecystectomy, the patient may be in the hospital from one to three days post surgery. Normal activity can be resumed in about four weeks. In complicated cases normal activity can be resumed in about four to eight weeks. The procedure is very common and is successful most of the time. However, any surgery involves risk factor associated with it, which can cause complications. The most common associated risk with Cholecsytectomy is the injury to the common bile duct (CBD) which is hidden, as it lies below a layer of fat. Thus, it is the surgeon's expertise and judgment for locating the CBD and avoiding any injuries.

A laparoscope is a long and rigid tube that is attached to a camera and a light source. Before the laparoscope is inserted, the patient's abdomen is distended with an injection of carbon dioxide gas, which allows the surgeon to see the internal organs of the patient. With the help of the laparoscope and a video display, which guides the surgeon for the procedure, the surgeon is able to locate and perform a cholecystectomy. Other small incisions are made in the abdomen; two of them on the right side below the rib cage and one in the upper portion below the sternum or the breast. Many other sophisticated instruments are used to perform the procedure. For example, two instruments are used to grasp and retract the gall bladder and a third is used to free the gall bladder from its attachment. Once the gall bladder is free, the surgeon then removes it from the patient.

Under normal conditions, patients recover within a day or two; however, complications may still occur. The most common complication that can occur is the injury to common bile duct (CBD). This complication occurs in about 0.5% of cholecystectomies. Even though this complication is rare, it demands a better imaging technique that provides the surgeon with the precise location of the CBD during a cholecystectomy. The imaging technique should also be able to distinguish between the CBD and other tissue, providing a good contrast image.

During a cholecystectomy, one of the important problems faced by the surgeon is visibility of structures below the fat layer. Thus, it is the surgeon's experience which determines the approximate location of the bile duct. An imaging aid currently available for intraoperative bile duct visualization is an Intraoperative Cholangiography (IOC). This technique has hardly undergone substantial changes since its introduction by Mirizzi in 1937. (See Mirizzi P L. 1937 Operative Cholangiography Surg Gynaecol Obstet. 1937; 65; 702-710). Routine IOC performed with every cholecystectomy is one of the strategies used to reduce bile duct injuries. The rapidly advancing technology of nuclear imaging, diagnostic ultrasound, MRI and CT have also been used for the purpose of visualizing the bile duct. For diagnosis of hepatobiliary disease imaging techniques such as ultrasound and Magnetic Resonance Cholangiography (MRC) are frequently used. Endoscopic Retrograde Cholangiography (ERC) is another standard for visualization of the bile duct. Ultrasound is tolerated by patients and is cost effective. MRC is superior in visualizing the biliary system, does not require any contrast agent to visualize the bile ducts and dilatation and gallstones in CBD are easily detected. For patients with choedocholithiasis, endoscopic retrograde cholangio-pancreatography (ERCP) can be utilized. Selective use of preoperative ERCP has proven to be a good diagnostic tool, as well as a way to allow clearance of CBD stones when present. (See Qasim Al-qasabi et al. "Operative Cholangiography in Laproscopic Cholecystectomy: Is it essential"). One of the faster and widely available techniques is Computed Tomography Cholangiography (CTC). A multi-detector CT reports a sensitivity of 65%-88% and a specificity of 84%-97% to detect gallstones. With the development of multi-detetcor CT, the resolution of CTC exceeds that of MR. (See A Persson, N Dahlstrom, Ö Smedby and T B Brismar: "Three-dimensional drip infusion CT cholangiography in patients with suspected obstructive biliary disease: a retrospective analysis of feasibility and adverse reaction to contrast material").

Most histological evaluation of living tissues typically involves fixation, sectioning, and/or staining to obtain samples which exhibit high quality images under microscopy. While this process is current the industry standard, the procedure is time consuming. It requires removal of tissue from the patient, processing time, and has inherent sampling error. In addition, the major limitation of this process is the delay in providing the surgeon with clinically relevant information at the time of surgery. Thus, new methods have been developed to complement existing modalities by providing the surgeon real-time information that could be used intra-operatively to identify suspect lesions.

One such method is hyperspectral imaging. Hyperspectral imaging is a method of imaging spectroscopy that generates a gradient map based on local chemical composition. Hyperspectral imaging has been used in satellite investigation of suspected chemical weapons production areas, geological features, and the condition of agricultural fields, and has recently been applied to the investigation of physiologic and pathologic changes in living tissue in animal and human studies. Hyperspectral imaging has also been used in medical applications and has been shown to accurately predict viability and survival of tissue deprived of adequate perfusion, and to differentiate diseased (e.g., tumor) and ischemic tissue from normal tissue.

One such example can be seen in United States Patent Application Publication No. 2007/0016079 (Freeman et al.). The '079 application describes methods and systems of hyperspectral and multispectral imaging of medical tissues. In particular, the '079 application is directed to new devices, tools and processes for the detection and evaluation of diseases and disorders such as diabetes and peripheral vascular disease, that incorporate hyperspectral or multispectral imaging.

Another example can be found in United States Patent Application Publication No. 2007/0002276 (Hirohara et al.). The '276 application describes spectral characteristics that reduce variation depending on the frequency of received light intensity, and is gentle on a subject's eye. The invention of the '276 application eliminates displacement between positions of respective spectral images of the same area even if a change in alignment occurs between the eye and apparatus during image capture. In the '276 application, an apparatus for measuring spectral fundus image includes: an illumination optical system having an illumination light source that emits a light beam in a specified wavelength range; a light receiving optical system for forming a fundus image on the light receiving surface of a photographing section; a liquid crystal wavelength tunable filter capable of choosing a wavelength of a transmitted light beam in a specified wavelength range; a spectral characteristic correction filter having a wavelength characteristic for correcting the wavelength characteristic of the emitted light intensity of the illumination light source and the transmission wavelength characteristic of the wavelength tunable filter so that the received light intensity on the light receiving surface is kept within the specified range; and, a data measuring section for taking the spectral fundus image data from the light receiving surface while changing the wavelength of the light beam passing through the wavelength tunable filter.

Yet another example is described in U.S. Pat. No. 7,199,876 (Mitchell) entitled "Compact Hyperspectral Imager". Here, the '876 patent details a hyperspectral imager including: a first optical sub-system; at least one slit element; a second optical sub-system; at least one reflective dispersive element located at a center plane; and, at least one detecting element located at substantially an image surface. During operation, the first optical sub-system images, onto the slit element(s), electromagnetic radiation originating at a source. The second optical sub-system substantially collimates, at a center plane, electromagnetic radiation emanating from the slit element(s). The second optical sub-system also images, onto the image surface, the electromagnetic radiation reflected from the reflective dispersive element(s). The detecting element(s) detect the dispersed electromagnetic radiation reflected from the reflective dispersive element(s).

Still yet another example is seen in U.S. Pat. No. 7,167,279 (Otten) entitled "High Efficiency Spectral Imager". The '279 patent describes optical instruments having, inter alia, optics to process wavelengths of electromagnetic radiation to produce an interferogram. The instruments described in the '279 patent include at least one optical path and optical elements positioned along this path for splitting and recombining the wavelengths which interfere with each other to produce a plurality of different fringes of different wavelengths. In one group, the optics include matched gratings which are positioned along the optical path outside of the interferometer optics to produce first and second sets of spectrally dispersed beams. The interferometer optics also include a beam splitter and first and second mirrors. The gratings may be positioned in a variety of locations along the optical path. In another group, the optics include a beam splitter having a plurality of surfaces, wherein each of the surfaces is either 100% reflective, 100% transmissive or 50% reflective and 50% transmissive. In a third group, the optics include the beam splitter having a plurality of reflective and transmissive surfaces and matched gratings. The instruments can all include a detector for detecting the interferogram and means for processing the detected interferogram to produce spectral information.

U.S. Pat. No. 6,198,532 (Cabib) discloses a spectral bioimaging method for enhancing pathologic, physiologic, metabolic and health related spectral signatures of an eye tissue. The method disclosed in the '532 patent includes the steps of: (a) providing an optical device for eye inspection being optically connected to a spectral imager; (b) illuminating the eye tissue with light via the iris, viewing the eye tissue through the optical device and spectral imager and obtaining a spectrum of light for each pixel of the eye tissue; and, (c) attributing each of the pixels a color according to its spectral signature, thereby providing an image enhancing the spectral signatures of the eye tissue.

Another example can be found in U.S. Pat. No. 6,992,775 (Soliz et al.). The '775 patent discloses an ophthalmic instrument for obtaining high resolution, wide field of area hyperspectral retinal images for various sized eyes which includes a fundus retinal imager (which includes optics for illuminating and imaging the retina of the eye); apparatus for generating a real time image of the area being imaged and the location of the hyperspectral region of interest; a high efficiency spatially modulated common path; a Fourier transform hyperspectral imager (a high resolution detector optically coupled to the hyperspectral and fundus imager optics); and, a computer (which is connected to the real time scene imager, the illumination source, and the high resolution camera) including an algorithm for recovery and calibration of the hyperspectral images.

Finally, in U.S. Pat. No. 7,118,217 (Kardon el al.) describes an optical imaging device of retinal function to detect changes in reflectance of near infrared light from the retina of human subjects in response to visual activation of the retina by a pattern stimulus. The device of the '217 patent measures changes in reflectance corresponding in time to the onset and offset of the visual stimulus in the portion of the retina being stimulated. Any changes in reflectance can be measured by interrogating the retina with a light source. The light source may be presented to the retina via the cornea and pupil or through other tissues in and around the eye. Different wavelengths of interrogating light may be used to interrogate various layers of the retina. Additionally, various patterns and methods of stimulation have been developed for use with the imaging device and methods.

The aforementioned hyperspectral imaging systems are slow for routine clinical practice. In addition, there are no methods for directly imaging the in vivo level of the biomolecules in live humans or animals during clinical visits or during surgical (open, endoscopic or laparoscopic) operations. Accordingly, there is a need for an improved microscopy system and method that incorporates superior speed for hyperspectral/multimodal imaging while offering high spatial resolution and optimized signal sensitivity for fast image acquisition. The present invention is directed to such a need.

BRIEF SUMMARY OF THE INVENTION

In one embodiment, the present invention is a hyperspectral imaging system that includes one or more optical tunable radiation sources configured to illuminate one or more fluorescent targets; one or more light dispersing elements positioned in the optical path between the one or more optical tunable radiation sources and one or more detectors; one or more spatial light modulators, capable of tuning light from the optical radiation source into at least one spectral band or the band spectrum, placed in the optical path before the one or more fluorescent targets; an optical microscope configured to collect the at least one spectral band or the band spectrum reflected from the one or more fluorescent targets positioned in the optical path between the optical tunable radiation sources and the one or more detectors; and a processor connected to the one or more optical tunable radiation sources, the one or more detectors to process the at least one spectral band or a band spectrum reflected from the fluorescent target into image data, or both. In one aspect, the fluorescent target comprises natural fluorescence of a tissue or fluid. In another aspect, the one or more optical tunable radiation sources produce electromagnetic radiations having wavelengths over the range of 250 nm-2,500 nm. In another aspect, the one or more optical tunable radiation sources is a supercontinuum laser. In one aspect, the hyperspectral imaging system is a microscope.

The system may further comprise at least one deconvolution algorithm that normalizes each of the at least one spectral band or the band spectrum at each pixel before image processing. In one aspect, the spatial light modulator is a digital micromirror device. In one aspect, the at least one spectral band or the band spectrum are processed at a video rate. One or more dispersing elements may be a grating, a prism, a tunable filter, an electromechanical optical filter wheel, an acousto-optical tunable filter, a liquid-crystal tunable filter, a digital micromirror device, or any combination thereof. One or more detectors may be selected from the group consisting of: a spectrometer, a two-dimensional array detector, a multi-array detector, an on-chip amplification CCD camera, a back-illuminated CCD, a liquid nitrogen cooled CCD detector or a focal plane array, e.g., a CCD, VisGaAs, InGas or ferromagnetic. In one aspect, the processor comprises an image data acquisition software that tunes the spatial light modulator, triggers the one or more detectors for collection of a series of spectroscopic images formatted as a hyperspectral image cube and processes the image data for visualization; and one or more converters to digitize image data, wherein the processor is connect to one or more displays. In another aspect, the processor tunes the one or more spatial light modulators, triggers the one or more detectors for collection of a series of spectroscopic images formatted as a hyperspectral image cube and processes the image data for visualization.

In another aspect, the fluorescence is natural fluorescence, a fluorescent dye, a fluorescence resonance energy donor, a fluorescence resonance energy acceptor, a fluorescence quencher or combinations thereof. Non-limiting examples of one or more fluorescence molecules for use with the present invention include indocyanine green, 5-carboxyfluorescein (5-FAM), 6-carboxyfluorescein (6-FAM), fluorescein-5-isothiocyanate (FITC), 2'7'-dimethoxy-4'5'-dichloro-6-carboxyfluorescein (JOE); rhodamine and rhodamine derivatives such as N,N,N',N'-tetramethyl-6-carboxyrhodamine (TAMRA), 6-carboxyrhodamine (R6G), tetramethyl-indocarbocyanine (Cy3), tetramethyl-benzindocarbocyanine (Cy3.5), tetramethyl-indodicarbocyanine (Cy5), tetramethyl-indotricarbocyanine (Cy7), 6-carboxy-X-rhodamine (ROX); hexachloro fluorescein (HEX), tetrachloro fluorescein TET; R-Phycoerythrin, 4-(4'-dimethylaminophenylazo) benzoic acid (DABCYL), and 5-(2'-aminoethyl)aminonaphthalene-1-sulfonic acid (EDANS) or combinations thereof.

In another aspect, the processor is defined further as: a computer having image data processing software capable of processing various fluorescence and digital signals; a digital signal processor comprising algorithms for fluorescence analysis; and, an algorithm library for visualizing chemistry on and/or within the imaged one or more fluorescent targets for detection, monitoring and diagnosis. In one aspect, the one or more illumination optics comprises lenses, microscopes, dissection microscopes, surgical microscopes, slit lamps, endoscopes, laparoscopes, colonoscopes or any combination thereof. In another aspect, the processor is in communication with a database comprising a library spectrum of fluorescent targets. In yet another aspect, the one or more fluorescent targets comprises a tissue, in the bloodstream, in the lymphatic system, in bodily secretions, in biopsies, on the skin, by fiber optic transdermal spectroscopy on a blood vessel, on the skin or at the retina, by laparoscopy, by endoscopy, in the central nervous system or combinations thereof. Moreover, in still yet another aspect, the one or more fluorescent targets comprises an organ. In another aspect, the system can be configured for real-time in vivo analysis of the one or more fluorescent targets.

Another embodiment of the present invention is an apparatus and method for obtaining spectral image data from one or more fluorescent targets in vivo comprising: generating a spectrum of electromagnetic radiation; separating the electromagnetic radiation into at least one spectral band or a band spectrum using a spatial light modulator; illuminating the one or more fluorescent targets with the at least one spectral band or the band spectrum; collecting the reflected at least one spectral band or the band spectrum resulting from the one or more fluorescent targets; and, directing the collected at least one spectral band or the band spectrum to one or more detectors that capture spectral image data. The method may further comprise the steps of: tuning the spatial light modulator; triggering the one or more detectors for collection; formatting and digitizing the spectral image data as a hyperspectral image; deconvoluting each pixel of the spectral image data using a signal processing algorithm; and, displaying the spectral image on one or more fluorescent targets. In one aspect, the one or more fluorescent targets comprise tissue components that have natural or native fluorescence.

Another embodiment of the present invention is a method for hyperspectral surgery by capturing image data of one or more fluorescent targets generating a wide spectrum electromagnetic radiation comprising: separating the electromagnetic radiation into at least one spectral band or a band spectrum using a spatial light modulator; illuminating the one or more fluorescent targets with the at least one spectral band or the band spectrum; collecting the reflected at least one spectral band or the band spectrum resulting from the one or more fluorescent targets; and, directing the collected at least one spectral band or the band spectrum to one or more detector to form the image data, wherein the hyperspectral surgery is used in surgical procedures selected from a cholecystectomy, amputation, burn, skin flap evaluation, visualizing areas of angiogenesis, probes that bind antigens and absorbs near-infrared during pathological evaluations and in vivo, quality control of pharmaceuticals, monitoring vascular changes and drug discovery in response to pharmaceuticals, monitoring diabetic retinopathy, diseases such as cancer, diabetes, sickle cell, anemia, bilirubin, raynauds, ulcers, burns, skin flaps, surgery, gallbladder, brain, monitoring wound healing, and early detection of wound infections.

Another embodiment of the present invention is a method for hyperspectral surgery of a human subject by capturing image data of one or more fluorescent targets generating a wide spectrum electromagnetic radiation comprising: covering the human subject with NIR transparent material to provide privacy, accessibility and maintain body heat; separating the electromagnetic radiation into at least one spectral band or the band spectrum using a spatial light modulator; illuminating the fluorescent target with the at least one spectral band or the band spectrum; collecting the reflected at least one spectral band or the band spectrum resulting from the one or more fluorescent targets; and, collecting at least one spectral band or the band spectrum to one or more detector to form the image data, wherein the hyperspectral surgery is used in surgical procedures selected from a cholecystectomy, amputation, burn, skin flap evaluation, visualizing areas of angiogenesis, probes that bind antigens and absorbs near-infrared during pathological evaluations and in vivo, quality control of pharmaceuticals, monitoring vascular changes and drug discovery in response to pharmaceuticals, monitoring diabetic retinopathy, cancer, diabetes, sickle cell, anemia, bilirubin, raynauds, ulcers, burns, skin flaps, surgery, gallbladder, brain, monitoring wound healing, measuring oxygenation of retina, measuring optic nerve oxygenation, measuring macular pigments, measuring pigments in retinal photoreceptors and retinal pigment epithelium, diagnosis of autoimmune retinitis, diagnosis of infectious retinitis, diagnosis of infiltrative neoplastic conditions, evaluating disease biomarkers, diagnosis of ocular trauma injuries, measuring oxygenation of a kidney and early detection of wound infections.

Most of the art discussed above can either collect all the spectral information and scan the field of view, or collect all the field of view and scan through the spectral range. Unlike the prior art, the present invention can collect all the spectral information and scan the field of view simultaneously by illuminating with a spectrum, a spectroscopic wavelength, or multiple wavelengths and collect the image data, along with chemometrics on the source side and/or on the detector side.

One embodiment of the present invention is a hyperspectral imaging system having one or more optical radiation sources configured to illuminate one or more objects, illumination optics, one or more dispersing elements, one or more spatial light modulators that are capable of tuning light from the optical radiation source into at least one spectral band or a band spectrum (in other words, one or more single wavelength bands or a single multi-wavelength band), and positioned in the optical path before the one or more objects, an optical microscope configured to collect the at least one spectral band or the band spectrum reflected from the one or more objects, one or more detectors; and, a processor to process the reflected at least one spectral band or the band spectrum to provide an enhanced image. The present invention system images may also include, but are not limited to, organs and tissue components.

The optical radiation source of the system is capable of producing photons having wavelengths in the range of 250 nm-2,500 nm. The spatial light modulator of the system may be a Digital Micromirror Device (DMD). In certain embodiments, the dispersing element of the present system may be a grating or a prism. The one or more detectors can also include at least one detector selected from: a spectrometer, a two-dimensional array detector, a multi-array detector, an on-chip amplification CCD camera, a back-illuminated CCD, a liquid nitrogen cooled CCD detector or a focal plane array, e.g., a CCD, VisGaAs, InGas or ferromagnetic.

In addition, the processor(s) of the present invention include, but are not limited to, a computer having image processing software that will tune the spatial light modulator and trigger the one or more detectors for collecting a series of spectroscopic images formatted as a hyperspectral image cube, one or more displays, and a database of characterized objects.

The present system may also have one or more liquid crystal tunable filters positioned in the optical path, and can even be configured as a portable endoscopic system. In certain embodiments, the present invention can be configured for real-time in vivo analysis of the one or more objects.

The present invention also relates to a method for obtaining spectral image data from an object by generating a wide spectrum electromagnetic radiation, separating the electromagnetic radiation into at least one spectral band or a band spectrum using a spatial light modulator, illuminating the object with the at least one spectral band or the band spectrum electromagnetic radiations, collecting the reflected at least one spectral band or the band spectrum electromagnetic radiations resulting from the object, and directing the collected at least one spectral band or the band spectrum electromagnetic radiation image to one or more detector array for forming the spectral image data.

In addition, the reflected one or more single wavelength electromagnetic radiations may include, but are not limited to: electromagnetic radiation reflected, refracted, luminescence, fluorescence, autofluorescence, Raman scattered, transmitted, scattered, adsorbed, or emitted by the sample. In one aspect, the present invention includes one or more slit lamps. The present invention can also operate as a dissection microscope for clinical and surgical applications. In another aspect, the present invention includes a laparoscopic system for creating a library of chemometric deconvolutions so that a clinician can simply switch through various algorithms depending on applications.

In another embodiment, the present invention includes a hyperspectral imaging system including: one or more optical tunable radiation sources configured to illuminate one or more objects, e.g., tissue components; one or more detectors; one or more dispersing elements positioned in the optical path between the one or more optical tunable radiation sources and the one or more detectors; one or more spatial light modulators, capable of tuning light from the optical radiation source into at least one spectral band or a band spectrum; an optical microscope configured to collect one or more single wavelength spectral band or a spectrum band reflected from the one or more objects positioned in the optical path between the optical tunable radiation sources and the one or more detectors; one or more processors connected to the one or more optical tunable radiation sources, the one or more detectors, the one or more dispersing element, the one or more spatial light modulator, the optical microscope, or any combination thereof, wherein the one or more processors process the reflected at least one spectral band or the band spectrum as image data and to provide enhanced images. The one or more optical tunable radiation sources are typically capable of producing electromagnetic radiations having wavelengths over the range of 250 nm-2,500 nm and can be a supercontinuum laser.

In some aspects, the spatial light modulator is a digital micromirror device, and the one or more dispersing element can be a grating, a prism, a tunable filters, an electromechanical optical filter wheel, an acousto-optical tunable filter, a liquid-crystal tunable filter, a digital micromirror device, or any combination thereof. In addition, the one or more detectors can have at least one detector selected from: a spectrometer, a two-dimensional array detector, a multi-array detector, an on-chip amplification CCD camera, a back-illuminated CCD, a liquid nitrogen cooled CCD detector or a focal plane array.

In another aspect, the processor of the present invention can further include at least one processor having an image data acquisition software that tunes the spatial light modulator, triggers the one or more detectors for collection of series of spectroscopic images formatted as a hyperspectral image cube and processes the image data for visualization; one or more transducer to digitize image data; and, one or more display. The processor can further include a dedicated processor that tunes the spatial light modulator, triggers the one or more detectors for collection of series of spectroscopic images formatted as a hyperspectral image cube and processes the image data for visualization. The processor may be further defined as a computer having image data processing software capable of processing various chemometric and digital signals; a digital signal processor comprising algorithms for chemometric analysis; and, an algorithm library for visualizing chemistry on and within the imaged one or more objects for detection, monitoring and diagnosis. In addition, the processor can be connected to a database having a library spectrum of characterized one or more objects. In another aspect, the one or more illumination optics of the present invention can include lenses, microscopes, dissection microscopes, surgical microscopes, slit lamps, endoscopes, laparoscopes, colonoscopes or any combinations thereof.

In some aspects, the system of the present invention can further include one or more liquid crystal tunable filter and can be configured as a portable endoscopic system. The present invention can also be configured for real-time in vivo analysis of the one or more objects.

Yet in another aspect, the present invention includes a method for obtaining spectral image data from one or more objects in vivo (e.g., tissue components) including: generating a spectrum of electromagnetic radiation; separating the electromagnetic radiation into one or more single wavelength bands or a spectrum band using a spatial light modulator; illuminating the one or more objects with the one or more single wavelength bands or the spectrum band; collecting the reflected one or more single wavelength bands or the spectrum bands resulting from the one or more objects; and, directing the collected single wavelength bands or the spectrum bands to one or more detectors that capture spectral image data. The method can further include the steps of: tuning the spatial light modulator; triggering the one or more detectors for collection; formatting and digitizing the spectral image data as a hyperspectral image; deconvoluting each pixel of the spectral image data using a signal processing algorithm; and, displaying the spectral image on one or more displays.

In some aspects, the method uses spectrum of electromagnetic radiation comprises photons having wavelengths over the range of 250 nm-2,500 nm, or a supercontinuum laser. The spatial light modulator of the present invention can include a grating, a prism, a tunable filter, an electromechanical optical filter wheel, an acousto-optical tunable filter, a liquid-crystal tunable filter, a digital micromirror device, or any combination thereof. The detector for the method can have at least one detector selected from: a spectrometer, a two-dimensional array detector, a multi-array detector, an on-chip amplification CCD camera, and a back-illuminated CCD, a liquid nitrogen cooled CCD detector or a focal plane array. It should be appreciated that the present invention is not limited to foregoing detectors, but may include any type of electro-optical detection elements.

The reflected one or more single wavelength band or the spectrum bands of the present invention can include reflected radiation, luminescence, fluorescence, autofluorescence, Raman scattered, transmitted, scattered, adsorbed or emitted electromagnetic radiation by the one or more objects.

In another aspect, the present invention includes a method for hyperspectral surgery by capturing image data of one or more object generating a wide spectrum electromagnetic radiation including, by not limited to the following steps: separating the electromagnetic radiation into one or more single wavelength bands or a spectrum band using a spatial light modulator; illuminating the object with the one or more single wavelength bands or the spectrum band; collecting the reflected one or more single wavelength bands or the spectrum band resulting from the one or more object; and, directing the collected or more single wavelength bands or spectrum band to one or more detector to form the image data, wherein the hyperspectral surgery is used in a surgical procedure selected from the group consisting of: a cholecystectomy, amputation, burn, skin flap evaluation, visualizing areas of angiogenesis, probes that bind antigens and absorbs near-infrared during pathological evaluations and in vivo, quality control of pharmaceuticals, monitoring vascular changes and drug discovery in response to pharmaceuticals, monitoring diabetic retinopathy, diseases such as cancer, diabetes, sickle cell, anemia, bilirubin, raynauds, ulcers, burns, skin flaps, surgery, gallbladder, brain, monitoring wound healing, measuring oxygenation of retina, measuring optic nerve oxygenation, measuring macular pigments, measuring pigments in retinal photoreceptors and retinal pigment epithelium, diagnosis of autoimmune retinitis, diagnosis of infectious retinitis, diagnosis of infiltrative neoplastic conditions, evaluating disease biomarkers, diagnosis of ocular trauma injuries, measuring oxygenation of a kidney and early detection of wound infections. The method can further include the step of covering the human subject with NIR transparent material to provide privacy, accessibility and maintain body heat.

The present invention further includes a hyperspectral imaging system having an optical path, where the system includes an illumination source adapted to output a light beam, the light beam illuminating a target, a dispersing element arranged in the optical path and adapted to separate the light beam into a plurality of wavelengths, a digital micromirror array adapted to tune the plurality of wavelengths into a spectrum, an optical device having a detector and adapted to collect the spectrum reflected from the target and arranged in the optical path and a processor operatively connected to and adapted to control at least one of: the illumination source; the dispersing element; the digital micromirror array; the optical device; and, the detector, the processor further adapted to output a hyperspectral image of the target. The dispersing element is arranged between the illumination source and the digital micromirror array, the digital micromirror array is arranged to transmit the spectrum to the target and the optical device is arranged in the optical path after the target.

In some embodiments, the present invention hyperspectral imaging system further includes collimating optics adapted to transmit the light beam from the dispersing element to the digital micromirror array as a collimated light beam. In other embodiments, the present invention hyperspectral imaging system further includes beam shaping optics adapted to transmit the light beam from the digital micromirror array to the target so that the light beam substantially illuminations all of the target.

The present invention further includes a method of obtaining a hyperspectral image of a target including the steps of: generating a beam of light; dispersing the light beam with a dispersing element; separating the dispersed light beam into a first complex spectrum using a spatial light modulator; illuminating the target with the first complex spectrum, wherein the first complex spectrum subsequently reflects off of the target as a first reflected light beam; collecting the first reflected light beam; directing the collected first reflected light beam to a detector to capture a first spectral image data; separating the dispersed light beam into a second complex spectrum using the spatial light modulator; illuminating the target with the second complex spectrum, wherein the second complex spectrum subsequently reflects off of the target as a second reflected light beam; collecting the second reflected light beam; directing the collected second reflected light beam to the detector to capture a second spectral image data; separating the dispersed light beam into a third complex spectrum using the spatial light modulator; illuminating the target with the third complex spectrum, wherein the third complex spectrum subsequently reflects off of the target as a third reflected light beam; collecting the third reflected light beam; directing the collected third reflected light beam to the detector to capture a third spectral image data; and, forming the hyperspectral image from the first, second and third spectral image data.

In some embodiments, the first, second and third reflected light beams each includes reflected, luminescence, fluorescence, autofluorescence, Raman scattered, transmitted, scattered, adsorbed, or emitted electromagnetic radiation. In other embodiments, the detector includes a processor having an image data acquisition software adapted to tune the spatial light modulator, trigger the detector for collection of the first, second and third spectral image data formatted as a hyperspectral image cube and process the hyperspectral image cube for visualization, a digital signal process algorithm for analyzing chemometrics of the target and a display device adapted to display the hyperspectral image. In still other embodiments, the method is adapted for use in hyperspectral surgery, and the hyperspectral surgery is used in surgical procedures selected from the group consisting of: a cholecystectomy; an amputation; a burn; a skin flap evaluation; visualizing areas of angiogenesis; probes that bind antigens and absorbs near-infrared during pathological evaluations; in vivo quality control of pharmaceuticals; monitoring vascular changes and drug discovery in response to pharmaceuticals; monitoring diabetic retinopathy and diseases such as cancer, diabetes, sickle cell, anemia, bilirubin, raynauds, ulcers, burns, skin flaps, surgery, gallbladder, brain; monitoring wound healing; measuring oxygenation of retina; measuring optic nerve oxygenation; measuring macular pigments; measuring pigments in retinal photoreceptors and retinal pigment epithelium; diagnosis of autoimmune retinitis; diagnosis of infectious retinitis; diagnosis of infiltrative neoplastic conditions; evaluating disease biomarkers; diagnosis of ocular trauma injuries; measuring oxygenation of a kidney; and, early detection of wound infections. In still yet other embodiments, the first, second and third complex spectrum each include a plurality of intensities of a plurality of wavelengths.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which:

FIG. 16 is a fluorescence image of bilirubin with excitation from 400 nm-500 nm compared to a blank capillary;

FIG. 21 is a diagram of an example binning in a CCD camera;

FIG. 22 is another diagram of an example binning in a CCD camera;

FIG. 47 is a comparison of images obtained using visible light and Near infrared (NIR) of the reperfusion of a foot following removal of the shoe;

FIG. 48 is the in vivo hyperspectral imaging of human tissue, spatial variation of percentage of $HbO_2$ and surface temperature in response to burn;

FIG. 69A is an image of a human hand having burned regions thereon;

FIG. 69B is a hyperspectral image of the human hand of FIG. 69A chemically encoded to show oxyhemoglobin;

FIG. 69C is a hyperspectral image of the human hand of FIG. 69A chemically encoded to show water;

DETAILED DESCRIPTION OF THE INVENTION

Figure 1:
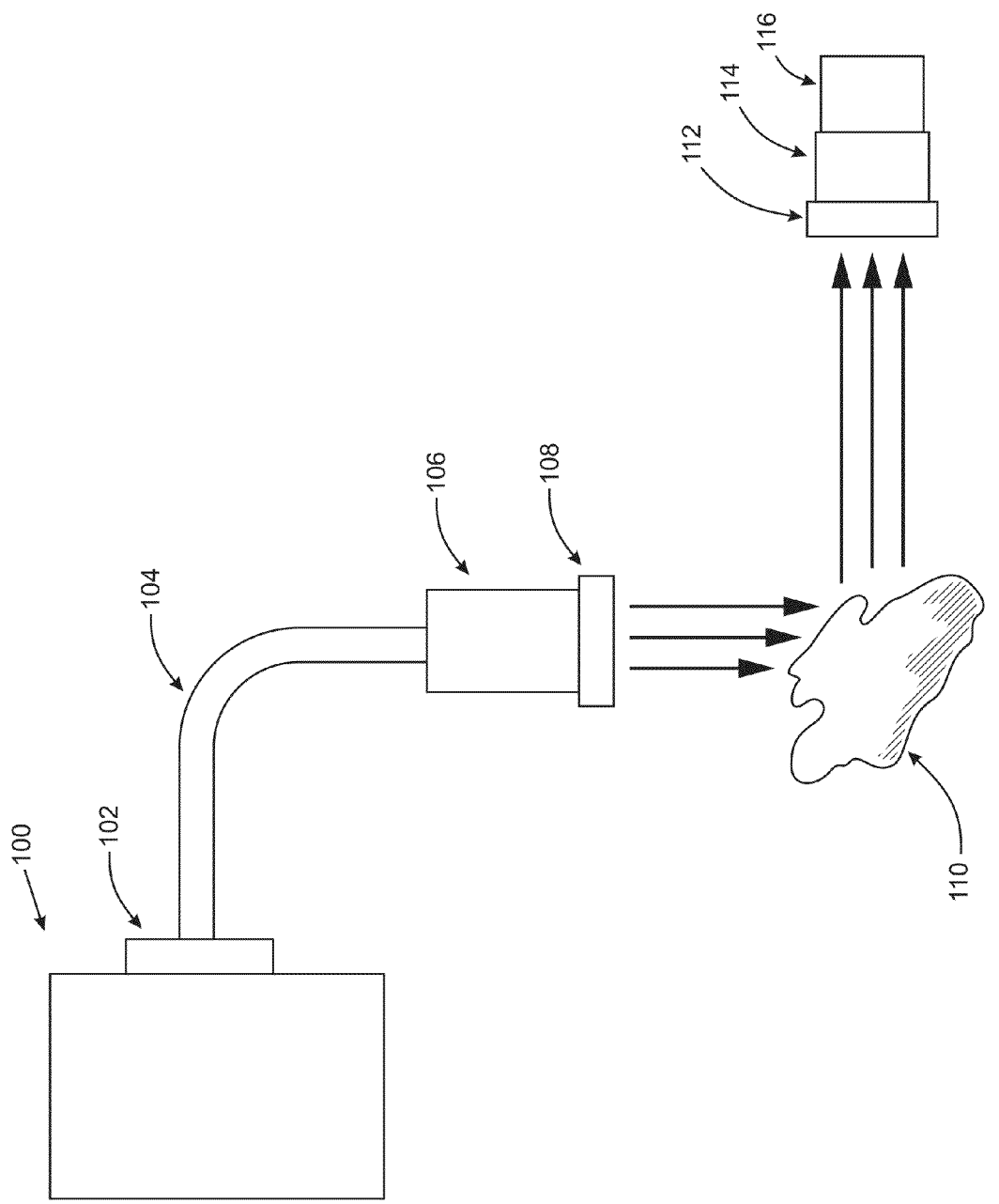
FIG. 1 is a fluorescent imager for detecting, for example, ICG and bilirubin.

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. As used herein, DLP® and Digital Micromirror Device (DMD) are used interchangeably. A DMD chip has on its surface several hundred thousand microscopic mirrors arranged in a rectangular array which correspond to the pixels in the image to be displayed. The mirrors can be individually rotated ±10-12°, to an on or off state. In the on state, light from the projector bulb is reflected into the lens making the pixel appear bright on the screen. In the off state, the light is directed elsewhere (usually onto a heat sink), making the pixel appear dark. It can be purchased commercially from Texas Instruments. As used herein, "hyperspectral" in reference to an imaging process or method is meant the acquisition of an image at more than one wavelength or bands of wavelengths. Furthermore, as used herein, "spectra" is defined as illumination with spectra of light with multiple wavelengths within a spectral range. Although any methods, devices or materials similar or equivalent to those described herein can be used in the practice or testing of the invention, the preferred methods, devices, and materials are now described. Still further, as used herein, "hyperspectral image" is defined as an image derived from hyperspectral image data, e.g., hyperspectral data cube, which includes but is not limited to, a chemically encoded image, a principle component analysis (PCA) image and wavelength dependent images.

A spectral illuminator using DLP technology may be used to excite fluorescence markers, which are native to the tissue (tissue fluorescence) or target, or markers that were injected or painted onto the tissue or target. An optical filter, Liquid Crystal Tunable Filter (LCTF) or other element can be used to pass emitted fluorescence light to a detector. For imaging bile ducts, e.g., ICG, indocyanine green can be injected or the native fluorescence properties of bile can be used. With improved imaging, surgical procedures can focus on the target for treatment (or the adjacent tissue) by visualization, e.g., the biliary tree. The system can be used for other surgical applications to perform in vivo pathology during surgery, i.e., in vivo hyperspectral pathology. The present invention can also be used in other methods or techniques, including but not limited to, in vivo pathology of cancer in real-time (e.g., before, during or after surgery), in the body (e.g., laparoscopically), without having to biopsy and/or fix the tissue or target to a slide. The example being a probe that binds to antigens. The techniques described infra are also applicable to fluorescence microscopy. Finally, chemometrics and digital signal processing may be used to produce chemically encoded images to enhance visualizations. Furthermore, it has been found that using a digital light processor (DLP), the present inventors were able to achieve video rate hyperspectral image capture and processing. Such video rate capture and processing is not possible with current illumination technology; however, is made possible by the use of DLP technology as set forth herein. The video capture rate also benefits from the chemometric illumination.

In addition to the above described disadvantages of present imaging apparatus and techniques, the following describes still further disadvantages. ERC is an invasive, user-dependent modality which may also induce pancreatitis. Though ultrasound is cost effective, the images are not clearly understood by clinicians. MRC is also often inconclusive in patients with air in the biliary system. Proponents of routine intraoperative cholangiography (IOC) claim that this practice lowers risk of CBD injuries and leads to fewer retained bile duct stones. (See Flowers J L, Zucker K L, Graham S M, et al. "Laparoscopic cholangiography: results and indications." Ann Surg 1992; 215:209-16; and, Gerber A, Apt MK. "The case against routine operative cholangiography. AM J Surg" 1982; 143:734-6). The disadvantages of routine IOC include increased costs, operative time and false positive findings, leading to unnecessary efforts to clear the CBD stones. Injecting contrast media for a CTC can led to adverse effects such as anaphylaxis, urticaria and respiratory distress. (See A Persson, N Dahlstrom, Ö Smedby and T B Brismar: "Three-dimensional drip infusion CT cholangiography in patients with suspected obstructive biliary disease: a retrospective analysis of feasibility and adverse reaction to contrast material"). These can be reduced if the contrast agents are diffused instead of injected. Possible explanations of infrequent use of CTC might be the low resolution of a single detector helical CT and reports of an unacceptable high number of adverse events after the injection of meglumine iotroxate. (See A Persson, N Dahlstrom, Ö Smedby and T B Brismar: "Three-dimensional drip infusion CT cholangiography in patients with suspected obstructive biliary disease: a retrospective analysis of feasibility and adverse reaction to contrast material"). It has been observed that selective preoperative ERCP was successful in showing CBD stones.

Fluorescence is the optical phenomenon of luminescence in which the molecular absorption of a photon triggers the emission of another photon of longer wavelength. The energy difference between the absorbed and the emitted wavelength ends up as molecular vibration or heat. A material that exhibits fluorescence is called a fluorophore. Different fluorophores have different absorption and emission wavelengths. Fluorescence imaging has found a number of applications in the field of biochemistry and medicine. Typically a fluorophore molecule, in the ground state $S_0$, absorbs energy $h\sigma$ provided by the excitation light. This energy takes the molecule to an excited state $S_1$. This is an unstable state; hence, the molecule returns to the ground state $S_0$ by emitting energy equivalent to hv. The return to the ground state can happen through many paths.

In the current research Indocyanine Green (ICG) and bilirubin are used as fluorophores. ICG has already been established as an injectible fluorophore for retinal angiography. Bilirubin on the other hand exists as a component of bile, thus, avoiding injection of an additional fluorophore.

One of the major hurdles during a cholecystectomy procedure, open or laparoscopic, is the visualization of the bile duct, which is hidden underneath fat layers, to avoid any bile duct injuries. As discussed above, the known imaging techniques are not fully satisfactory.

As described supra, the critical issue while performing a Cholecystectomy is injury to the Common Bile Duct (CBD) which can cause post procedural complications. Since the CBD is under a fat layer it is important to image and locate the CBD during the procedure. The present invention fluorescence imager helps visualize the CBD by using the fluorescence properties of Indocyanine Green, which is injected into the body, or by using the fluorescence properties of bilirubin, already existing in bile. An instrument using ICG as a fluorophore has been characterized for its penetration depth to view fluorescence using an intralipid model, thereby determining the best possible fluorescence concentration that would give maximum fluorescence photons at the same time remaining within the limits of the concentration prescribed for human dosage. The system incorporates unique short pass-long pass filter combinations at the source and detector ends, respectively, to provide excitation illumination and detect emission. The filters are designed in accordance with the absorption and emission characteristics of individual fluorophores in different mediums.

The best fluorescence concentration was found to be 0.015 mg/ml. Depth analysis was performed for ICG mixed with water, going deeper in a 1% intralipid solution used as a model to mimic tissue and fat properties. A vernier height gauge was coupled to a capillary holder, which held the capillary containing the fluorophore. Two separate analyses were carried out, ICG mixed with human bile and aqueous ICG solution, both having an approximate concentration of 0.015 mg/ml. Contrast to background and signal to noise ratios were computed at each depth to find the maximum depth the system can visualize. The maximum depth of penetration was found to be 11 mm below the surface of the intralipid solution when ICG was mixed with bile and 20 mm below the surface of the intralipid solution for aqueous ICG. The threshold for contrast to background was set based on beef fat measurement.

Thus, the present invention includes devices and methods for fluorescence imaging that allows the user to visualize the bile duct either by injection of a fluorophore into the bile duct or by exciting the fluorophore inherently present in the bile duct. As described above, this can be accomplished by the use of fluorophores either existing inside the bile duct (bilirubin) or through external injection into the bile duct (Indocyanine Green). A unique design of short pass-long pass filters enables viewing all emitted photons due to fluorescence. The excitation fluorescence filter is coupled to a broadband QTH source, which provides the energy for excitation of the fluorophore. The fluorophore absorbs this energy and emits photons of a higher wavelength than the one being absorbed. These photons are detected by the FPA which is coupled to the emission fluorescence filter, designed uniquely to prevent the transmission of any excitation light. The FPA produces an image of the fluorescence of the fluorophore, which is then used for further analysis and to determine the location of the bile duct.

The present invention includes a novel fluorescence imagery system for visualizing the biliary tract, in-vivo, using Indocyanine Green and Bilirubin as fluorophores. The present invention imaging system includes a focal plane array (FPA) sensitive in the near infrared region for imaging Indocyanine green (ICG). The present invention imaging system helps surgeons visualize the bile duct real-time by exploiting the fluorescence properties of ICG.

The system includes of a broadband illumination source of light from a 250 W Quartz Tungsten Halogen (QTH) lamp placed in a housing (Oriel, Stratford, Conn.). The source is powered by a radiometric power supply to maintain a stable lamp output with minimum light ripple, making it an excellent long term, stable illuminator. The condensing lens assembly includes a molded Pyrex® aspheric which focuses light through the filters and to the optical couplers. A liquid light guide (Oriel, Stratford, Conn.), which also acts as an UV filter, i.e., attenuates wavelengths below 420 nm, is coupled to the condenser. The other end of liquid light guide is coupled to a Pyrex® aspheric expander which converts a fiber optic light beam to a collimated light beam. The broadband illumination is attenuated by a low pass filter mounted in front of the aspheric expander. The low pass filter (Omega Optical, Brattleboro, Vt.) was selected taking the ICG absorption characteristics into account. The lowpass filter (LPF) has a cut off (50% Transmittance) wavelength at 795 nm. The detector includes a high pass filter (HPF) coupled to a 50 mm, f/1.4 lens (Nikon, Tokyo, Japan) which is placed in front of the focal plane array.

The foregoing embodiment is represented in FIG. 1. Lamp 100 transmits light through collector optics 102 and into light guide 104. The light is then transmitted from light guide 104 through beam shaping optics 106 and filter 108. After exiting filter 108, the light reflects off of surface 110 and the reflected light is subsequently passes through filter 112 and lens 114 which in turn transmits the light to camera 116.

The high pass filter (Omega Optical, Brattleboro, Vt.) was selected according to the emission characteristics of ICG. The HPF has a cut off (50% Transmittance) wavelength at 805 nm. The CCD includes a Focal Plane array. The system utilizes a PIXIS 400 BR (Princeton Instruments, Trenton, N.J.). The PIXIS 400 BR FPA is a fully integrated system with a permanent vacuum and deep cooling arrangement. It uses a high performance, back illuminated, spectroscopic format CCD. The CCD incorporates deep depletion technology to extend the sensitivity in the near infrared (NIR). These special devices are thermoelectrically cooled (air) down to −75° C. to provide the lowest dark charge and thereby reduction of dark current noise. The FPA has a 1340×400 pixel array having an 8 mm chip height and 27 mm spectral coverage. This arrangement makes the FPA ideal for multistripe spectroscopy and maximum light collecting area. Each pixel has a size of 20

μm×20 μm with a total imaging area of 26.8 mm×8.0 mm. The device's sensitivity ranges from 220 nm to 1100 nm, with a peak efficiency of about 85% at 800 nm. This device has a 16 bit Analog to Digital Converter (ADC) coupled to the FPA which provides a maximum of $2^{16}$ (655356) shades of gray. A high end laptop (e.g., Dell Latitude D610, Austin, Tex.) is connected to the camera for image rendering and analysis. The foregoing example system is helpful for a surgeon to visualize the common bile dust during cholecystectomy; however, this system is presented only as an example and does not limit the scope of the claimed invention.

The fluorescence imaging system using bilirubin as a fluorophore includes a Focal Plane Array which is sensitive in the visible region. The system also includes a broadband illumination of light from a 250 W Quartz Tungsten Halogen (QTH) lamp placed in a housing (Oriel, Stratford, Conn.). The source is powered by a radiometric power supply to maintain a stable lamp output with minimum light ripple, making it an excellent long term, stable illuminator. The condensing lens assembly contains a molded Pyrex® aspheric which focuses light toward the filters and optical couplers. A liquid light guide (Oriel, Stratford, Conn.), which also acts as an UV filter, i.e., attenuates wavelengths below 420 nm, is coupled to the condenser. The other end of the liquid light guide is connected to a beam expander/collimator. A low pass filter (Omega Optical, Brattleboro, Vt.) with a cut off (50% Transmission) at 500 nm, selected on the basis of the absorption properties of bilirubin, is coupled to the collimating assembly. A high pass filter (Omega Optical, Brattleboro, Vt.) with a cut off (50% Transmission) at 515 nm, selected on the basis of the emission properties of bilirubin, is coupled to a 50 mm, f/1.4 lens (Nikon, Tokyo, Japan) which is placed in front of the focal plane array.

The present invention fluorescence system includes Cool-Snap$_{ES}$ (Photometrics, Tucson, Ariz.) which contains a Sony ICX 285 focal plane array. Higher sensitivity is one of the distinct advantages of this CCD which enables it to have a reduced time for data collection. The analog to digital converter (ADC) is 12 bits with a speed of 20 Mpixels/s, thereby decreasing the acquisition time by a factor of 20 when digitizing the same number of pixels.

Again, the foregoing embodiment is represented in FIG. 1. Lamp 100 transmits light through collector optics 102 and into light guide 104. The light is then transmitted from light guide 104 through beam shaping optics 106 and filter 108. After exiting filter 108, the light reflects off of surface 110 and the reflected light is subsequently passes through filter 112 and lens 114 which in turn transmits the light to camera 116.

The specific system components described infra are for illustrative purposes only and are not intended to limit the scope of the claimed invention. The QTH source (Lamp and Housing) along with the radiometric power supply are manufactured by Spectra-Physics, a division of Newport Corporation. The research Grade lamp housing (Model: 66884) houses a 250 W QTH lamp source (Model: 6334) and the Radiometric power supply (Model: 69931) drives the source.

The Oriel Radiometric Power Supply is a highly regulated source of constant current or constant power for QTH lamps. The control and monitoring features of the power supply include powering the supply on and off, set the current/power preset and limit, monitor the current, voltage, power and operating time. The power supply is run in current mode with a current setting at 10.42 Amps, which drives the QTH lamp. (See 'The Newport Resource' 2008-2009. Newport Corporation pp 140-141). The Research grade lamp housing holds the QTH lamp. The housing includes condensing optics to produce a collimated or focused beam. Asphere condensers are used for superior uniformity. The housing also incorporates rear reflectors to collect the lamp's back radiation, external lamp and reflector adjustments to fine position the filament and a power regulated fan to cool the lamp and the housing. (See 'The Newport Resource' 2008-2009. Newport Corporation pp 137-138). Re-imaging onto the filament does increase the collimated output a little and changes the power balance of the system.

TABLE 1

Specification of Radiometric Power Supply (Model 69931)

| Parameters | Model 69931 |
|---|---|
| Power Factor | >0.99 |
| Input Voltage | 90-264 VAC |
| Input Current | 5 A |
| Input Frequency | 47-63 Hz |
| Output Power | 40-300 W |
| Output Current | 3-24 A |
| Output Voltage Range | 0-45 VDC |
| Line Regulation | 0.01% |
| Output Voltage Ripple | <0.05% r.m.s. |
| Light Ripple | <0.05% r.m.s. |
| Meter Accuracy (% of full scale) | <0.05% |
| Digital Meter Resolution, Voltage | 0.1 VDC |
| Digital Meter Resolution, Current | 0.01 A |
| Digital Meter Resolution, Power | 1 W |
| Safety Interlock Voltage | 12 VDC/GND |
| Operating Mode | Constant current or constant power |
| Ambient Operating Temperature | 0-45° C. |
| Weight | 20 (9) |
| Dimensions (W × D × H) [in. (mm)] | 12.0 × 16.0 × 5.18 (305 × 406 × 132) |

Quartz Tungsten Halogen lamps are popular visible and near infrared sources because of their smooth spectral curve and stable output. ICG has a molecular formula of $C_{43}H_{47}N_2NaO_6S_2$. The filter designs have to be selected based on the emission and absorption spectrum of ICG. ICG has a bimodal absorption spectrum from 650 nm-800 nm, with peaks occurring at 685 nm and 775 nm in distilled water. In plasma, ICG has two absorption peaks at around 710 nm and 805 nm. The absorption spectrum changes according to the concentration of ICG and solvent. For example, higher concentrations have a maximum absorption at 685 nm, while lower concentrations have a maximum absorption at 775 nm in an aqueous solution. (See M. L. J. Landsman, G. Kwant, G. A. Mook, W. G. Zijlstra, "Light-Absorbing Properties, Stability and Spectral Stabilization of Indocyanine Green", Jour. Applied Physiology, Vol. 40, No. 4, April 1978). Thus, separate filters were designed for ICG with water as a solvent and ICG with blood as a solvent. Instead of a conventional band pass filter combination for emission and excitation filters, unique low pass and high pass filters are used as excitation and emission filters.

The filter combination (excitation and emission) of low pass and high pass filters are used. The low pass filter has a cut off (50% Transmission) wavelength at 790 nm. This filter coupled with the source (mentioned above) is used to excite ICG with all possible absorption wavelengths of ICG including the peak absorption wavelength. The high pass filter (coupled with the detector) was used to collect the fluorescence photons coming from ICG. In an aqueous solution ICG, has an emission peak at 820 nm. (See R. C. Benson, H. A. Kues, "Fluorescence properties of Indocyanine Green as Related to Angiography", Vol. 23, No. 1, 159-163, Phys. Med. Biol. 1978). Thus, a high pass emission filter with a cut-off (50% Transmission) at 805 nm is used. This enables us to avoid any excitation light reflected back. These curves were obtained by using a standard calibrated USB2000+ spectrometer (Ocean Optics, Dunedin, Fla.) and using the filter in the transmission mode and illuminating with the broad band source discussed above. During the entire study all the parameters including distance, exposure time and other pre-processing remained the same.

ICG in blood follows a similar pattern as that for ICG in an aqueous solution with changes in the Excitation and Emission cut-off filters. The low pass excitation filter has a wavelength cut off (50% Transmission) at 810 nm. This filter coupled with the source enables illuminating the target (ICG) with its entire absorption wavelength. ICG emission occurs at 830 nm when in blood. (See R. C. Benson, H. A. Kues, "Fluorescence properties of Indocyanine Green as Related to Angiography", Vol. 23, No. 1, 159-163, Phys. Med. Biol. 1978). Thus, the high pass emission filter has a filter cut-off (50% Transmission) at 815 nm allowing the viewing of only the fluorescence photons coming into the detector.

Bilirubin stands as one of the important constituents of bile. The pH of bile ranges from 7.5-9.5, which indicates that bile is alkaline. This is due to the presence of bicarbonates. Bilirubin is a major product of heme catabolism. Bilirubin is a yellow tetrapyrrole pigment which is water soluble as it possesses two propionic side chains, which might be expected to render it highly polar. Bilirubin may be water insoluble as the bilirubin molecule can adapt to various configurations. Bilirubin is mostly found in the conjugated form in bile. Unconjugated bilirubin is normally 5% of total bilirubin. Bilirubins are also susceptible to oxidation and are photosensitive thereby leading to a variety of derivatives. (See Francesco Baldini, Paolo Bechi, Fabio Cianchi, Alida Falai, Claudia Fiorillo, Paolo Nassi "Analysis of Optical Properties of Bile" J. Biomedical Optics 5(3), 321-329, July 2000). The quantum yield of free bilirubin at room temperature is low ($<10^{-4}$). (See M. A. Rosci, "Fluorescence of free bilirubin at room temperature", Experimentia Vol: 39 (1983)). Thus, fluorescence of free bilirubin is difficult to observe. However fluorescence of bilirubin is enhanced in the presence of albumin. (See Humra Athar, Nisar Ahmad, Saad Tayyab, Mohammad A. Qasim "Use of Fluorescence enhancement technique to study bilirubin-albumin interaction" Int. J. Biological Macromolecules, 25, 353-358, 1999).

Figure 2:
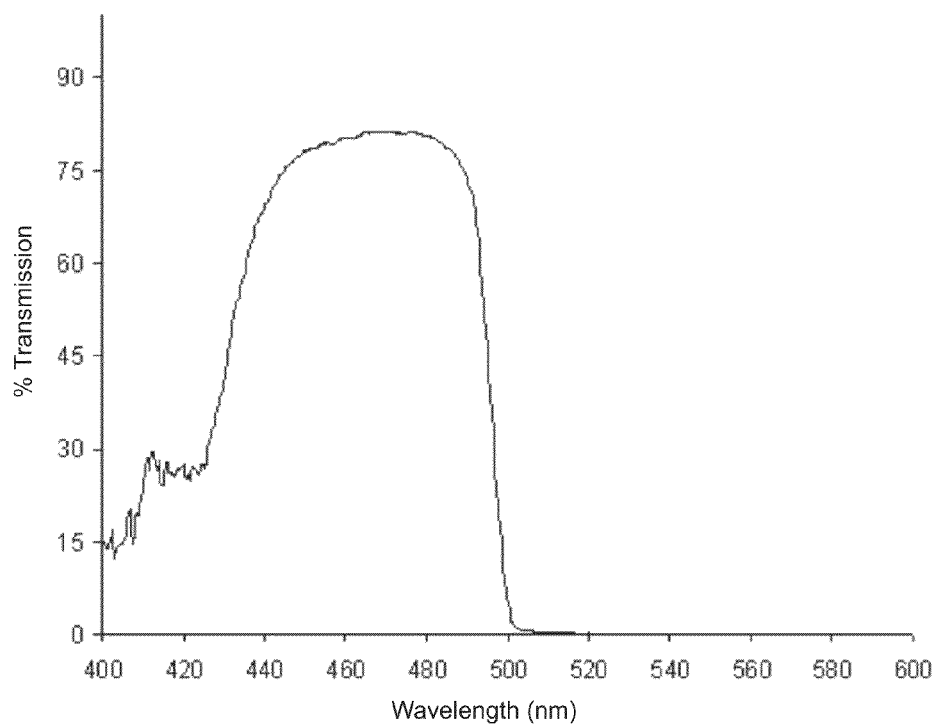
FIG. 2 is a short pass filter transmission characteristics used as an excitation filter for bilirubin.
Figure 3:
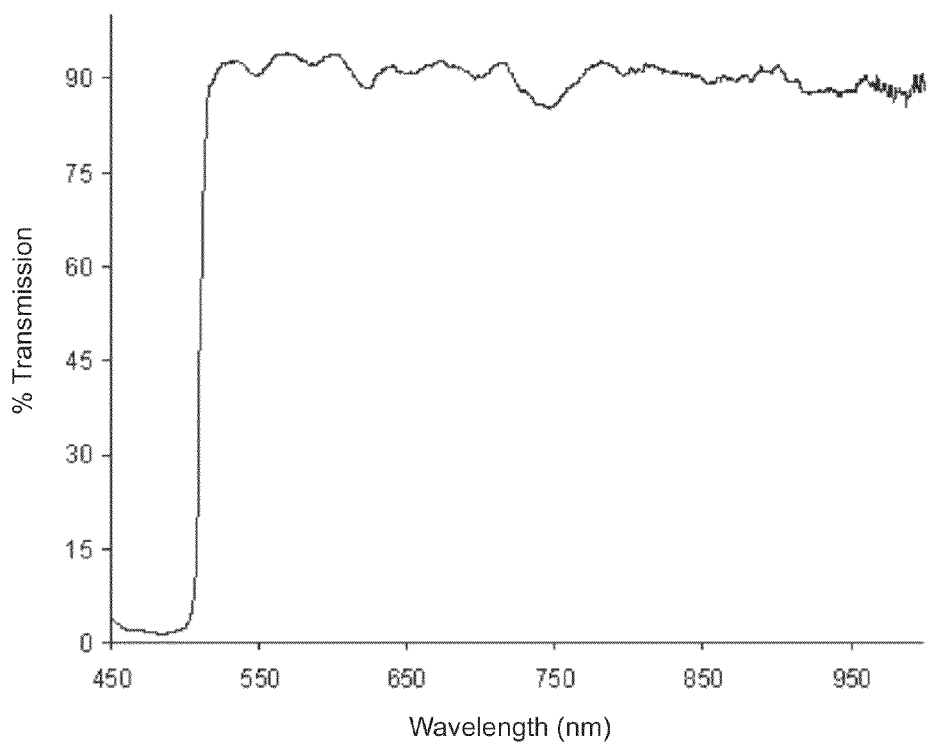
FIG. 3 is a long pass filter transmission characteristics used as an excitation filter for bilirubin.

Bilirubin in bile fluoresces as a result of its interactions with other bile components and albumin. Thus, imaging this fluorescence is an indicator for the position of bile duct, which contains bile in it. Bilirubin has a strong absorption of visible light between 400 nm-500 nm. (See Francesco Baldini, Paolo Bechi, Fabio Cianchi, Alida Falai, Claudia Fiorillo, Paolo Nassi "Analysis of Optical Properties of Bile" J. Biomedical Optics 5(3), 321-329, July 2000). Thus, a filter designed to allow ideally all the wavelengths below 500 nm would become an excellent excitation filter for fluorescence of bilirubin in bile. This was the basis of the excitation filter selection in the present example. The transmission characteristics of such a filter are shown in FIG. 2. The fluorescence of bilirubin in bile is observed to peak around 528 nm. (See Humra Athar, Nisar Ahmad, Saad Tayyab, Mohammad A. Qasim "Use of Fluorescence enhancement technique to study bilirubin-albumin interaction" Int. J. Biological Macromolecules, 25, 353-358, 1999). Thus, a filter capable of eliminating the excitation wavelengths and able to measure or see the fluorescence was selected. Such a filter was implemented through a long pass filter with its cut off (50%) at 515 nm. The transmission of such a filter is shown in FIG. 3.

The emission filter is coupled to a 50 mm, f/1.4 Nikon Lens manufactured by Nikon. This lens helps in focusing the target onto the CCD. This lens is fast enough for shooting virtually all types of light. It produces distortion free images with high resolution and color rendition. This lens incorporates a wide variety of f-stops or apertures. The maximum aperture is f/1.4, while the minimum aperture is f/16. The back end of the lens is coupled to a C-F mount, which is used to fit a variety of lenses onto the CCD.

The Charged Coupled Device or Focal Plane Array is an analog shift register that enables analog signals to be transported through successive stages controlled by a clock signal. An image is projected by a lens onto the photoactive region of the CCD which includes photodiodes and capacitors that accumulate charges based on the intensity of light at that location. This image is then transferred to the transmission region, which includes shift registers. Once the array has been exposed to the image, a control circuit causes each capacitor to transfer its content to its neighbor. The last capacitor dumps the charge to a charge amplifier, which converts the charge into a voltage and is finally read out.

The Focal Plane Array used for imaging Indocyanine Green (ICG) is the PIXIS 400 BR. The specifications for PIXIS 400BR is given in Table 2 below.

TABLE 2

| Specification for PIXIS 400 BR Specification PIXIS 400 BR | |
| --- | --- |
| CCD Format | 1340 × 400 imaging pixels |
| | 20 × 20-μm pixels |
| | 100% fill factor |
| | 26.8 × 8.0-mm imaging area |
| System Read Noise | 5 e-rms @ 100-kHz digitzation (max) |
| | 16 e-rms @ 2 MHz digitization (max) |
| Spectrometric Well Capacity | 300 ke-(High Sensitivity-Typical) |
| | 1 Me-(High Capacity-Typical) |
| Deepest Cooling Temperature | −70° C. (High Sensitivity) Minimum |
| | −75° C. (High Sensitivity) Typical |
| Dark Current @ −75° C. | 0.25 e-/p/s (Typical) High Sensitivity |
| | 0.5 e-/p/s (Maximum) |
| Dynamic Range | 16 Bits |
| Vertical Shift Rate | 30 μsec per row |
| Operating Environment | +5 to +30° C. non-condensing |

PIXIS 400 BR has controlling software that controls and maintains the set temperature allowing a deviation of ±0.05° C. from the set temperature by controlling the camera's cooling circuit. Dark charge is thermally induced into the FPA over time. This statistical noise is called the dark noise. Dark noise tends to change depending on the exposure time, temperature and gain. Dark noise could be measured when there is no light passing through the FPA. The longer the exposure time and warmer the temperature, the background becomes larger and less uniform. (See PIXIS User Manual). The camera has controller gain software which allows setting three different gain levels. Level 1 (low) is used for high signal intensities. Level 2 (mid) is used for mid intensity levels and Level 3 (high) is used for low intensities.

From the specification table one can see that the camera has a dual digitization rate available (100 KHz/2 MHz). The 2 MHz digitization rate is used for the fastest possible data collection, while the 100 KHz is used when noise performance is of greatest concern. Thus, multi digitization allows complete freedom between 'Slow Operation' for low noise and high SNR and 'Fast Operation' for rapid spectral acquisition. (See PIXIS User Manual).

Megapixel resolution and smaller pixel size allows imaging very fine details. Sensitivity can be improved by binning, but at the expense of resolution. The camera has a 1340×400 pixel CCD array that provides superior resolution over the industry standard '1024' pixel format. Binning increases the frame rate. The camera has a dynamic range of 16 bits allowing bright and dim signals to be quantified in a single image with 216 shades of gray.

The PIXIS 400 BR has a back illuminated FPA. This means that light enters from a back surface through a thinned (etched) silicon layer. This has an advantage that no light absorption or reflection takes place at the polysilicon gate structure enabling the CCD to have higher quantum efficiency (almost twice the efficiency). Due to this etching, the layer becomes transparent to NIR wavelengths causing fringe effects for NIR spectroscopy. To overcome the disadvantages of etaloning, the CCD is made of thicker silicon (roughly twice the thickness of a normal back-illuminated CCD). This contributes significantly to the absorption of NIR light, reducing the amount of light that survives a round trip path to cause interference and increasing the quantum efficiency. This reduces the amount of light into the CCD that is reflected back from the polysilicon side of the back surface. It also increases the quantum efficiency by increasing the amount of light into the CCD and reducing stray light in the spectrometer.

The CoolSnap$_{ES}$ camera is used as a detector for measuring the fluorescence of bilirubin. This camera has high quantum efficiency in the visible region which makes it a perfect choice for fluorescence measure of bilirubin. This camera is used in applications requiring high speed and high spatial resolution in the visible region. It is manufactured by Roper Scientific (Now Princeton Instruments). The CoolSnap$_{ES}$ offers higher sensitivity and lower read noise to produce high quality 12-bit monochrome images. (See CoolSnap$_{ES}$ user manual). Exemplary specifications are provided is Table 3 (below).

TABLE 3

Specifications of CoolSnap$_{ES}$ FPA
Specification CoolSnap$_{ES}$

| | |
|---|---|
| CCD Format | 1392 × 1040 imaging pixels |
| | 6.45 × 6.45-μm pixels |
| | 8.77 × 6.6-mm imaging area |
| | (Optically Centered) |
| System Read Noise | <8 e-rms @ 20 MHz |
| Well Capacity | 16000 e-(Single Pixel) |
| | 30000 e-(2 × 2 Binned Pixel) |
| Cooling | Thermoelectric, 5° C. below |
| | ambient Temperature |
| Dark Current | 1 e-/p/s |
| Dynamic Range | 12 Bits @ 20 MHz |
| Dimensions | 4.5" × 5.0" × 2.5" (1.9 lbs) |
| Operating Environment | 15° C. to 30° C. ambient |
| Frame readout | 91 ms/frame |

The CoolSnap$_{ES}$ incorporates a SONY ICX285AL silicon chip array with interline transfer capability. The interline transfer CCD has a parallel register that is subdivided into alternate columns of sensor and storage areas. The image accumulates in the exposed area of the parallel register and during CCD readout the entire image is shifted under interline mask into a hidden shift register and then proceeds in normal CCD fashion. Since the signal is transferred in microseconds, smearing is undetectable for typical exposures. However, a drawback to interline transfer CCD's has been their relatively poor sensitivity to photons since a large portion of each pixel is covered by the opaque mask. As a way to increase the detector's fill factor, high quality interline transfer devices have microlenses that direct the light from a larger area down to the photodiode. The quantum efficiency is about 60% in the region of bilirubin-albumin fluorescence (500 nm-550 nm), hence these CCDs are used as detectors for measuring the fluorescence of bilirubin-albumin.

Both the above mentioned detectors are driven by Photometrics Virtual Camera Access Method (PVCAM) software. The PVCAM application programming interface for high performance digital cameras is a set of software library routines that implement a camera's operations in a hardware independent, platform independent suite of function calls. This software is used to control and acquire data from the camera. The data collection is done using Vpascal programming integrated in V++ which internally communicates with PVCAM for controlling the detectors.

Figure 4:
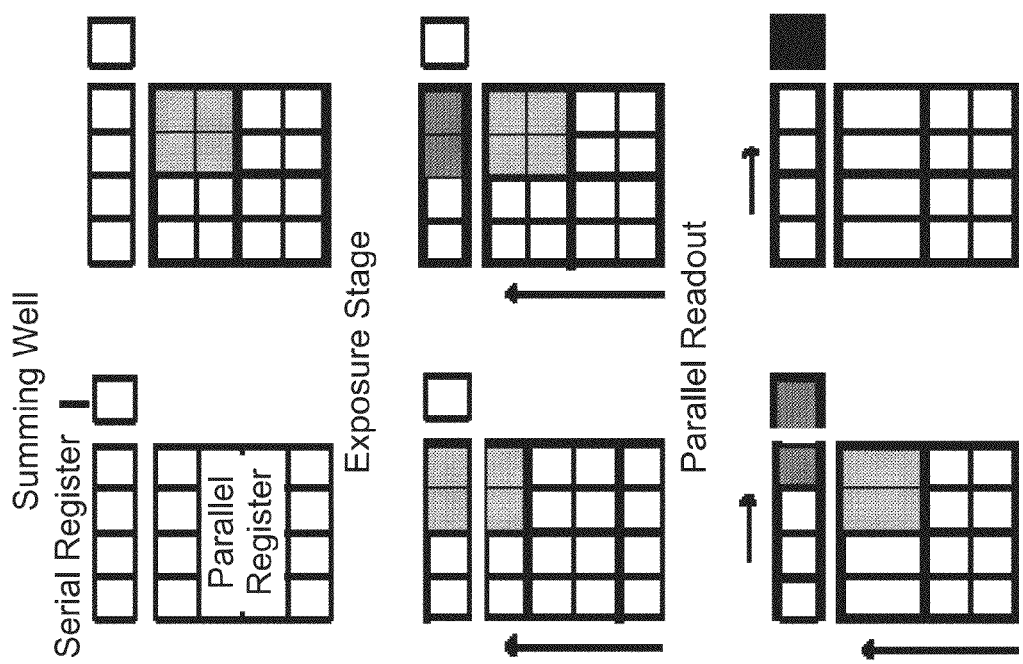
FIG. 4 is a diagram of a 2×2 binning process.

Binning is a process of combining charge from adjacent pixels in a CCD during readout. This process is performed prior to digitization in the on-chip circuitry of the CCD by specialized control of the serial and parallel registers. The two primary benefits of binning are improved signal-to-noise ratio (SNR) and the ability to increase frame rate, at the expense of spatial resolution. Binning 1×1 has the maximal spatial resolution. No charges are combined in this case. In the case of 2×2 binning, during parallel readout, the charges from two rows of pixels, rather than a single row, is shifted into the serial register. Next, charge is shifted from the serial register, two pixels at a time, into the summing well. It then goes to the output amplifier. This process is iterated until the entire array is read. One of the prime advantages of binning is high SNR. In normal operation, CCD read noise will be added to each pixel, whereas during binning, the CCD read noise is added to each super pixel thereby increasing the SNR. A 2×2 binning process is shown in the FIG. 4.

The following characterization of indocyanine green fluorescence imager is provided for clarification. Indocyanine green (ICG) ($C_{43}H_{47}N_2O_6S_2Na$), having a molecular weight of 775, is a trycarbocyanine type of dye with infrared absorbing properties. ICG has little or no absorption in the visible spectrum. ICG may be used for recording dye dilution curves, in particular for determination of cardiac output. The principle advantages of using ICG as a dye are its absorption maximum at the isobestic point of hemoglobin and oxyhemoglobin, the confinement to the vascular compartment through plasma protein binding, low toxicity and rapid excretion into the bile. (See M. L. J. Landsman, G. Kwant, G. A. Mook, W. G. Zijlstra, "Light-Absorbing Properties, Stability and Spectral Stabilization of Indocyanine Green", Jour. Applied Physiology, Vol. 40, No. 4, April 1978). Moreover, ICG is readily soluble in water. Following intravenous injection, ICG binds to plasma proteins with albumin as its principle carrier. ICG undergoes no significant extra hepatic or entero hepatic circulation. ICG is taken up by plasma almost exclusively by the hepatic parenchymal cells and is rapidly excreted into the bile. Due to its properties, ICG is used extensively for the study of hepatic function. ICG is FDA approved and can be used with proper dosages as per FDA regulations. IC-Green™ is available in vials from Akorn Inc. Dosages for ICG can also be taken from the same.

It has been demonstrated that ICG can be used as a contrast agent in animals for visualizing biliary tract during Laparoscopic Cholecystectomy. (See Araki, K. Namikawa, J. Mizutani, M. Doiguchi, H. Yamamoto, Arai T. Yamaguchi, et al. "Indocyanine Green Staining for Visualization of Biliary System during Laparoscopic Cholecystectomy"; and, D. Persemlidis, A. Barzilai, et al. "Enhanced Laparoscopic Visualization of Extrahepatic Bile duct with Intravenous ICG"). The present invention uses the fluorescence properties of ICG for viewing the biliary tract during cholecystectomy.

Figure 5:
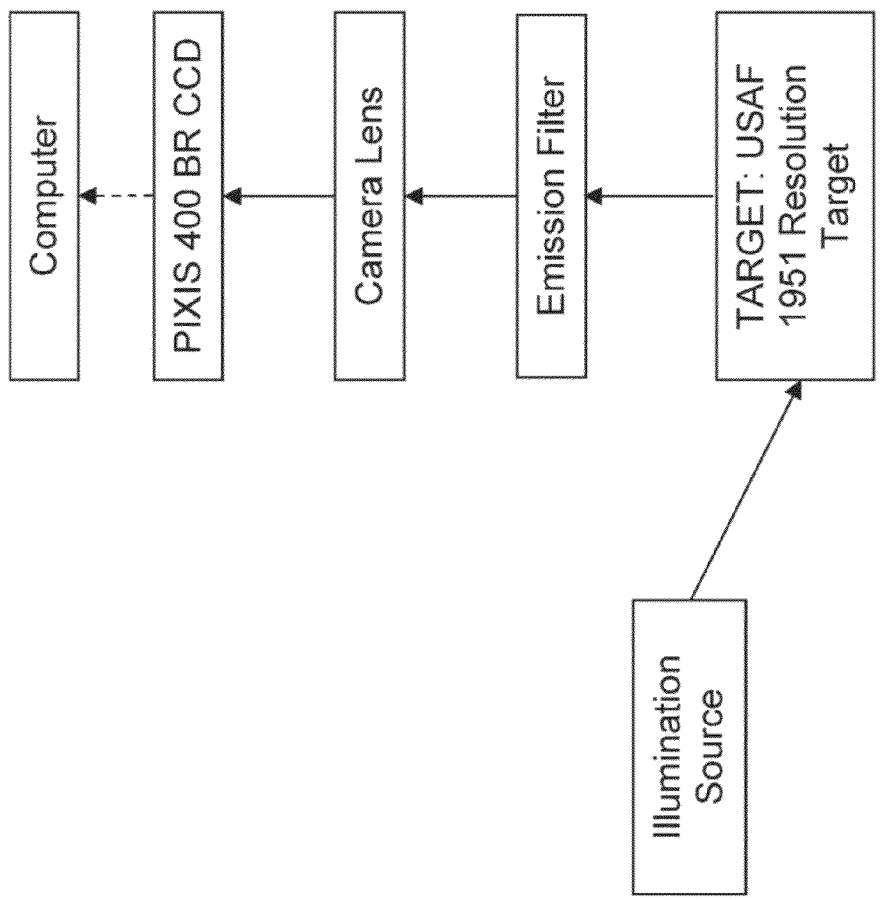
FIG. 5 is a block diagram depicting a method for computing the spatial resolution of the system.

The spatial resolution of the fluorescence imager was established by computing the percent contrast by imaging a standard USAF 1951 resolution target. The block diagram for the set up is given in FIG. 5. The distance between the source and the target was set as 22 inches. The results are plotted for multiple bins. The percent contrast, C, where $I_{max}$ is the maximum intensity reflected by a line of the resolution target (i.e., a white bar) and $I_{min}$ is the minimum intensity from the non reflecting area between the white bars (i.e., dark bars).

Percent contrast is calculated by using equation (1):

$$C = \left(\frac{I_{max} - I_{min}}{I_{max} + I_{min}}\right) \quad (1)$$

Figure 6A:
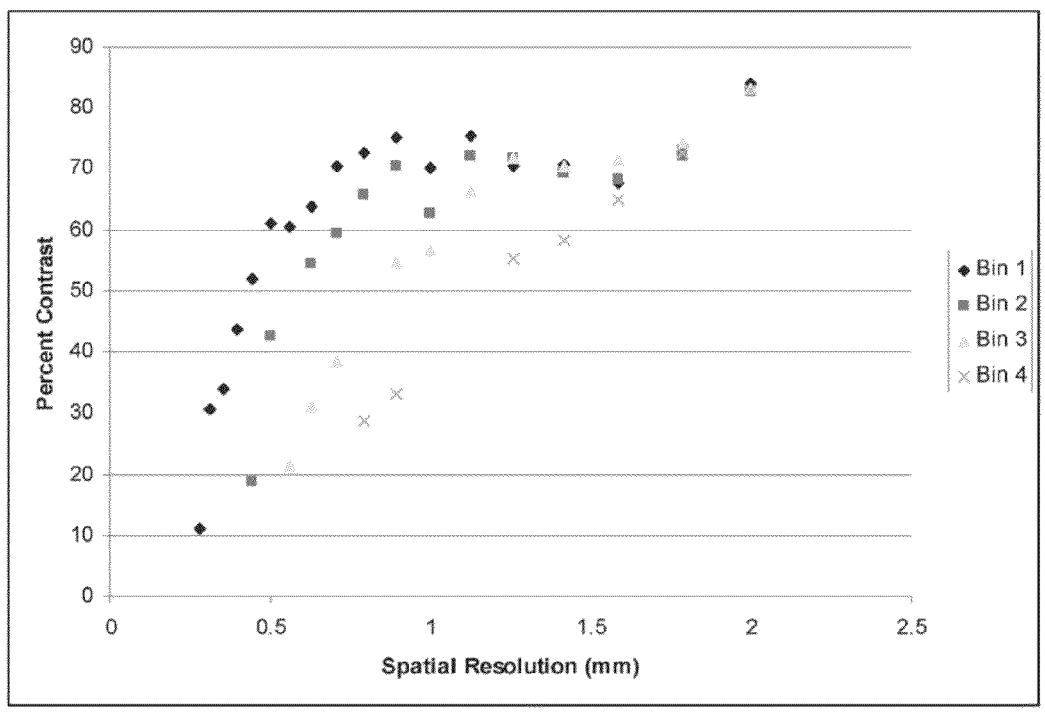
FIG. 6A is a percent contrast against spatial resolution without an emission filter at the detector.
Figure 6B:
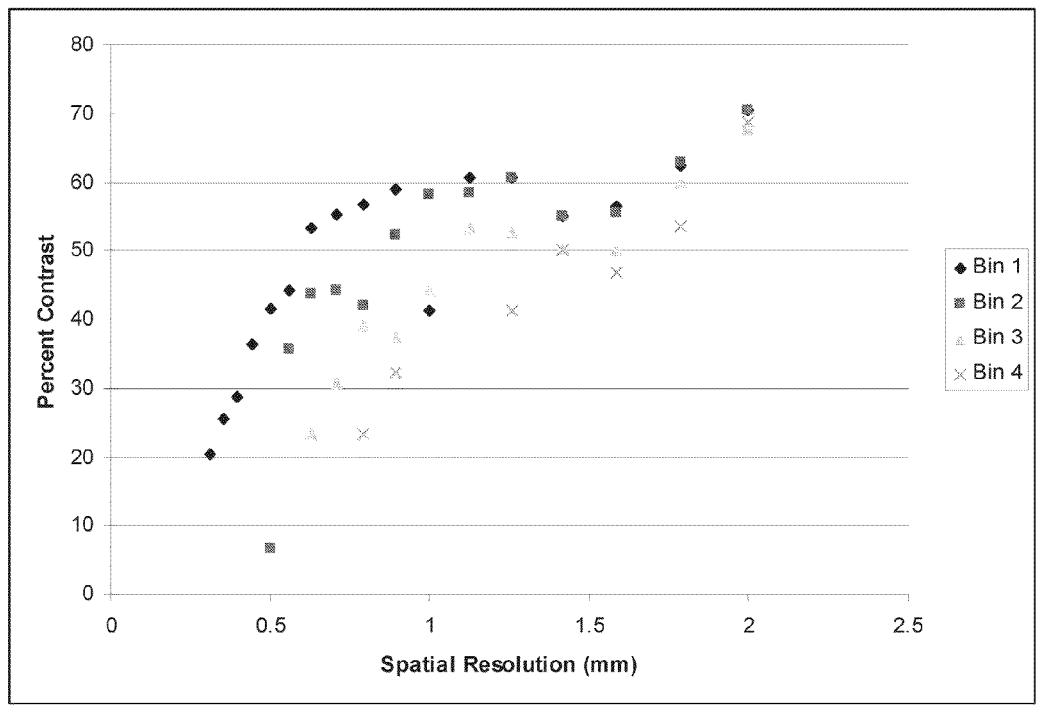
FIG. 6B is a percent contrast against spatial resolution with an emission filter at the detector.

This percent contrast measurement is carried out with and without the emission filter on the detector end, to observe any effects on spatial resolution due to the filter. FIG. 6A shows the percent contrast measurements carried out without the emission filter on the detector end, while FIG. 6B shows the percent contrast measurements carried out with the emission filter on the detector end.

It was found that there is a slight reduction in percent contrast when the emission filter is placed in the path. This can be attributed to the way the filters are manufactured. The surface of the filters is not always smooth and hence there can be a reduction in the spatial resolution. With the filter in place, the spatial resolution of the system (not for fluorescence) turns out to be 0.4 mm when used with the lowest bin value (Bin 1).

Figure 7:
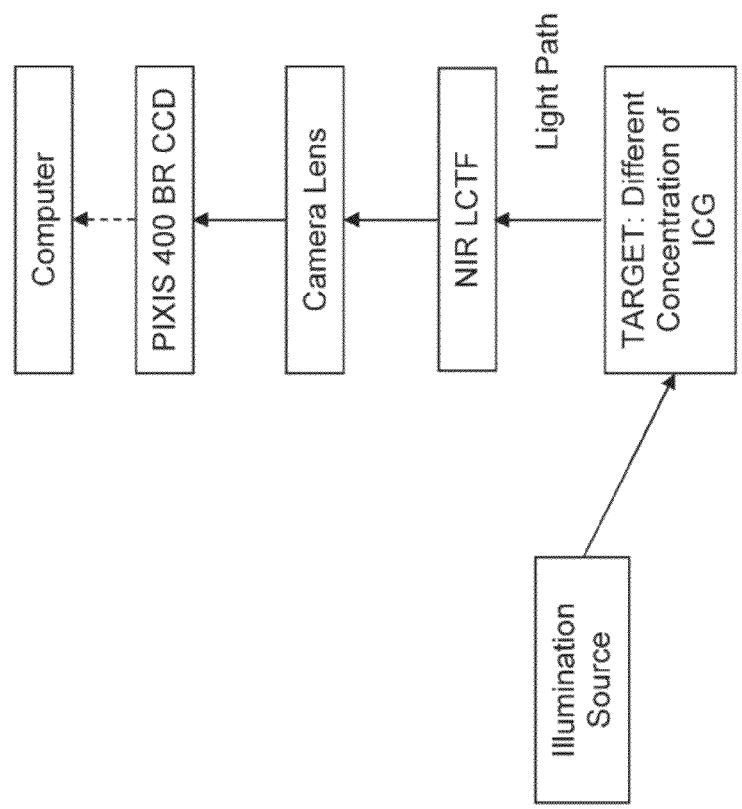
FIG. 7 is a block diagram depicting the set up used for measurement of absorption spectrum of ICG.

The following describes the quantification of the absorption spectrum of ICG. The first step in determination of ICG as a potential fluorophore for visualizing biliary tract during Cholecystectomy is to find its absorption spectrums and wavelengths needed for ICG to get excited for fluorescence. ICG has a bimodal absorption peak when in an aqueous solution (e.g., distilled water). The absorption spectrum changes with different solutes of ICG and different concentrations. This observation leads to the conclusion that ICG does not obey Beer Lamberts law. There is however a low concentration region where it does obey Beer Lamberts law. (See M. L. J. Landsman, G. Kwant, G. A. Mook, W. G. Zijlstra, "Light-Absorbing Properties, Stability and Spectral Stabilization of Indocyanine Green", Jour. Applied Physiology, Vol. 40, No. 4, April 1978). The set up for measuring the absorption spectrum of ICG is shown in FIG. 7.

A QTH lamp, as discussed above, along with all its optical components is coupled to a low pass filter (e.g., an excitation filter having a cutoff of 790 nm), which acts as an excitation filter for the fluorophore ICG. Cardio Green (Sigma Aldrich, St. Louis, Mo.) was used. Three different concentrations of ICG (0.078 mg/ml, 0.015 mg/ml and 0.005 mg/ml) were prepared. An initial solution of 0.078 mg/ml was prepared and the other concentrations were obtained by dilution of this initial solution. Thus, any error in the measurement of ICG is consistent. These were filled inside capillaries having a 1.5 mm bore diameter. The detector (PIXIS 400 BR) is coupled to a NIR Liquid Crystal Tunable Filter (LCTF) (Cambridge Research & Instrumentation, Boston, Mass.) which is already calibrated. The distance between the source and the target was set to 22 inches for all concentrations. It is possible to tune the LCTF for different wavelengths and get images at each of those wavelengths. The wavelengths and interval between wavelengths is user defined through software. In this embodiment, the LCTF was tuned for wavelengths from 650 nm to 900 nm with increments of 2 nm. Images were obtained at every 2 nm increment of wavelength starting from 650 nm and ending at 900 nm. Thus, a 3-D hyperspectral image cube is obtained with two spatial dimensions and one spectral dimension. These cubes were obtained for each three different concentrations and also for spectralon (i.e., a material having 100% reflectance). Each of these concentration cubes were then divided by the spectralon cube to obtain absorptions of the different ICG concentrations. The resultant cube was then filtered using a savitsky-golay filter and the spectrum was plotted by taking a sample area from the cube that matches the position of the capillary. ICG in distilled water has a bimodal peak absorption spectrum with maximum absorption occurring at 705 nm and 775 nm, respectively. One important observation is the change in the shape of the curves with changes in concentration. As the concentration of ICG in distilled water increases, the peak at 775 nm tends to become a shoulder and only one peak at 705 nm remains. Contrarily, as the concentration decreases the peak at 705 nm tends to become a shoulder and only one peak at 775 nm remains. This effect can be attributed to the aggregate formation of ICG when the concentration is higher. (See M. L. J. Landsman, G. Kwant, G. A. Mook, W. G. Zijlstra, "Light-Absorbing Properties, Stability and Spectral Stabilization of Indocyanine Green", Jour. Applied Physiology, Vol. 40, No. 4, April 1978).

Figure 8:
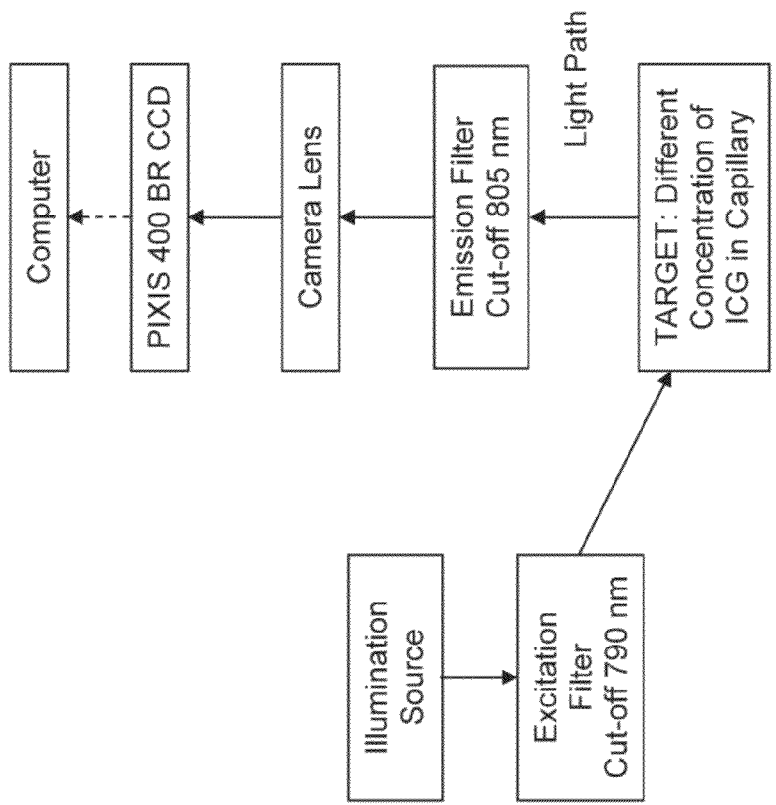
FIG. 8 is a block diagram depicting the set up used for measuring the best concentration of ICG in Water.

Determination of the fluorescence concentration that produces the best emission was required. The set up for determination of best fluorescence concentration is shown in FIG. 8. A QTH source is coupled to a low pass filter having a cutoff of 790 nm, which provides all excitation wavelengths for ICG. Different concentrations of ICG in distilled water were used. An ICG solution having a concentration of 0.03 mg/ml was first made by carefully measuring from an Adventurer™ (Ohaus). This solution was further diluted to form the other concentrations (0.02 mg/ml, 0.015 mg/ml, 0.010 mg/ml and 0.005 mg/ml). These solutions were put in different capillaries. A NIR detector (PIXIS 400 BR) coupled to an emission filter having a cutoff of 805 nm was used to measure the fluorescence. The five capillaries were kept parallel to each other and were excited by the QTH source coupled to the excitation filter as mentioned previously. Care was taken to make sure that the capillaries each received approximately the same intensity of illumination by keeping the capillaries closer to each other. Fluorescence photons emitted by ICG were then detected using the detector mentioned above. The best concentration was decided based on the maximum fluorescence photons detected by the detector. Higher concentrations were eliminated as there was a reduction in fluorescence emission and due to restrictions on the dosage.

Fluorescence for 0.03 mg/ml, 0.02 mg/ml and 0.015 mg/ml ICG are almost identical with the peak fluorescence at 0.03 mg/ml and 0.015 mg/ml. Thus, either concentration can be used for injecting into humans. However, dosage regulations restrict the concentration to 0.015 mg/ml. ICG forms aggregate at higher concentrations. The total dose of dye injected should be kept below 2 mg/kg. Thus, for an average adult having a weight of 70 kg, the concentration of dye with blood as a solvent is 0.025 mg/ml.

Maximum depth of fluorescence inside tissue was then determined. Human tissue has both scattering and absorbance properties. Thus, light falling on tissue gets partly scattered and partly absorbed. This depends on the absorbing properties of the tissue. Different tissues have different absorption and scattering properties. As described above, one of the issues related to viewing the bile duct is that the CBD lies underneath a thick fat layer. Thus, it is important to determine the depth that the fluorescence imager can see, to enable the user to accurately determine the position of bile duct.

An intralipid model was then considered, which model mimics tissue properties. A 1% intralipid solution was prepared by diluting a 20% intralipid solution (obtained from Fresenius-Kabi) with distilled water. This 1% intralipid solution mimics the properties of skin tissue. (See I Driver, J W Feather, P R King, J B Dawson "The optical properties of aqueous suspensions of Intralipid, a fat emulsion" Phys. Med. Biol., 1989 Vol:34, No 12, 1927-1930). 0.03 mg of ICG was carefully weighed using an Adventurer™ (Ohaus) and then mixed with 10 ml of distilled water. This solution was then diluted to get a concentration of 0.015 mg/ml. This fresh ICG solution was filled into capillaries having 1.5 mm bore diameters using a 1 cc syringe. The capillary was then fitted to a stand, which was coupled to a vernier height gage such that each capillary could be moved with precision in the vertical direction. The vernier height gage enables data to be produced at each millimeter. The fresh intralipid solution, previously prepared, was then filled into a tub. The setup was arranged in such a way that the center point of the bore of each capillary was at the surface of the 1% intralipid solution. A QTH source coupled with the low pass excitation filter having a cut off of 795 nm was used as an excitation source for the ICG in the capillary. The detector (PIXIS 400 BR) was coupled to a high pass emission filter. The distance between the source target and the detector is also illustrated in the figure. A distance of 22 inches between the source and target was fixed because of clinical constraints during cholecystectomy surgery. The detector was focused on the surface of the intralipid solution. At each step, each capillary was carefully moved into the intralipid solution in increments of 1 mm using the vernier scale. Care was taken not to disturb the alignment of the capillary tube with respect to the detector. Two different studies were done using the same setup: (1) with a constant exposure time; and, (2) with variable exposure time. In the constant exposure method, the exposure time and aperture of the detector was adjusted to measure maximum fluorescence without getting saturated, when each ICG filled capillary was at the surface of intralipid solution. The same exposure time and aperture were used for all depths. Background (i.e., plain intralipid solution using both filters) images were also collected using the same exposure and aperture. In the variable exposure time method, the exposure time was varied at each depth to get maximum fluorescence photons out of the ICG. Thus, each depth had a different exposure time. This difference in exposure time was accounted for during the analysis of the images. Background (i.e., plain intralipid solution using both filters) images were also collected using the same aperture but different exposure times to obtain maximum counts from the intralipid solution. The entire study was conducted in the dark to maximally avoid any stray light from the background into the detector.

Data acquisition was also taken from beef fat. Data was taken with capillaries having aqueous ICG, at 2 mm from the surface of the fat and at 2 cm from the surface of the fat. The second data point can be used as a threshold to determine the penetration depth in the intralipid model as shown in FIGS. 9A and 9B.

Images at different depths were collected in both methods. Images collected using method 1 (i.e., with constant exposure), were ratioed with the background image obtained with all parameters being the same. However, in the case of method 2 (i.e., variable exposure time), each image was first divided by its exposure time to obtain an Intensity/sec at each pixel. The background image was also divided by the corresponding exposure time and then each image was ratioed with the processed background image. Ratioing with the background image removes any source patterns associated with the original images. Thus, the fluorescence signals can then be processed. Beef fat was obtained and a capillary filled with ICG having the optimal concentration obtained above at approximately 2 mm to 3 mm below the surface of fat. The images obtained are shown in FIGS. 9A and 9B.

Figure 9B:
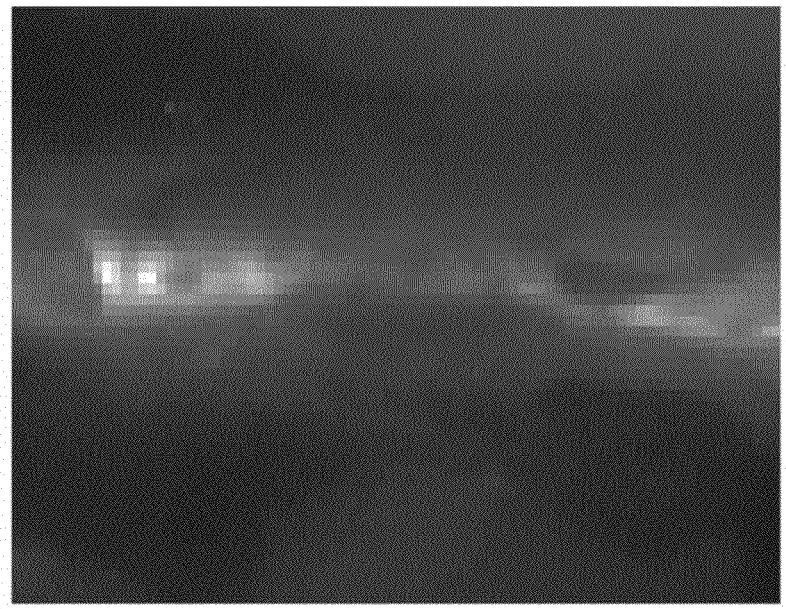
FIG. 9B is an image of beef fat with an ICG in water filled capillary taken using a present invention surgical fluorescence imager.
Figure 9A:
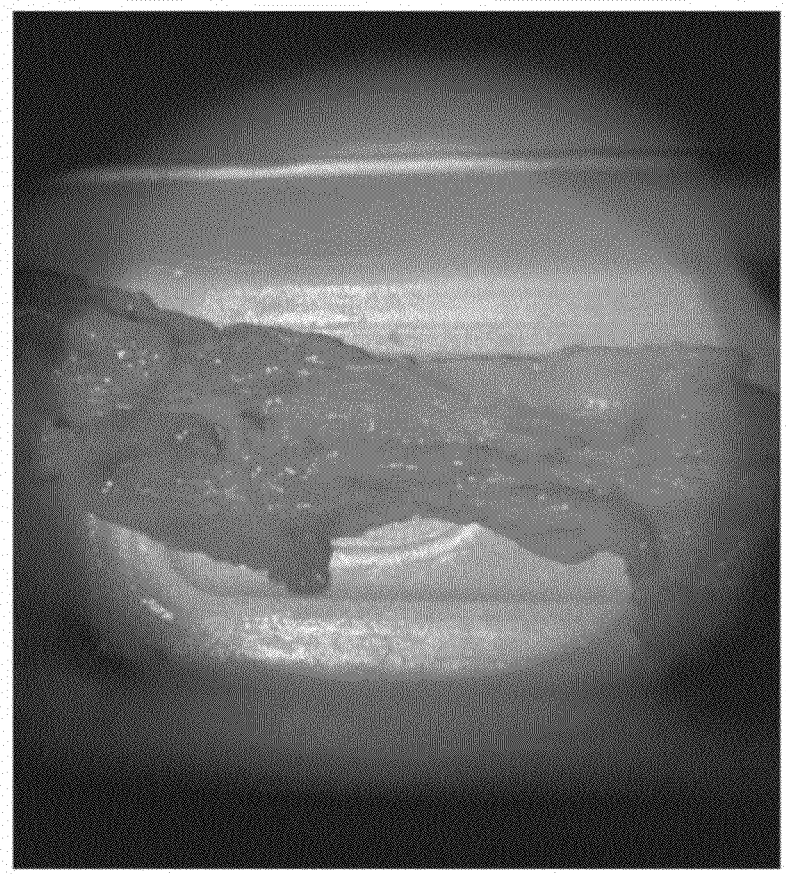
FIG. 9A is a digital image of beef fat with an ICG in water filled capillary taken from a digital image.

FIGS. 9A and 9B show images of beef fat with an ICG in water filled capillary taken from two cameras. FIG. 9A shows a digital image of beef fat with a capillary having ICG with water in it. FIG. 9B shows a digital image taken using the Surgical Fluorescence Imager of the same beef fat with the same capillary. The fluorescence glow can be clearly seen.

Figure 10:
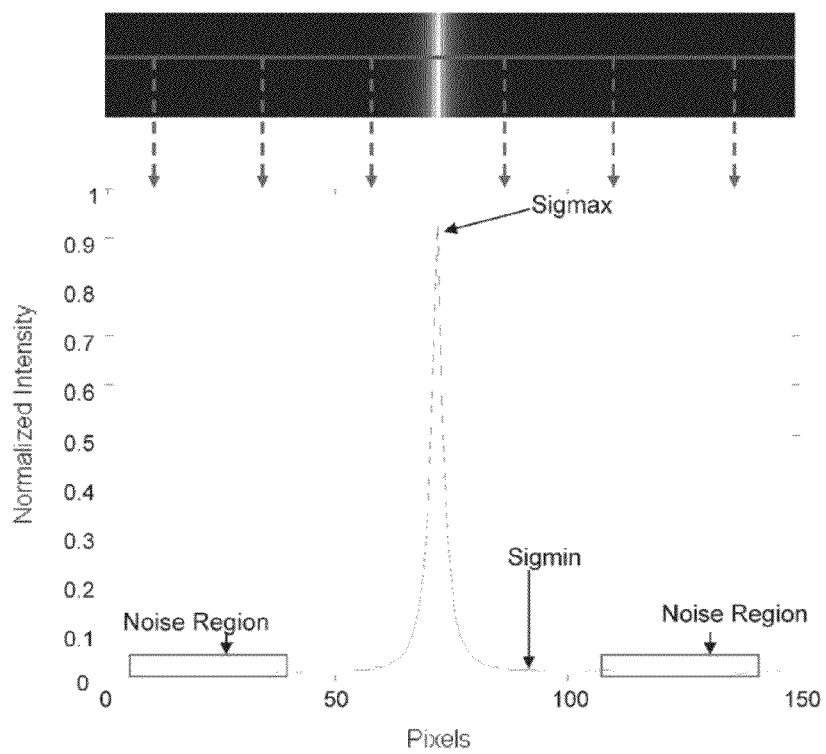
FIG. 10 is a SNR and contrast to background calculation wherein a profile is taken from each row of the image and SNR and contrast to background are then calculated for each row and averaged.

In both methods, the processed images were then cropped for the region of interest, and then a row profile of each row was obtained. This profile was median filtered with a filter window of 3. The signal to noise and contrast to background at each row were then averaged and plotted along with their error bars. FIG. 10 shows SNR and contrast to background calculations. This profile is taken from each row of the image. SNR and contrast to background are then calculated for each row and then averaged.

SNR (Signal to Noise Ratio) is the ratio of signal power to the noise power. From the profile obtained above, signal to noise was calculated by selecting the noise region, getting the standard deviation and then dividing the signal by this noise. This is depicted in FIG. 10, and described by equation (2):

$$SNR = \left(\frac{Sig_{max} - Sig_{min}}{StdDev\_of\_Noise\_Region}\right) \quad (2)$$

where $Sig_{max}$ is the maximum fluorescence signal; and, $Sig_{min}$ is the baseline fluorescence signal.

Figure 11A:
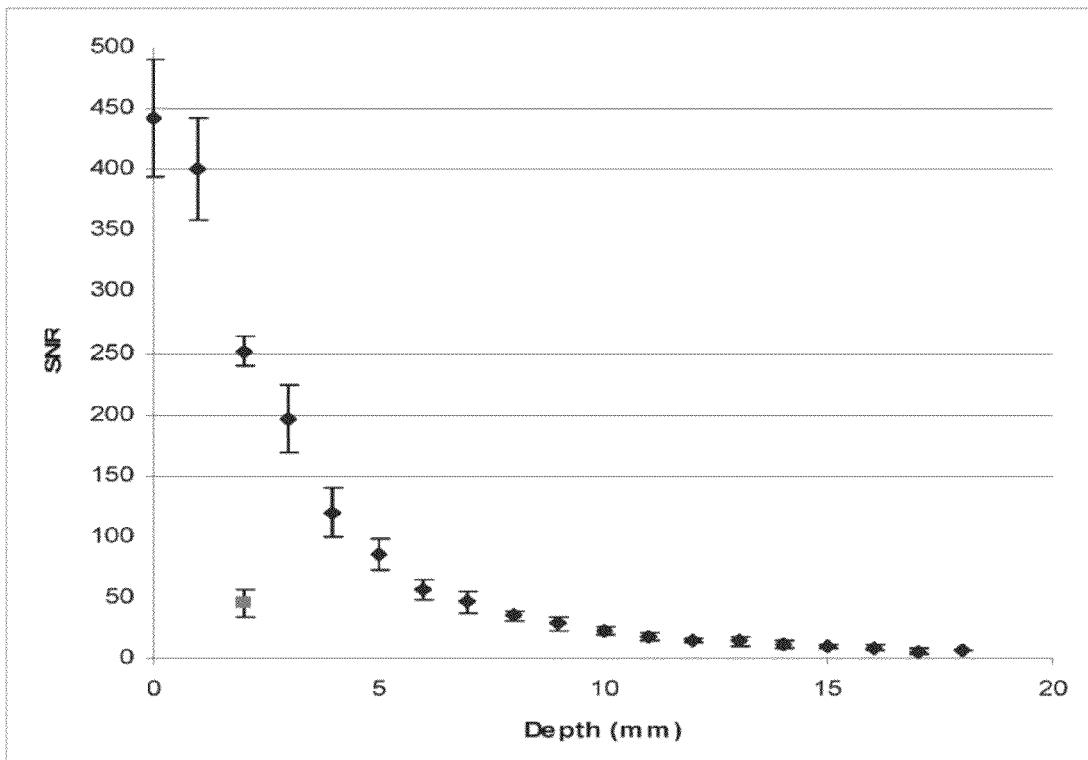
FIG. 11A is a plot depicting the signal to noise ratio against penetration depth in intralipid of Aqueous ICG with constant exposure.
Figure 11B:
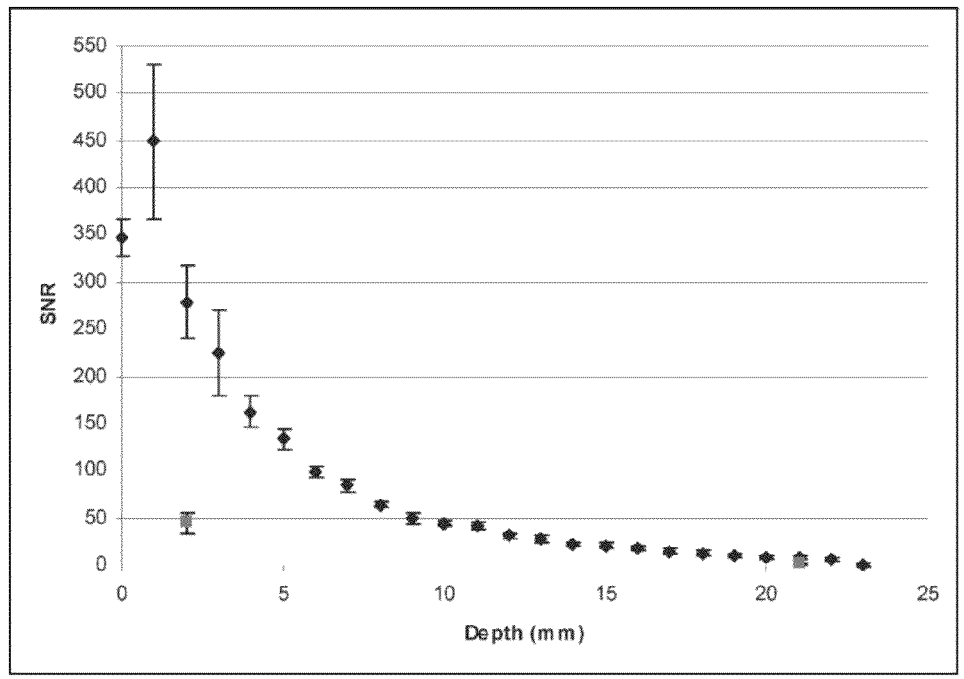
FIG. 11B is a plot depicting the signal to noise ratio against penetration depth in intralipid of Aqueous ICG with variable exposure.

The plots for the SNRs using both of the above mentioned methods are shown in FIG. 11A and FIG. 11B. SNR was calculated for each row from the cropped, processed image. A Mean SNR was calculated along with the standard deviation. FIG. 11A shows the signal to noise ratio against penetration depth in the intralipid solution of aqueous ICG with constant exposure, while FIG. 11B shows the signal to noise ratio against penetration depth in the intralipid solution of aqueous ICG with variable exposure. The square data points depict aqueous ICG in beef fat at two different depths.

Moreover, FIGS. 11A and 11B show that the signal to noise decreases as the capillary goes deeper. As discussed supra, intralipid has both absorption and scattering properties. When the fluorescence signal goes deeper, scattering and absorption takes place in the intralipid leading to lower signal and higher noise. Another factor that could affect the signal is the excitation source. The penetration depth of the excitation light itself is lower due to intralipid absorption and scattering thereby leading to lower fluorescence signal and a reduction in SNR. Typically the threshold for SNR is taken as five (5). As shown in the figures, a SNR of five (5) is reached at 18 mm below the surface with constant exposure and at 21 mm below the surface with variable exposure.

Figure 12:
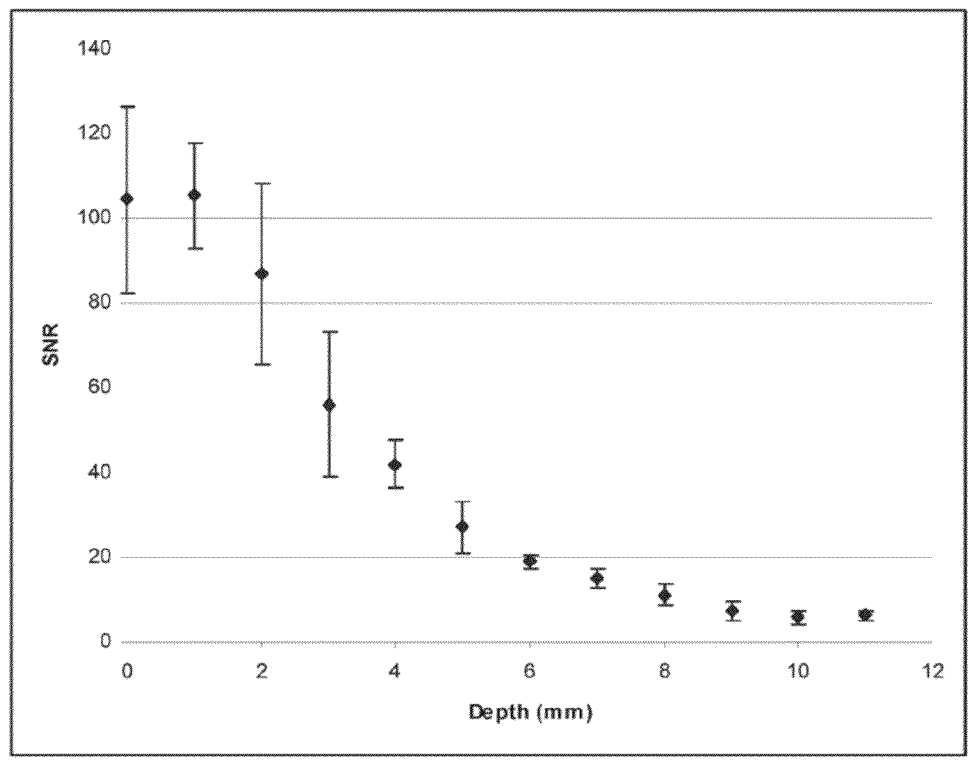
FIG. 12 is a plot depicting the signal to noise ratio against penetration depth in intralipid of ICG with Human Bile with Constant Exposure.

Another measure of depth analysis, with the same set up was taken for ICG with bile. Care was taken to maintain the concentration of ICG in bile to be 0.015 mg/ml. This was carried out with the constant exposure method. FIG. 12 is a plot depicting the signal to noise ratio against penetration depth in intralipid of ICG with Human Bile using the constant exposure method.

When bile is mixed with ICG, the penetration depth reduces due to various effects of the bile, e.g., quenching. Thus, from the plot, we can see that an SNR of five (5) is reached at 11 mm below the surface. Beyond this depth, it is difficult to distinguish between signal and noise, and thus data analysis was terminated.

Figure 13A:
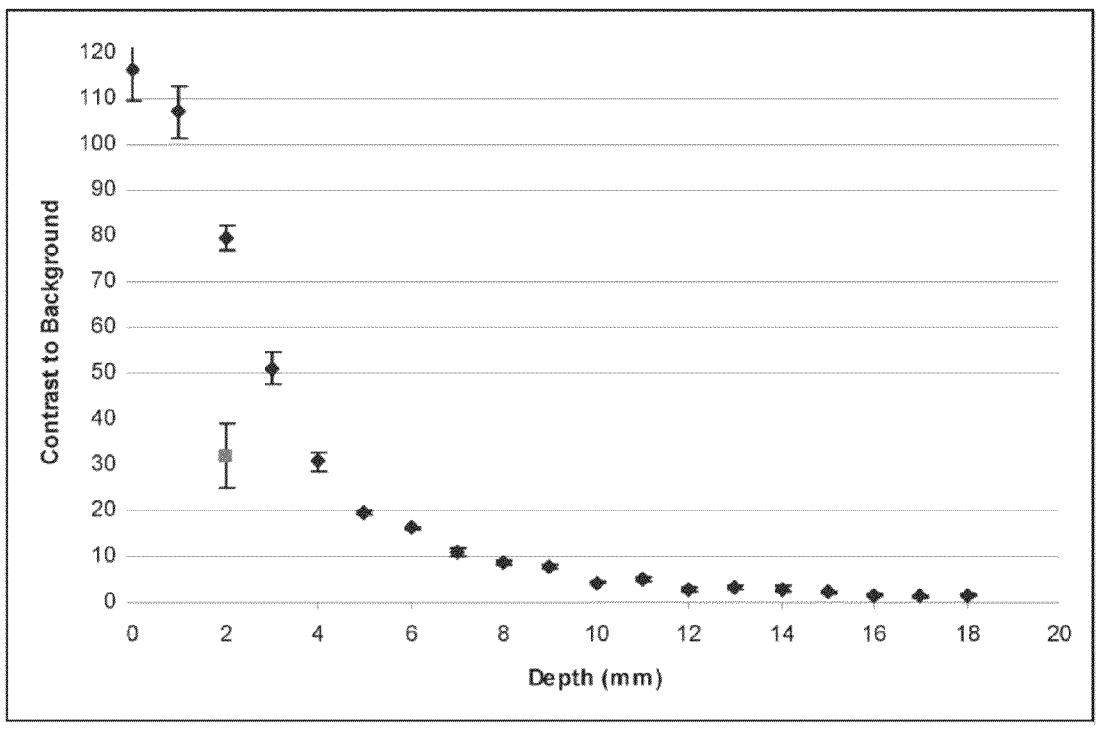
FIG. 13A is a plot depicting the contrast to background ratio against penetration depth in intralipid of Aqueous ICG with constant exposure.
Figure 13B:
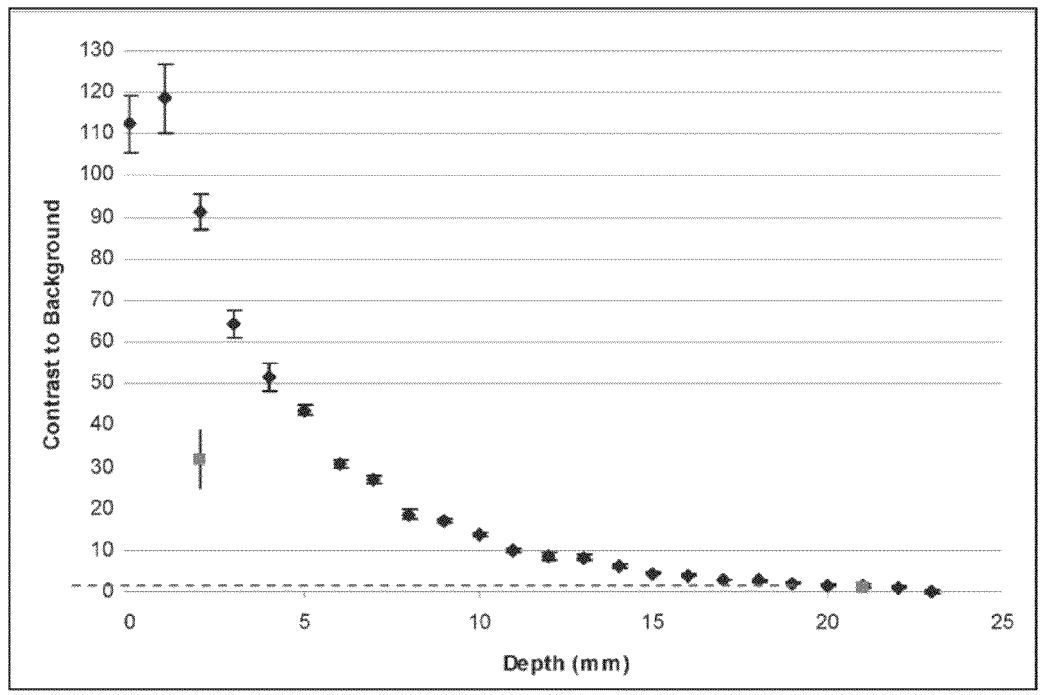
FIG. 13B is a plot depicting the contrast to background ratio against penetration depth in intralipid of Aqueous ICG with variable exposure.

Contrast to Noise was calculated using the same value of signal as for SNR and dividing it by the mean of the noise region. This parameter can also be used as a deciding factor for finding the penetration depth of ICG in intralipid. The plots for contrast to background are shown in FIGS. 13A and 13B. FIG. 13A shows a plot depicting the contrast to background ratio against penetration depth in intralipid of aqueous ICG using the constant exposure method, while FIG. 13B shows a plot depicting the contrast to background ratio against penetration depth in intralipid of aqueous ICG using the variable exposure method. Square data points show data with aqueous ICG in beef fat at two different depths.

Figure 14:
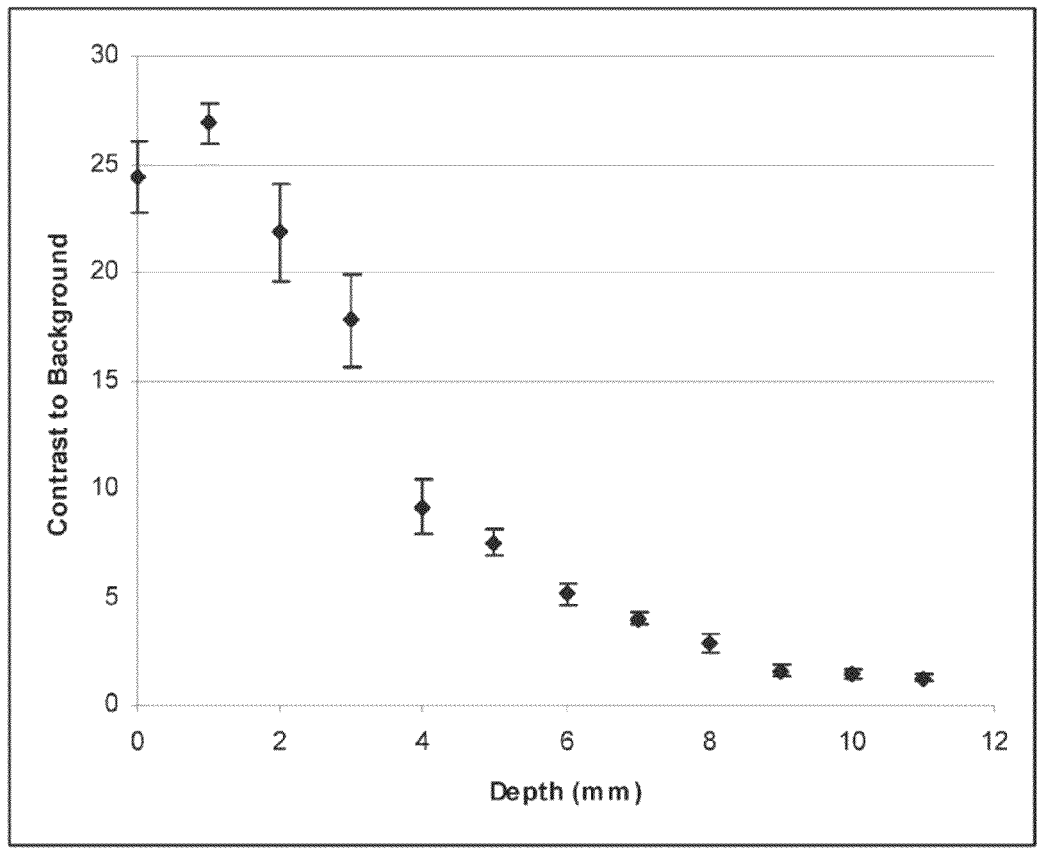
FIG. 14 is a plot depicting the contrast to background ratio against penetration depth in intralipid of ICG with human bile under constant exposure.

Similar to signal to noise ratio, contrast to background ratio was also computed for ICG with Bile in an Intralipid solution. FIG. 14 is a plot depicting the contrast to background ratio against penetration depth in intralipid of ICG with Human Bile using the constant exposure method.

From FIG. 14, it is clear that the contrast to background ratio decreases with penetration depth. From FIGS. 11A-14, it can be concluded that the penetration depth of ICG with water in a 1% intralipid solution is approximately 21 mm from the surface of intralipid. The dashed line in the plot (FIG. 13B) determines the threshold value of contrast to background taken from aqueous ICG in beef fat. However, since a 1% intralipid solution is a homogenous medium and ICG in aqueous solution is also homogenous, the penetration depth is high. Analysis of beef fat revealed a contrast to noise threshold of 1.0.

From FIG. 14 it is clear that the penetration depth is approximately 11 mm below the surface of intralipid beyond which the contrast to background ratio is below 1.

As described above, free bilirubin does not have high fluorescence and conjugated bilirubin has a better quantum yield. Bilirubin has a strong and main absorption spectrum in the visible region with wavelengths ranging from 390 nm to 460 nm and a molar absorption coefficient of approximately $50 \times 10^3$ $mol^{-1}$ $cm^{-1}$ in aqueous solvents. The position of maximum absorption, the shape of the spectrum and the molar absorption coefficient depends greatly on the conformational structure.

The fluorescence of bilirubin increases in the presence of albumin. (See Humra Athar, Nisar Ahmad, Saad Tayyab, Mohammad A. Qasim "Use of Fluorescence enhancement technique to study bilirubin-albumin interaction" Int. J. Biological Macromolecules, 25, 353-358, 1999). Bilirubin dianions combine reversibly with human albumin in neutral or alkaline solution. (See Jorgen Jacobsen, Rolf Broderson "Albumin-Bilirubin Binding Mechanism" Jour. Of Biological Chemistry, Vol 258, No. 10, Issue of May 25, pp. 6319-6326, 1983). A bilirubin albumin solution has an absorption spectrum from 500 nm-600 nm, with an emission occurring at around 528 nm.

Figure 15:
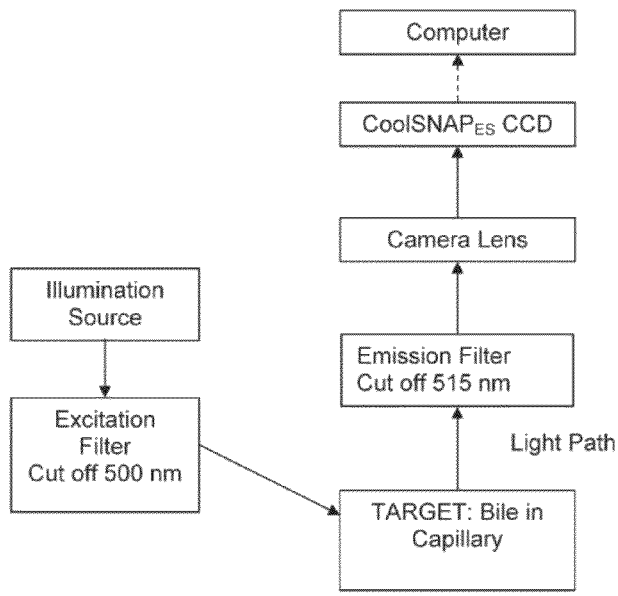
FIG. 15 is a block diagram depicting a set up for measurement of fluorescence from bilirubin.

Measurement of fluorescence was done using the source detector combination as shown in FIG. 15. FIG. 15 is a block diagram depicting a set up for measurement of fluorescence from bilirubin.

Bile was taken from a patient with the patient's consent. The raw bile was used for filling the capillary through a syringe. The capillary was kept over a black cloth to avoid any reflection as this would affect the fluorescence. A source coupled to an excitation filter (i.e., a short pass filter having a cut off of 500 nm) was used to excite the bile inside the capillary. The source was a broad band QTH source as discussed above. The source-filter combination was at a distance of 15 inches from the capillary. The detector used was CoolSnap$_{ES}$ (Princeton Instruments). The detector was coupled to the bilirubin emission filter (i.e., a long pass filter having a cut off of 515 nm) along with a 50 mm, f/1.4 Nikon lens. The detector and the source were arranged in reflective mode geometry as shown in FIG. 15. The detector was further connected to the laptop for data acquisition. In such a mode, light emitted through fluorescence was collected at the detector which then amplified and provided an image. FIG. 16 is a fluorescence image of bilirubin with excitation from 400 nm-500 nm. The fluorescence is clearly seen as compared to the blank capillary.

The above described image was obtained by subtracting the raw image against its background (i.e., image without the bile capillary). From the image, the fluorescence of bilirubin is clearly seen. This can be used as one of the parameters in the detection of biliary duct. From this experiment, it has been found that the bilirubin in the bile fluoresces. This provides another method of visualizing the bile duct in a cholecystectomy procedure.

Figure 17A:
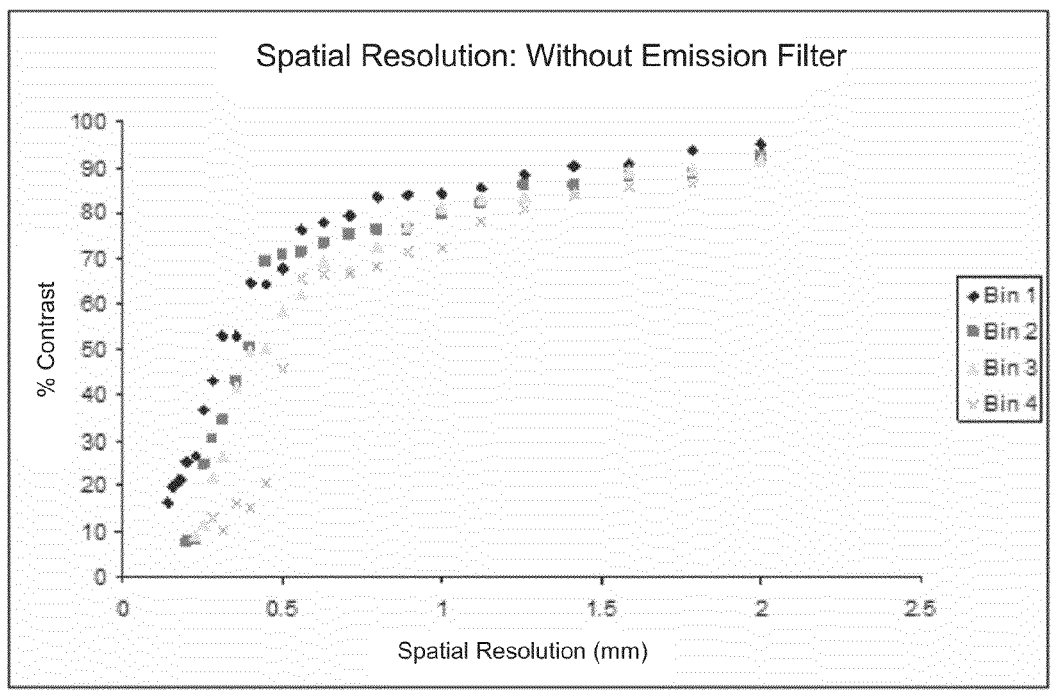
FIG. 17A is a plot depicting percent contrast against spatial resolution, when no emission filter is used.
Figure 17B:
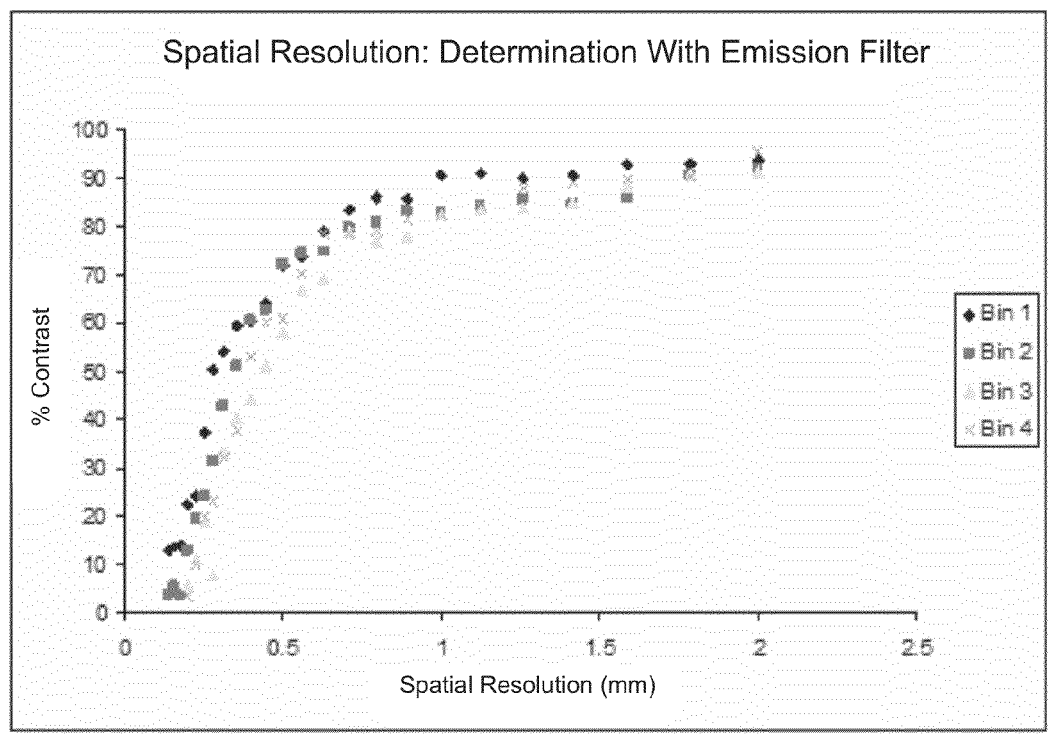
FIG. 17B is a plot depicting percent contrast against spatial resolution, when an emission filter is used.

The spatial resolution of the bilirubin fluorescence imager was established in a similar manner as it was done for determining percent contrast using the ICG fluorescence imager. However, in this embodiment, the detectot was the CoolSNAP$_{ES}$. Excitation filters having a cut off of 500 nm and emission filters having a cut off of 515 nm were used. The results are shown in FIGS. 17A and 17B. FIGS. 17A and 17B are plots depicting percent contrast against spatial resolution, when no emission filter is used (FIG. 17A), and when an emission filter is used (FIG. 17B). FIGS. 17A and 17B show that there is a slight decrease in the percent contrast when the emission filter is used in the optical path. This is possible as, there can be non-uniformity generated due to the filter from certain manufacturing issues. Additionally, the spatial resolution with the emission filter is approximately 0.25 mm (at a percent contrast of 26%). This does not reflect the spatial resolution when measuring fluorescence and just reflects the spatial resolution of the CCD coupled to the filter.

It has been demonstrated that Indocyanine Green and Bilirubin can be used as a latent contrast agent for visualizing an anteriorly placed biliary structure. This is evident from the analysis of penetration depth in an intralipid model. However, ICG mixed with bile resembles closer to real data imaging. Thus, it has been shown that the penetration depth of Indocyanine Green is approximately 11 mm below the surface of a 1% intralipid. Plain aqueous ICG was used for depth analysis in a 1% intralipid solution, and the penetration depth is almost doubled. This demonstrates that when bile is mixed with ICG, aggregates are formed. Moreover, bile itself absorbs some of the incident radiation that falls on it, thereby reducing the excitation energy for ICG. However, this forms a more realistic model that can be used for clinical studies.

Another potential method is to perform multimodal imaging using a DLP hyperspectral imager that is capable of imaging fluorescence signals from ICG, bile and NIR reflectance radiation. Moreover, the present invention comprises a method of performing multimodal imaging using a DLP hyperspectral imager which includes but is not limited to visualization of biomarkers and/or biochemical markers that absorb, reflect and/or fluoresce by using digital signal processing and chemometric algorithms, or alternatively, complex spectral illumination can be used to collect complex spectral data thereby providing chemically encoded information. Accordingly, an embodiment of the present invention includes a method of confirming the location of the bile ducts by video rate or near video rate imaging of the area and switching between various methods such as the hyperspectral imaging method using NIR spectral illumination and fluorescing ICG and bile.

Figure 18:
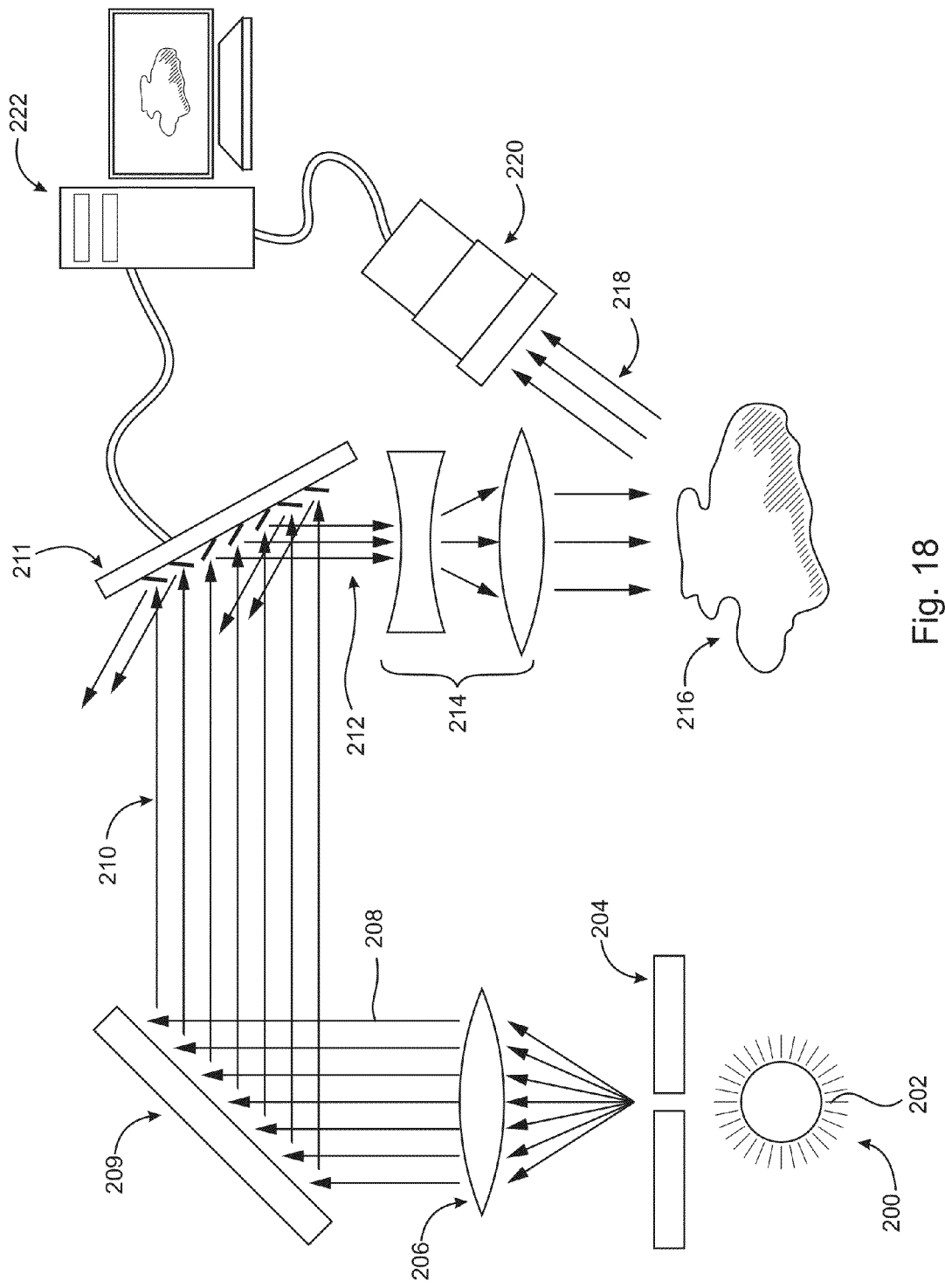
FIG. 18 is a hyperspectral imager for use with the present invention.

FIG. 18 is yet another embodiment of the hyperspectral imager of the present invention. Briefly, the hyperspectral imager includes Xenon lamp assembly (Optronic Labs) 200, broadband light 202 emitted from lamp 200, passes through sub-millimeter slit (Optronic Labs) 204 and in turn passes through collimating lens 206. Collimated light 208 then reflects off of diffraction grating 209 which creates diffracted light 210, i.e., light separated into a plurality of bandpasses of light. It should be appreciated that slit 204, in combination with collimating lens 206 and grating 209 may also be a prism, a tunable filters, an electromechanical optical filter wheel, an acousto-optical tunable filter, a liquid-crystal tunable filter, a digital micromirror device, an electro-optical filter, a holographic filter, and combinations thereof. The diffracted light strikes a DLP® digital micromirror array 211, which reflects projected light 212. Projected light 212 includes intensities of wavelengths of a complex spectrum reflected back into the optical path by array 211. In other words, diffracted light 210 falls on array 211 in such a way that the columnar bands of discrete wavelengths of light each fall on a specific column of micromirror on array 211. Then, by selecting particular rows within the columns of micromirrors, the spectral content of projected light 212 may be controlled forming a complex spectral illumination. For example, as shown in FIG. 18, rows within the columns of micromirrors corresponding to wavelengths ranging from 380 nm to 1600 nm are "turned on" while rows within other columns of micromirrors are "turned off". Thus, projected light 212 includes varying light intensity ranging in wavelength from 550 nm to 600 nm. Subsequently, projected light 212 passes through beam shaping optics 214 and strikes tissue sample 216. Reflected light 218 from tissue sample 216 is received by CCD Focal Plane Array detector 220 and the detected data is communicated to computer 222 for data processing. Computer 222 can also be arranged to control digital micromirror array 210 and the detector 220.

As described supra, the present invention includes a spectral illuminator using DLP technology to excite fluorescence markers (which can be native to the tissue (tissue fluorescence) or target, or that was injected or painted onto the tissue or target) and an optical filter, LCTF or other element used to pass emitted fluorescence light to a detector. With the improved imaging provided by the present invention, surgical procedures can focus on the target for treatment (or its adjacent tissue) by visualization, e.g., the biliary tree. The present invention system can be used for other surgical applications to perform in vivo pathology during surgery, or alternatively, in vivo hyperspectral pathology. The present invention can also be used in methods, including, in vivo pathology of cancer in real-time (e.g., before, during or after surgery), in the body (e.g., laparoscopically) without having to biopsy and/or fix the tissue or target to a slide. Other examples include a probe that binds to antigens. The techniques are also applicable to fluorescence microscopy. Finally, chemometrics and digital signal processing may be used to enhance the visualization. Furthermore, it has been found that using a digital light processor the present inventors were able to achieve video rate hyperspectral image capture and processing. Video rate capture and processing is not possible with current illumination technology and made possible by including DLP. The video capture rate also benefits from the chemometric illumination.

Clinical results have shown visible reflectance hyperspectral imaging is capable of visualizing chemical changes using inherent chromophores within the microvasculature. These results have created the opportunity to apply this cutting-edge imaging modality in a variety of clinical applications. As an example, the surgeon needs a system for helping determine the degree of amputation and monitoring vascular healing after surgery in order to reduce the risk of an amputation failure. Similarly, plastic and reconstructive surgeons have a need for a reliable system indicating tissue viability of skin flaps and transplanted tissue, as well as, determining how much tissue to extract when removing a cancerous skin tumor. Moreover, the laparoscopic gastric bypass surgeon needs a system for detecting hemorrhage and ischemic tissue during gastric bypass procedures to avoid catastrophic complications. To that end, hyperspectral imaging is useful in monitoring and assessing vascular healing after performing a lower limb amputation, in determining the degree of amputation and tumor removal, monitoring tissue viability of skin flaps and transplanted tissue and detecting strictures and leaks during gastric bypass surgery. There were approximately 82,000 lower-limb amputations reported in the year of 2002; 105,000 bariatric gastric bypasses; 500,000 cholecystectomy surgeries were performed in 2003; and, approximately 59,350 new cases of skin cancer, all of which are expected to increase over time.

Figure 19:
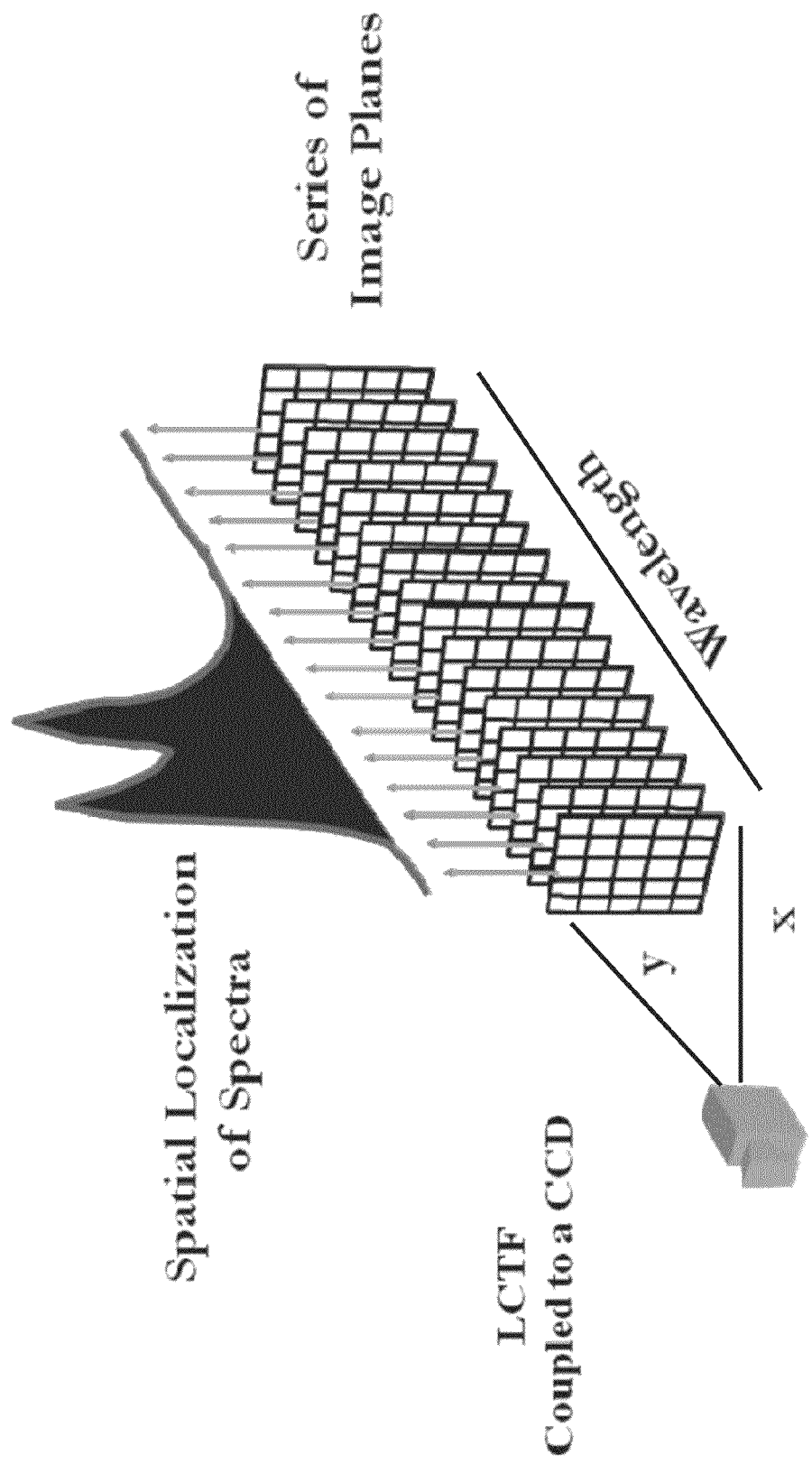
FIG. 19 is an illustration of hyperspectral image cube visualization.

As described supra, hyperspectral imaging is an optical imaging technique that captures the spatial and spectral information from the source target, typically capturing hundreds, of contiguous wavelength bands for each pixel. The hyperspectral data would be rendered useless, until the recorded data is precisely analyzed and processed using tools borrowed from spatial image processing, chemometrics and spectroscopy to yield information that can be presented in an image form. Thus, the hyperspectral imaging approach provides a "data cube" consisting of two dimensional images with each desired wavelength being represented by one of the images from the stack of images collected. The image cube thus obtained, has three dimensions: two (2) spatial (X and Y) and one (1) spectral dimension (wavelength). A basic hyperspectral imaging system consists of a broadband light source, with the desired spectral band of interest; optics arranged to focus light on the source target; an electronically tunable filter to spectrally discriminate the imaged light from the source target; and, a sensitive array detector or focal plane array, which collects the light, converts it into a two dimensional gray scaled image and transfers it to a computer. The image acquisition process continues until all images at desired wavelengths have been collected, generating the hyperspectral image cube. An overview of a hyperspectral image cube is depicted in FIG. 19.

Hyperspectral imaging has been used in satellite technology to identify features on the earth surface; however, there has been little application to biology and almost none to clinical medicine. The present inventors address this with the next generation of hyperspectral imaging systems that are "source based".

The present invention incorporates DLP® technology and increases the speed of image data acquisition. The DLP® is used in conjunction with a source lamp, and is capable of tuning different wavelengths of light within microseconds versus milliseconds required by current systems in the industry. In addition, the placement of the liquid crystal tunable filter (LCTF) within the slit lamp beam path and the spectral deconvolution are unique features of this invention.

The current invention source based system can collect data 60 to 100 times faster that previous known detector based systems. With the increased speed, the present invention may be applied to practical clinical and surgical uses. Additionally, the increased speed reduces movement artifacts, producing real time video images, with the capability of displaying both normal and hyperspectral video simultaneously.

The present invention includes integrating DLP® technology with Focal Plane array technology, collecting and storing digital hyperspectral image data and analyzing the data using chemometric analysis methods. Visualizing tissue chemistry are features unique in the field of clinical hyperspectral imaging. This technology enables clinicians to visualize the levels of chemicals within the tissue, for example, visualizing anteriorly placed or hidden structures during open, endoscopic and laparoscopic surgery detecting retinal disease early, guiding laser therapy, monitoring patients during pharmacologic therapies for preventing blindness, helping guide and monitor wound healing and amputations as well as skin flaps during recovery. Other applications include research grade devices for animal research and in quality control of pharmaceuticals and food.

Another example application of the present invention is to visualize tissues and organs in the human body using chemometric techniques and sophisticated signal processing methods. The system has a wide range of clinical applications such as enabling surgeons to see through tissues before they cut into them during cholecystectomies, chromoendoscopy facilitating cancer detection, plastic surgical skin flap viability and burn wound healing evaluation, skin cancer detection, retinal blood perfusion in diabetic retinopathy, assessing and monitoring wound healing in lower limb amputations, monitoring anastomotic viability in gastric bypass operation, dental evaluation, measuring oxygenation of the kidneys and monitoring pressure sores. The present invention can also be used as an integral component to the smart bed and smart hospital for measurement of vital signs and monitoring a patient's tissue oxygenation.

The present invention consists primarily of a spectral light engine with DLP® technology providing the spectroscopic illumination, a digital camera with a scientific grade CCD for imaging, and software designed and developed to manage the data acquisition and the chemometric visualization. The data acquisition software automatically tune the DLP® technology and trigger the camera for collecting a series of spectroscopic images formatted as a hyperspectral image cube. Next, the spectroscopic image data are deconvoluted using chemometric analysis methods. The resulting gray scale or color encoded images provides the clinician with a non-invasive visualization of the chemical state within the micro vasculature perfusing the tissue while the patient is in the clinic or surgery.

One of the many goals of the present invention is to demonstrate a DLP®-based Visible Hyperspectral Imaging Systems can be used routinely for a variety of medical applications. In certain embodiments, a DLP spectral light engine can be used for illuminating the tissue with different wavelengths, colors of light and light reflected back to the detector are measured as a spectrum at each image pixel and using different chemometric methods to determine relative levels of inherent chromophors within the tissue can be visualized. In addition, the chemometric methods can be performed on the detector instead of on the source, or the combination of both. Furthermore, the present invention can illuminate the object to be analyzed with spectroscopic light, tuned by DLP®. The speed of the present invention reduces the current acquisition time from minutes to seconds making hyperspectral imaging a practical everyday surgical and clinical tool for imaging.

In some embodiments, the present invention may be used in the field of opthalmology. Here, a hyperspectral slit lamp, which involves the integration of electro-optics and a clinical slit lamp, enables clinicians to image psychopathological aspects of the retina, including the oxygenation status and the level of macular pigments. This in turn allows the clinician to assess the need for treatments earlier than is currently possible. Additional examples of the clinical applications of hyperspectral imaging include: (a) the determination of areas of ischemia in diabetic retinopathy and retinal vascular occlusive diseases. This helps the clinician to decide if laser therapy or intraocular injections of pharmacologic agents would be helpful to prevent or treat retinal neovascularization or macular edema. In the case of laser therapy, this imaging technique would also help delineate the specific areas of the retina that require treatment; (b) the measurement of macular pigment levels to help in the early diagnosis and therapeutic interventions of diseases like parafoveal telangiectasis and, most importantly, age-related macular degeneration; and, (c) monitor patients for determining the best pharmacological therapy for maximizing favorable patient outcomes. Consequently, hyperspectral imaging may help prevent or decrease the vision loss from these highly prevalent diseases.

In some embodiments, the present invention capitalizes on different levels of chemicals, for example the relative amount of oxyhemoglobin, deoxyhemoglobin, carboxyhemoglobin, and met perfusing the retinal tissue. Imaging not only the vasculature structure but the relative amount of chemicals within such structure to help detect and diagnose eye disease early. The present invention can directly imaging the level of the above mentioned molecules particularly oxygenation of the retina. This enables monitoring effectiveness of a therapy of a patient during treatment.

This embodiment enables clinicians to visualize the levels of chemicals (oxyhemoglobin, deoxyhemoglobin and carboxyhemoglobin within the retina, to detect retinal disease early, to guide laser therapy and to monitor patients during pharmacologic therapies for preventing blindness. In this embodiment, a liquid crystal tunable filter is placed into the beam path of a slit lamp source illuminating the eye with different wavelengths of light and light reflected back to the detector are measured as a spectrum at each image pixel. This is a unique configuration designed specifically for measuring the chemical levels within the retina.

Typically, the wavelengths to be used depend on the tissue type due to the penetration of tissue depth. For example, in visible spectra, $HbO_2$, Hb and $HbCO_2$ can be measured. In near-infrared (NIR) spectra, $HbO_2$, Hb, water and lipids can be measured.

In another embodiment, the present invention can be used for detecting, diagnosing and monitoring disease in live human patients visiting the clinic or during open and closed (endoscopic and laparoscopic) surgical procedures. The system can also be used for animal research applications. A hyperspectral imaging system integrating DLP technology to illuminate the area of interest with wavelength bands of light ranging over a spectral range from the visible to the near-infrared that is interfaced with a digital focal plane array for acquisitioning and storing a series of digital spectroscopic images (a hyperspectral data cube) that is analyzed using chemometric methods providing chemical information within the area of interest aiding the clinician in detecting, diagnosing and monitoring disease. Clinicians can also monitor patients with this technology for determining the best pharmacological therapy and maximize favorable patient outcomes. The present invention utilizes DLP technology with a focal plane array and chemometric deconvolution for visualizing the biochemical levels within a human non-invasively for clinical and surgical applications. The present invention can also be illuminated with spectrum of light.

In yet another embodiment, the present invention enables the clinician to visualize anatomical structure and the chemistry within live human patients or research animals within seconds during a visit to the doctor or during open, laparoscopic and endoscopic surgery. These images are useful to the clinician or surgeon for detecting, diagnosing, and monitoring disease and the effectiveness for identifying hidden structures during surgery and help clinicians determine the best therapy. The present invention provides unique capability to image relative levels of inherent chromophors within the tissue noninvasively without contrast agents in live humans during clinical visits or during surgery. A DLP spectral light engine may be used for illuminating the tissue with different wavelengths spectrum of light, and the light reflected back to the detector are measured as spectrum at each image pixel and using different chemometric methods to determine relative levels of inherent chromophors within the tissue can be visualized.

In certain embodiments, the system of the present invention has multiple modalities that include UV light, visible light, near infrared light, infrared light, and fluorescence excitation. In the DLP®-based Visible Hyperspectral Imager (DVHI) embodiment, the present invention may be coupled with standard surgical and clinical devices, for example a laparoscope, slit lamp, or with lens for microscopic imaging. In particular, a quick release mechanical coupling between the DVHI and a standard laparoscope is developed allowing the system to image both laparoscopically during closed surgical procedures and removing the laparoscope for open surgery imaging. The DVHI system is calibrated at NIST and to NIST standards. For visible to 2500 nm applications, the present invention may use TI Discovery 1100 electronics board with an Accessory Light Processor (ALP) electronic board.

In another embodiment, the DVHI is used in vivo using an animal model during open surgical procedures and during closed laparoscopic procedures. Spectral light illuminating the animal tissue are evaluated for safety by measuring the temperature of the tissue. A variety of tissues can be imaged and identified by measuring spectroscopy and the chemometrics, as well as, imaging before and after inducing ischemia and hemorrhaging the tissue. The system can be assessed by comparing hyperspectral and chemometric images with an evaluation made by the attending veterinarian using standard clinical methods.

Yet in another demonstration, the DVHI is translated to human surgery and clinic establishing its efficacy for a variety of human applications. Here, the present inventors translate Visible DLP® Hyperspectral Imaging for imaging during live human surgery, and monitoring the progression of clinical disease for determining feasibility. Also, surgical and clinical hyperspectral data is monitored to observe the progression of disease and changes in tissue chemistry during wound healing due to trauma, amputations, tumor removals, plastic surgery skin flaps and visualizing ischemia and hemorrhage during gastric bypass. For these purposes, the present inventors utilized the existing chemometric analysis algorithms and develop new visualization methods, chemometric and statistical analysis. In addition, the present inventors continue collected clinical hyperspectral image data using existing system and existing hospital protocols for building our clinical hyperspectral image database that can be populated over time specifically on spectral properties of composite structures for example the gallbladder and extrahepatic bile ducts, determined additional clinical applications, and refined new chemometric algorithms. The end results provide better imaging algorithms for better clinical visualizations that can be implemented into the software of the new DLP® Visible Hyperspectral Imaging System.

The DLP® Hyperspectral Imaging and Chemometric deconvolution can be applied to all products that use light, for example, the fields of clinical endoscopy, clinical chemistry, microscopy, surgical microscopy, drug discovery, microarray scanners and microplate readers.

In certain embodiments, the multi-modal microscopic reflectance Hyperspectral Imaging system developed provides enhanced diagnosis in a clinical environment. The system developed has the capability to measure relative contributions of oxyhemoglobin in the microvasculature in the visible as well as the near infrared region, hence it is multi-modal. An example was formulated to measure contributions of oxyhemoglobin in the microvasculature perfusing the dermal tissue of the palm in the near infrared region. The system was also used to image the human eye measuring the relative contributions of oxyhemoglobin perfusing the scleral surface. The instrumentation used for this imaging system is shown in the FIG. 20.

Figure 20:
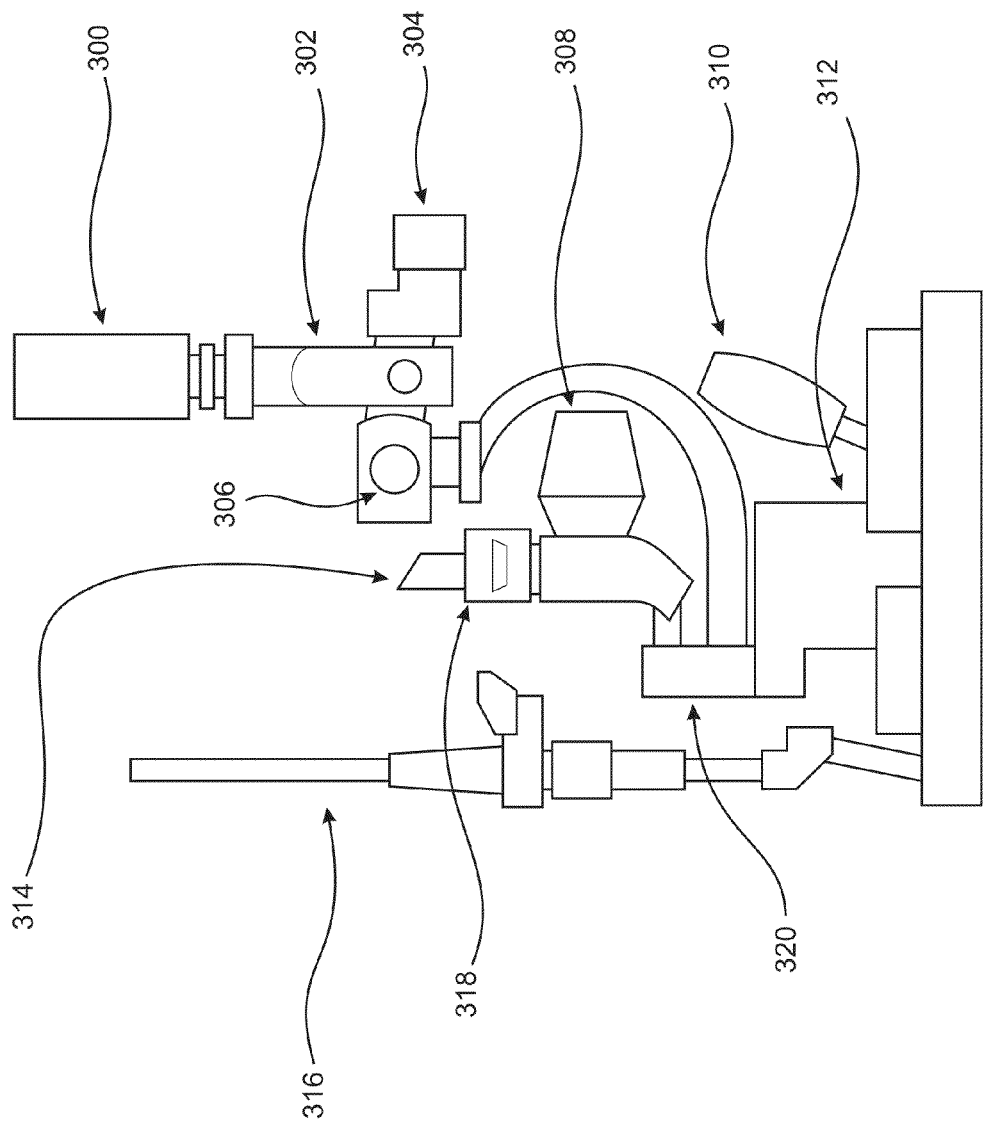
FIG. 20 is an embodiment of the present invention hyperspectral imaging system.

FIG. 20 depicts one embodiment of the above mentioned hyperspectral imaging system of the present invention having charged coupled device 300 (CCD), beam splitter 302, eye pieces 304, magnification knob 306, light source 308, joystick 310, intensity control knob 312, illumination mirror 314, subject position 316, liquid crystal tunable filter (LCTF) 318, and common center for rotation 320. In another embodiment, the LCTF may be replaced with a digital micromirror device, and can be located anywhere along the optical path of the present apparatus.

In certain embodiments, the instrumentation shown in FIG. 20 may contain a slit lamp (light source 308) that illuminates the target using an in-built 12V/30W illumination Halogen lamp source. The light from the source is focused onto the target which is placed on the Y-shaped headrest. The diffused reflected light from the target is passed back through the slit lamp microscope optics onto a beam splitter 302 which allows a part of light into eyepiece 304 for the observer and the remaining part of light to the relay optics which further pass light into the LCTF 318, which is an electronically tunable filter discriminating the reflected light into individual wavelengths passing it onto the camera lens which then focuses it onto Charged Coupled Device or HQ2 (CCD) camera 300. It should be appreciated that the foregoing arrangement, which includes a LCTF, may alternatively include a DLP illumination device as described throughout this application. Thus, the LCTF can be removed, and the DLP illumination device coupled to this system at the location shown for light source 308. The images formed on the CCD are then digitized and stored in a laptop computer for further analysis. In some embodiments, the system can be applied to collect data in the near infrared region or in the visible region. The visible and near infrared application differ in the use of a unique CCD camera, i.e., the CooLSNAP$_{ES}$ camera instead of the PIXIS camera, and a unique LCTF, visible LCTF instead of near infrared LCTF, or visible versus a NIR DLP® spectral illuminator.

The slit lamp is a microscope having an illumination system and an observation system, which are mounted on a rotated drum with a common centre of rotation. The slit lamp is binocular; that is, it has two eyepieces 304, giving the binocular observer a stereoscopic (i.e., three dimensional) view of the eye. These devices are sometimes referred to as Biomicroscope or stereomicroscopes. The Galilean magnification changer allows increasing the magnifying power between three stages, e.g., 10×, 16×, 25×, by simply turning a knob which is designed with a flat area so that the operator can change the power by feel, without looking at the markings, since the higher magnification is achieved when the flat portion is on top, while lowers magnification is achieved when the flat portion is at the bottom. The actual magnification of what is seen through the slit lamp is derived by multiplying the power of the eyepieces, which are fixed, with the power of the objective lens.

Thus, if the eyepieces 304 are 10× and the objective lens is 1.6×, the total magnification is 16×. The non-radiometric light source of the slit lamp is a 12V/30W halogen lamp providing broadband white light. The light is controlled by a transformer which provides continuous light intensity with the help of rheostat placed next to the joystick 310. The slit width and the slit height can be continuously varied from 1-14 mm. A Beam splitter 302 is effectively a semi-silvered mirror which is placed in-between the eyepiece and the microscope optics to partially transmit light to the eyepiece and partially reflect light to the attached CCD camera 300. In another embodiment, the detector can be a focal plane array. Typically, for macroscopic and endoscopic embodiments, the present invention uses a non-radiometric source system. This non-radiometric source provides significant advantages for the use in standard clinical operations due to its safety characteristics. However, in the embodiments of the hyperspectral imaging system which include DLP®, a radiometric power supply is used due to it stable current as a light source.

Attaching LCTF 318 and CCD camera 300 onto beam splitter 302 of the slit lamp does not use a lot of CCD chip area, i.e., the spot created by the reflected light from the slit lamp falling onto the CCD after passing through the LCTF is very small. Hence there is a need to magnify the reflected light coming out of the beam splitter before passing onto the LCTF. Thus, a relay optic module was designed which is composed of two optics namely an eyepiece and a photo eyepiece placed in a machined metal cylinder. An eyepiece lens is an optical system which is used to magnify images in optical instruments such as telescopes, microscopes, etc. A photo eyepiece performs the function of focusing the images onto a plane. These two optical components are housed in a metal cylinder 18 cm in length.

Light passes through a Liquid Crystal Tunable Filter (LCTF) 318 having solid-state construction and no-moving parts or vibrations, which works by applying voltage to its liquid crystal elements, to select a transmitted wavelength range, while blocking the rest of the wavelengths. The 60 mm, f/2.8 D micro-Nikon camera lens focuses the light filtered by LCTF 318 onto CCD camera detector 300. Typically, the 60 mm is the dimension for a slit-lamp in spectral detection. The 50 mm lens is used for macroscopic imaging spectral detector, and no lens is used with the LCTF as the spectrum illuminator. It has the ability to produce distortion-free images with superb resolution, sharpness and contrast. The lens has a good depth of field and a small working distance.

The charge coupled devices (CCD's) or focal plane arrays (FPA) perform three essential functions: photons are transduced to electrons, integrated and stored, and finally read out. They can be roughly thought of a two-dimensional grid of individual photodiodes (called pixels), with each photodiode connected to its own charge storage "well." Each pixel senses the intensity of light falling on its collection area, and stores a proportional amount of charge in its associated "well." Once charge accumulates for the specified exposure time, the time between start acquisition and stop acquisition (also known as integration time), the pixels are read out serially.

As described in part above, the CoolSNAP$_{ES}$ monochrome camera typical incorporates a SONY ICX-285 silicon chip with Interline-transfer capability. The interline-transfer CCD has a parallel register subdivided into alternate columns of sensor and storage areas. The image accumulates in the exposed area of the parallel register and during CCD readout the entire image is shifted under the interline mask into a hidden shift register. Readout then proceeds in normal CCD fashion. Since the signal is transferred in microseconds, smearing is undetectable for typical exposures. However, a drawback to interline-transfer CCDs has been their relatively poor sensitivity to photons since a large portion of each pixel is covered by the opaque mask. As a way to increase a detector's fill factor, high-quality interline-transfer devices have microlenses that direct the light from a larger area down to the photodiode. Blooming is the migration of electronic charge to the adjacent pixels; however, the incorporated Sony chip by Roper Scientific provides protection against blooming by having built in drains that remove any excessive charge generated from an overexposed pixel. This Sony interline chip provides anti-blooming for optical signals greater than 1000 times the full well capacity. The spectral response for the CoolSNAP$_{ES}$ camera within the visible region is of interest for the visible system application. The quantum efficiency is always beyond 45% in this region, peaking to over 60% between wavelength regions of 475 nm to 625 nm.

The CCD cameras, PIXIS 400 BR (or 1024 BR), CoolSNAP$_{ES}$ or HQ2 are driven by PVCAM software which stands for Photometrics Virtual Camera Access Method. HQ2 has a 20 MHz analogue to digital digitizer which is faster. This software is used to control the cameras and acquire data from them. The data collection process is automated using Vpascal programming language integrated in V++, a precision digital image processing and enhancement software. V++ has been designed to control any PVCAM-compatible feature using the V++ interface and the VPascal built-in programming language. The HQ2 system typically has a 20 MHx A/D digitizer that is faster than the others. Another computer codec has been written to configure a portable computer to provide mobile data collection. The software further controls and synchronizes the speed of illumination, data collection, analysis and/or deconvolution.

In an embodiment, the software performs the following steps for analysis and deconvolution. First, ratio data for each pixel is calculated.

$$RD_{ij} = \text{Log}_{10}\left(\frac{BKG_{ij} - DF_{ij}}{SD_{ij} - DF_{ij}}\right) \quad (3)$$

where
$RD_{ij}$ is the ratio data for each pixel i at wavelength j
$BKG_{ij}$ is the reflectance of a 100% reflectance standard
$DF_{ij}$ is a dark field (the value being read when no light is coming into the camera)
$SD_{ij}$ is the reflectance from the sample The ratioed spectra are then filtered using a Savitsky-Golay filter, which filter is well known in the art and therefore is not discussed in detail herein. Next, the spectrum at each pixel is normalized.

$$ND_{ij} = \left(\frac{RDF_{ij} - \min(RDF_{ij})}{\max(RDF_{ij}) - \min(RDF_{ij})}\right) \quad (4)$$

where
ND$_{ij}$ is the normalized spectrum at each pixel
RDF$_{ij}$ is the ratioed data The effect of such normalization is that each spectrum will then range from 0 to 1. Then, the data is further modified by a multivariate least squares deconvolution. It should be appreciated that such a deconvolution requires two or more reference spectra in order to be performed. In short, a least squares fit is performed, at each pixel, of the measured spectrum by performing linear combinations of the reference spectra to obtain a best fit curve. Then, the resulting relative linear contributions are scaled to produce a gray scale image. The following equations are used to performed the foregoing multivariate least squares deconvolution.

$$S_{i\lambda} = (A_{\lambda,i}^T \cdot A_{\lambda,i})^{-1} \cdot A_{\lambda,i}^T \quad (5)$$

where
S is the pixel sensitivity matrix
A represents the matrix of i pure component spectra composed of λ wavelengths Then, substitution of the sensitivity matrix, S, into the multivariate regression determines C, comprising linear contributions of the pure components in the unknown sample, namely:

$$C_{ij} = S_{i\lambda} R_{j\lambda} + e_{ij} \quad (6)$$

where
R is the matrix of the experimentally determined sample spectra j
$e_{ij}$ represents the residuals.

In another embodiment, the software performs the following steps for determining the illumination spectra and subsequent analysis. First, at least two reference spectra, as measured at the detector, are obtained for targets of interest, e.g., 100% oxyhemoglobin and 100% deoxyhemoglobin. It should be appreciated that the targets of interest may include but are not limited to reference spectra, a patient, a portion of a patient, a purified substance, etc. Additionally, a reference spectrum, as measured at the detector, is obtained for 100% illumination from the illumination source. In other words, a measurement of the spectral content of the illumination source is determined. Then, each spectrum is ratioed according to the following equations:

$$\text{ratioed\_spectrum}_1 = \left( \frac{\text{spectrum}_1 - \text{spectrum}_2}{\text{spectrum}_{100}} \right) \quad (7)$$

$$\text{ratioed\_spectrum}_2 = \left( \frac{\text{spectrum}_2 - \text{spectrum}_1}{\text{spectrum}_{100}} \right) \quad (8)$$

where
ratioed_spectrum$_1$ is the ratioed spectrum from the first target of interest
ratioed_spectrum$_2$ is the ratioed spectrum from the second target of interest
spectrum$_1$ is the measured spectrum of the first target of interest
spectrum$_2$ is the measured spectrum of the first target of interest
spectrum$_{100}$ is the measured spectrum of the illumination source The ratioed spectra are then used to illuminate an unknown sample, e.g., a kidney. In other words, the spectra calculated by equations (7) and (8) are used to illuminate the unknown sample and the reflected illumination are measured with the detector. Then, pixel by pixel, the second image, i.e., the image obtained from the illumination of ratioed_spectrum$_2$, is subtracted from the first image, i.e., the image obtained from the illumination of ratioed_spectrum$_1$. The resulting image is a chemically encoded image providing a quantitative assessment of the targets of interest. It should be appreciated that each of the foregoing measurements occur on a pixel by pixel basis and therefore differences in illumination and/or pixel response can be accounted for.

As described above, binning is the practice of merging charge from the adjacent pixels in a CCD prior to digitization in the on-chip circuitry of the CCD by specific control of the serial and parallel registers. Binning reduces the readout time and the burden on computer memory, increases the signal to noise ratio, but at the expense of image resolution. To comprehend the binning practice in the Roper scientific cameras, consider the examples shown below in FIG. 21 (binning 1×1 where no charges are summed provides the maximal resolution) against FIG. 4 (binning 2×2 where charges from 4 neighboring pixels are summed). FIG. 21(1) shows the CCD at the end of an exposure, wherein the capital letters represent different charge accumulated on the CCD pixels. Readout of the CCD begins with the parallel readout phase. FIG. 21(2) shows simultaneous shifting of all pixels in a bottom row towards the serial register followed by the serial readout phase, FIG. 21(3) and FIG. 21(4) shown shifting of charge in the serial register into the summing well which is then digitized. Only after all the pixels in the bottom row are digitized is the second row from the bottom moved into the serial register. Thus, for example above, the order of shifting is therefore A1, B1, C1, D1, A2, B2, C2, D2, A3, . . . D6.

Figure 23:
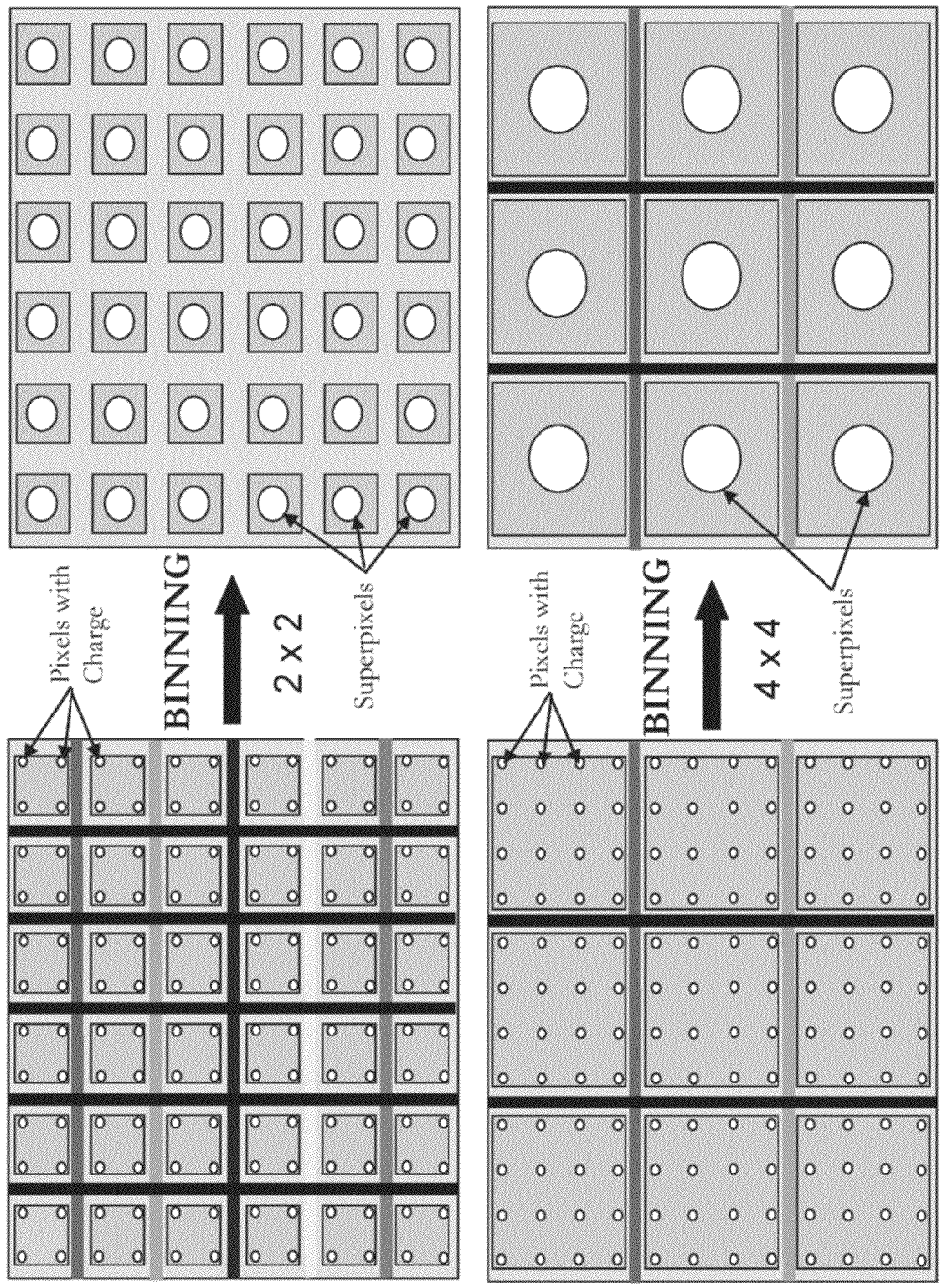
FIG. 23 is yet another diagram of example binnings in a CCD camera.

The charge that has integrated during the exposure is shown as capital letters in FIG. 22(1). Readout begins with a parallel readout, as shown in FIG. 22(2); however, since binning of 2×2 is required, charge from two rows of pixel, rather then a single row during 1×1 binning, is shifted into the serial register. Next, charge is shifted from the serial register, as shown in FIG. 22(3) and FIG. 22(4), two pixels at a time, into the summing well rather then a single pixel as in binning 1×1. The result is that each readout event from the summing well contains the collected charge from four pixels on the CCD, i.e., a superpixel. This procedure is iterated until the entire array has been read and the formation of superpixels shown below for binning of 2×2. FIG. 23 shows similarly superpixel formations for 2×2 binning and 4×4 binning.

Figure 24A:
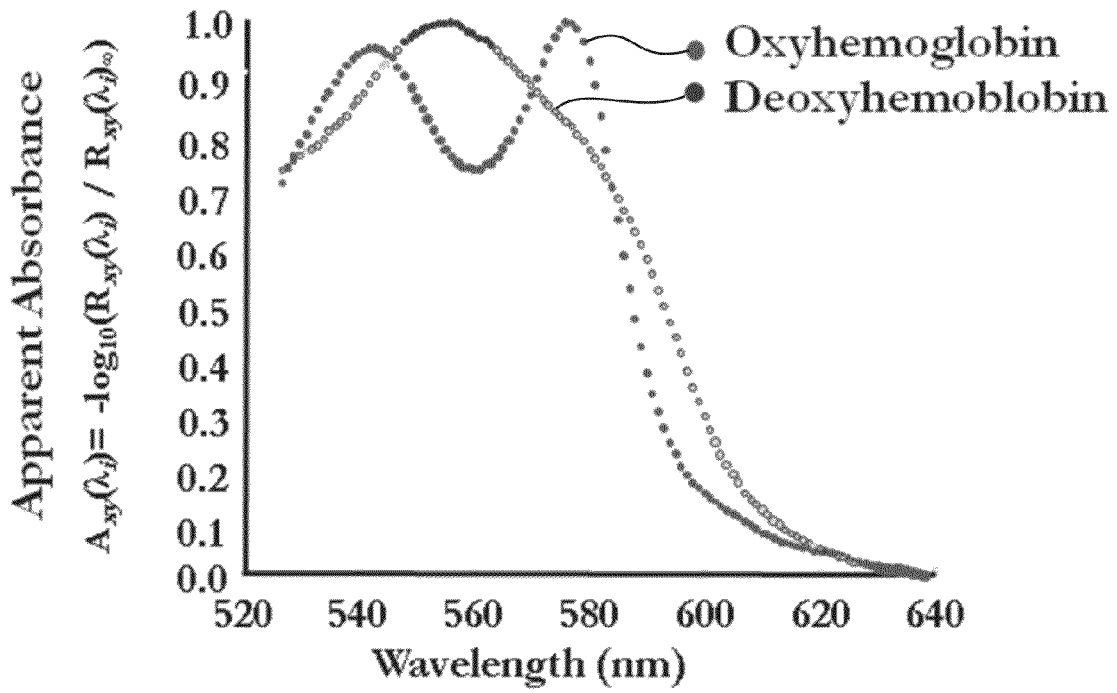
FIG. 24A is a graph showing a comparison of actual measured hemoglobin versus the predicted hemoglobin using pure hemoglobin samples and the actual measured hemoglobin using the present invention.
Figure 24B:
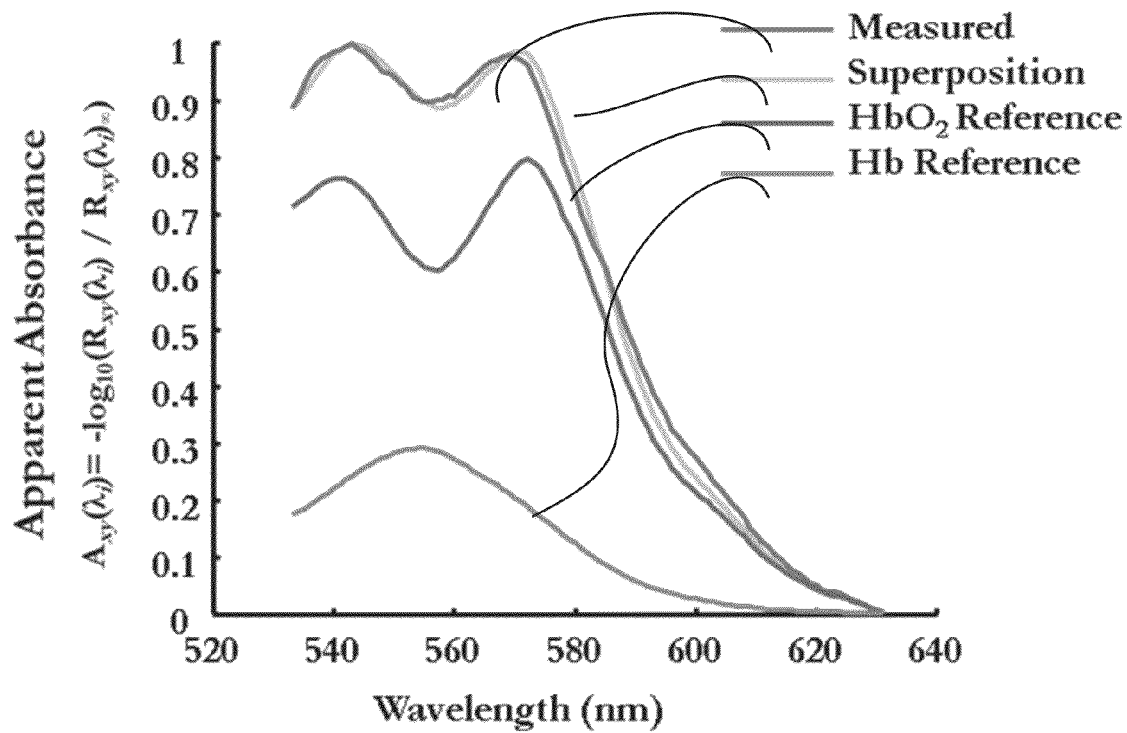
FIG. 24B is a graph showing a comparison of actual measured hemoglobin versus the predicted hemoglobin using pure hemoglobin samples and the actual measured hemoglobin using the present invention.

In certain embodiments, hyperspectral data analysis provides spatially distributed contributions of oxyhemoglobin, which are obtained based upon oxy- and deoxyhemoglobin reference spectrums. FIGS. 24A and 24B show a comparison of actual measured hemoglobin versus the predicted hemoglobin using pure hemoglobin samples and the actual measured hemoglobin using the present invention. The system requires two or more reference spectra, followed by a least squares fit, at each pixel, of the measured spectrum by performing linear combinations of the reference spectra to obtain best fit curve. The resulting relative linear contributions are scaled to produce a gray scale image.

Pure HbO$_2$ and Hb solutions were prepared at NIH by standard methods using blood collected from a healthy individual and reference spectra were obtained from the original imaging system developed at NIH for the Visible region (400 nm-700 nm). A region of interest (520 nm-645 nm) containing the peaks for oxy- and deoxyhemoglobin was selected and used for imaging purposes in the visible region, see FIG. 24A. Similar methods are used for HbO$_2$, Hb, H$_2$O, and lipids by scanning the NIR regions. References can be taken for HbO$_2$, Hb, HbCO and HbNO in the visible regions. In addition, an unsupervised method can also be used, e.g., data can be pre-processed using a filter, and then normalized thereafter.

Here, each individual spectrum can be normalized first. The typical steps include, but are not limited to, measuring a spectrum, filtering the spectrum, normalizing the spectrum data, deconvoluting the spectrum data, and calibrating the corresponding data. The present invention does not concentrate or only measure the spectral amplitude; the present invention observes the changes in spectral broadening or narrowing in addition to amplitude change.

In some embodiments, the protocol used may involve the following: An example involving seven subjects, for imaging the Human eye after seeking approval from the Institutional Review Board, IRB. In this example, the sclera of the eye was illuminated using the light source from the slit lamp for five (5) seconds while acquiring the Hyperspectral image cube. The imaging was achieved in two steps, firstly on entering the lab, the subjects were asked to rest their chin on the chin rest of the slit lamp with closed eyes and light from the slit lamp was shone onto one of the closed eyelid which was brought in focus of the slit lamp. Secondly, upon getting the eyelid in focus using the slit lamp optics, the subjects were then asked to open their eyes, look in the opposite direction from where the light was shone into the eye, and the slit lamp was made to focus on the scleral vessels upon which, hyperspectral image data cube was obtained for five (5) seconds.

Figure 25:
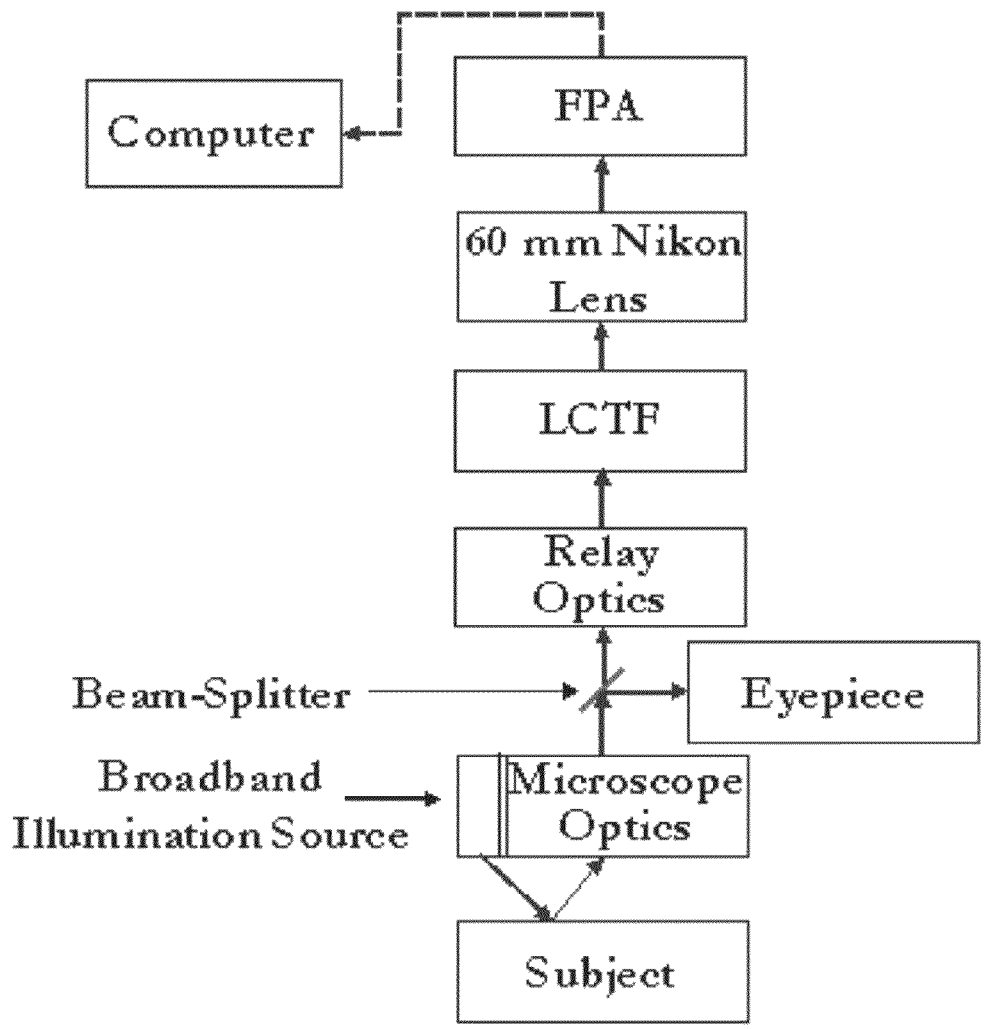
FIG. 25 is a schematic diagram of a microscopic system.

The setup for an embodiment of the present invention noninvasive non-DLP® microscopic reflectance hyperspectral imaging system consisting of a source, optics, filter and detector as shown in FIG. 25. The slit lamp contains a 12V/30 W halogen source providing broad band illumination, that illuminates the target and the reflected light from the target is guided by the microscopic optics onto a beam splitter, a semi-silvered mirror transmitting light to the eyepiece and to the attached hyperspectral imaging system. The radiation from the beam splitter is directed towards the LCTF using relay optics. The LCTF collects reflected light provided by the source into individual band passes of wavelengths that are placed on the focal plane array (FPA) detector with the use of a 60 mm Nikon lens fitted in front of the FPA. The FPA has an analog to digital, A/D, converter for digitizing the data, which is transferred to a high end laptop PC for post processing. A computer program automatously manages the data collection by synchronizing the timing between individual hardware components, for example, tuning the LCTF and triggering the FPA, and setting parameters (e.g., image size, exposure time, spectral range and resolution, image binning, gain, filename) using a GUI that was built in V++. To sum up the data acquisition, various parameters are inputted initially using the GUI developed in V++, after which the LCTF initializes and the desired voltages calculated for the selected spectral range are stored in the palette. Upon initialization, the LCTF tunes to the first wavelength specified in the palette, the camera is triggered, the CCD is exposed for the duration of the exposure time, and ADC digitizes the image information storing it onto the laptop. This process is repeated for the remaining wavelengths. For the visible application, the focal plane array (FPA) used was the HQ2 CCD in combination with the visible low resolution LCTF. The raw hyperspectral image data was collected over a spectral range of 520 nm-602 nm with a spectral resolution of 2 nm increments with the magnification set at 10× and CCD binning of 2×2 for increasing readout speed. Thus an entire reflectance hyperspectral image cube was acquired and saved to hard disk in around five (5) seconds.

The microscopic hyperspectral imaging system was then characterized. The characterization of the system involved the characterizing the LCTF, the FPA and the slit lamp source. The LCTF was characterized for its spectral band-pass, tune delay, and the tuning wavelength capability of the filter. The FPA was characterized for its ability to differentiate between objects, i.e., spatial resolution.

The spectral capabilities of the near infrared LCTF were determined using a calibrated Perkin Elmer Spectrometer. The spectrometer was scanned in increments of 1 nm with the near infrared LCTF that was tuned to a specific wavelength placed in the collimated optical path of the spectrometer. This procedure was repeated for a series of sequential wavelengths spanning the range of the near infrared LCTF, 650 nm to 1000 nm, at every 50 nm and the corresponding transmittance spectra of the LCTF were noted. The transmission spectra from the spectrometer were then analyzed in Matlab to measure the center wavelength the LCTF actually tuned to.

The desired wavelengths that were electronically sent to the LCTF controller are plotted on the X axis and the measured wavelengths, the spectrometer transmission spectral analysis to which the LCTF tuned, are plotted on the Y axis. Example data shows a linear regression curve fit ($Y=1.00X-0.20$, $R2=1$). From the example data, it is believed that an error exists between the desired tuning and the actual tuning of the LCTF. To rectify this small error, a look-up table in the V++ software was established from the relationship that was derived above which makes sure that the LCTF gets tuned to the wavelength which the operator desires.

Figure 26:
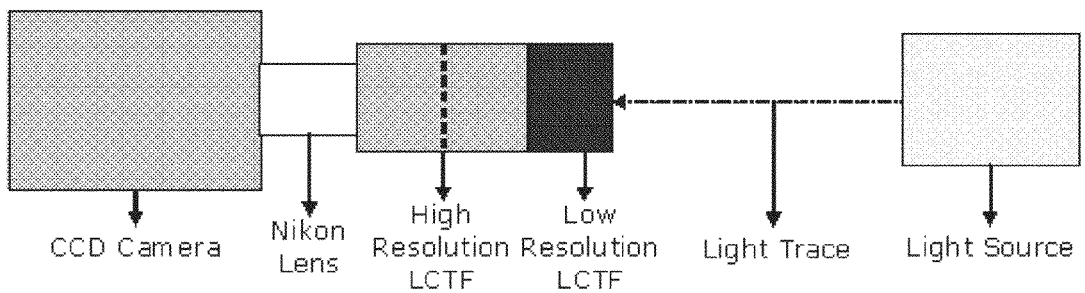
FIG. 26 is a diagram of the visible low resolution LCTF calibration setup.
Figure 27:
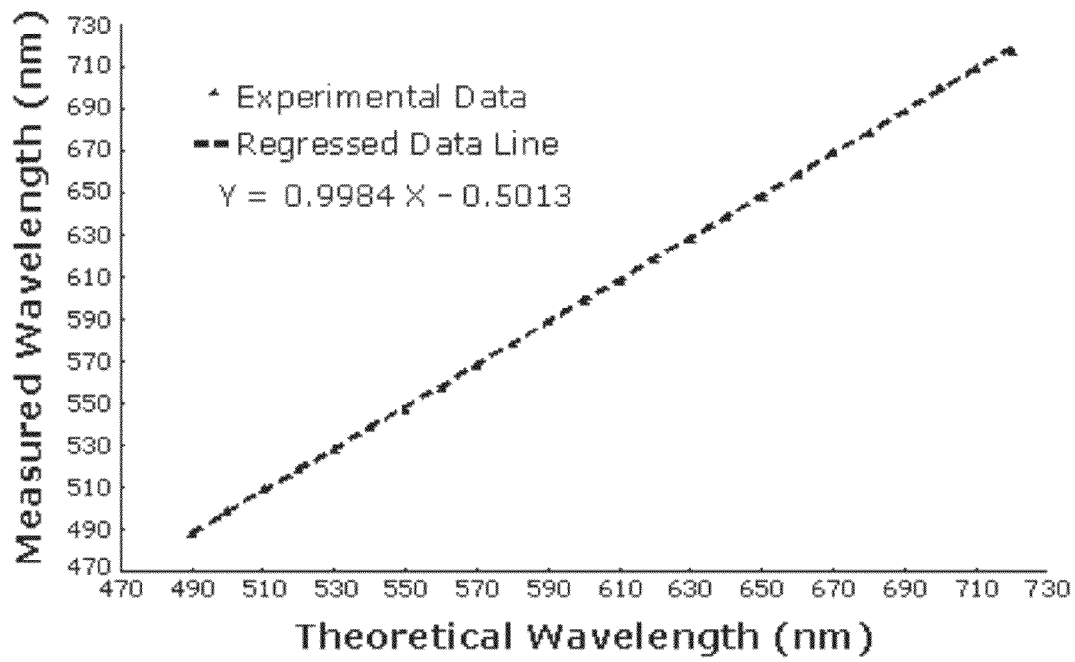
FIG. 27 is a plot of visible low resolution LCTF calibration curve.

The visible low resolution LCTF similarly was calibrated, however, a high resolution LCTF was used having a band-pass lying between 0.19 nm at 500 nm and 0.75 nm at 700 nm. As shown in FIG. 26, the input light from the source is passed through the low resolution LCTF, which is to be calibrated, tuned to a particular wavelength onto the high resolution LCTF which is scanned with an increment of 1 nm over its spectral range of 480 nm-720 nm, and focused using the 60 mm Nikon camera lens onto the CCD camera generating a series of images, i.e., a hyperspectral image cube. This procedure was repeated until the low resolution LCTF was tuned in the wavelength range 500 nm-700 nm at every 10 nm and a hyperspectral cube captured. The hyperspectral cubes generated were then analyzed in Matlab to locate the center wavelength the LCTF was actually tuned to. As in the near infrared LCTF calibration plot, here also the desired wavelengths sent to the LCTF controller were plotted on the X axis and the measured wavelengths from the hyperspectral analysis were plotted on the Y axis, see FIG. 27. Points in FIG. 27 are example values and the dashed line represents a linear regression curve fit ($Y=0.9984X-0.5013$, $R2=0.9999$). From this relationship, a small look-up table was generated in the V++ software tuning the LCTF to the desired wavelength that the operator desires.

Figure 28:
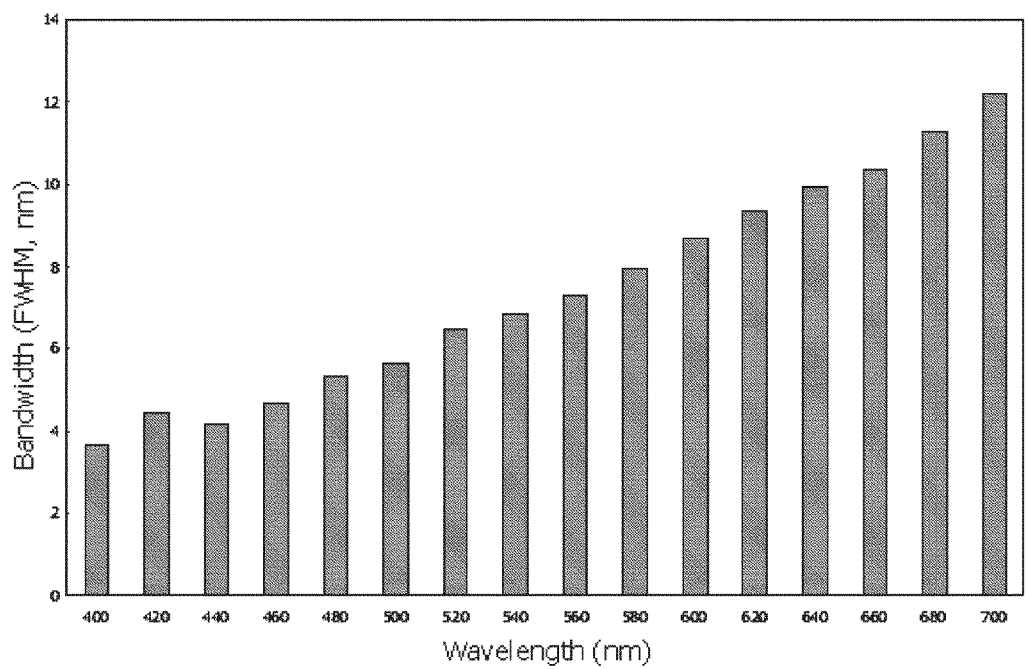
FIG. 28 is a plot of bandpass and wavelength.

Similarly the spectral band-pass for the visible low resolution filter varies from 3.7 nm at 400 nm to 12.2 nm at 700 nm, see FIG. 28. The conclusion from these Figures is that the LCTF band-pass is wavelength dependent. This bandwidth is more than sufficient to spectroscopically resolve $HbO_2$ and Hb which have spectral characteristics that are several times broader than the broadest band-pass.

Figure 29:
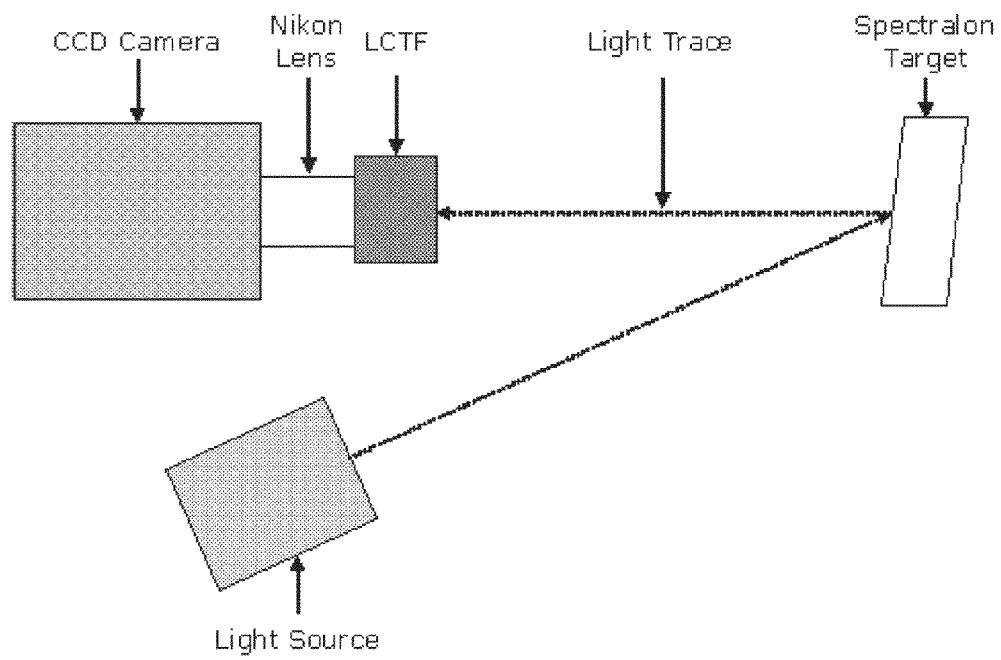
FIG. 29 is a schematic of tune-wait example setup.

In the hyperspectral imaging system images are collected sequentially at wavelengths differentiated continuously by the LCTF that tunes from one wavelength to another. LCTF takes typically 50 to 150 ms to switch from one wavelength to another, i.e., the response time. Any imaging application collecting sequential image data through the LCTF must account for the response time required to tune the LCTF. In the V++ program developed to control the acquisition of the hyperspectral imaging system, a tune-delay time is introduced that accounts for the LCTF tune time. An example was done to determine this tune-delay or tune-wait time for the LCTF's;

the setup for which is shown in FIG. 29. In this example, light focused on a spectralon target is reflected onto the FPA through the LCTF and a hyperspectral cube was collected. Hyperspectral cubes were collected for varying tune-delay time starting from 0 ms to 100 ms in increment of 10 ms.

Figure 30:
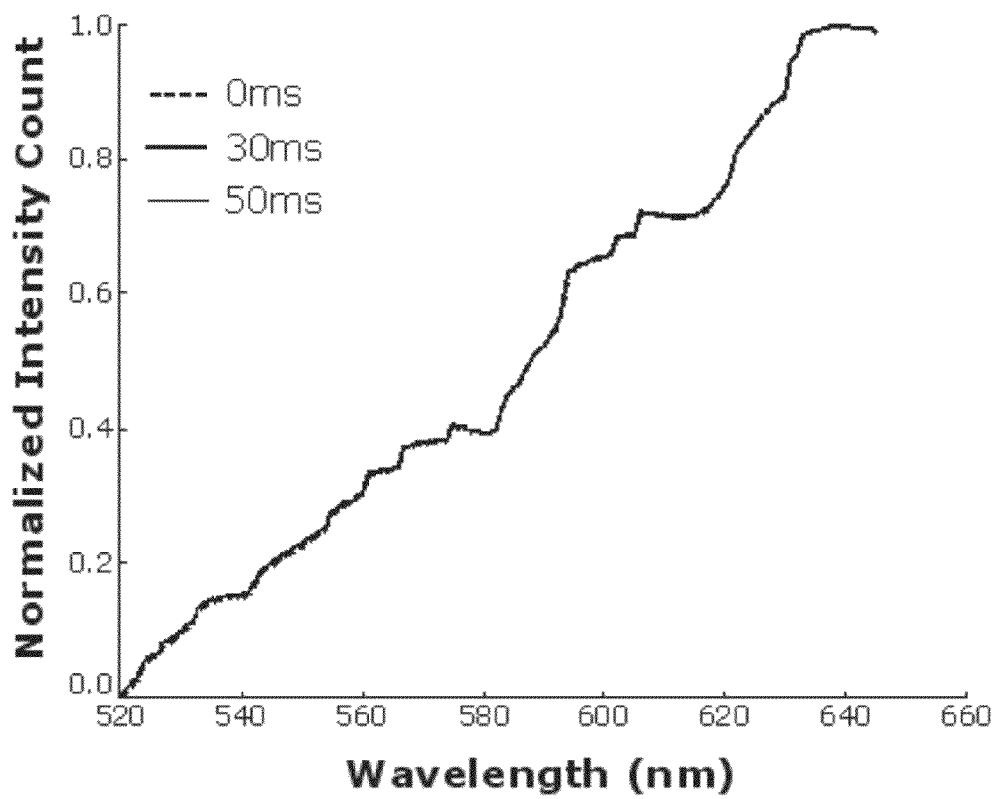
FIG. 30 is a graph of visible LCTF tune-wait with normalized intensity and its relationship with wavelength.

Similarly, spectral analysis was performed on the visible LCTF, and as shown in FIG. 30 there is little or no difference between 0 ms, 30 ms and 50 ms, thus suggesting a tune-delay of 0 ms for the visible LCTF.

The tune-delay time increases the exposure time for collecting the hyperspectral, hence keeping it to a minimum is advantageous. Tune-wait/Tune-delay time depends on various factors such as the liquid crystals and the electronic components in the circuitry. Thus, tune-wait time is typical for each LCTF.

The following describes the calibration of the FPA. The spatial resolution of the microscopic hyperspectral imaging system was characterized, which is defined as the ability to distinguish between two closely spaced objects within an image. The spatial resolution of the system was established by computing the percent contrast which depends on various factors such as the focal plane array, filter, slit lamp magnification, type of camera lens, f-stop, depth of field, and degree of pixel binning. Modifications of any of the factors alter the spatial resolution of the system. In view of the foregoing, spatial resolution was evaluated with various degrees of binning and magnification. The percent contrast, C, was determined using the expression equation (9) shown below, and plotted as a function of spatial resolution in millimeter.

$$C = \left(\frac{I_{max} - I_{min}}{I_{max} + I_{min}}\right) \times 100 \quad (9)$$

where:
$I_{max}$ is the maximum intensity reflected by a line of the resolution
target (white bar) of the resolution target are shown in FIG. 31; and,
$I_{min}$ is the minimum intensity from the nonreflecting area between the lines (dark bar) of the resolution target are shown in FIG. 31.

Figure 31:
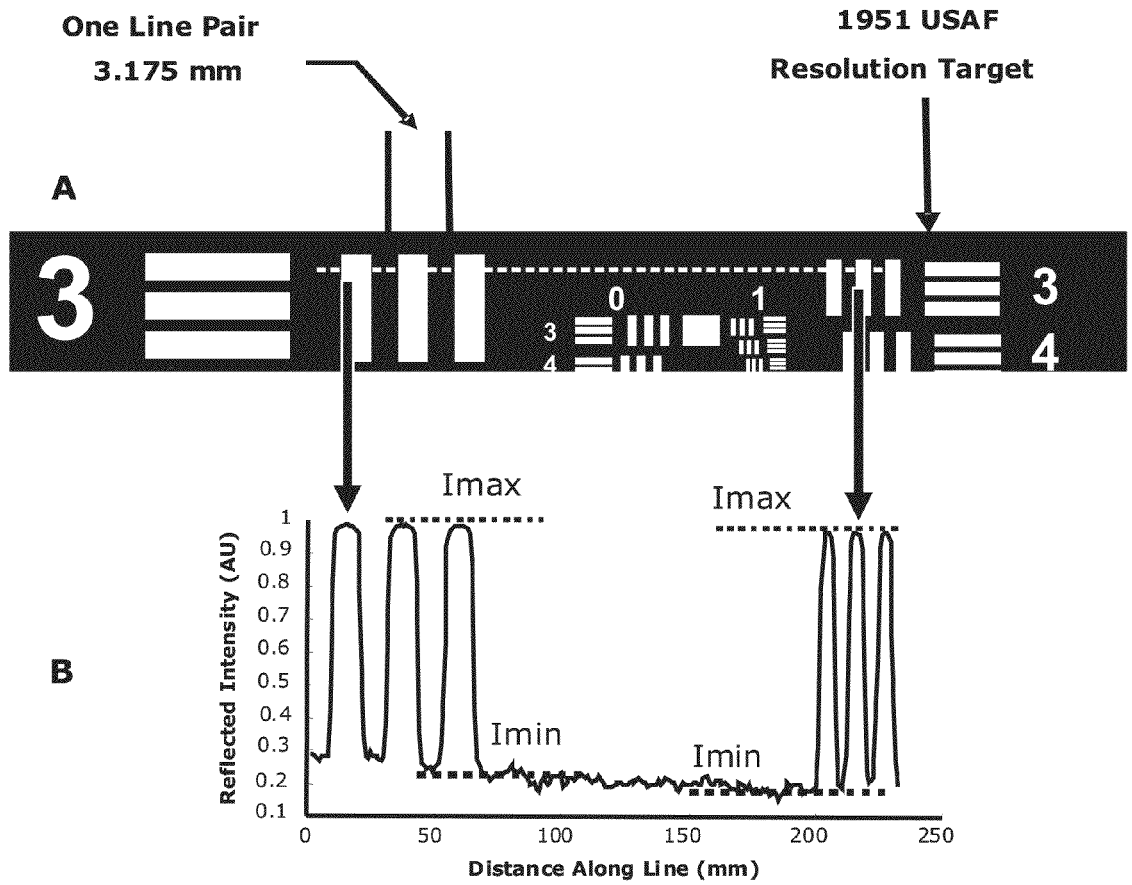
FIG. 31A is an image of a portion of the resolution target.
FIG. 31B is a graph of the reflected intensity corresponding to the target.

A 1951 quartz USAF resolution target is depicted in FIG. 31 where A depicts a portion of the target and the corresponding reflected intensity taken along a row of pixels is depicted in B was used to determine the spatial resolution. It should be appreciated that a line pair is defined as the distance between the first edge of a white bar and the second edge of a dark bar. Generally, the spatial frequency, or number of line pairs, increases (the number of pairs/unit length) as the percent contrast decreases. The quartz target was placed in the imaging path and a single image was collected which was then analyzed to determine the percent contrast by using equation (7). This procedure was followed for determining spatial resolution of the near infrared imaging as well as visible imaging system. Binning and magnification were changed keeping other parameters the same, and images were collected and analyzed to obtain the percent contrast. Percent contrast calculations were done for the near infrared microscopic hyperspectral imaging system and plotted as a function of spatial resolving power (mm) in FIG. 32. The graph of FIG. 32 includes percent contrast as the dependent variable (y-axis) and spatial resolution in millimeter as the independent variable (x-axis) and it has been determined from the regression curve fit models when various binning embodiments cross the 20% contrast threshold set by the Rayleigh criterion, i.e., the horizontal dashed line.

Figure 32:
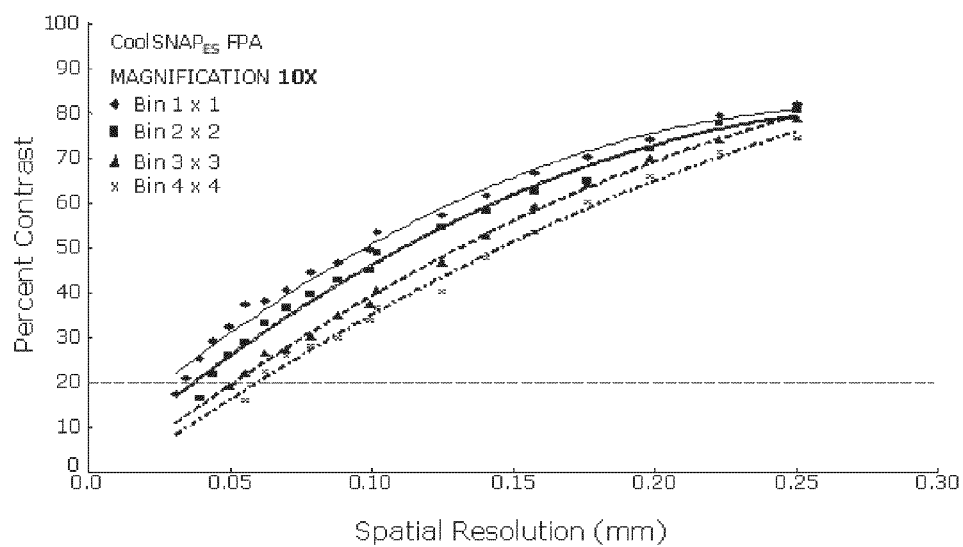
FIG. 32 is a graph of percent contrast and its relationship with spatial resolution with relay optics.

Percent contrast of the visible microscopic hyperspectral imaging system is plotted as a function of spatial resolving power (mm) in FIG. 32. Each embodiment shown in FIG. 32 has a polynomial regression curve fit model. For a magnification of 10× and binning of 1×1 (diamond shaped data points), the regression equation is y=−996.04x2+548.86x+5.7296. Keeping the magnification same but changing the binning to 2×2 (square shaped data points), the regression equation is y=−919.92x2+544.64x+0.8112. For a binning of 3×3 (triangle shaped data points), and 4×4 (cross shaped data points), the respective regression equations are y=−660.48x2+498.39x−4.0232 and y=−531.26x2+458.81x−5.5901. Again, in all the above embodiments, the dependent variable (y-axis) is percent contrast and the independent variable (x-axis) is spatial resolution in millimeter, and it is determined from the regression curve fit models when it crosses the 20% contrast threshold set by the Rayleigh criterion, i.e., the horizontal dashed line. The spatial resolution for the visible hyperspectral imaging system with the magnification at 10× is 0.027 mm at binning 1×1, 0.038 mm at binning 2×2, 0.052 mm at binning 3×3 and 0.06 mm for binning 4×4. As mentioned above, the binning decreases the spatial resolution which is verified by the spatial resolution numbers obtained.

Figure 33:
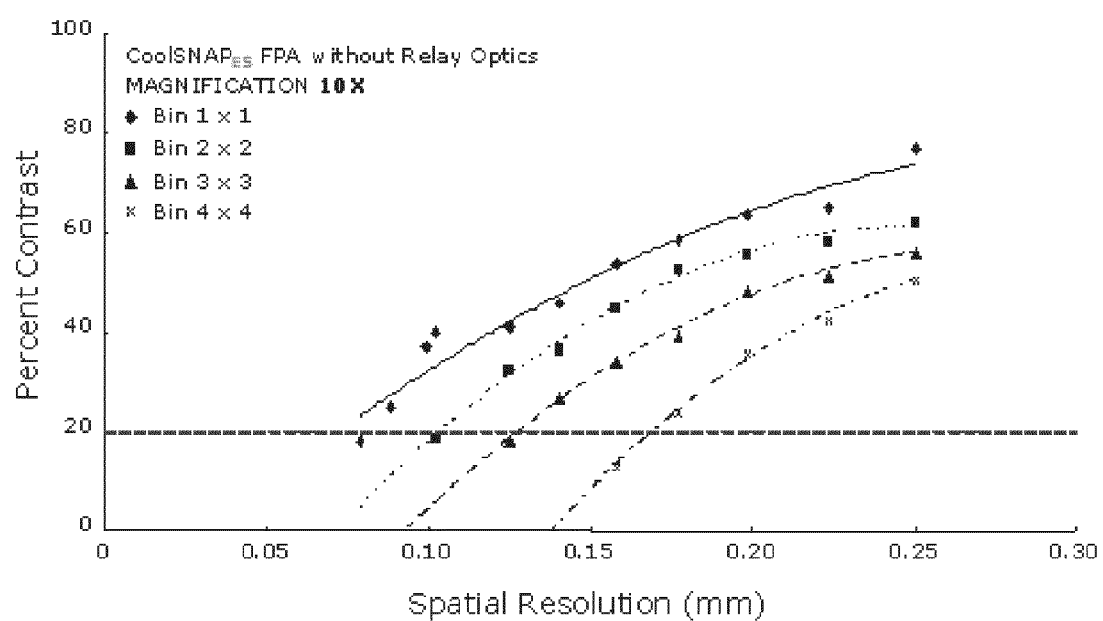
FIG. 33 is a graph of percent contrast and its relationship with spatial resolution without relay optics.

Another interesting comparison was made using the visible microscopic hyperspectral imaging system by obtaining percent contrast measurements for the visible system without the presence of the relay optics in the light path. These measurements are plotted in FIG. 33. Regression equations were obtained and analyzed keeping the Magnification at 10×, and changing the binning on the FPA to find out the spatial resolution for the system without the relay optic, yielding spatial resolutions of 0.072 mm for binning of 1×1, 0.104 mm for binning of 2×2, 0.129 mm for binning of 3×3 and 0.169 mm for binning of 4×4. The spatial resolution for the system without the relay optics was found to be worse then that for the system with the relay optics in the light path. The relay optics were introduced in the system to increase the magnification of the system and allow the system to occupy a larger area of the CCD chip thus improving the overall spatial resolution of the system as verified by the spatial resolution numbers for the system with and without the relay optics.

The following describes the system performance of an embodiment of the present invention. Hyperspectral imaging is emerging as a powerful imaging tool to exemplify spectral as well as the spatial characteristics. An embodiment of a present invention microscopic near infrared hyperspectral imaging system was used to image, non-invasively, microvascular perfusion of the dermal tissue, in vivo, for assessing oxyhemoglobin contribution during a resting condition for ten subjects. The hyperspectral data deconvoluted for the contribution of oxyhemoglobin is gray scale encoded, meaning the greater the pixel intensity the greater the oxyhemoglobin contribution as depicted by the gray scale bar associated with an image.

The microscopic hyperspectral system was further applied towards imaging the microvasculature structure present in the anterior region of the human eye, especially the sclera, which required imaging in the visible spectrum, i.e., 520 nm-602 nm. A hyperspectral image cube was obtained using the visible slit lamp microscopic imaging system, with parameters such as setting the magnification to 10×, setting the binning to 2×2 and varying the wavelength from 520 nm-602 nm, incremented at 2 nm. These parameters successfully reduced the acquisition time for the hyperspectral image cube to within 5 seconds which is critical for imaging the eye since the subjects involved in the data collection are not allowed to blink or move their eye since that would create artifacts in the images.

Figure 34:
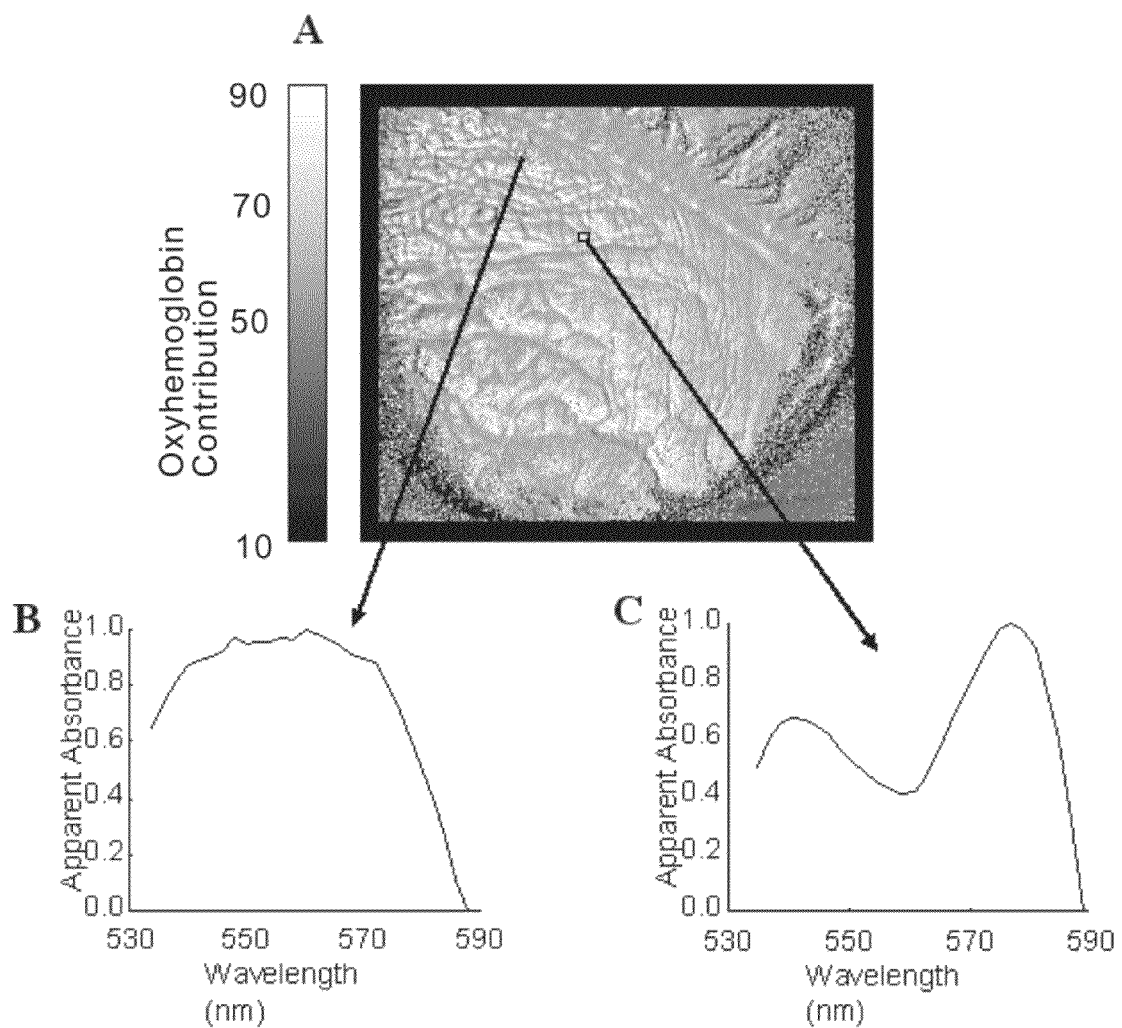
FIG. 34 is an image of color coded hyperspectral image.

The hyperspectral cube was deconvoluted for oxyhemoglobin contribution values that are color encoded and spatially depicted in FIG. 34A. A small region over a high oxyhemoglobin contribution region, shown within the small black box, as suggested from the color bar, i.e., red areas, was selected and pixels under the region were averaged to obtain a spectrum shown in FIG. 34C which resembles the oxyhemoglobin spectrum. Similarly, the spectrum under the area of the small pink box was selected and pixels under the region were averaged to obtain a spectrum shown in FIG. 34B, and represents a deoxyhemoglobin spectrum.

Seven healthy subjects were imaged to obtain scleral tissue oxyhemoglobin contributions for assumed arterial and venous structures in the image as displayed by the spectroscopic information. The average oxyhemoglobin contribution values for these seven subjects were obtained. The regions from under which the above average values evaluated were not random but visually selected depending on the spectroscopic information the region yielded.

Qualitative values with quantitative evaluations pending were obtained. These values demonstrate that there exist marked differences between arterial and venous structure oxyhemoglobin contributions and that the system is capable of distinguishing between arterial and venous structure in the tissue being imaged.

The following description sets forth embodiments of a present invention microscopic visible hyperspectral imaging systems. After demonstrating capabilities of the microscopic hyperspectral imaging system using dermal microvasculature imaging, other applications of the present invention are now discussed, in particular, imaging of the human eye, especially the sclera. The sclera is the white portion of the eye, covered by the episclera, tenon's capsule, and the conjunctiva. The blood vessels seen on the scleral surface are actually found between these various regions. Scleral disease such as scleritis and episcleritis, are uncommon in opthalmology patients, however they present symptoms for serious, painful and life threatening systemic diseases such as rheumatoid arthritis, syphilis, spondylitis, etc.

The anterior region of the human eye was imaged using the microscopic visible hyperspectral imaging system. The visible system uses the CoolSNAP$_{ES}$ CCD in conjunction with the visible low resolution LCTF and the slit lamp microscope. The CoolSNAP$_{ES}$ CCD's spatial resolving power at a binning of 2×2 and a magnification of 10× is 0.038 mm, which is better then the resolving power of the PIXIS 400 BR with the same parameters, i.e., 0.083 mm. Since speed is an important trade off with the imaging of the eye, the 20 MHz readout rate is preferred against 2 MHz readout rate of the PIXIS FPA. Also to decrease the acquisition time of the system the spectral range and spectral resolution were reduced to 520 nm-602 nm at increments of 2 nm, instead of the previously reported macroscopic version of the visible hyperspectral system that used a spectral range of 520 nm-645 nm, at increments of 1 nm. These were the two major trade offs considered to reduce the data acquisition time to 5 seconds, which acquisition time is clinically suitable for eye imaging applications. Inputting these example parameters with the slit lamp magnification set to 10×, the sclera of the subject was imaged to obtain a hyperspectral data cube that upon deconvolution with the visible range reference spectra of oxyhemoglobin and deoxyhemoglobin rendered an image that contained spatially distributed contributions of oxy-hemoglobin.

Figure 35:
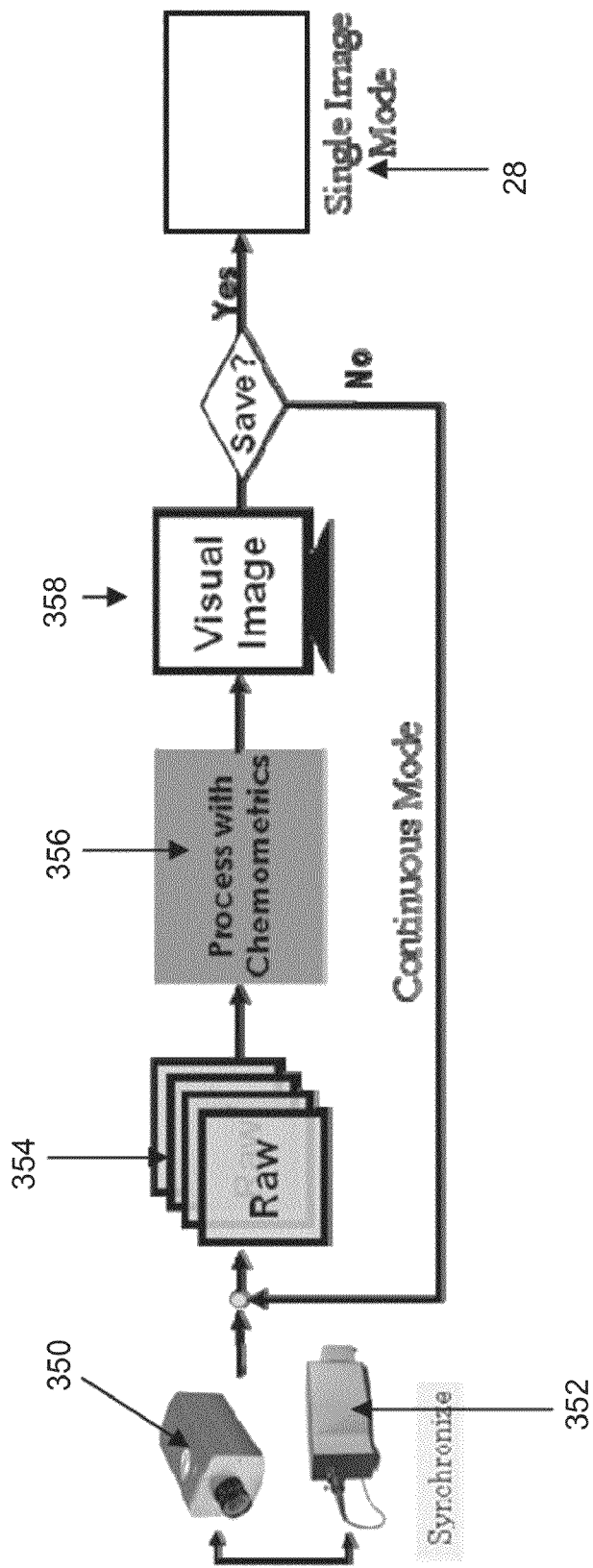
FIG. 35 is a schematic of an embodiment of the present invention.

FIG. 35 is an illustration of the basic setup of a DLP hyperspectral imaging system of the present invention. The setup for noninvasive DLP® microscopic reflectance hyperspectral imaging system consisting of a spectrally-tunable source, optics, a detector, a computer, and a DLP®. The radiometric radiation source can be a 12V/30 W halogen source and/or a QTH (quartz tungsten halogen) source providing broad band illumination. The radiation is directed towards the DLP® using relay optics. The DLP® differentiates the broadband reflected light into individual band passes or provides a spectrum of wavelengths and is directed to the object to be analyzed. Major components include, but not limited to: white laser source 350 and spatial light modulator 352, such as a DLP®, used to create one or more light wavelengths or a band spectrum which are captured as raw images 354. Raw images 354 are then processed to detect known chemometrics 356, which are then output as visual image 358. The user is then able to determine if they wish to save or discard the image, which image may be stored on storage device 360, e.g., hard drive, CD-ROM, etc.

Figure 36:
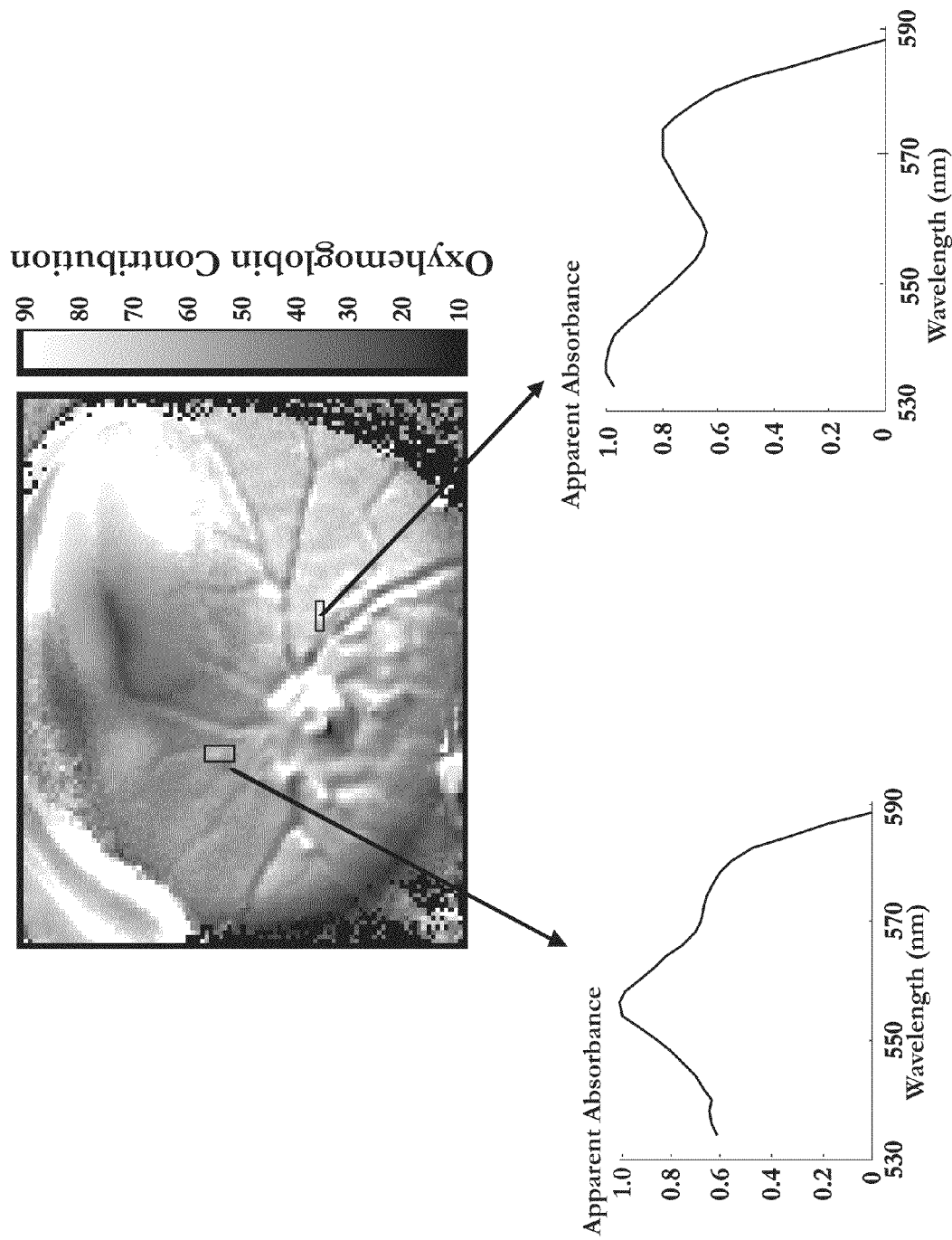
FIG. 36 is an image of oxyhemoglobin contribution taken with reflectance hyperspectral imaging system of the present invention.
Figure 37:
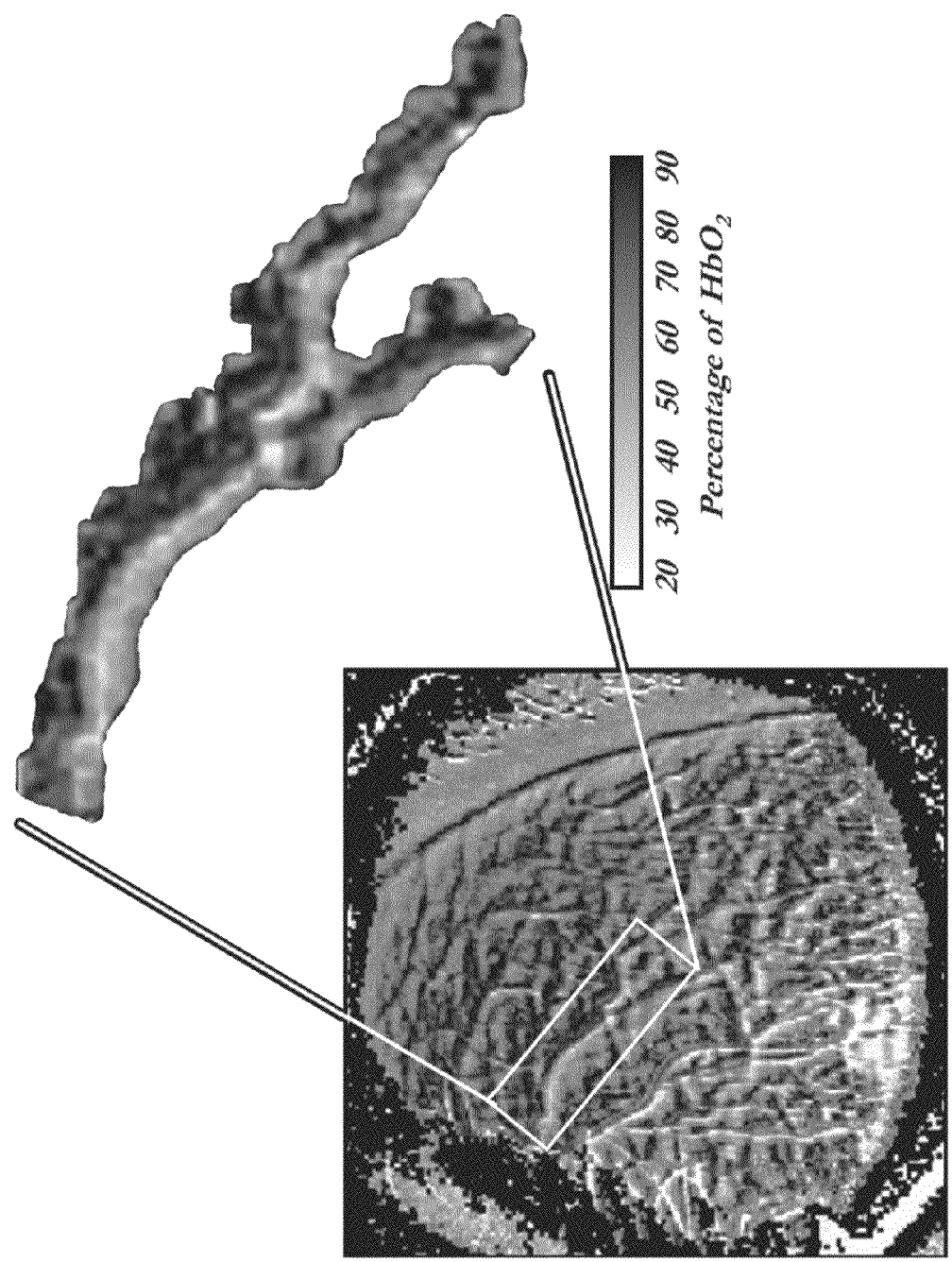
FIG. 37 is an image of small vessels within a human conjuctive of an eye taken with hyperspectral imaging system.

Another example of the present invention is demonstrated as follows. The hyperspectral slit imager acquisitions hyperspectral data that is gray scale encoded as the percentage of oxyhemoglobin at each pixel of the image along with its associated spectrum. Spectra were selected from darker pixels indicating a venous structure, the purple spectrum, versus bright pixels indicating an artery, the red spectrum, as shown in FIG. 36. FIG. 36 demonstrates retinal imaging of oxyhemoglobin contribution using visible reflectance hyperspectral imaging system. Other part of the eye, for example the conjunctiva, can also be imaged and can also be color encoded, the redder the pixel, the greater the percentage of oxyhemoglobin, and a variety of image processing techniques may be applied, for example, feature extraction or optical biopsy, for future evaluation (see FIG. 37). FIG. 37 is a hyperspectral imaging of small vessels within human conjuctiva of the eye.

Figure 38:
FIG. 38 is an example image taken on an occluded fingers using a DLP HSI two-shot method.

FIG. 38 is an image taken using one embodiment of the present invention by using a DLP system with a "2 shot" illumination scheme. The results were obtained using illumination with a spectrum of light. This embodiment includes illumination with the difference of two (2) principle component spectra (one spectrum that is consistent with the positive values and the other in which the negatives are multiplied by negative one, illuminated and then the image multiplied by negative one again). The resulting images are then normalized and processed.

In another embodiment, the present invention includes using optical filters as a method for fluorescing indocyanine green dye (ICG). The embodiment enables the identification of organs such as the biliary structures when ICG is injected into a blood vessel such as the femoral artery of an animal or human. This embodiment enables fluorescence of biliary structures. Here, the illuminator can be a Texas Instrument's DLP illuminator and the fluorescence image of the ICG can more precisely illuminate the exact spectrum for maximizing the fluorescence of the ICG and imaging it in the biliary structures. The present Applicants have completed the optical filter system and have successfully imaged ICG and bile fluorescence in capillary tubes. This embodiment can further be modified to be used in animals and humans or clinical trials.

In certain embodiments, the present invention can be used in conjunction with using a supercontinuum laser instead of a plasma source to illuminate the DMD chip. The laser used in this embodiment does provide greater intensity, smaller band passes, and larger spectral range. Supercontinuum or white-light laser sources are recognized in the art. Briefly, they are typically suitable for applications in spectroscopy and microscopy. It can include a pump laser and a microstructured fiber (either a photonic-crystal fiber or a tapered fiber). Although 80 fs pulses from a Ti:sapphire laser and 200 fs pulses from an ytterbium (Yb):glass laser have been used to generate supercontinuum light, researchers have demonstrated a more-compact and lower-cost portable femtosecond supercontinuum source with a small footprint. Moreover, in other embodiments, the present invention can include a light emitting diode (LED) based illumination source. The source may include a single LED or a plurality of LEDs.

In some embodiments, the present invention includes image analysis of a patient wearing a silk gown. Near infrared light is known to see through silk. Wearing a silk gown allows the patient to cover them selves while letting the NIR camera see through to the tissue for analysis. In this embodiment, the patient can lay on a piece of clear material, e.g., plexiglass or glass. A layer of oil can help negate index or refraction effects and improve imaging similar to an oil immersion microscope objective lens. This embodiment provides maximum privacy to the person being imaged, preserves body heat and provides accessibility for the surgeon.

In another embodiment, the present invention can also include at least one deconvolution algorithm. The algorithm is typically used for normalizing each spectrum at each pixel as a step in the pre-processing. This algorithm is counter-intuitive to the skilled artisan in the art or for the general spectroscopist. The skilled artisan would not consider and would question this unique and unexpected algorithm.

In yet another embodiment, the present invention can be used during kidney surgery. The kidney is highly vascularized and tends to bleed copiously during surgery, as such, surgeons minimize this bleeding by clamping off the blood supply. However, clamping off this organ also limits greatly the time permitted to perform the surgery without affecting long-term kidney function. The present invention allows a small amount of blood to leak past the clamp to perfuse the kidney, thereby giving the surgeon more time to perform the surgery before permanent kidney tissue damage takes place. The hyperspectral imager of the present invention aids in visualizing and determining when the kidney is at risk of permanent damage before damage occurs by providing the surgeon real-time information regarding kidney cell and tissue status.

The present invention can be applied in various field, e.g., in cholecystectomy, amputations, burns, skin flap evaluation, visualizing areas of angiogenesis, probes that bind antigens and absorbs NIR during pathological evaluations and in vivo, quality control of pharmaceuticals, monitoring vascular changes and drug discovery in response to pharmaceuticals, monitoring diabetic retinopathy, diseases such as cancer, diabetes, sickle cell, anemia, bilirubin, raynauds, ulcers, burns, skin flaps, surgery, gallbladder, brain, monitoring wound healing, and early detection of wound infections.

Figure 39:
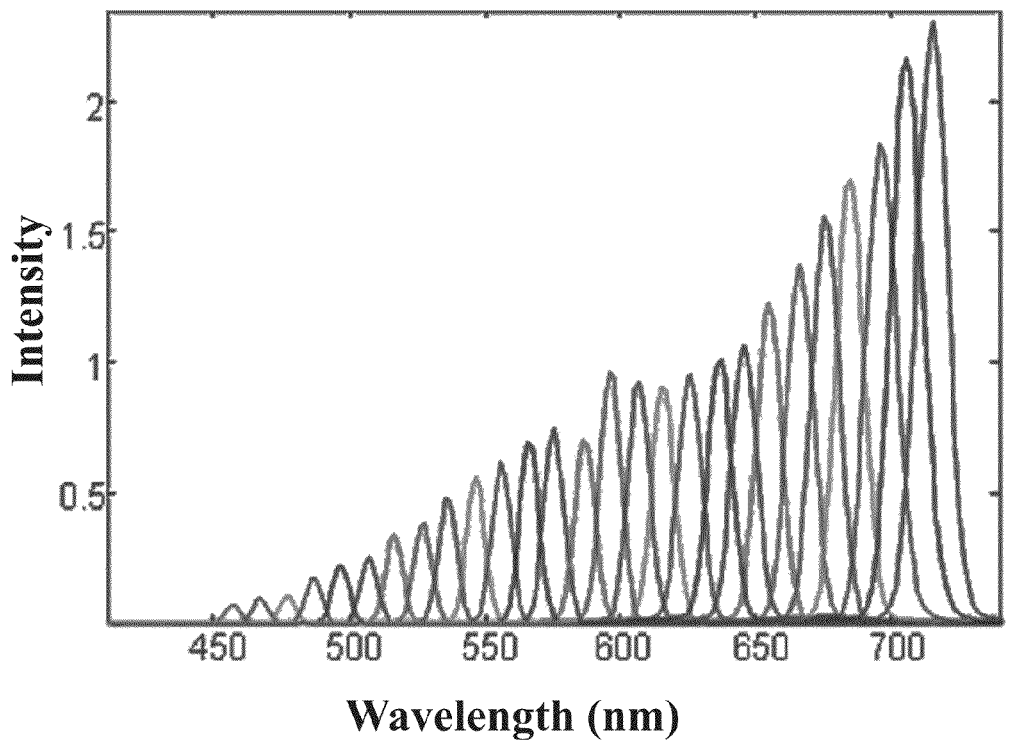
FIG. 39 is a graph that shows one hundred twenty six (126) separate wavelengths using an LCTF to separate the bands prior to illumination, after which an image is captured with each bandpass or with a single frame including up to one hundred twenty six (126) images.
Figure 40:
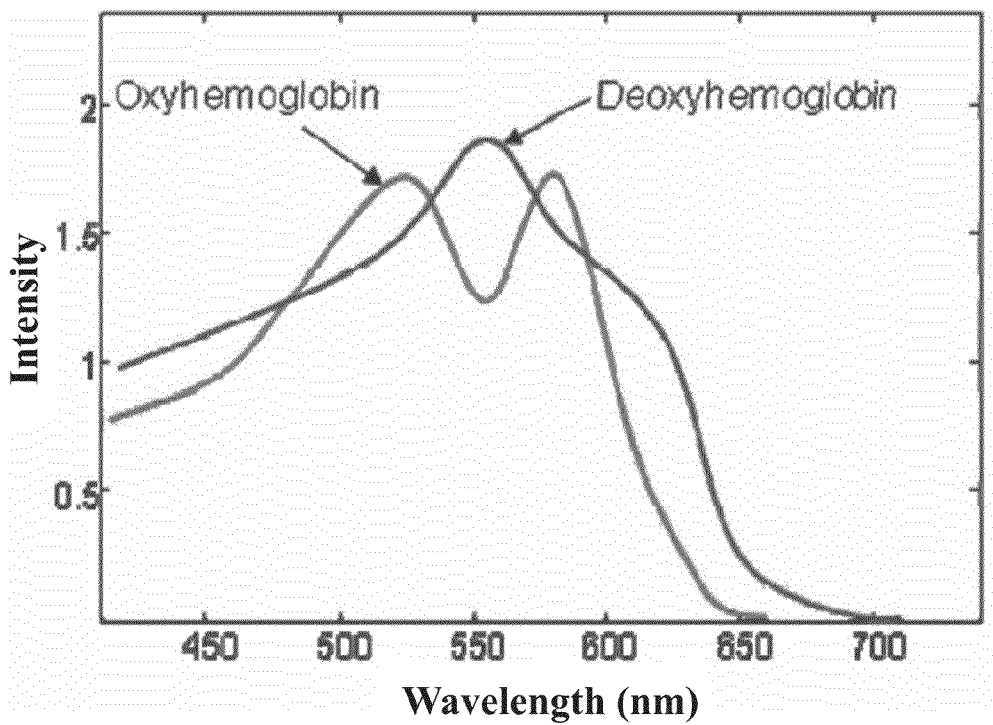
FIG. 40 is a graph showing a band spectrum in which a digital micromirror array was used to create spectral illumination that allows for a lower number of images per frame.
Figure 41:
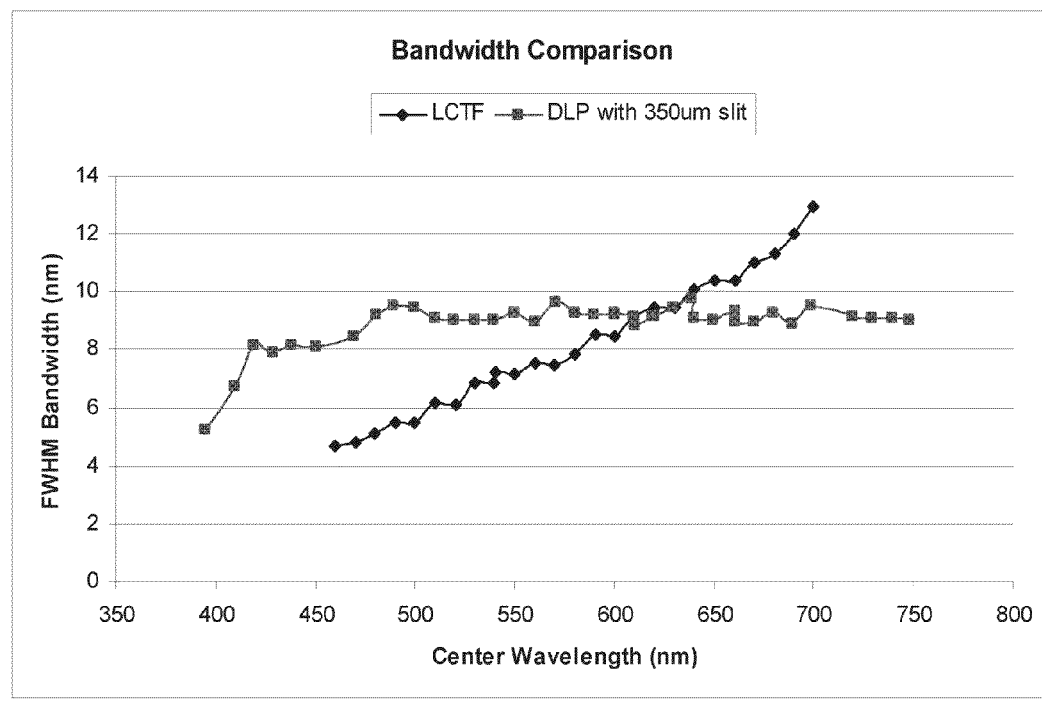
FIG. 41 is a graph of a comparison of data obtained with the LCTF and the digital Micromirror array illumination using the single bandwidths of FIG. 39.
Figure 42:
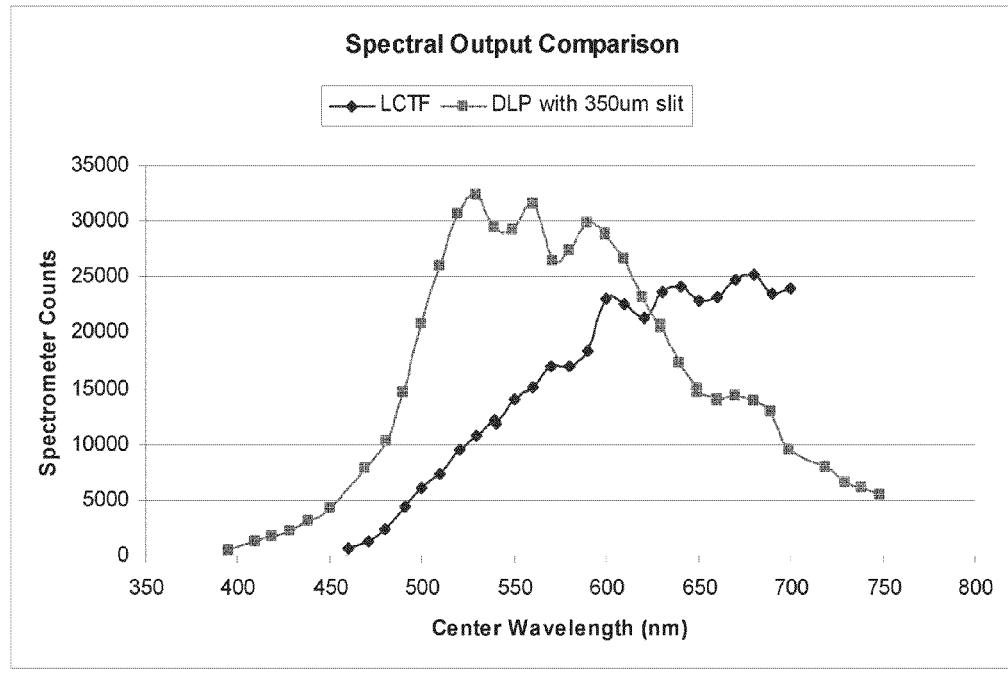
FIG. 42 is a graph of a comparison of data obtained with the LCTF and the digital Micromirror array illumination using the single bandwidths of FIG. 40.

FIG. 39 is a graph that shows one hundred twenty six (126) separate wavelengths using a LCTF to separate the bands prior to illumination, after which an image is captured with each bandpass or with a single frame including up to one hundred twenty six (126) images. FIG. 40 is a graph that shows a band spectrum in which a digital micromirror array was used to create spectral illumination that allows for a lower number of images per frame. FIG. 41 shows a comparison of data obtained with the LCTF and the digital micromirror array illumination using the single bandwidths of FIG. 39. FIG. 42 shows a comparison of data obtained with the LCTF and the digital micromirror array illumination using the single bandwidths of FIG. 40.

Figure 43:
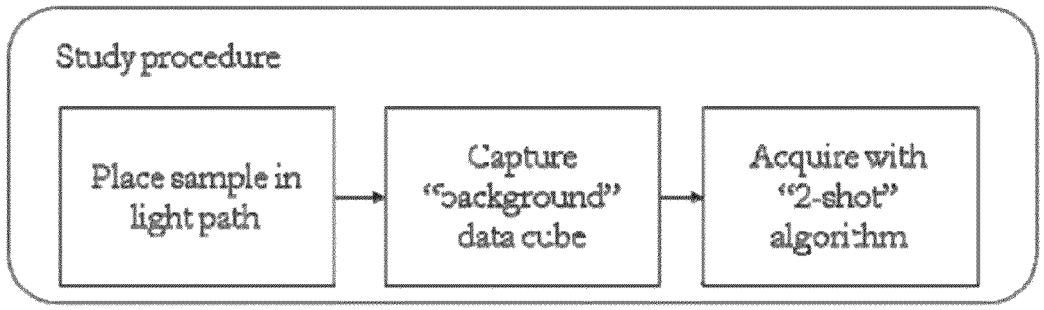
FIG. 43 is a flow chart of the basic 2-shot algorithm.
Figure 44:
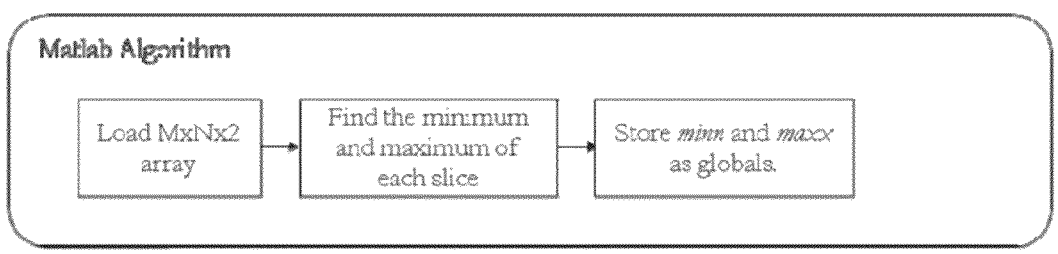
FIG. 44 is a flow chart of the processing of the data cube obtained using the basic 2-shot method.

FIG. 43 is a flow chart of the basic "2-shot" algorithm. FIG. 44 is a flow chart of the processing of the data cube obtained using the basic "2-shot" method.

Figure 45:
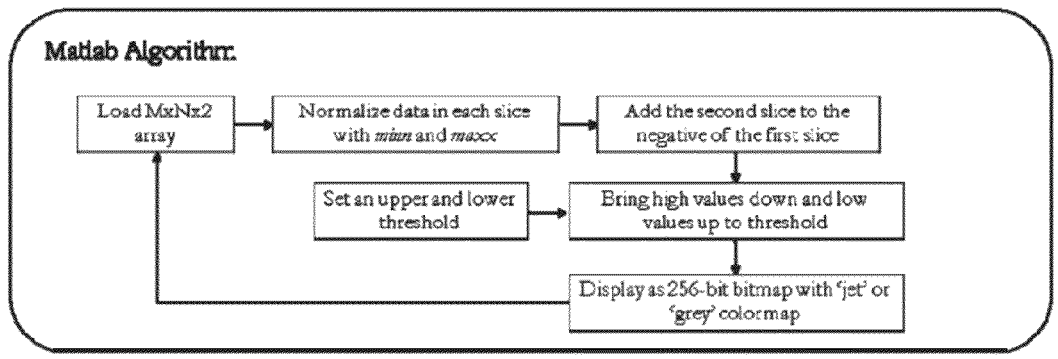
FIG. 45 is a flow chart of the acquisition method of the basic 2-shot method.

FIG. 45 is a flow chart of the acquisition method of the basic "2-shot" method. Briefly, normalized absorption spectra in the 520 nm-645 nm wavelength range for $HbO_2$ and Hb are subtracted from each other, and the positive areas become the two illumination spectra. The relative intensity of each illumination spectrum is stretched from 0 to 100 to maximize the overall light intensity and match the required OL-490 input format. Each data cube (M×N×2) consists of one M×N pixel image taken in the first image capture and one M×N pixel image or shot captured, taken for the second image or shot captured.

Figure 46:
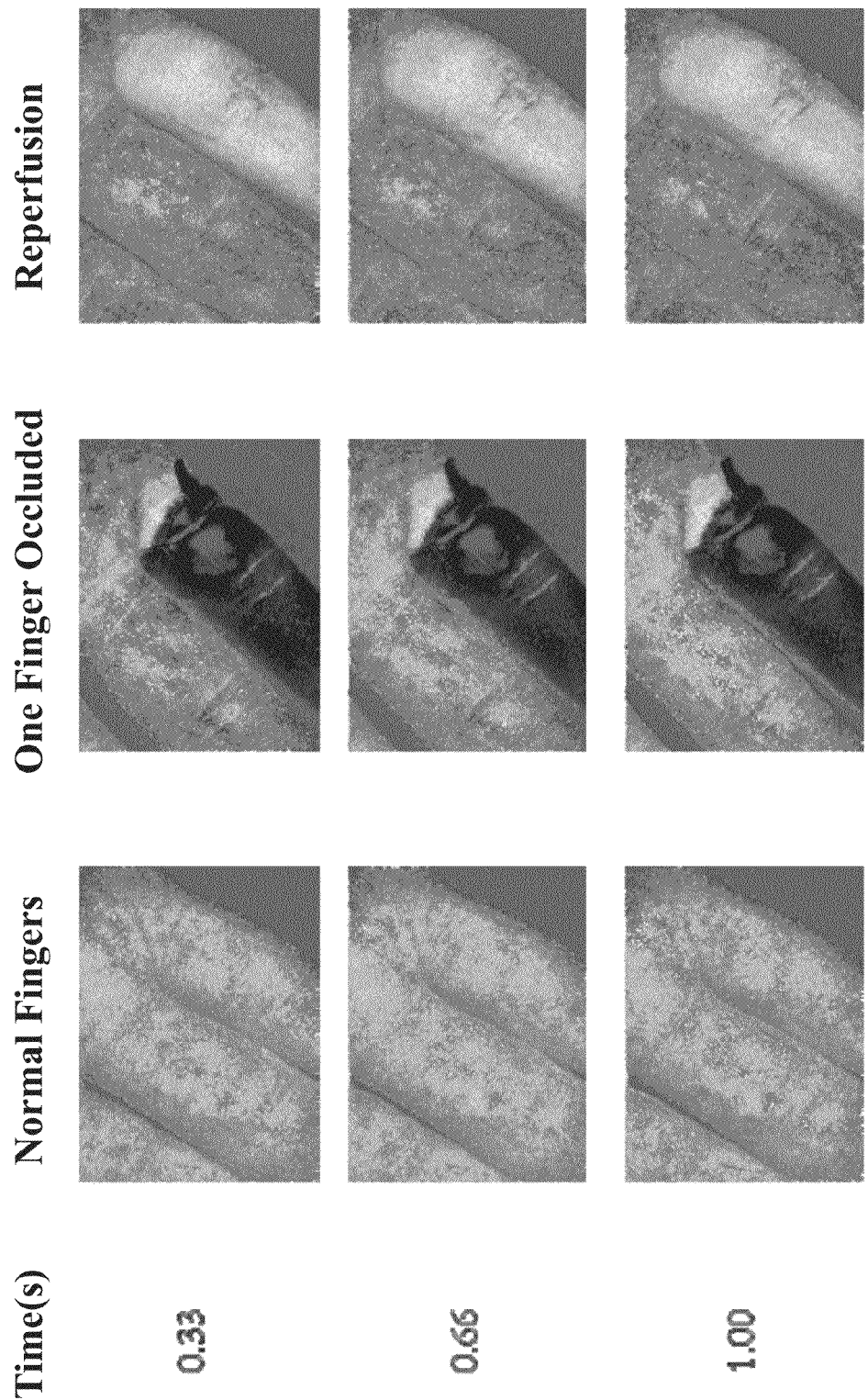
FIG. 46 is a sample of images obtained for a finger occlusion at different times using the present invention.

FIG. 46 shows sample images obtained for finger occlusion at different times using the present invention. FIG. 47 compares the images obtained using visible light and near infrared (NIR) of the reperfusion of a foot following removal of the shoe. FIG. 48 shows the in vivo hyperspectral imaging of human tissue, spatial variation of percentage of $HbO_2$ and surface temperature in response to a burn.

The present invention describes a "3 shot" illumination method in an integrated DLP hyperspectral imaging (HSI) system which reduces the number of image frames required to generate a processed image that is color-coded based on matching the reflectance of each pixel in an image to known reflectance spectra. The "3 shot" method of the present invention can replace traditional hyperspectral imaging which requires many frames to be acquired at contiguous wavelengths throughout a wavelength range of interest.

In the "3 shot" method of the present invention, a sample is illuminated with three complex spectra which have varying levels of intensity at each wavelength across the wavelength range of interest. Traditional hyperspectral imaging captures images for discrete wavelengths with narrow bandwidths. Contrarily, in the "3 shot" method, a series of narrow bandwidths is replaced with a broadband spectrum, in which the relative intensity of each wavelength is attenuated according to reference spectra. Without explicitly measuring the reflectance spectrum of a tissue, the "3 shot" method implicitly determines how closely the sample matches one of a pair of reference spectra.

After illuminating a sample with three broadband components of reference spectra, the "3 shot" method of the present invention subtracts and divides the resulting three images, and outputs several processed images per second. Present technology, on the other hand, illuminates or filters multiple narrow bandwidths, measures the sample reflectance for each of those discrete bandwidths, compares the reflectance spectrum to known reference spectra, and outputs, at most, one processed image per several seconds.

The advantages of the "3 shot" method of the present invention over traditional hyperspectral imaging makes the present invention ideal for real-time visualization of the molecular components of tissue for clinicians and surgeons. In addition the "3 shot" method of the present invention can be implemented in any hyperspectral imaging device which has the ability to illuminate with a variable intensity spectrum.

The present invention describes a "3 shot" illumination method in an integrated DLP HSI instrument. The "3 shot" method generates an image of the target very quickly in comparison to the more commonly used and previously described spectral sweep illumination method.

The data acquisition software automatically tune the DLP® technology and trigger the camera for collecting a series of spectroscopic images formatted as a hyperspectral image cube. Next, the spectroscopic image data are deconvoluted using chemometric analysis methods. The resulting gray scale or color encoded images provide the clinician with a non-invasive visualization of the chemical state within the micro-vasculature perfusing the tissue while the patient is in the clinic or surgery.

Hyperspectral imaging is the equivalent of reflectance spectroscopy at many discrete points arranged in a spatial pixel array. Reflectance spectroscopy involves collecting the reflectance of light at each wavelength, in the spectral dimension. Projecting the spectral dimensions to each pixel in an image results in a 3D data cube that contains the intensity spectrum for each pixel in a 2D spatial array. A hyperspectral data cube can be acquired in two fundamental ways: scanning a point spectrometer over a spatial area, or sweeping the wavelengths of light incident on an array detector. With the 2-dimensional array detectors available today, the reflectance of light can be collected in two spatial and one spectral dimension.

The first way to capture a hyperspectral image cube is by moving a sample on a mechanical stage to raster-scan a point spectrometer through the image field of view (FOV). (See Sellar R G, Boreman G D, Classification of imaging spectrometers for remote sensing applications. 2005; 44:1-3). A point spectrometer couples a very small area of broadband light into a prismatic grating. The grating spatially disperses polychromatic light into its monochromatic components, which are then uniquely detected to quantify the intensity spectrum as a function of wavelength. The spectrum measured by a point spectrometer is a measurement of all the light coupled into the spectrometer. To generate a 3D hyperspectral image cube, the point spectrometer must capture an intensity spectrum at each spatial pixel in the image FOV.

The second fundamental method of hyperspectral imaging is acquiring all spatial information at a wavelength of interest and scanning through a spectral range using optical or electro-optical filters. A liquid crystal tunable filter (LCTF) or acousto-optic tunable filter (AOTF) is used to cut off all broadband light except for a precisely tuned narrow bandpass. (See Sellar R G, Boreman G D, Classification of imaging spectrometers for remote sensing applications. 2005; 44:1-3). A scientific grade camera captures an image of a full 2D scene (e.g., tissue sample) at each narrow bandpass through a sweep of contiguous wavelengths, resulting in a 3D hyperspectral image cube.

Figure 49:
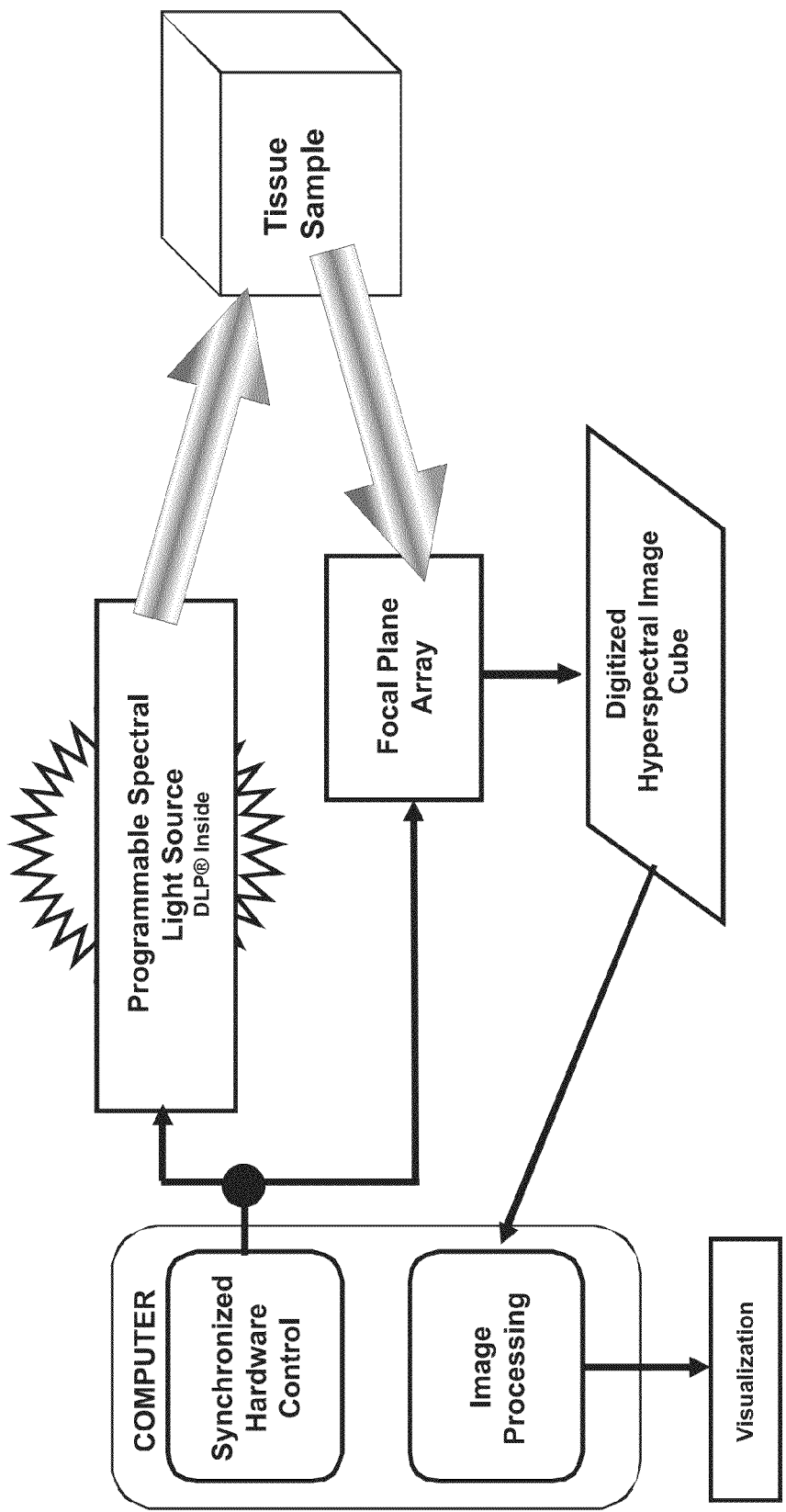
FIG. 49 is a schematic illustration of the different elements of a DLP® hyperspectral imaging system of the present invention.

The instrumentation in the present invention consists primarily of a spectral light engine with DLP® technology providing the spectroscopic illumination, a digital camera with a scientific grade CCD for imaging, and software designed and developed to manage the data acquisition and the chemometric visualization. The hyperspectral imaging system comprises an OL 490 spectral light engine created with Texas Instruments' "Digital Light Processor" (DLP®) technology. In the OL 490, polychromatic visible light is dispersed onto the micromirror array of a DLP chip so that each column of micromirrors corresponds to a narrow band of monochromatic light. Programming the mirrors individually allows the user to precisely define the intensity of each wavelength in the light engine's optical output spectrum. The OL 490 can illuminate with narrow bandpasses of light as in traditional hyperspectral imaging, but the novelty of the DLP HSI is using the OL 490 to illuminate with complex broadband illumination spectra. Regardless of the illumination scheme, the light from the OL 490 is reflected from a tissue sample of interest and detected by a scientific grade CCD focal plane array. The data acquisition software automatically tunes the DLP® technology and triggers the camera for collecting a series of spectroscopic images formatted as a hyperspectral image cube. Then, the spectroscopic image data are deconvoluted using chemometric analysis methods. The resulting gray scale or color encoded images provide the clinician with a non-invasive visualization of the chemical state within the micro-vasculature perfusing the tissue while the patient is in the clinic or surgery. A simplified schematic of the instrumentation described above is presented in FIG. 49.

One of the many goals of the present invention is to demonstrate that the "3 shot" illumination method in a DLP®-based visible hyperspectral imaging system can be used routinely for a variety of medical applications. The speed afforded by the "3 shot" illumination method of the present invention reduces the current acquisition time from minutes to seconds making hyperspectral imaging a practical everyday surgical and clinical tool for imaging.

The DLP® HSI with "3 shot" illumination and chemometric deconvolution can be applied to all products that use light, for example, the fields of clinical endoscopy, clinical chemistry, microscopy, surgical microscopy, drug discovery, microarray scanners and microplate readers.

As described above, the present invention can be used during kidney surgery. The kidney is highly vascularized and tends to bleed copiously during surgery, as such, surgeons minimize by clamping off the blood supply. However, clamping off this organ also limits greatly the time permitted to perform the surgery without affecting long-term kidney function. The present invention allows a small amount of blood to leak past the clamp to perfuse the kidney, thereby giving the surgeon more time to perform the surgery before permanent kidney tissue damage takes place. The hyperspectral imager with "3 shot" illumination of the present invention aids in visualizing and determining when the kidney is at risk of permanent damage before damage occurs by providing the surgeon real-time information regarding kidney cell and tissue status.

Currently there are three illumination methods implemented in the DLP HSI for hyperspectral imaging: Full Spectral Sweep, Spectral Sweep, and the "3 Shot" method described in the present invention. These illumination methods will be discussed in the remaining sections; however, new illumination methods are easily created by programming the spectral light engine. In fact, the integrated DLP HSI system of the present invention has the ability to change the illumination spectrum to any imaginable narrow or broadband spectrum in the wavelength range of the OL 490. This versatility means that the DLP HSI can be used for any number of imaging applications.

The full spectral sweep method is now described. To utilize the practical wavelength range of the system, the full spectral sweep method sweeps bandpass illuminations having 10 nm bandwidths from 450 nm to 650 nm in 4 nm increments. A hyperspectral image cube acquired with this method consists of 51 slices and is generally used to explicitly measure the absorbance spectroscopy of an area of interest. Formally, the following series of illuminations is programmed into the OL 490:

$$\{L_{1,FullSweep}=L_{OL490}(\lambda_1), L_{2,FullSweep}=L_{OL490}(\lambda_2), \ldots L_{51,FullSweep}=L_{OL490}(\lambda_{51})\} \quad (10)$$

for, $$\lambda_n = 450 + 4(n-1), n=\{1:51\} \quad (11)$$

where, $L_{OL490}(\lambda_n)$ is the total radiant power emitted from the OL 490 at a center wavelength, $\lambda_n$, with a 10 nm full width half maximum (FWHM) bandwidth.

After proportioning with the background, each slice in the cube represents the absorbance of the bandpass illumination at which the image is acquired. Thereby, each spatial pixel in the processed cube represents a discrete absorbance spectrum of the tissue or other material in the physical position corresponding to that pixel. The wavelength limits of the full spectral sweep method intentionally truncate the wavelength limits of the OL 490 since the output intensity of the OL 490 is very low near the extremes of its wavelength range.

This illumination method is only used to help calibrate the system as a spectrophotometer, and no algorithms currently exist to process its image cubes for visualization of tissue chemistry. However, with the spectral information acquired using full spectral sweep illumination, it is possible to search for spectral signatures of chemical chromophores and develop new processing algorithms.

The spectral sweep method is now described. To mimic the illumination of LCTF-based hyperspectral imaging systems, the spectral sweep method sweeps bandpass illuminations with 10 nm bandwidths from 520 nm to 645 nm in 1 nm increments. A hyperspectral image cube acquired with this method consists of 126 slices and explicitly measures the absorbance spectroscopy of an area of interest. Formally, the following series of illuminations is programmed into the OL 490:

$$\{L_{1,Sweep}=L_{OL490}(\lambda_1), L_{2,Sweep}=L_{OL490}(\lambda_2), \ldots \\ L_{126,Sweep}=L_{OL490}(\lambda_{126})\} \quad (12)$$

for, $$\lambda_n = 520+(n-1), n=\{1:126\} \quad (13)$$

where, $L_{OL490}(\lambda_n)$ is again the total radiant power emitted from the OL 490 at a center wavelength, $\lambda_n$, with a 10 nm FWHM bandwidth.

Figure 50A:
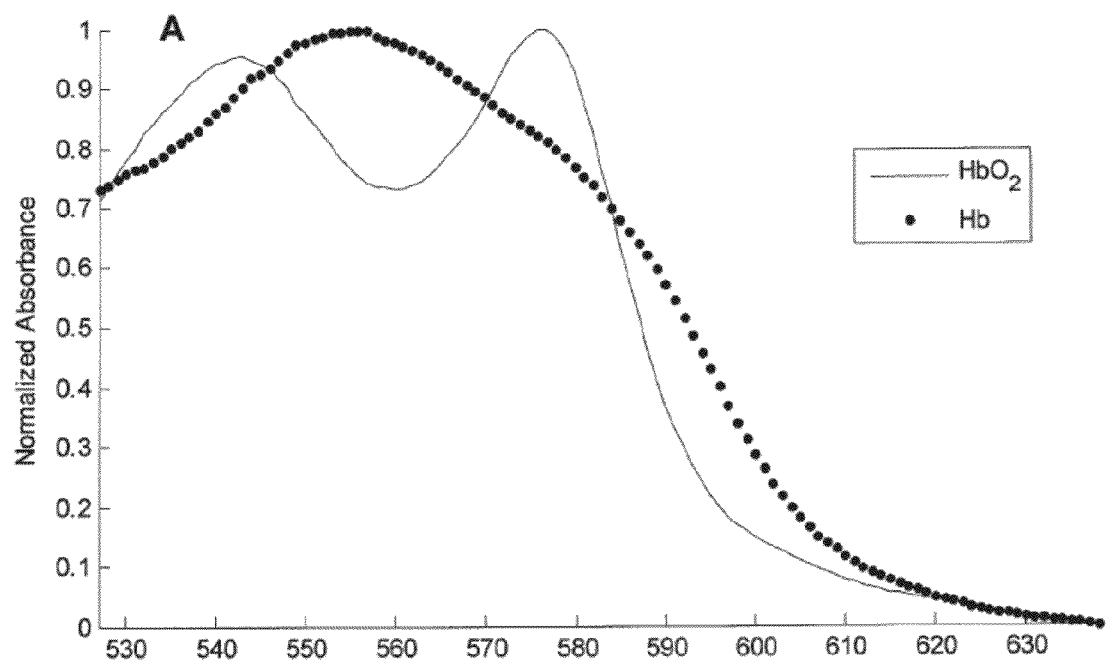
FIG. 50A is the normalized absorption spectra of $HbO_2$ and Hb used as references for multivariate deconvolution of spectral sweep absorbance cubes.

After proportioning out the background, each slice in the cube represents the absorbance of the bandpass illumination at which the image is acquired. Thereby, each spatial pixel in the processed cube represents a discrete absorbance spectrum of the tissue or other material in the physical position corresponding to that pixel, identical to the full spectral sweep method, but with better spectral resolution and narrower wavelength range. Each pixel absorbance spectrum is then compared to reference spectra for oxy-hemoglobin ($HbO_2$) and deoxy-hemoglobin (Hb) in FIG. 50A by multivariate least squares analysis to calculate the percent $HbO_2$ for that pixel. The output bitmap, after processing with 'Oxyz—Jet', is a color-coded two-dimensional image, where more intense pixels (red) signify that the pixel absorbance spectrum more closely resembles the $HbO_2$ reference and less intense pixels (blue) signify that the pixel absorbance spectrum more closely resembles the Hb reference.

Spectral sweep illumination is slow for two fundamental reasons: acquisition of 126 frames takes 126 times longer than acquisition of a single frame and processing of such large data cubes takes considerable time. One suggested solution to this speed issue has been selecting only a few narrow illumination bands to significantly reduce the number of slices in the cube, thereby reducing the acquisition time and processing time. (See Guo, B, Gunn, S R, Damper, R I, Nelson, J D B, Band selection for hyperspectral image classification using mutual information. 2006; 3:522-526; and, Du, Z, Jeong, M K, Kong, S G, Band selection of hyperspectral images for automatic detection of poultry skin tumors. 2007; 4:332-339). This solution has been shown to speed up data acquisition and processing, but does not necessarily gather the same spectral information as a spectral sweep.

The present invention "3 shot" method is now described. The "3 shot" method of the present invention enables the gathering of spectral information equivalent to the spectral sweep method with fewer images being captured. The "3 shot" method sequences through three complex broadband illumination spectra in the 527 nm to 638 nm wavelength range. A hyperspectral image cube acquired with this method consists of three (3) slices and is used to calculate the percent $HbO_2$ for each spatial pixel without explicitly measuring the absorbance spectra. Formally, the following illuminations are programmed into the OL 490:

$$L_{1,3shot} = \sum_{n=8}^{119} L_{OL490}(\lambda_n) V_1(\lambda_n) \quad (14)$$

$$L_{2,3shot} = \sum_{n=8}^{119} L_{OL490}(\lambda_n) V_2(\lambda_n) \quad (15)$$

$$L_{3,3shot} = \sum_{n=8}^{119} L_{OL490}(\lambda_n) \quad (16)$$

Figure 50B:
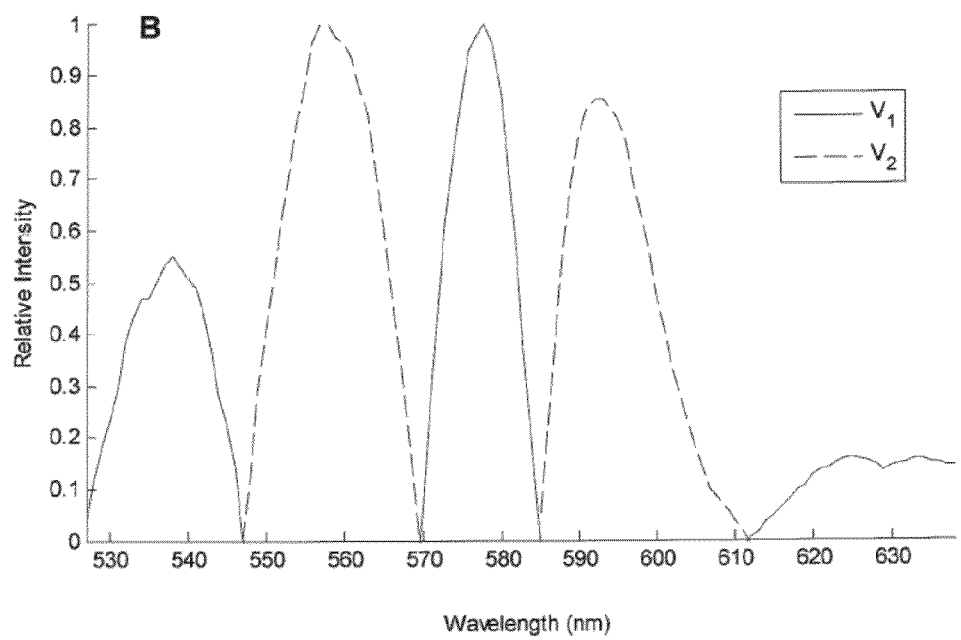
FIG. 50B is the positive and negative subtraction of spectra used for "3 shot" illumination.

For the wavelengths described by equation 8, $V_1(\lambda_n)$ represents the positive subtraction of normalized reference spectra and for the wavelengths described by equation 9, $V_2(\lambda_n)$ represents the negative subtraction of normalized reference spectra as shown in FIG. 50B. The limits of summation are intentionally n=8 and n=119, because the reference spectra have been filtered by a moving average filter that trims seven discrete values from the beginning and end of each spectrum.

Figure 51:
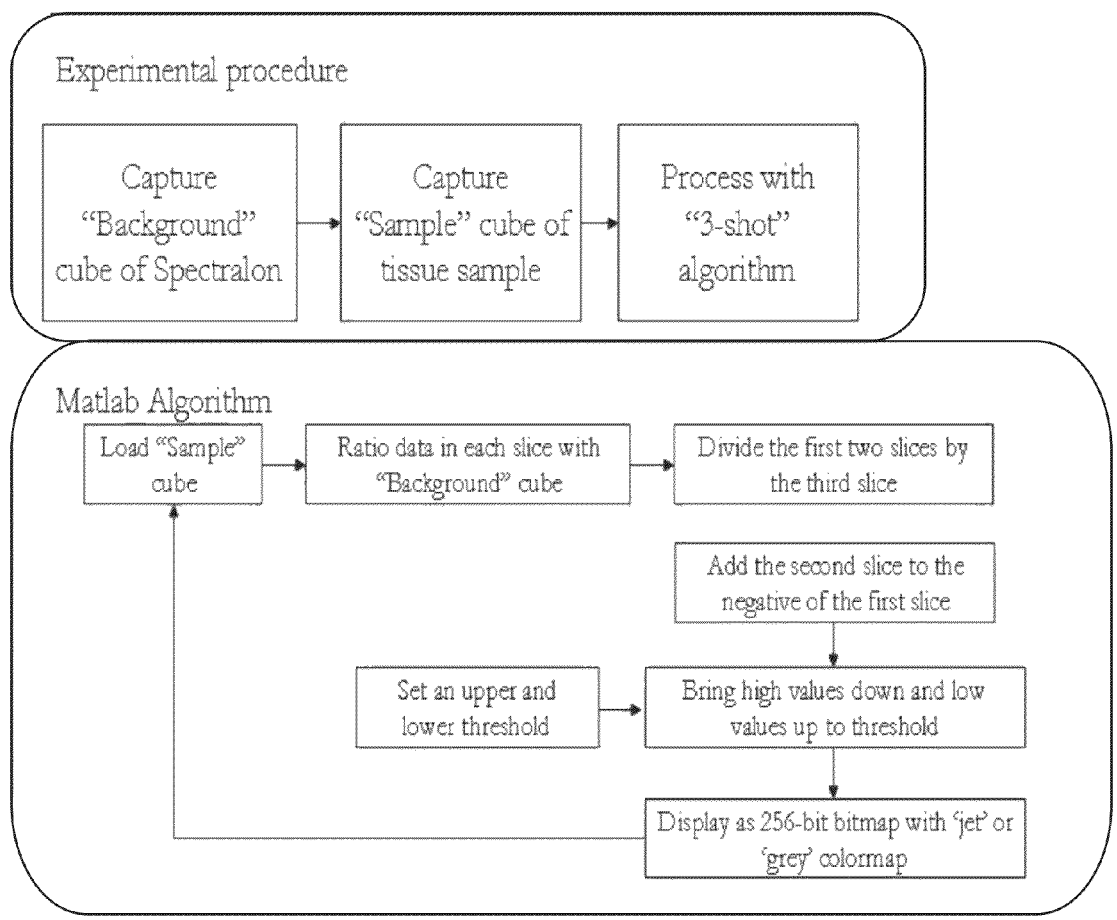
FIG. 51 is a block diagram that shows the experimental procedure used to capture images using the "3 shot" method of the present invention and the MATLAB® algorithm used to process the images captured using the "3 shot" method of the present invention.

FIG. 51 is a block diagram that shows the experimental procedure used to capture images using the "3 shot" method of the present invention and the MATLAB® algorithm used to process the images captured using the "3 shot" method of the present invention.

Figure 52A:
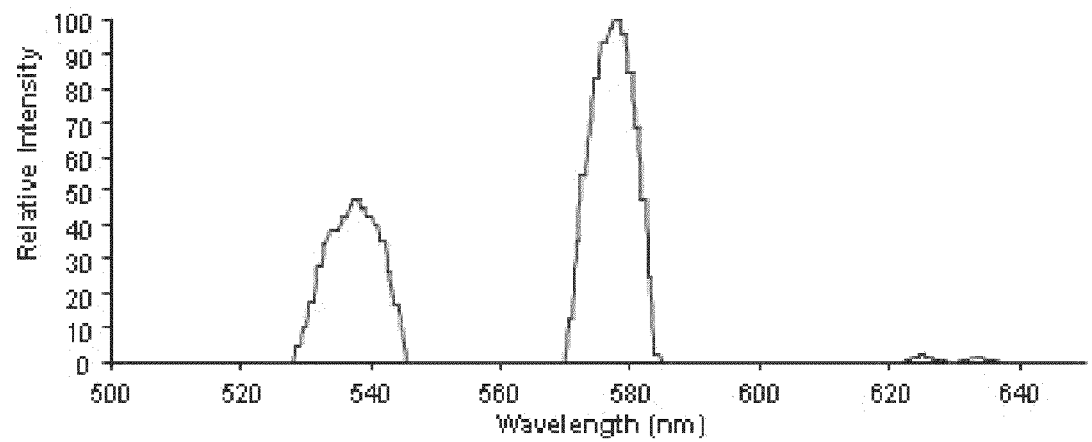
FIG. 52A is an illustration of the "3 shot" illumination method of the present invention used for visualizing blood oxygenation showing the normalized absorbance spectra in the 520 nm-645 nm wavelength range for $HbO_2$ and Hb subtracted from each other, and the positive areas become the two illumination spectra.
Figure 52B:
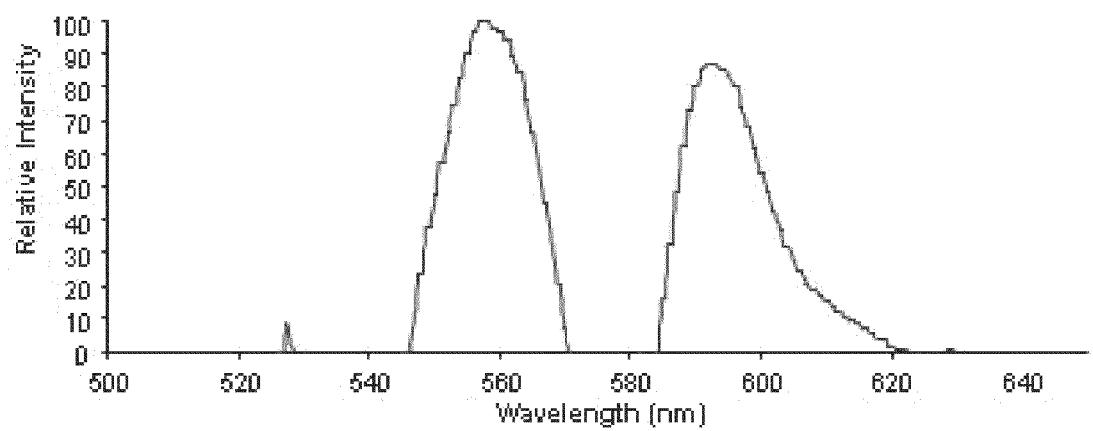
FIG. 52B is an illustration of the "3 shot" illumination method of the present invention used for visualizing blood oxygenation showing relative intensity of each illumination spectrum is stretched from 0 to 100 to maximize the overall light intensity and match the required OL-490 input format.
Figure 52C:
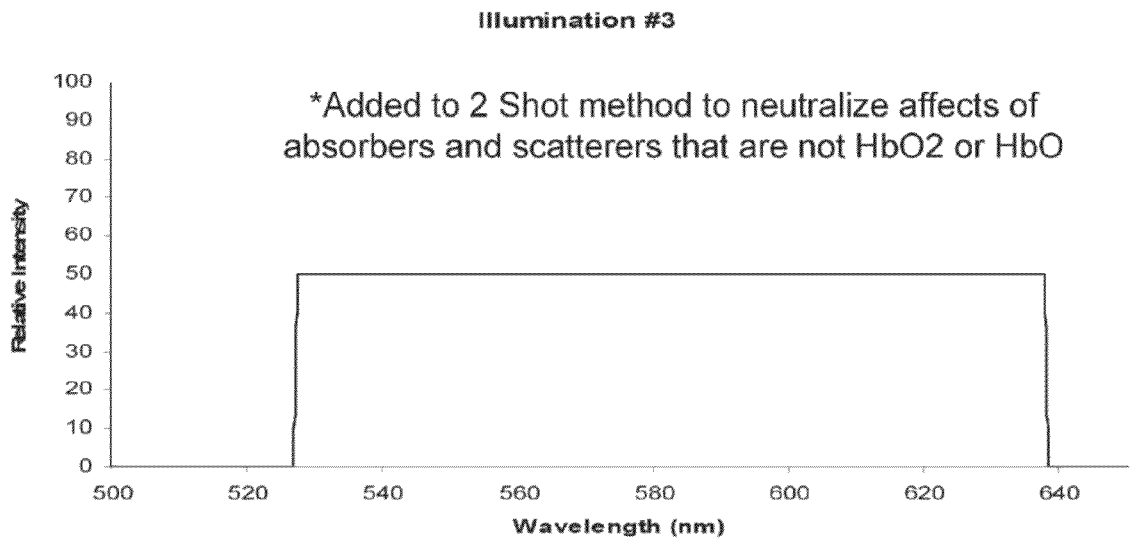
FIG. 52C is an illustration of the "3 shot" illumination method of the present invention used for visualizing blood oxygenation showing the absorbers and scatterers that are not $HbO_2$ and Hb.

FIGS. 52A-52C are an illustration of the "3 shot" illumination method of the present invention used for visualizing blood oxygenation. FIG. 52A shows the normalized absorbance spectra in the 520 nm-645 nm wavelength range for $HbO_2$ and Hb subtracted from each other, where the positive areas become the two illumination spectra. FIG. 52B shows that the relative intensity of each illumination spectrum is stretched from 0 to 100 to maximize the overall light intensity and match the required OL-490 input format. FIG. 52C shows the absorbers and scatterers that are not $HbO_2$ and Hb.

After proportioning out the background, each slice in the cube represents the absorbance of the broadband illumination at which the image is acquired. Absorbance spectra are not explicitly measured, but a mathematic combination of the three slices results in a single two-dimensional image where higher pixel values indicate absorbance similar to $HbO_2$ and lower pixel values indicate absorbance similar to Hb. The data cube is forty two (42) times smaller than the spectral sweep data cube, the processing algorithm is considerably simpler, and the resulting visualization of tissue oxygenation is the same. Thus, a color-coded bitmap image that appears nearly identical to one generated by the spectral sweep method can be generated by the "3 Shot" method much more quickly.

Figure 53A:
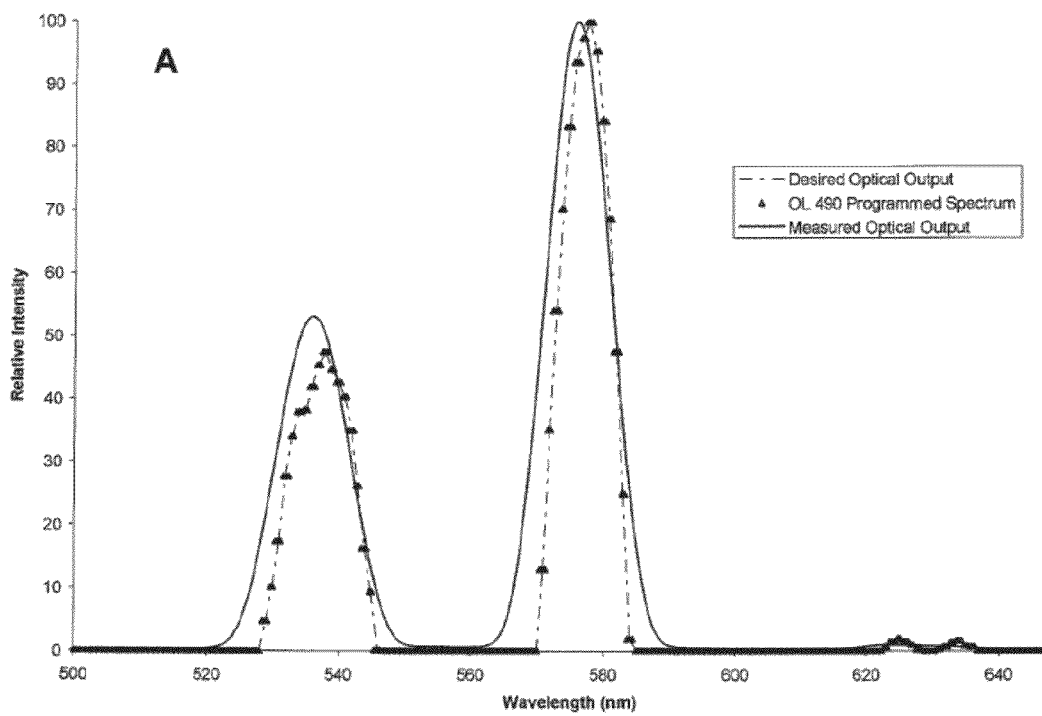
FIG. 53A is a graph illustrating the comparison of optical output measured by a spectrometer and desired optical output for first illumination spectrum of the "3 shot" method before applying center wavelength calibration and intensity adjustment.

Three complex broadband illumination spectra were derived from the reference absorbance spectra of Hb and $HbO_2$ for the "3 Shot" method described in the present invention. Initially the OL 490 was programmed to illuminate with these spectra by directly copying the spectra into Gwectra files. The optical output measured by a spectrometer when these spectra were explicitly programmed is seen in FIG. 53A. Explicitly using the calculated spectra, the measured optical output was significantly different than the desired illumination. In the plot, the solid line (measured optical output) is shifted horizontally from the dotted line (desired optical output), and the measured first peak is not as intense as the desired first peak.

Figure 53B:
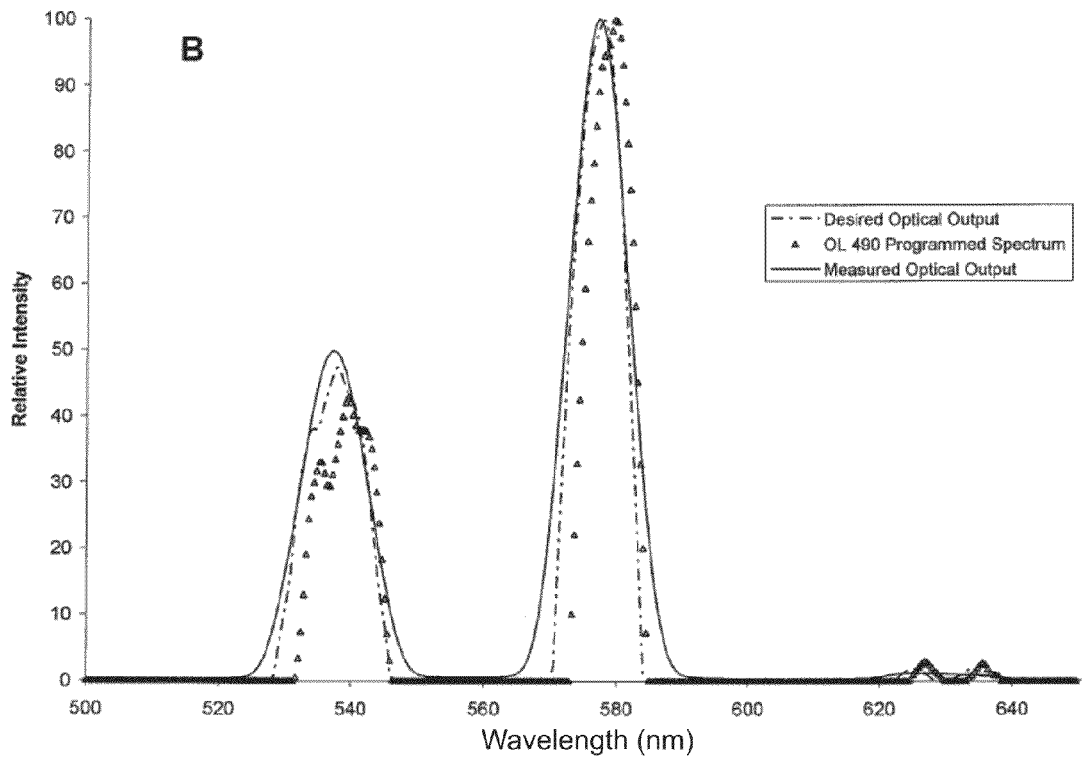
FIG. 53B is a graph illustrating the comparison of optical output measured by a spectrometer and desired optical output for first illumination spectrum of the "3 shot" method after applying center wavelength calibration and intensity adjustment.

In order to generate an illumination spectrum that more closely matches the desired optical output, a new Gwectra file was written. In the new file, the intensities at each wavelength were shifted horizontally according to the center wavelength calibration curves mentioned earlier and vertically according to the error between the measured and desired intensities. Programming the OL 490 with the new Gwectra file, the optical output is seen in FIG. 53B. In the plot, the solid and dashed lines (measured optical output and desired optical output, respectively) coincide much better than in the previous plot.

Reprogramming the mirrors of the DMD in the OL 490 allows for refinement of illumination spectra for the "3 Shot" method. The same wavelength calibration and intensity adjustment was performed for the other two complex broadband illuminations. For most of the wavelength range, the actual optical output matches well with the desired optical output. Due to the minimum bandpass limitation when using the 350 µm slit, it is fundamentally impossible to mimic the two bumps desired between 620 nm and 640 nm. If lower overall light intensity is adequate, the 150 µm slit, which has a smaller minimum bandpass limitation, can be used to further refine the actual optical output.

Speed is a key requirement in the DLP hyperspectral imaging system design. Camera selection is often based primarily on speed. The purpose of the "3 Shot" method of the present invention is speed. One of the main reasons hyperspectral imaging is not a primetime medical imaging modality is its inherent lack of speed. The DLP HSI prototype of the present invention is purposefully versatile. The user can adjust exposure times (constant or variable), binning of the CCD array, processing algorithms for chemometric visualization, lens aperture, and OL 490 illumination methods. To address the need for speed, it is important to understand the role each of these parameters play in determining the final frame rate of the system.

Several fundamental bottlenecks limit the maximum speed of the DLP HSI. The minimum exposure time of the OL 490 is 80 µs, the minimum exposure time of the HQ2 is 210 µs, the maximum transfer rate of the camera to the computer is 20 MHz, and the image processing time is significant.

Theoretically, increasing exposure time in each slice will increase acquisition time for each image thereby increasing total acquisition time for the hyperspectral cube. Practically, exposure time is varied to achieve near 12,000 counts at the maximum intensity when capturing a background cube, so exposure time is not considered an independent variable. Rather, exposure time depends on lens aperture, camera binning, gain, illumination intensity, and focal distance. Illumination intensity is dependent on illumination method and is fixed for either the spectral sweep illumination method or the "3 shot" illumination method of the present invention. Focal distance is variable and is adjusted depending on the physical constraints of the clinical or surgical setup. In surgery, the camera must be at least 1 m away from the subject and should be unobtrusive to the surgeon. On the lab bench, the camera is set to a focal distance of 45 cm. Camera gain can be varied according to CoolSNAP HQ2 specifications while the lens aperture can be varied from f/16 to f/1.4. The two parameters in concert affect the exposure time primarily, with side effects of focus range and detector noise. For the following speed tests, 'high gain' refers to a camera gain of 3 and a lens aperture of f/1.4, while 'low gain' refers to a camera gain of 1 and a lens aperture of f/8. Camera binning affects both exposure time and spatial resolution. For the following speed tests, bins of 2×2 and 4×4 are set. In the clinic, 'low gain' and 4×4 binning is typically used to ensure good quality imaging at reasonable speeds.

A final parameter that does not affect exposure time but still affects the speed of the system is the processing algorithm. The most basic processing algorithm reads the hyperspectral image cube into MATLAB and outputs one of the raw images as a Windows bitmap file for display. For visualization of oxygenation, "Oxyz Jet" and "3shot Jet—*," where * can be any pair of thresholds, are the processing algorithms used. In each of the oxygenation algorithms, the hyperspectral image cube and background cube in the same parent directory are read into MATLAB for calculating absorbance. Chemometric analyses transform the absorbance cube into a chemically relevant image which is output as a bitmap for display.

To measure the effect of each parameter on the overall speed of the DLP HSI, the system was set to a focal distance of 45 cm with the Spectralon target filling the detector field of view (FOV), and a combination of parameters based on the 2×2×2×2 factorial analysis model presented above are programmed into the GUI. Temporary data cubes are acquired to set the exposure time that allows for a maximum response near 12,000 counts as seen in Table 4. Due to the illumination intensity of the "3 Shot" illuminations the exposure time could not be adequately lowered to keep the detector from saturating under 'high gain' conditions.

TABLE 4

Exposure time (µs) required to get maximum response near 12,000 counts for the given combination of parameters.

| | | Spectral Sweep | | 3 Shot | |
|---|---|---|---|---|---|
| | | Raw | Oxy | Raw | Oxy |
| 2 × 2 | Low Gain | 980 | 980 | 5750 | 5750 |
| | High Gain | 184000 | 184000 | saturates | saturates |
| 4 × 4 | Low Gain | 200 | 200 | 1250 | 1250 |
| | High Gain | 40000 | 40000 | saturates | saturates |

After the exposure times are determined, the system is set to acquire continuously for a period of ten (10) minutes. The number of output bitmaps created within that ten (10) minutes is counted, and the time to output one processed image for the set parameters is calculated by equation 17.

$$t = \frac{600}{\# \text{ bitmaps}} \quad (17)$$

Table 5 shows the results of all 12 runs. As expected from casual observations, the fastest time to output one "3 Shot" image visualizing oxygenation is near ⅓ of a second (0.33 seconds), which means that under these conditions, the system is operating a nearly 3 frames per second (fps). Acquiring Spectral Sweep images with 2×2 binning causes an exception violation in the software because the resulting image cube is too large for MATLAB to process (696×520×126). Comparing Oxy to Raw, it appears that the processing algorithm has an increased effect on speed when binning is reduced, but no differential effect on speed when gain is increased. From the spectral sweep results, it also appears that the processing algorithm has a greater effect on speed than does gain level.

These observations may be helpful in determining how to make image acquisition and processing most efficient with the DLP HSI.

TABLE 5

Time (sec) to output one processed image for the given combination of parameters.

| | | Spectral Sweep | | 3 shot | |
|---|---|---|---|---|---|
| | | Raw | Oxy | Raw | Oxy |
| 2 × 2 | Low Gain | exception | exception | 0.48 saturates | 0.71 saturates |
| | High Gain | exception | exception | saturates | saturates |
| 4 × 4 | Low Gain | 14.63 | 23.08 | 0.32 saturates | 0.39 saturates |
| | High Gain | 9.68 | 18.75 | saturates | saturates |

Figure 54:
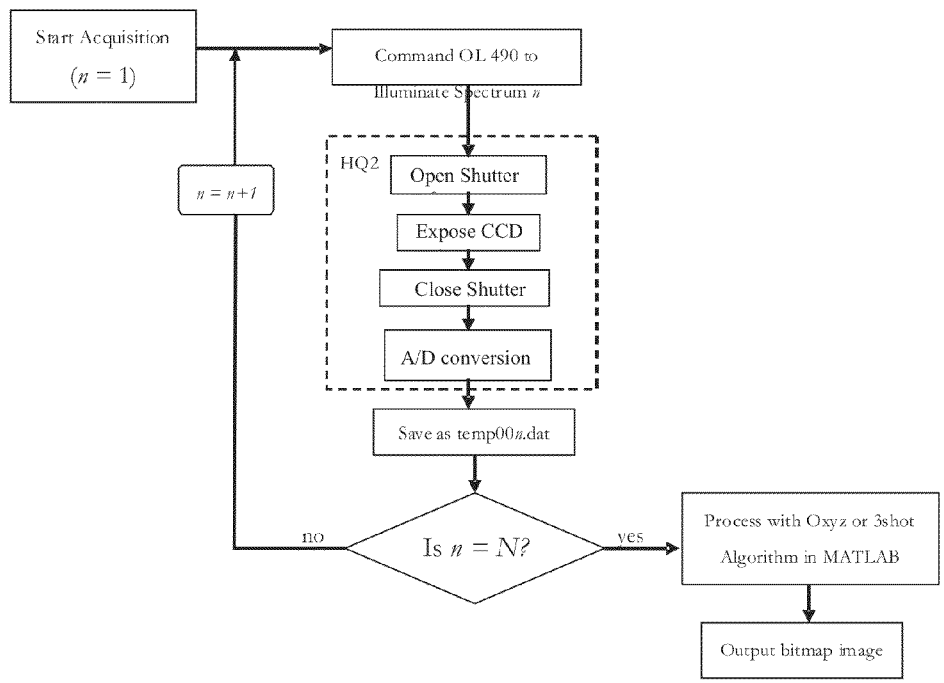
FIG. 54 is a timing diagram of hyperspectral acquisition where N is the total number of slices to be acquired, for a spectral sweep, N=126, and for a "3 shot", N=3.

To further illustrate the timing of each process in the hyperspectral image acquisition sequence, the timing diagram in FIG. 54 follows the flow of data from initializing acquisition to visualization of a processed bitmap. The closed loop describes acquisition of a single slice of a hyperspectral cube, thus the time required to complete that loop must be multiplied by the number of slices or illumination spectra in order to calculate acquisition time. By examining the time log of the GUI during acquisition, processing time for each algorithm is deduced. This processing time is subtracted from the output time in Table 5 for 4×4 binning and low gain for "3 Shot" (high gain for spectral sweep) to determine the total acquisition time. Dividing the total acquisition time by the number of slices equals the time to complete one cycle of the closed loop. For spectral sweep, the acquisition time is 116 ms/slice, and for "3 Shot", the acquisition time is 93 ms/slice. This difference, 23 ms/slice, is less than the difference in exposure time for the two methods, 38.75 ms/slice, indicating that initialization of the camera or light source plays a large factor in acquisition time.

Figure 55A:
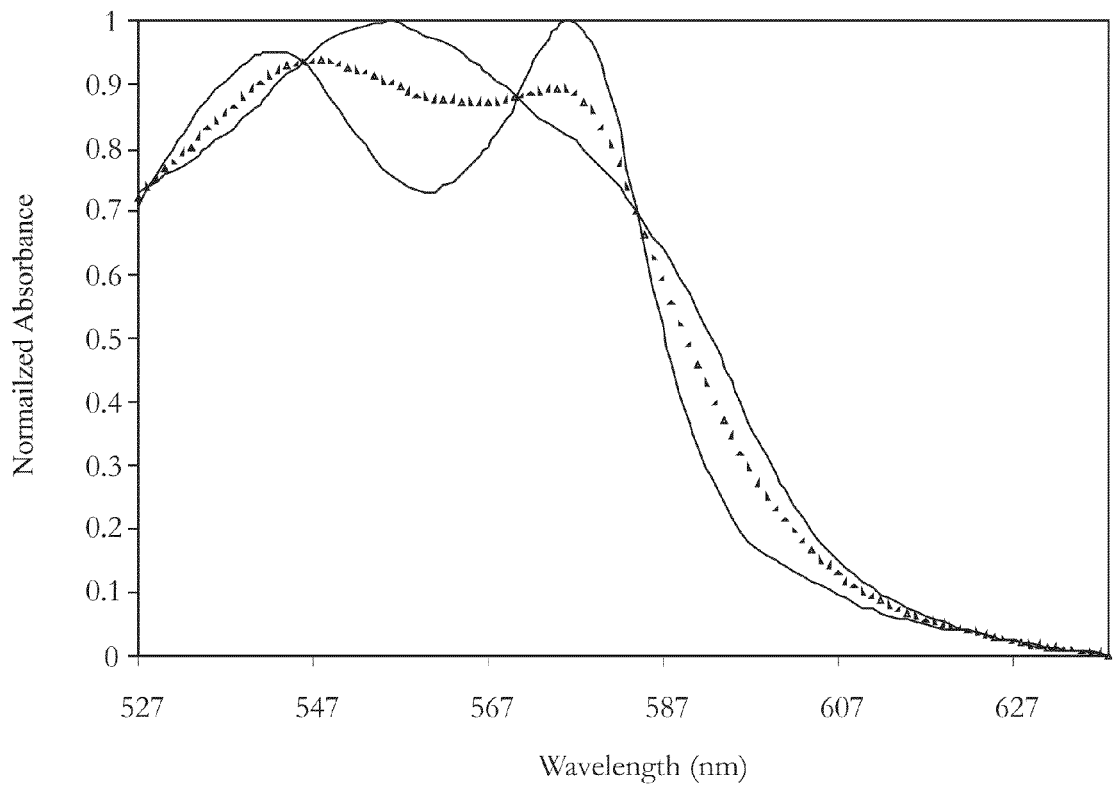
FIG. 55A is a diagram illustrating the processing algorithms for visualizing the images of blood oxygenation captured using the spectral sweep method comparing measured spectrum to reference spectra via multivariate least squares analysis to quantify relative concentration $HbO_2$.
Figure 55B:
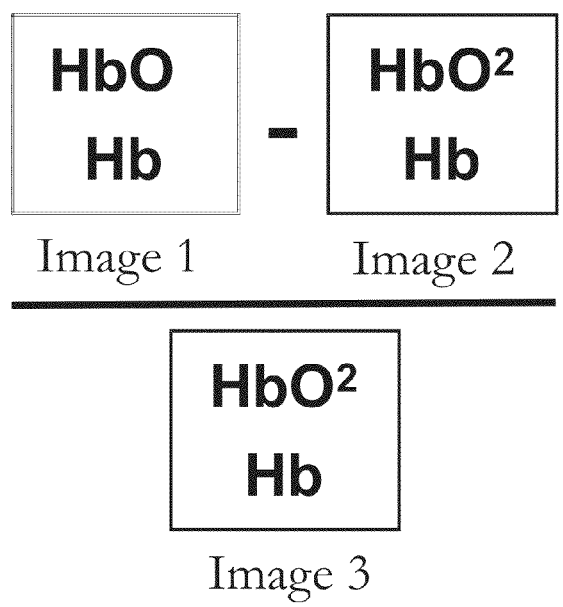
FIG. 55B is a diagram illustrating the processing algorithms for visualizing the images of blood oxygenation captured using the "3 shot" method of the present invention which subtracts the image representing Hb absorbance from the image representing $HbO_2$ absorbance and dividing the broadband absorbance to quantify relative concentration of $HbO_2$.

FIGS. 55A and 55B are diagrams illustrating the processing algorithms for visualizing the images of blood oxygenation captured using the spectral sweep and the "3 shot" method of the present invention. FIG. 55A shows the spectral sweep comparing measured spectrum to reference spectra via multivariate least squares analysis to quantify relative concentration $HbO_2$. FIG. 55B shows the "3 shot" method which subtracts the image representing Hb absorbance from the image representing $HbO_2$ absorbance and dividing the broadband absorbance to quantify relative concentration of $HbO_2$.

Figure 56A:
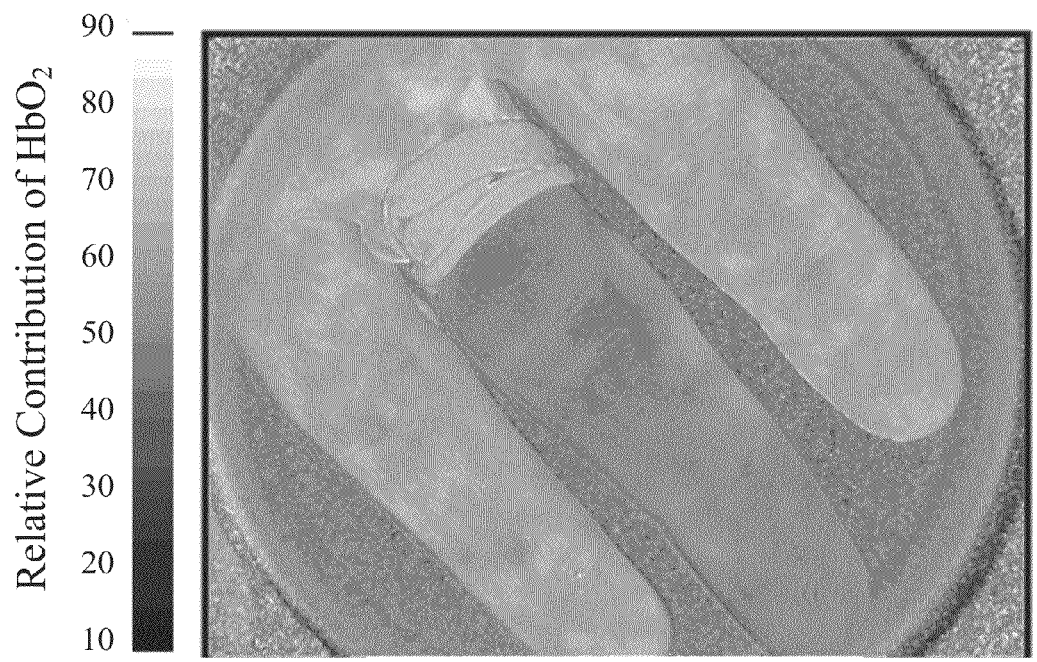
FIG. 56A is the visualization of an ischemia induced by occluding blood flow to a finger imaged with the DLP HSI in spectral sweep mode.
Figure 56B:
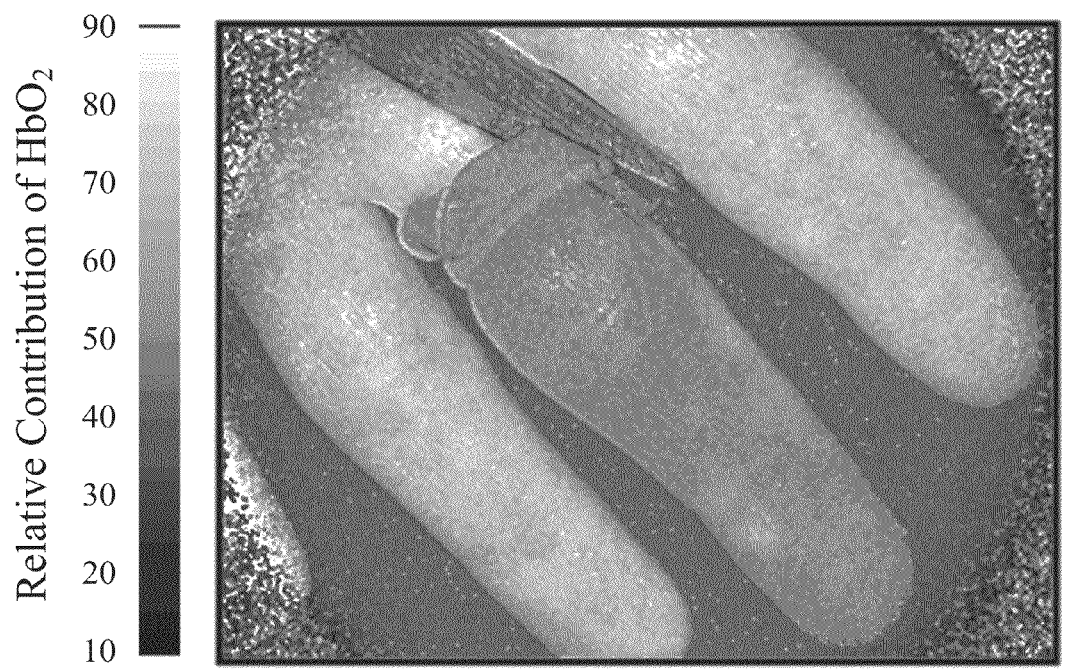
FIG. 56B is the visualization of an ischemia induced by occluding blood flow to a finger imaged with the DLP HSI in "3 shot" mode.

The methods are further described infra. To visualize the ischemia induced by occluding blood flow to a finger and the ensuing reactive hyperemia upon removal of the occlusion, a subject's hand is imaged with the DLP HSI in spectral sweep and "3 Shot" modes (FIGS. 56A and 56B, respectively). The system is warmed up, focused at a distance of 18 cm, and set to capture a background cube. The subject's hand was placed palm up in the FOV of the camera so that three fingers and part of the palm were imaged. 'Control' hyperspectral image cubes, i.e., five spectral sweep cubes and five "3 Shot" cubes, were acquired of the non-occluded fingers. Each spectral sweep cube was analyzed with 'Oxyz Jet' and each "3 Shot" cube was analyzed with '3 shot jet (mid)17' processing algorithms, resulting in five output bitmap images color-coded for percent $HbO_2$ for each illumination method. After acquiring 'Control' images, a rubber band is wrapped three times around the base of the subject's middle finger and five 'Occluded' hyperspectral image cubes for each method were acquired and processed in the same way as the 'Control' images.

To visualize the real-time progression of reactive hyperemia after removal of the occlusion, "3 Shot" images were acquired and processed continuously after acquiring the 'Occluded' images. While the system continued outputting "3 Shot" images color-coded for percent $HbO_2$, the rubber band was cut with a pair of scissors. After a period of three minutes, the system was switched to spectral sweep mode to collect five 'Reperfusion' hyperspectral image cubes.

The spectral sweep hyperspectral images were averaged for each time point in the experiment (n=5, for 'Control', 'Occluded', and 'Reperfusion'). The "3 Shot" output bitmaps are averaged for 'Control' and 'Occluded' time points (n=5), and the mean pixel value for a constant 49 pixel area represents percent $HbO_2$ at each time point. For the real-time progression of reactive hyperemia, the mean pixel value for the 49 pixel area was plotted versus time for several seconds prior to cutting the rubber band and 180 seconds immediately thereafter.

Figure 57A:
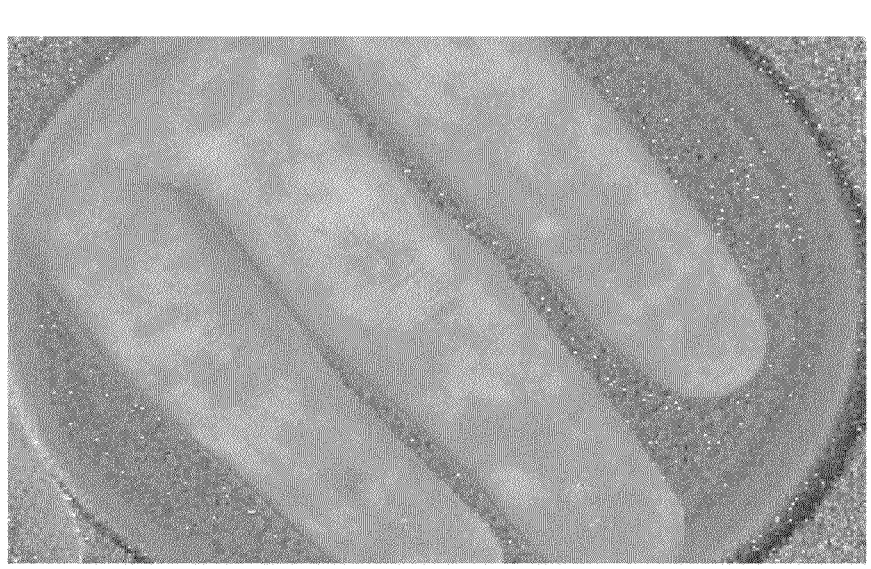
FIG. 57A is the average of five spectral sweep oxyz output images captured as 'Control'.
Figure 57B:
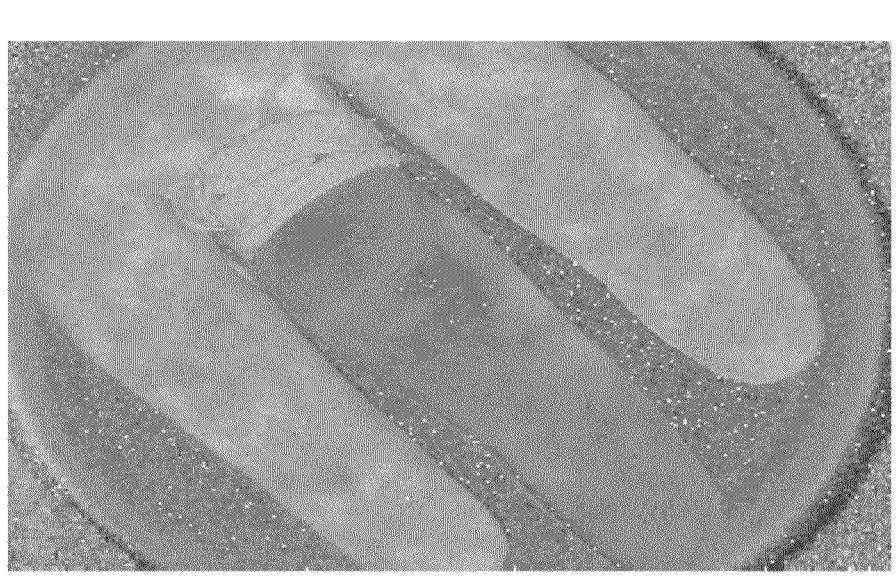
FIG. 57B is the average of five spectral sweep oxyz output images captured while 'Occluded'.
Figure 57C:
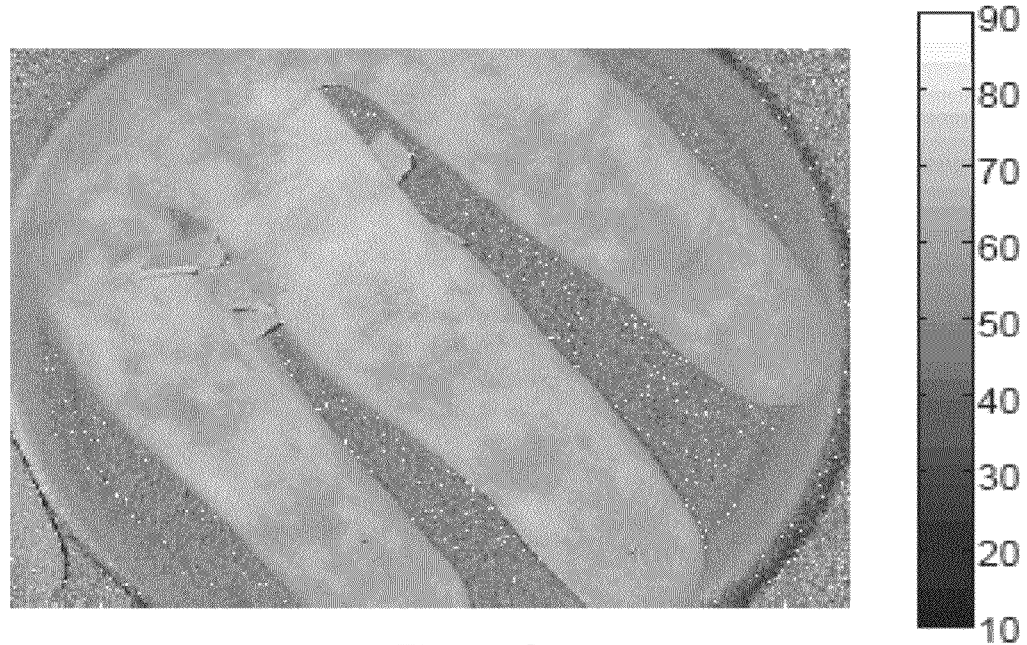
FIG. 57C is the average of five spectral sweep oxyz output images captured for 'Reperfusion'.

The results are now discussed infra. Visual inspection of the processed spectral sweep images (See FIG. 57A) showed that the DLP hyperspectral imaging system can differentiate between oxygenated and deoxygenated tissue. In FIG. 57A, all three fingers were colored shades of red, orange, and yellow, which corresponded to a percent $HbO_2$ between 60 and 80%, as indicated on the colorbar at the right. As expected under 'Control' conditions, there was no difference in the surface oxygenation amongst the three fingers. In FIG. 57B, the middle finger was colored blue-green, which corresponds to a percent $HbO_2$ between 40 and 50%, while the other two fingers appeared the same as they did in the 'Control' image. As expected under 'Occluded' conditions, the rubber band tourniquet inhibits blood flow to the finger and effectively de-oxygenates the tissue. In FIG. 57C, the middle finger was colored red-orange, corresponding to a percent $HbO_2$ higher than 75%. As expected under 'Reperfusion' conditions, the DLP HSI visualizes an overshoot in tissue oxygenation related to reactive hyperemia most likely caused by vascular autoregulation of the previously occluded finger.

Figure 58A:
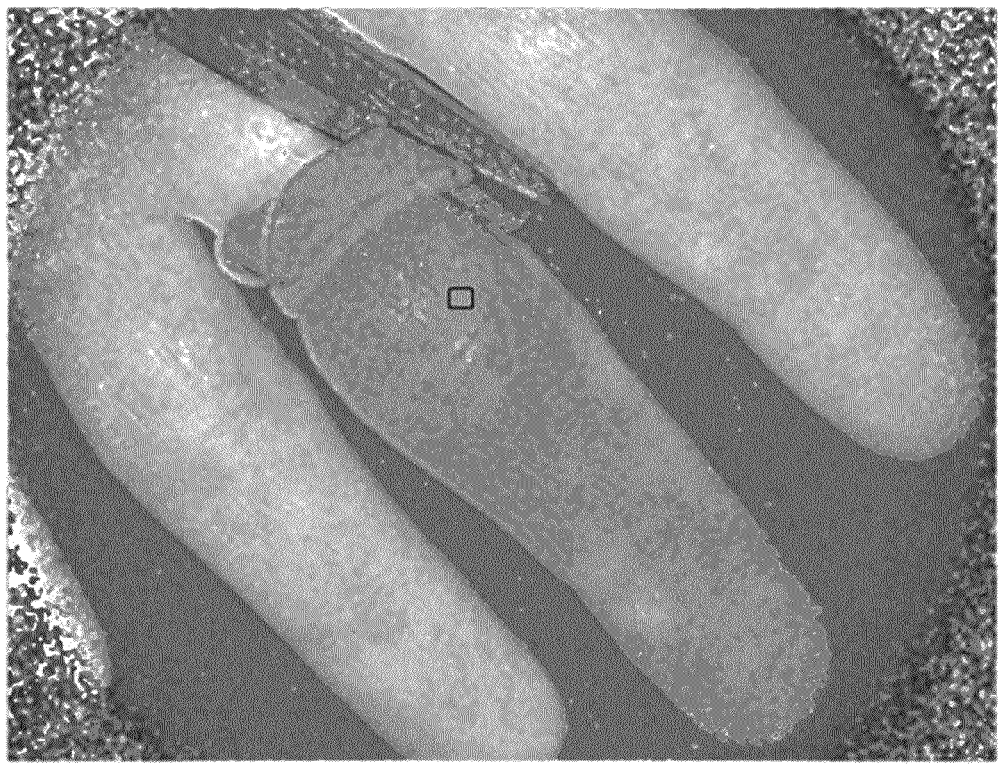
FIG. 58A is a color-coded "3 shot" output images captured immediately before cutting the rubber band.

To quantify this overshoot related to reactive hyperemia, inspection of the 3 Shot output images was necessary. In FIG. 58A, the processed "3 Shot" output image under 'Occluded' conditions matched its counterpart spectral sweep image (FIG. 57B). The non-occluded fingers appeared redder than those in the spectral sweep image, indicating a higher percent $HbO_2$ than measured by the spectral sweep method. The two methods were calibrated further to determine the truer method of measuring absolute oxygenation. Because of this discrepancy in absolute measures, all results must be considered in relative terms rather than in absolute oxygen percentages.

Figure 58B:
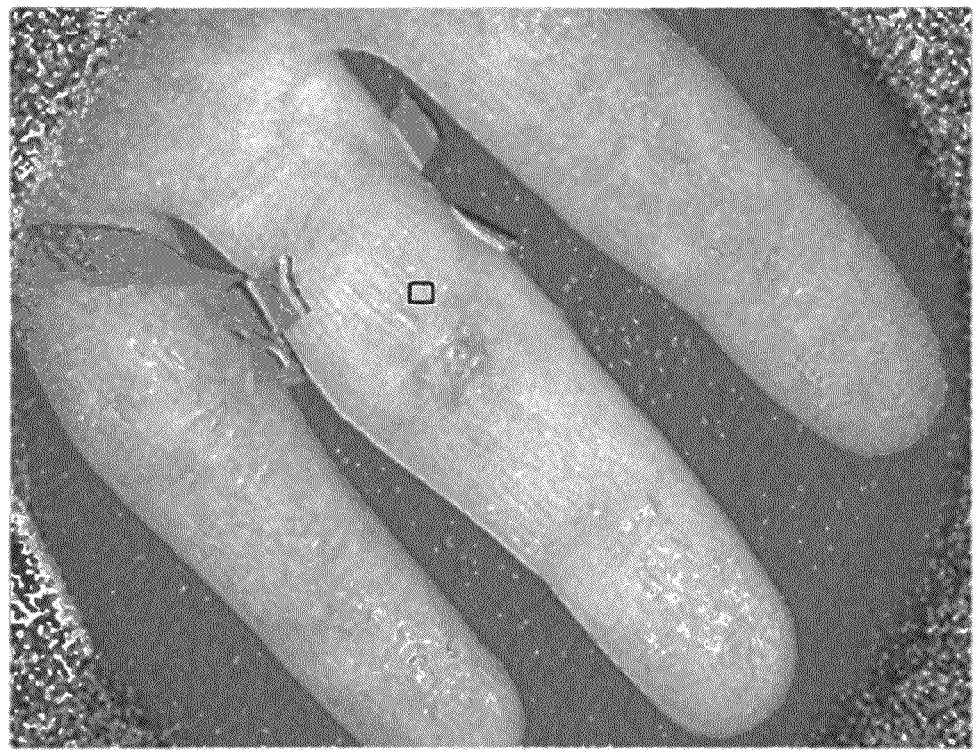
FIG. 58B is a color-coded "3 shot" output images captured 10 seconds after cutting the rubber band.
Figure 58C:
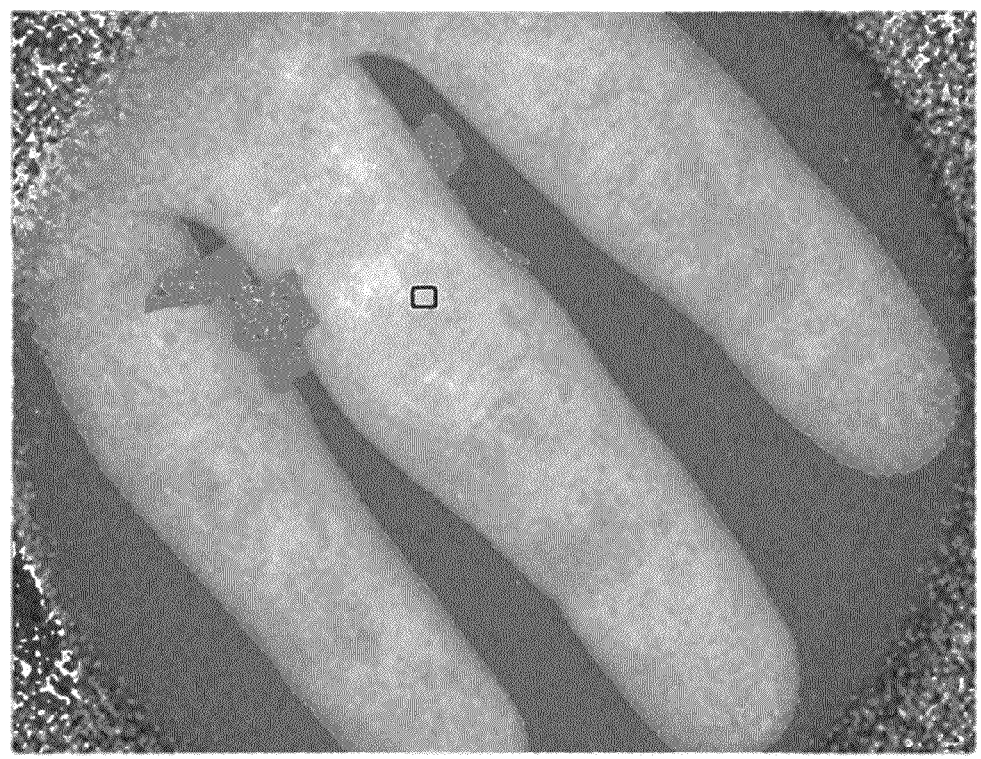
FIG. 58C is a color-coded "3 shot" output images captured 2 minutes after cutting the rubber band.
Figure 59:
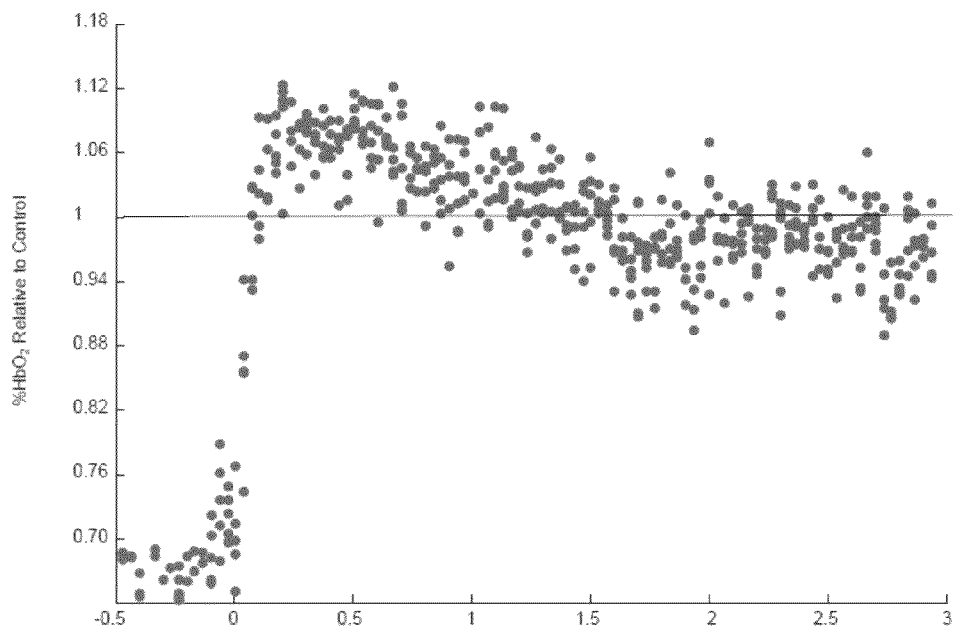
FIG. 59 is the real-time progression of reactive hyperemia after cutting rubber band from finger shown as a plot of average pixel values from "3 shot" images acquired during removal of tourniquet from finger which shows reactive hyperemia in at 3 frames per second.

Inspecting the "3 Shot" images immediately after the occlusion is removed and several minutes later (FIGS. 58B and 58C, respectively), it appeared that there is an immediate overshoot of percent $HbO_2$ in the previously occluded middle finger and a subsequent return to normal tissue oxygenation levels. This overshoot is quantified by calculating the mean of the pixel values in the black sample area of each image divided by the average 'Control' values for the same pixel area. With this calculation, the transient response of reactive hyperemia in the middle finger was examined. In FIG. 59, the average percent $HbO_2$ relative to control for the black sample area is plotted for every "3 Shot" output image acquired between occlusion and reperfusion. While occluded, the surface oxygenation was less than 70% of the control oxygenation, but in the first ten (10) seconds after removing the tourniquet the surface oxygenation raises to 112% of control.

Variability in consecutive images was apparent when viewing the output images in real-time and is also apparent in the wide vertical spread of the data points in FIG. 59. This image to image variability is not entirely understood, but may be an artifact of the OL 490 output variability. Even with the variability, the overall trend of oxygenation appeared to mimic an under-damped 2nd order system response. There is an initial overshoot, then undershoot after about 1.5 minutes, with percent $HbO_2$ eventually returning to the control level after longer than 3 minutes.

The DLP HSI can be used to visualize ischemia and reactive hyperemia, as evidenced by the proof-of-principle finger occlusion test. Processed Spectral Sweep output images showed high contrast between oxygenated and de-oxygenated tissue and indicated gross physiological changes. Processed "3 Shot" output images showed the same contrast between oxygenated and de-oxygenated tissue, but the two illumination and processing methods do not give identical absolute measurements of percent $HbO_2$.

Images acquired and processed by the "3 Shot" method were generated at about 3 frames per second, while spectral sweep images are generated at about 3 frames per minute. Both are useful methods for visualizing the spatial distribution of surface tissue oxygenation, but the "3 Shot" method is preferable when visualizing short duration physiological changes. Analyzing several minutes of continuous "3 Shot" outputs shows reactive hyperemia of the surface tissue in a previously occluded middle finger.

The following descriptions detail particular examples of procedures, conditions, etc. which are applicable to utilizing the present invention "3 Shot" methods.

Partial nephrectomy is a surgical procedure in which a section of a patient's kidney is removed, usually to eliminate a tumor. Sparing the remainder of the kidney often requires vascular occlusion in order to temporarily interrupt renal blood and prevent hemorrhage. Two methods of renal vascular occlusion: artery-only occlusion (AO) and artery and vein occlusion (AV), have demonstrated differential effects on renal tissue viability during 2 to 24 hour long periods of ischemia. (See Gong, E M, Zorn, K C, Orvieto, M A, Lucioni, A, Msezane, L P, Shalhav, A L, Artery-only occlusion may provide superior renal preservation during laparoscopic partial nephrectomy. Urology 2008; 72:843-846). To understand the effects of competing clamping methods during shorter periods of ischemia, the DLP HSI was used to image the renal tissue oxygenation during partial nephrectomies in pigs and then humans for periods of ischemia less than one hour long.

The following describes the results of the study involving pigs. Following approval by the UTSW Institutional Animal Care and Use Committee (IACUC), four female Yorkshire pigs, weighing between 60-80 kg, underwent AO or AV occlusion of each kidney. At the beginning of the study, one kidney was used to perfect the investigational technique and, therefore, was not included in the analysis. In order to verify the images obtained by the prototype DLP HSI, hyperspectral image cubes are acquired by sweeping 126 contiguous bandpasses, identical to the spectral sweep illumination method, with an already characterized LCTF-based hyperspectral imaging system. The primary difference between the two systems is the method of filtering light. In the LCTF system broadband light is reflected from the tissue sample and then filtered by a liquid crystal tunable filter (LCTF) before being detected by a CoolSNAP HQ2 array detector. In the DLP system's spectral sweep method, narrowband light from the spectral light engine is reflected from the tissue sample and directly detected by a CoolSNAP HQ2 array detector. There is no LCTF equivalent to the DLP "3 Shot" method as a LCTF is incapable of providing complex spectra as provided by the DLP.

Figure 60:
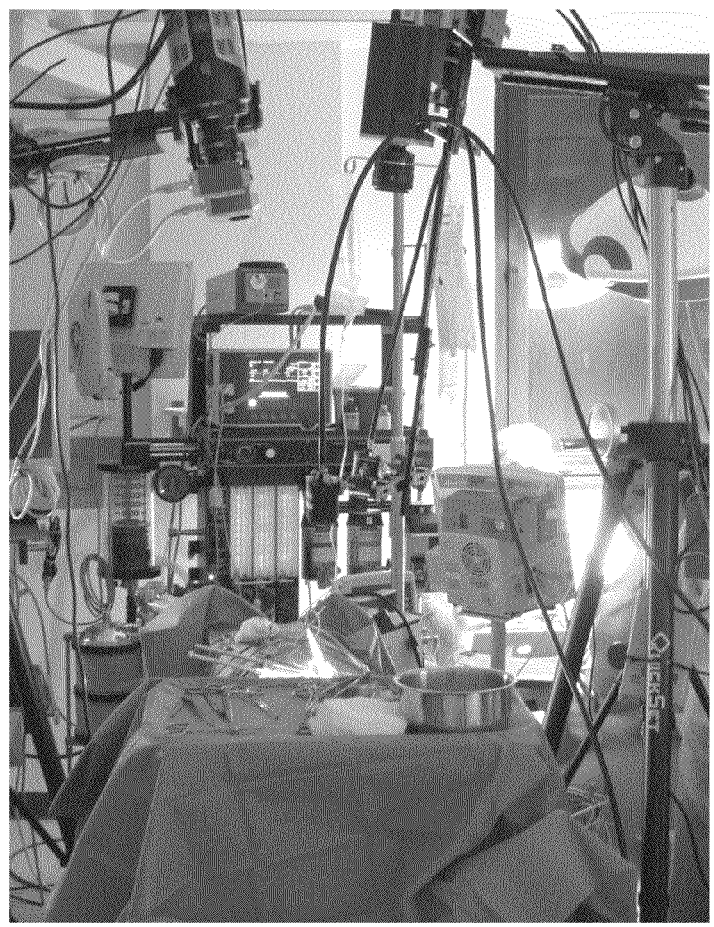
FIG. 60 is an image of a hyperspectral imaging setup in animal lab surgical suite at UTSW for imaging porcine partial nephrectomy.

After anesthetizing each subject according to protocol, the surgeon approached the right kidney through an open midline incision and pulled the peritoneum away from the visible surface of the kidney. While the surgeon exposed the kidney, background cubes for both illumination methods are acquired in a dark corner of the surgical suite. The DLP HSI tripod was then abutted to the surgical bedside (See FIG. 60) and the friction head was adjusted so that the exposed kidney is fully visible in the camera's FOV. The wheels of the tripod dolly were locked in place so that all images are acquired from the same angle and distance. 'Control' hyperspectral image cubes are acquired and processed by spectral sweep and "3 Shot" methods as in the finger occlusion test described above. The surgeon then dissected the hilem and clamped either the artery only (AO) or the artery and the vein (AV) with a curved Satinsky clamp.

The renal vasculature remained occluded for one hour before removing the clamp. Spectral sweep 'Occluded' image cubes are acquired and processed in approximately 5 minute intervals throughout the occlusion. "3 Shot" image cubes were acquired and processed continuously during application of the clamp, several times during the hour of occlusion, and continuously during removal of the clamp. After one minute of reperfusion, spectral sweep 'Reperfusion' image cubes were acquired at 5 minute intervals for 30 minutes. Following ischemia and reperfusion of the right kidney, the identical procedure was carried out on the left kidney using the opposite clamping technique. During the procedure, the subject's rectal temperature was maintained between 37° C. and 39° C. and its serum oxygenation, as measured by a pulse oximeter on the animal's ear, was kept between 98% and 100%.

Percent $HbO_2$ was measured over a uniform 81 pixel area chosen from the center of each kidney at each time point during the study. An average of the pixels for each region was calculated along with a standard deviation for each image cube. Images from each 10 minute time frame during ischemia were grouped as a single dataset in order to determine differences between AV and AO clamping conditions at each of six time periods. A regression model was fit to the individual levels using SAS statistical software (SAS Institute, Cary, N.C.) in order to determine whether there is a statistically significant difference between clamping methods with regard to kidney tissue ischemia over a period of one hour.

Real-time progression of ischemia and reactive hyperemia was measured in a 225 pixel area for all of the "3 Shot" output bitmaps acquired during tightening and removal of the Satinsky clamp in one pig subject. The mean pixel value in each image's sample area was plotted as a function of the time the output image was originally processed. This plot showed the transient behavior of the initial decline of percent $HbO_2$ after occlusion and the extent of reactive hyperemia after the occlusion is removed. It is unknown whether these immediate transient effects will be different between AV and AO clamping.

Figure 61:
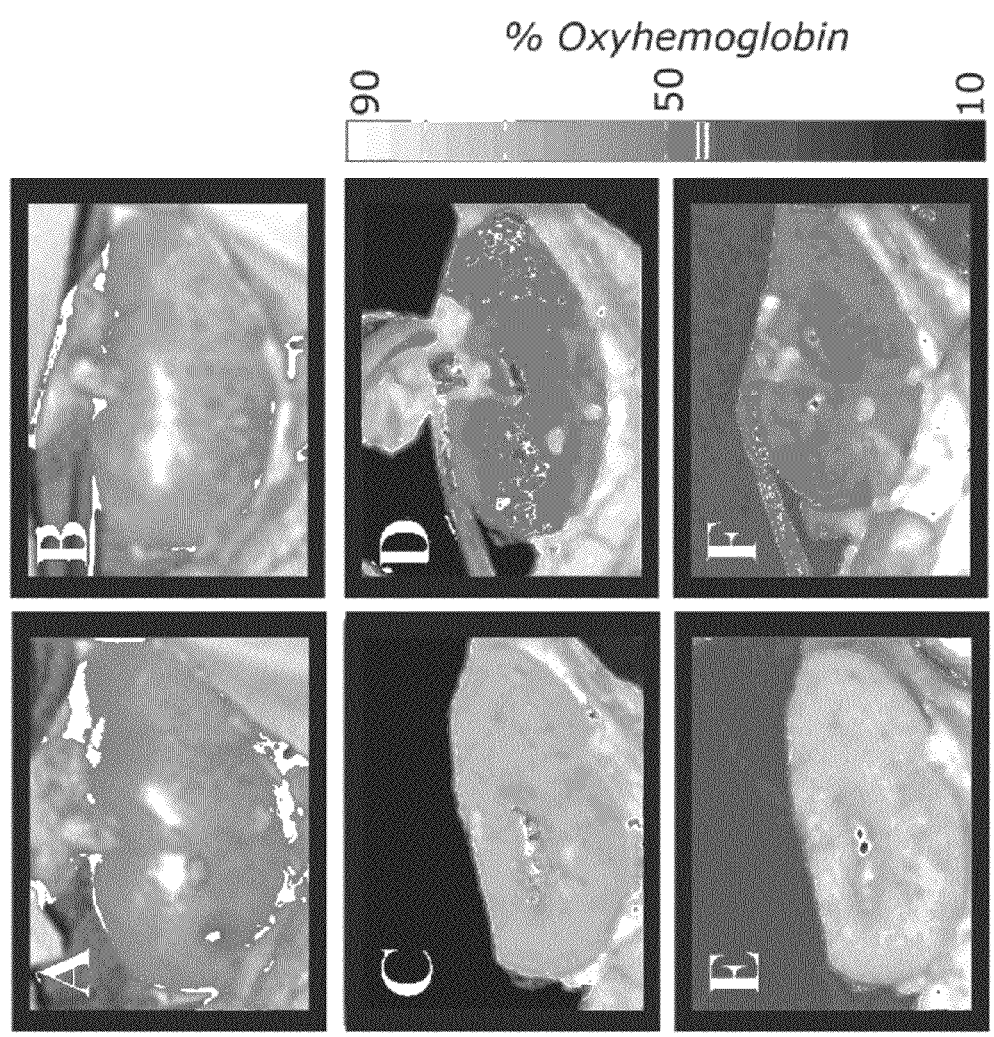
FIG. 61A is an image of a kidney showing a 'Control'.
FIG. 61B is an image of a kidney showing 'Occluded'.
FIG. 61C is a spectral sweep image of a kidney showing a 'Control'.
FIG. 61D is a spectral sweep image of a kidney showing 'Occluded'.
FIG. 61E is a "3 Shot" image of a kidney showing a 'Control'.
FIG. 61F is a "3 Shot" image of a kidney showing 'Occluded'.

In the porcine kidney studies, "3 Shot" images appear similar to spectral sweep images (See FIG. 61). Comparing FIGS. 61C and 61D to FIGS. 61E and 61F, the relative tissue oxygenation is the same for both illumination methods. It is obvious that between 'Control' and 'Occluded' states there is a drop in surface oxygenation for the renal unit, but the surrounding muscle and adipose tissue remains highly oxygenated. The major difference between spectral sweep and "3

Shot" processed images is the threshold vector by which the final image is mapped to percent $HbO_2$. For the spectral sweep method, the spectral information stored in the 126 slice data cube allows a wider range of values, so the background is truly blue, representing virtually no oxygenation. For the "3 Shot" method, the range of pixel values in a processed image is much less than that for a spectral sweep image, so a tighter threshold must be applied to visualize the same contrast. This tighter threshold causes the mapped percent $HbO_2$ values to be slightly different than those mapped in the spectral sweep images, so the detectable range and resolution of percent $HbO_2$ may be less with the "3 Shot" method than with the spectral sweep method.

The overall trend of pixel intensities in "3 Shot" output images is identical to the trend of spectral sweep images and matches the expected oxygenation trend. Therefore, "3 Shot" output images are sufficient for mapping the spatial distribution of tissue oxygenation over time. For the first three pig subjects, continuous acquisition of "3 Shot" images during application and removal of the Satinsky clamp was not performed because the primary concern was capturing quality images to test hour long effects of clamping. Before imaging the fourth pig subject, data from the other subjects indicated that a majority of tissue chemistry changes occur during the first minute after clamping and during the first few minutes after removing the clamp. So, for the fourth pig subject, continuous "3 Shot" images are acquired during both critical time periods for each kidney.

Figure 62:
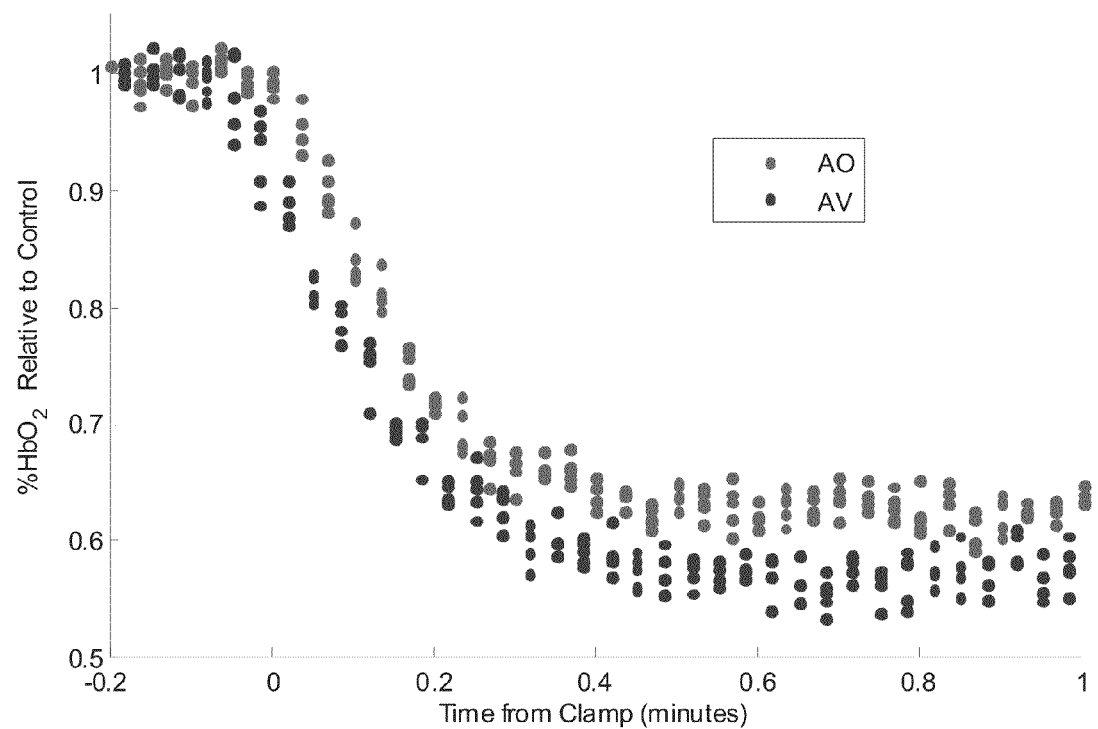
FIG. 62 is a graph plotting monitoring the time progression percentage of oxyhemoglobin perfusing the kidney before and during renal AO and AV occlusion.

A 225 pixel area from the center of the kidney is averaged in each image and divided by the average of the same area for the first 20 control images to result in the percent $HbO_2$ relative to control. In FIG. 62, this value is plotted for the kidney clamped AO (n=247) and for the kidney clamped AV (n=217) for 12 seconds prior to tightening of the clamp and about one minute following application of the clamp. For the first 10 seconds of occlusion both methods of clamping result in a linear decline of oxygenation. The transient response then becomes non-linear, and flattens after 30 seconds in both cases. There is a zero-order time delay between the two responses, with the AO decline lagging behind the AV decline. This lag may be due to the flow of blood through the renal vein, which would not occur under AV clamping. There is also a steady-state difference between the oxygenation levels, with AO being higher than AV.

The "3 Shot" outputs acquired during the removal of the Satinsky clamp are analyzed using the same procedure for the AO clamped kidney (n=1540) and the AV clamped kidney (n=269). Images are continuously acquired until it visually appears that there is no longer any fluctuation in kidney oxygenation levels. From the number of images in each case, it is apparent that visual fluctuations cease more quickly in the AV case than in the AO case. Another interesting observation is that the AO case has an overshoot of oxygenation associated with reactive hyperemia and then declines to a steady state lower than its control value, and lower than the AV steady state. This may be a potential detriment to clamping the artery only instead of the artery and the vein. Perhaps, there is a longer term oscillation that is not captured due to lack of images in the AV case.

Figure 63:
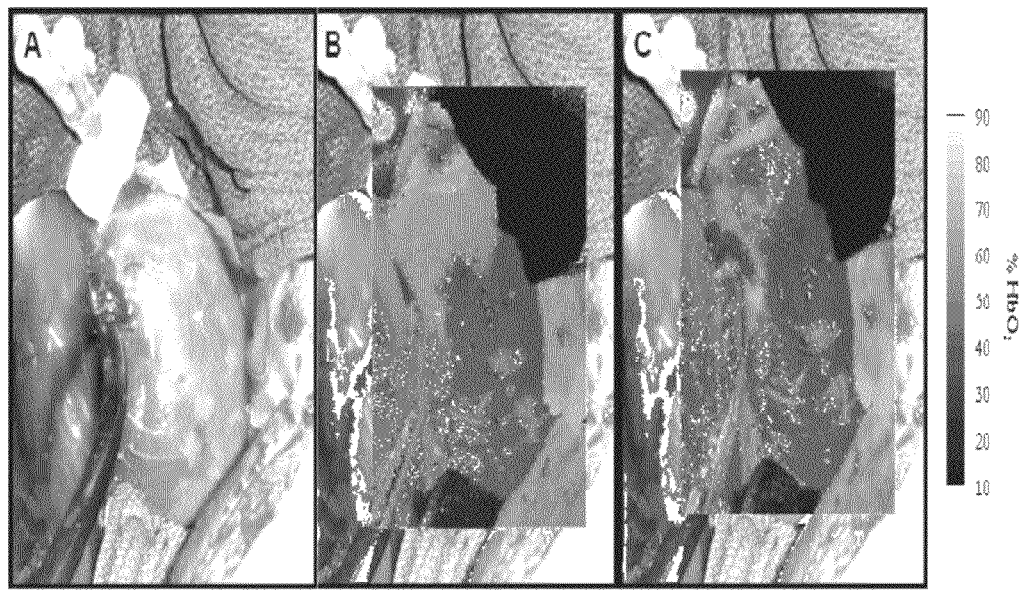
FIG. 63A is a raw image of a bilateral ischemia exhibited in a pig kidney having two renal arteries taken immediately after clamping one renal artery.
FIG. 63B is an image of a bilateral ischemia exhibited in a pig kidney having two renal arteries taken with the "3 shot" method after clamping one renal artery showing that the lower pole is ischemic, but the upper pole is still highly oxygenated.
FIG. 63C is an image of a bilateral ischemia exhibited in a pig kidney having two renal arteries taken with the "3 shot" method after clamping the second renal artery showing that the upper pole becomes ischemic as well.

An unanticipated advantage of near real-time "3 Shot" images showing the surgeon the spatial distribution of tissue oxygenation is illustrated when clamping fails to cause the entire kidney to become ischemic. In pig 3, the surgeon clamped the renal vasculature AO as in previous pig subjects. Raw views of the kidney seem to imply the clamping is successful (See FIG. 63A), but as the surgeon watches the real-time "3 Shot" output display in the GUI, he notices that the upper pole is still highly oxygenated but the lower pole has become ischemic (See FIG. 63B). This prompts a re-examination of the renal vasculature, in which the surgeon finds a second artery supplying oxygenated blood to the renal unit. Apparently, in this case, the clamped artery supplies blood to the lower pole, and an unclamped second artery supplies blood to the upper pole. Upon clamping the second artery, the upper pole also becomes ischemic, but never reaches the same level of ischemia as the initially occluded lower pole (See FIG. 63C). Therefore, the DLP HSI can also be used to determine the precise tissue areas that are supplied by an artery, which helps surgeons to know which arteries to occlude during partial nephrectomies.

Hyperspectral imaging with the DLP HSI is useful for comparing competing renal vasculature clamping methods with regard to kidney tissue oxygenation during nephron-sparing surgery. Analyzing spectral sweep images indicates that the percent $HbO_2$ of the kidney is higher when the artery only (AO) is clamped than when the artery and vein (AV) is clamped between 10 and 40 minutes. Images from other time periods indicate no difference in percent $HbO_2$ between AO and AV clamping. The spectral sweep image cubes captured by the prototype system visualize the same spatial oxygenation map as other hyperspectral imaging systems, even though the spectrum measured at each pixel is not always consistent between systems.

Generating "3 Shot" output images at 3 frames per second allows the surgeon to visualize real-time physiologic changes in tissue oxygenation. This is useful in determining whether or not blood flow is adequately inhibited from the entire kidney. Analyzing "3 Shot" images captured during the process of tightening and releasing the clamp shows the transient response of renal tissue at the onset of ischemia and during reactive hyperemia. Though only one subject was sufficiently imaged during this time period, it appears that AV clamping may be advantageous to AO clamping when immediate ischemia or no hyperfusion is desired.

The following discussion is related to similar studies performed on human subjects. Animal studies are necessary to ensure the safety and utility of prototype medical devices, but the end use of the DLP HSI is for human imaging, so its utility in live human surgeries must also be tested. An Institutional Review Board (IRB) approved protocol at UTSW permits the prototype hyperspectral imaging system to image open cavity partial nephrectomies in human subjects.

The following methods were used in the human studies. The surgical procedure for humans is different than that for the porcine study, because human subject survival is of the utmost importance. The surgeon makes an incision in the side of the subject to expose the kidney. 'Control' hyperspectral data cubes are acquired with the DLP HSI in spectral sweep and "3 Shot" modes. Then, the surgeon clamps the renal vasculature with a predetermined method (AO or AV) to occlude blood flow to the kidney. 'Occluded' hyperspectral data cubes are acquired at non-critical points in the surgery, when the surgeon allows all other room lights to be turned off. After the kidney is sufficiently bereft of blood to prevent hemorrhage, the surgeon removes the tumor and stitches the exposed renal tissue closed. One more 'Occluded' data cube is acquired before the clamp was removed. The surgeon removed the clamp, and 'Reperfusion' hyperspectral data cubes are acquired prior to closing the abdominal cavity.

To date, three human subjects have been imaged. The following results section is focused on the first of these human subjects. The subject is an otherwise healthy male, about 60 years old, with a tumor on his right kidney.

In human surgery, the room lights and operating lights cannot be switched off for minutes at a time as is possible during animal surgeries. Therefore, only one spectral sweep data cube was captured as a control to verify the image results of the "3 Shot" illumination method. Subsequent hyperspectral images were captured with the "3 Shot" method so that the room and operating lights only remain off for several seconds.

Figure 64A:
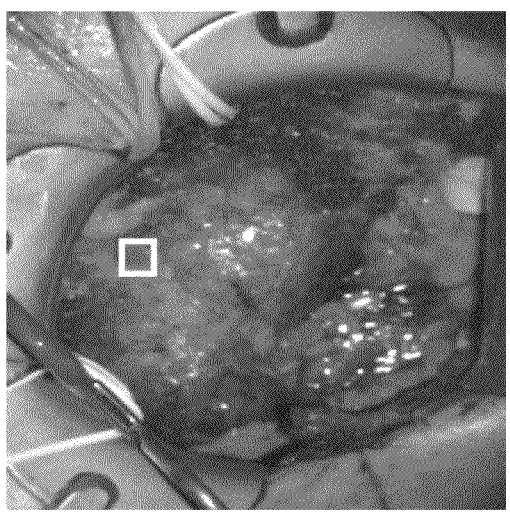
FIG. 64A is a raw image of a human kidney having partial nephrectomy.
Figure 64B:
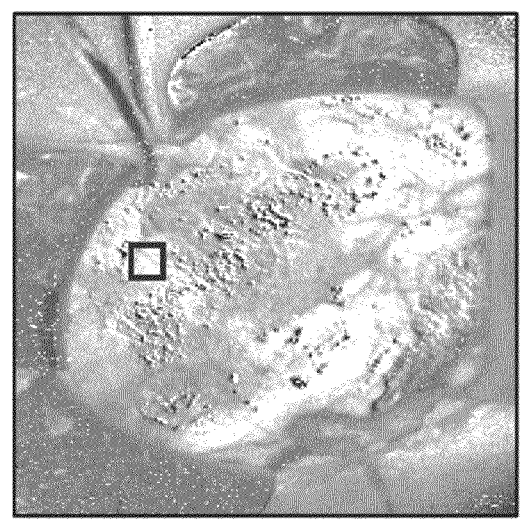
FIG. 64B is an image of a human kidney having partial nephrectomy taken using the "3 Shot" method before clamping.
Figure 64C:
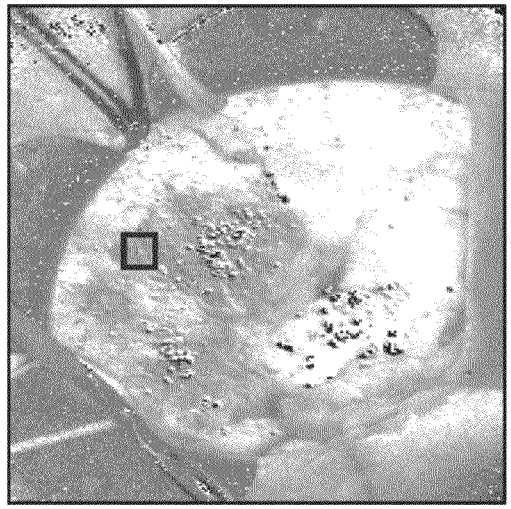
FIG. 64C is an image of a human kidney having partial nephrectomy taken using the "3 Shot" method immediately after clamping.
Figure 64D:
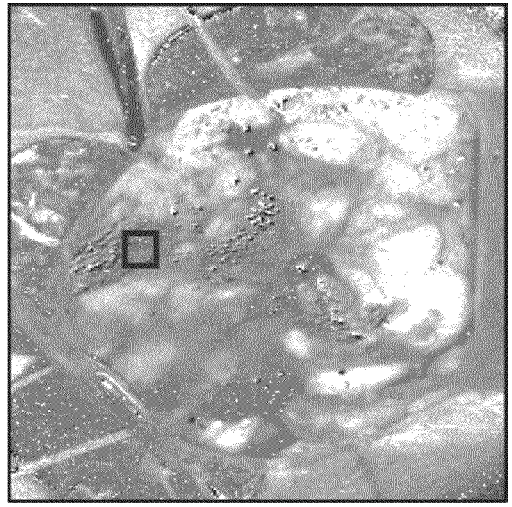
FIG. 64D is an image of a human kidney having partial nephrectomy taken using the "3 Shot" method after the tumor is removed and still clamped.
Figure 64E:
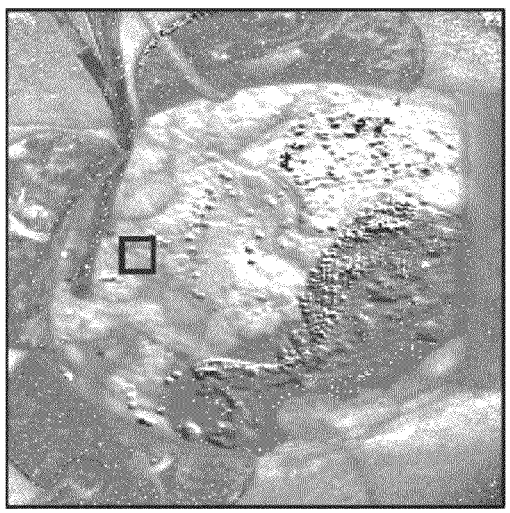
FIG. 64E is an image of a human kidney having partial nephrectomy taken using the "3 Shot" method immediately after clamping.
Figure 64F:
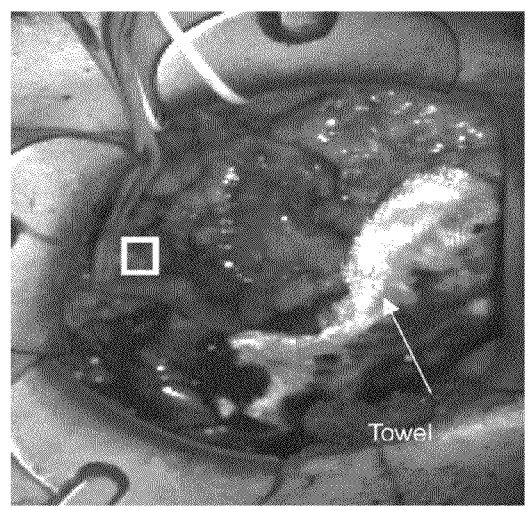
FIG. 64F is an image of a human kidney having partial nephrectomy taken using the "3 Shot" method after dissection.

View finder pictures of the kidney show the gross anatomy before and after the tumor is removed, and "3 Shot" image outputs show the relative oxygenation of the kidney throughout the surgery. In FIG. 64A, the blue sample area highlights a uniform region of the kidney tissue. The sample area is used to trace the trend of oxygenation throughout the surgery.

Hyperspectral images are acquired at five different time points during the surgery. One of the images is unreliable due to light pollution from the headlamp worn by the surgeon, and the other four images are shown in FIGS. 64B-64E. In the 'Control' image, FIG. 64B, the kidney is highly oxygenated and the spatial distribution of tissue oxygenation is fairly uniform. In the first 'Occluded' image, FIG. 64C, most of the kidney exhibits lower oxygenation levels. After the tumor is removed and the clamp is still tightened, FIG. 64D, the kidney shows decreased oxygenation levels in all areas. When the clamp is finally removed, FIG. 64E, the kidney oxygenation levels return to near those measured in the 'Control' image.

Figure 65:
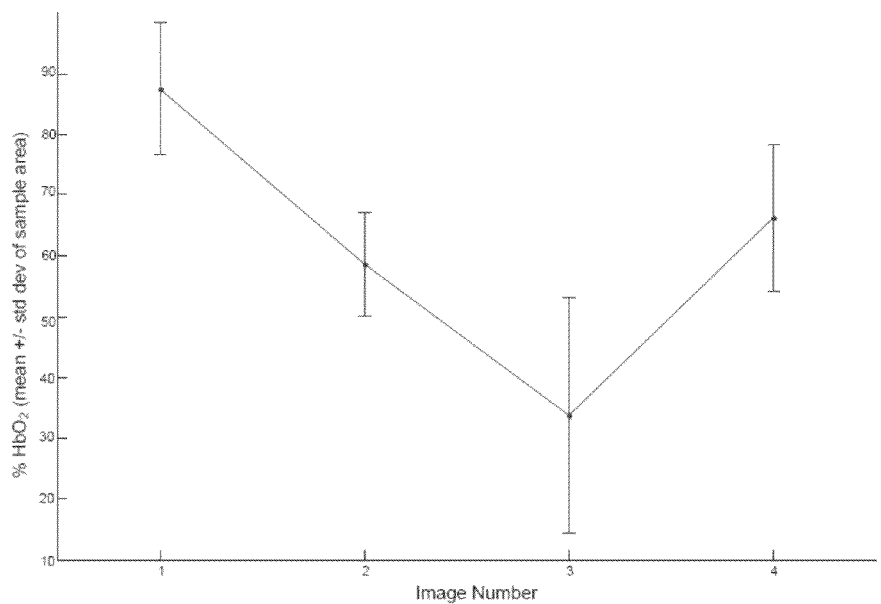
FIG. 65 is a graph showing the progression of relative oxygenation measured from output images in FIGS. 23B-23E.

In FIG. 65, the average and standard deviation of the 81 pixel values in each sample area are plotted to show the trend of oxygenation throughout the surgery. The overall trend implies that the kidney becomes most ischemic in image three and then recovers to a level similar to control.

The DLP HSI can successfully map the spatial distribution of tissue oxygenation during a human partial nephrectomy. Light pollution from the operating room lights and the surgeons head lamp interferes with hyperspectral imaging, so fewer images can be captured in human cases than in animal cases. However, the "3 Shot" output images acquired during the human study are useful for the surgeon to visualize which areas of the kidney are higher and lower oxygenated. Analysis of many more subjects is needed in order to compare AO versus AV clamping in human nephron-sparing surgeries.

Nerve damage may be correlated to the loss of blood flow in the surrounding tissue bed. To diagnose nerve damage in the lower limb of patients, physicians probe the leg with a mechanical or electrical prick and ask the patient if they can feel it. If the patient cannot feel the prick, that area is diagnosed as neuropathic. This process is time consuming, and the spatial resolution of the diagnosed neuropathy is a function of the number of discrete point measurements made by the physician. With the DLP hyperspectral imaging system it may be possible to map the spatial distribution of neuropathy along the entire lower limb by mapping its tissue oxygenation.

The following discussion is related to measurements of lower limb neuropathy. A clinical study is devised to test the utility of hyperspectral imaging for monitoring wound care in amputees and for studying their neuropathy. Amputees and patients exhibiting lower limb neuropathy are voluntarily enrolled in the clinical study at a weekly wound care clinic in the Dallas Va. After signing the consent forms, each subject is seated in a room reserved for hyperspectral imaging, the overhead lights are turned off, and the DLP HSI is used to capture spectral sweep and "3 Shot" images along the entire limb of interest.

To date, five human subjects have been enrolled in the study. The following results section is focused on the first of these human subjects. The subject is a male over 50 years old who has previously been diagnosed with neuropathy in the lower half of his left leg, as measured by the prick test.

Figure 66:
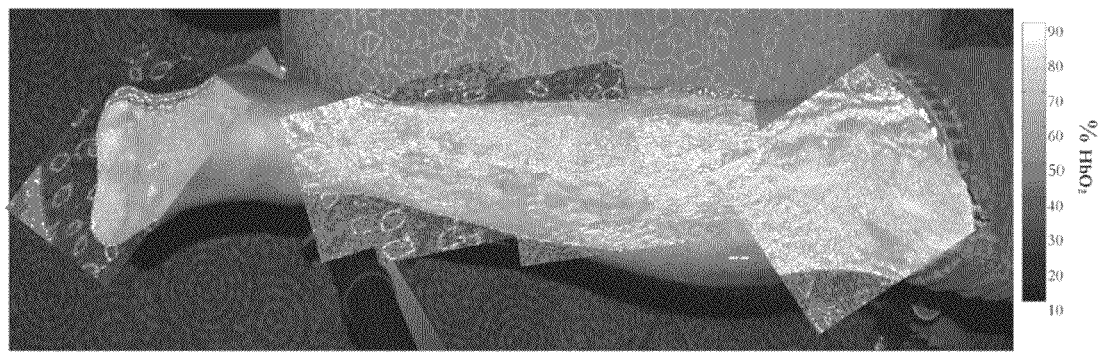
FIG. 66 is a digital image of a full leg with a superimposed spectral sweep image mapping the surface oxygenation of a patient with lower limb neuropathy.

Spectral sweep and "3 Shot" hyperspectral image cubes are acquired from the subject's toes to his knee in the lower limb's frontal plane. The output images color-coded for percent $HbO_2$ with the "3 Shot" method shows similar relative oxygenation levels to the color-coded outputs of the spectral sweep method. Overlaying the spectral sweep images on a picture of the subject's leg creates a surface tissue oxygenation map for the entire leg (See FIG. 66).

Due to the curvature of the ankle, the detected absorbance images captured between the foot and the shin contain an unreal intensity gradient and are not shown. Those images unsuccessfully predicted the spatial map of tissue oxygenation, emphasizing an important constraint of the prototype: the topography of the tissue being imaged. Tissue planes further from the camera and light source optics may appear less oxygenated than closer tissue planes, when their real oxygenation is the same.

Figure 67:
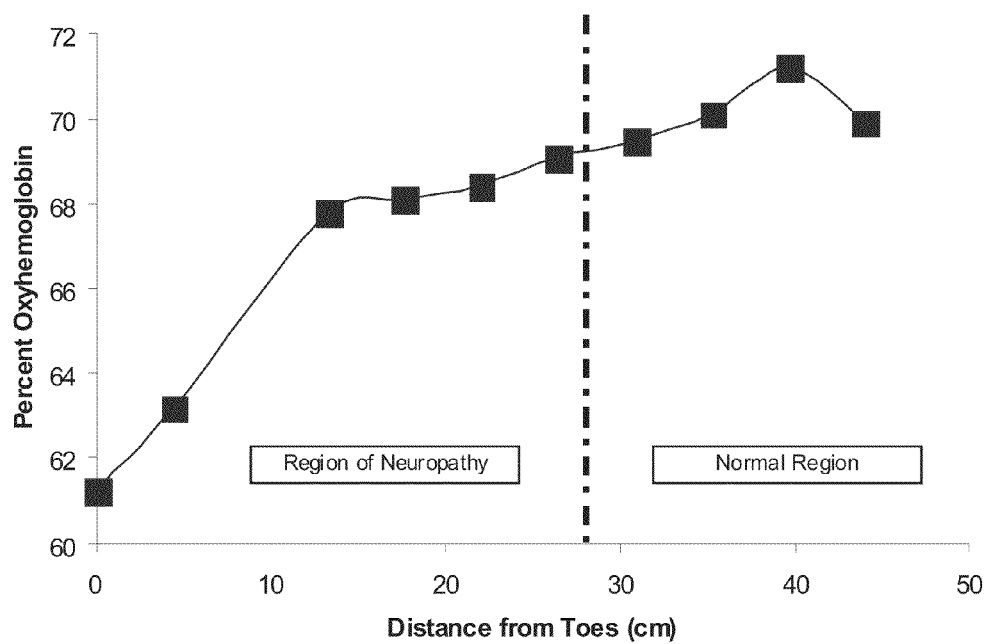
FIG. 67 is a graph showing the spatial progression of surface oxygenation as measured along the centerline of the leg in the hyperspectral images in FIG. 66 wherein the dashed line represents the limit of neuropathy as determined by a physician administering a clinical nervous response exam on the leg.

It is difficult to see any difference in oxygenation from the bottom half of the leg to the top half of the leg in the images alone. A sample area of pixel values along the midline of the leg is plotted versus the axial distance from the toes (See FIG. 67) to quantify this difference. This plot indicates that there is an increase in surface tissue oxygenation progressing from the toes to the knee. However, this increase does not seem to match the results of the prick test. If surface tissue oxygenation mimics underlying neuropathy, there should be a jump in oxygenation between the region of neuropathy and the normal region, but the hyperspectral images do not show this jump. This emphasizes another important constraint of the prototype: the depth of the tissue being imaged. The DLP HSI relies on measuring the absorbance of light in the visible wavelength range, and visible light does not penetrate deep into the tissue, so the measured percent $HbO_2$ is only indicative of epithelial tissue oxygenation. Epithelial tissue is highly regulated and its oxygenation levels do not correspond to neuropathy like deeper tissue oxygenation does. Development of a prototype that operates in the near infrared wavelength range may be useful for visualizing deeper tissue oxygenation.

The DLP HSI is useful for mapping the spatial distribution of tissue oxygenation for areas that are larger than the field of view of the camera. Several image cubes are captured in overlapping regions, and the resulting output images are overlain to create a large spatial map.

When acquiring images with the DLP HSI, it is important to know the topography and depth of the tissue of interest. The tissue area should be a uniform distance from the system's detector and light source illumination optics to eliminate unreal effects of distance on measured percent $HbO_2$. The tissue of interest should also be on the surface of the subject (e.g., epithelium), since visible light does not penetrate past the surface layers of tissue. In the case presented, epithelial oxygenation does not seem to correlate exactly with neuropathy, but a larger sample size is needed to confirm these results.

The following discussion is related to measurements taken during brain surgery. Neurosurgeons investigate brain behavior by dissecting the scalp and viewing the cerebral cortex with surgical microscopes. Current imaging only visualizes the physical anatomy of the cortex, or by introducing dyes as contrast agents some functionality can be visualized. Point measures of cerebral $HbO_2$ content are possible with near infrared spectroscopic techniques, but they do not show a spatial image of oxygenation. (See Quaresima, V, Sacco, S, Totaro, R, Ferrari, M, Noninvasive measurement of cerebral hemoglobin oxygen saturation using two near infrared spectroscopy approaches. 2000; 5:201-205.) By coupling the DLP hyperspectral imaging system to a surgical microscope, neurosurgeons may be able to visualize the spatial profile of cerebral tissue chemistry.

The CoolSNAP HQ2 is directly mounted to the C-mount of a Zeiss surgical microscope at the UTSW animal laboratory, and the OL 490 liquid light guide is coupled to the microscope's ring illumination optics. After setting the focal distance of the microscopic system, a background cube is captured with the DLP HSI and the surgeon dissects a small cross-section of an anesthetized rabbit's scalp. Imaging through the optics of the microscope, the DLP HSI is set to continuously acquire "3 Shot" images of the exposed cortical tissue. Several seconds of control images are captured while an external pump supplies oxygen to the subject. Continuous "3 Shot" images are acquired while the external oxygen supply for the subject is cut off for a period of 20 minutes and turned back on.

Figure 68:
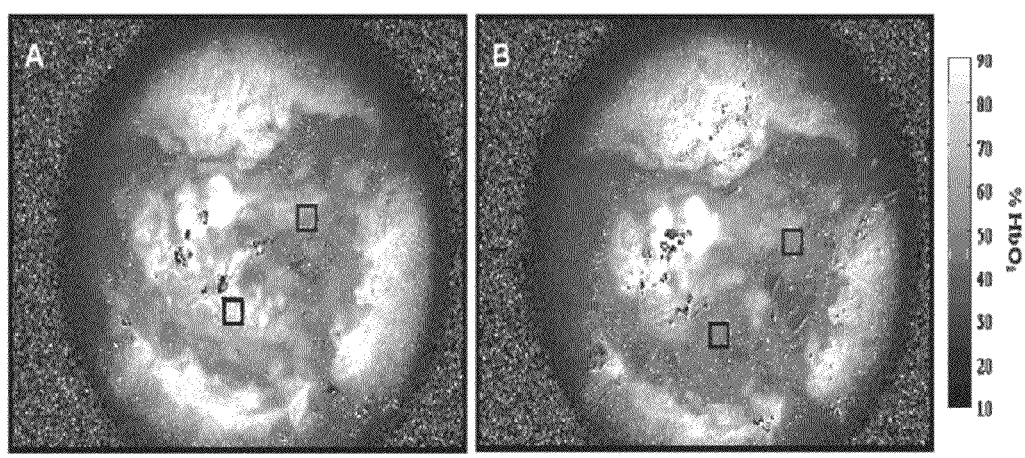
FIG. 68A is a control image of a rabbit brain taken with the "3 shot" method with the black sample area showing normal tissue and blue sample area showing damaged tissue.
FIG. 68B is an image of a rabbit brain taken with the "3 shot" method after oxygen supply is cut off to the rabbit wherein the normal tissue becomes ischemic and there is no change in the damaged tissue.

Watching the spatial distribution of tissue oxygenation, and drawing from his own experience, the surgeon notices one area of the exposed cortex is damaged at the beginning of the imaging session. In FIG. 68A, the central region is the cortical tissue and the three red regions around the circumference are scalp and other tissues. The black sample box surrounds an area of healthy brain tissue and the blue sample box surrounds an area of damaged brain tissue. In the control image, the damaged tissue appears ischemic compared to the normal tissue's level of oxygenation. There are no noticeable changes in the damaged tissue oxygen levels shown in the hyperspectral images during the period of external oxygen cutoff. However, after the oxygen is cut off for several minutes, the normal brain tissue begins to show ischemia as indicated by the lower percent $HbO_2$ in the black sample area of FIG. 68B.

Initial brain imaging with the DLP HSI coupled to a Zeiss surgical microscope suggests neurosurgery is another viable application for this novel medical imaging platform. The digital visualizations of oxygenation generated by hyperspectral imaging correspond with what the surgeon expects to see. Even though conclusive medical results cannot be derived from the initial imaging session, the results indicate that DLP HSI can enable surgeons to visualize cerebral tissue chemistry in near real-time.

In view of the foregoing description of the present invention, it should be appreciated that a variety of procedures and diagnostic techniques may be improved by incorporation of the present invention. The following discussion describes some of such procedures and diagnostics techniques. This discussion is not intended to limit the scope of the invention as set forth in the appended set of claims.

There are a variety of applications of hyperspectral imaging of the retina. For example, measuring oxygenation of the retina as may be effected by diabetic retinopathy, central retinal vein occlusion, branch retinal vein occlusion, central retinal artery occlusion, branch retinal artery occlusion, sickle cell retinopathy, retinopathy of prematurity and retinal vascular inflammatory diseases. Diabetic retinopathy is the most common cause of new cases of blindness in adults 20-74 years of age. Retinal vascular occlusions, sickle cell retinopathy and retinopathy of prematurity can also lead to irreversible severe visual loss. These conditions often lead to retinal ischemia and subsequent retinal neovascularization with the associated blinding complications of retinal detachment, vitreous hemorrhage and neovascular glaucoma. Laser photocoagulation of the peripheral retina can markedly reduce the risk of these complications. Targeting the areas of retina that are suffering from ischemia improves the clinical outcomes while reducing peripheral visual field loss. Furthermore, these conditions can also lead to macular edema (i.e., swelling of the central retina) and macular ischemia. Distinguishing between these two causes of visual loss helps to target patients that would benefit from light macular laser therapy versus pharmacologic interventions. Traditionally, fluorescein angiography (FA) has been used to evaluate for both peripheral retinal ischemia and macular ischemia. However, FA is painful, has risks associated with intravenous injections, leads to discoloration of the skin for twenty four (24) hours, can lead to allergic reactions of all degrees of severity, often leads to nausea and vomiting, and may be impossible to perform in patients with poor vein access. Furthermore, the technique evaluates vascular flow and permeability rather than retinal oxygenation. It is believed that hyperspectral imaging of the retina measuring oxyhemoglobin and deoxyhemoglobin may allow for earlier identification of areas of ischemia before permanent loss of capillary perfusion has occurred. It also would allow for a non-invasive determination of retinal oxygenation. This would speed up and simplify the process of obtaining this clinically important piece of information, while reducing the risk of complications and eliminating the associated pain and discomfort.

The present invention hyperspectral imaging system may also be used for measuring optic nerve oxygenation. Such information may be useful in evaluating such conditions as glaucoma, ischemic optic neuropathy and optic neuritis. It is believed that assessment of optic nerve head oxygenation may help diagnose patients with increased risk for glaucoma or ischemic optic neuropathy. It may also help differentiate between patients with ischemic optic neuropathy versus optic neuritis.

The present invention may also be used for measuring macular pigments thereby providing information regarding age-related macular degeneration and juxtafoveal telangiectasis. Age-related macular degeneration (AMD) is the most common cause of irreversible blindness in patients over sixty (60) years of age. Despite advances in therapeutics, clinical outcomes are still suboptimal. There is no effective therapy for atrophic AMD. Macular pigments including lutein and zeaxanthin are pigments that are present in the retina in the macular region. They absorb particularly harmful wavelengths of light (i.e., blue light) and protect the retina from phototoxicity. These pigments have been shown to decrease with age and more rapidly in patients with AMD and juxtafoveal telangiectasis. It is believed that the present invention provides an easy modality to measure the levels of macular pigments which in turn may help to identify patients that would benefit from dietary supplements with lutein before they develop clinical disease.

The present invention may also be used for measuring pigments in the retinal photoreceptors and retinal pigment epithelium thereby providing information related to retinitis pigmentosa and other hereditary retinal degenerations, e.g., age-related macular degeneration. Hereditary retinal degenerations and age-related macular degeneration lead to abnormalities in the photoreceptors and underlying retinal pigment epithelium (RPE). The health of the photoreceptors and the retinal pigment epithelium can be correlated to the levels of pigments (i.e., rhodopsin, lipofuscin and melanin). It is believed that the present invention will permit measuring these pigments accurately thereby allowing better monitoring of the clinical course in these patients. Moreover, it is believed that the present invention will also allow measurement of the response to prophylactic interventions. Finally, it is believed that the present invention may aid in the early diagnosis of these conditions or subclassification into clinically relevant subgroups due to its ability to obtain the foregoing measurements.

The present invention may also be used for the diagnosis of autoimmune retinitis, infectious retinitis and infiltrative neoplastic conditions. There are a limited number of physical changes that the retina can undergo in response to injury. The clinical presentation of retinal autoimmune infiltration (e.g., Wegener's granulomatosis, sarcoidosis, etc.), infectious retinitis (e.g., cytomegalovirus, toxoplasmosis and herpetic retinitis as in acute retinal necrosis or progressive outer retinal necrosis), and neoplastic infiltration (e.g., lymphoma and leukemia) can sometimes be indistinguishable from one another. In those cases, surgical intervention to obtain vitreous and/or retinal tissue for diagnostic purposes is often necessary. There are significant risks associated with this procedure. However, lack of therapy would often lead to blindness or loss of the eye. Furthermore, an erroneous diagnosis leading to an erroneous therapeutic intervention can precipitate acute exacerbation of the disease (e.g., treating a viral infection with steroids) or delayed diagnosis (e.g., anti-inflammatory therapy for a neoplastic condition) resulting in loss of vision, loss of the eye or progression of a life-threatening disease. It is believed that the present invention hyperspectral imaging system and methods can look for spectral signatures of pathogens thereby helping to ascertain a diagnosis in a non-invasive and rapid way.

The present invention may also be used for non-invasive evaluation of disease biomarkers. It has been said that the eye is a window to the body. The eye provides the clinician with an unobstructed view of vessels. This has for years allowed medical professionals to diagnose systemic conditions like diabetic and hypertensive retinopathy. It is believed that hyperspectral imaging will allow medical professionals to tap deeper into this invaluable resource. Not only can the spectrum of substances in the visible light spectrum be identified like oxyhemoglobin and deoxyhemoglobin. The spectral signatures of a wide range of biomarkers both in the visible and invisible light spectrum can also be identified. This will allow medical professionals to diagnose and non-invasively monitor a wide range of conditions, including but limited to depth of anesthesia during surgical cases, systemic intoxications, drug overdose, pancreatitis, liver disease, prostate and other cancers with known biomarkers, metabolic diseases, infectious diseases with pathogens that produce specific spectral signatures, etc. Furthermore, it is believed that it will allow medical professionals to discover new spectral signatures that correlate with common and uncommon diseases and that could serve as new biomarkers in the diagnosis and management of those conditions.

Moreover, the present invention may also be used to monitor the clinical course of battlefield blast injuries based on retinal vasculature diameter changes. It should be appreciated that the foregoing description of opthalmological applications are but some of the procedures and diagnostic methods that can be improved by the incorporation of the present invention hyperspectral imaging system and methods. For example, as discussed supra, real-time diagnostic measurements of the kidneys provides surgeons with never before available information to use during surgery.

Surgery is the mainstay treatment for patients diagnosed with kidney cancer. As such, removal of the tumor by either partial or total nephrectomy will inherently decrease renal function and risk the development or progression of chronic kidney disease. Chronic kidney disease (CKD) is prevalent in 11% of the adult population, including 17% of patients older than 60 years. It is associated with an increased risk of hospitalization, cardiovascular event, and mortality from any cause. In fact, patients with moderate kidney disease (CKD, stage 3-GFR<60 ml/min/1.73 m$^2$) have a 40% increased risk of cardiovascular events and 20% increased risk of death. As such, for patients who have been diagnosed with kidney cancer, most of which are over 60 years old and require surgery, preserving as much renal function as possible is the standard of care and may prevent cardiovascular morbidity and mortality.

As approximately 80% of renal tumors identified are small (i.e., Stage Ti which are typically <7 cm), kidney sparing surgery (e.g., partial nephrectomy) is the preferred technique to maximally preserve functioning kidney tissue. However, to comfortably and safely perform this procedure, the urologic surgeon routinely clamps the renal artery to stop blood flow to the kidney (i.e., ischemia). This improves visualization and minimizes blood loss. However, the resulting ischemia risks kidney injury so that surgeons often will cover the kidney with ice slush for 7-10 minutes prior to tumor excision in an effort to decrease kidney metabolism which is highly oxygen dependent (i.e., aerobic metabolism). Nevertheless, warm ischemia (i.e., no ice) of more than 20 minutes, and cold ischemia of more than 30 minutes can result in irreversible damage in the remaining kidney. Therefore, despite the good intent of preserving as much kidney as possible during cancer surgery, the patient and surgeon still risk decreased kidney function secondary to the surgical technique.

Thus, if partial nephrectomy can be performed with only partial occlusion of the renal artery such that the kidney still gets oxygen the kidney is less likely to suffer from irreversible kidney damage. Unfortunately, there is no guideline as to what degree should the artery be occluded and, more importantly, what is the minimum oxygen necessary to protect the kidney. This is critical information since incomplete artery occlusion could increase blood loss and diminish visualization during surgery. Although the ability to monitor tissue oxygen levels in real-time is now available using tissue probes that are often used in neurosurgery, the present invention hyperspectral imaging system and methods provides a viable and effective alternative to these probes. Additionally, the present invention, unlike the probes, provides such information in a non-invasive manner. As described above in view of the porcine and human studies, using the present invention which includes advanced camera technology and novel software, light reflected off the surface of an imaged tissue or organ can be used to measure oxygen levels. This is an improvement over existing tissue oxygen monitors which must use a needle probe and can only measure oxygen at one location. Incorporation of oxygenation and blood flow monitoring technology in partial nephrectomy can warn surgeons when oxygen levels are dangerously low and perhaps guide them in how long and to what degree the renal artery is partially or completely clamped. Recent laboratory data gathered using an animal model has demonstrated that 50% occlusion of the renal artery maintained kidney oxygen levels longer and at higher values during partial nephrectomy. Though blood loss was increased slightly, it did not increase operative time or surgery difficulty. Most importantly, when compared to conventional partial nephrectomy, the cases where tissue oxygen levels were higher (e.g., 50% artery occlusion) had less immediate and sustained kidney dysfunction after surgery. In view of the foregoing, it is believed and shown in part above that the present invention hyperspectral imaging system and methods can be used to monitor the vascular blood flow and monitor tissue oxygen in clinical use and determine if kidney function can be protected and improved when performing partial nephrectomy with real-time monitoring of kidney oxygen levels.

The present invention will thus ensure that the recovery of kidney function after partial nephrectomy will be improved by real-time monitoring and minimization of the ischemic insult routinely incurred. This present invention has the potential to alter the way kidney surgery for cancer is performed. The preservation of renal function during and after partial nephrectomy would be incrementally improved benefiting many patients with compromised kidney function.

The present invention may also be used to monitor, analyze and diagnose blast brain injury (BBI) and traumatic brain injuries (TBI). Overpressure brain injury is one of the most common injuries experienced by soldiers. Soldiers are exposed to various levels of blast pressure ranging from relatively low pressure that occurs from firing of weapons systems to very high pressures that occur from explosions of IEDs and mortar rounds. Damaging pressure waves are magnified by reflection from adjacent structures or the ground resulting in exposure of human tissues to extremely high pressure. Pressure can also be transmitted to the brain via the thorax when body armor is struck by high velocity projectiles.

Blast pressures can cause neural injury by several mechanisms. Pressure waves can cause substantial pulmonary injury with alveolar disruption. High pressure air injected into the blood can cause air emboli resulting in brain ischemia. Brain tissues can be injured directly from pressure waves passing through the cranial vault. High pressure can also be transmitted to the brain through the blood when high pressure occurs in the thoracic cavity. Lastly, brain function may be depressed by circulating metabolites and cytokines that are released into the blood stream by non-neural tissues that are injured by the blast wave.

Monitoring the severity and progression of blast-induced brain injury is critical to ensuring optimal care for wounded soldiers. The present invention can be used in the battlefield to objectively assess the degree of these injuries to facilitate appropriate triage of soldiers exposed to explosions. The present invention can scan the retina to detect appropriate biomarkers associated with the brain injury and determine the extent of injury.

The present invention may take one of several embodiments for performing the foregoing analysis. A direct fundoscope will enable imaging of the retina to examine for retinal hemorrhage. This system may be augmented to wirelessly connect to trained personnel in any location in the world who can interpret these images. Alternatively, hyperspectral measurements of retinal oxygenation may be taken with the present invention. It is known that retinal hyperemia is associated with blast injury and therefore overall and regional differences in retinal oxygenation can be measured. Moreover, measurement of air emboli may be taken with the present invention. Air emboli have been implicated as a cause for blast injury associated brain injury. Using the present invention, air bubbles in the retinal arterial blood supply may be identified and quantified. Further, it is believed that hyperspectral images of corneal surface blood vessels provide another means for analyzing traumatic brain injury.

Lastly, the present invention may be used to measure blood chemistry. Blast injuries cause widespread tissue damage resulting in elevated serum levels of leukotrienes C4, D4 and E4 and of 6-keto-PGF1 alpha and TxB2, the stable products of prostacyclin (PGI2) and thromboxane A2 (TxA2). These substances are elevated to a much greater extent in blast injury than blunt head trauma suggesting that these and other chemicals may serve as specific markers for the presence, extent and progress of blast injury to the brain. The eye can serve as a window to the microcirculation. Using visible spectroscopy, chemicals in the blood will be detected and quantified in the retinal microcirculation. It is believed that the chemical environment of the retinal microcirculation correlates to the magnitude of brain dysfunction experienced after blast injury. This complex chemical environment will be manifested as complex spectra that will be unique for the blood chemical environment associated with various stages of blast injury. It is further believed that the statistical classification of these spectra will enable the diagnosis and characterization of various stages of blast injury.

Further diagnosis may be performed by a near infrared version of the present invention. Such a system will enable chemometric assessment of tissues as deep as 1 centimeter and provide more informative spectral information than exists in the visible light range. This system will enable imaging of the retina and may provide information about blood flow changes in the face that occur as a result of blast injury. In a further embodiment, the present invention may include an infrared imaging system operating in the thermal range (5-15 micron) that will facilitate tissue spectroscopy in the wavelength range where molecular vibrations attenuate infrared energy. Attenuation of black body radiation by molecular vibration will enable development of scanning devices that will detect blood and tissue chemical composition with a high degree of discrimination for various disease states. It is believed that minor changes in blood chemistry associated with various disease states will result in highly unique spectral signatures in this region of the electromagnetic spectrum.

The foregoing measurements may be obtained by combining a conventional fundus camera and the present invention hyperspectral imaging illumination system.

A further embodiment of the present invention provides a convenient means for threat detection. The present invention hyperspectral imaging system provides for the detection of pathogens and poisons on surfaces of equipment, assembly lines, etc. For example, the present invention may be used to screen a food supply for toxic agents, e.g., salmonella (which has a known strain-specific IR spectra), anthrax, botulina, small pox, E. coli, shigella, etc. Further the present invention may be used to detect various chemicals, such as, organophosphates pesticides, ricin toxin, sarin, soman, tabun or VX gas.

A novel hyperspectral imaging system has been developed for real-time, non-invasive, in vivo imaging of tissue chemistry in surgical and clinical applications.

Using a spectral light engine to illuminate with simple narrow bandpasses or complex broadband spectra and a CCD FPA to detect the reflectance image from a tissue sample, the DLP hyperspectral imaging system remotely visualizes tissue oxygenation in live human and animal subjects. Illuminating with many narrow bandpasses in the spectral sweep mode results in large data cubes with full spectral information for each pixel in the image, but requires 20 to 30 seconds to generate a single chemically-encoded image. Spectral sweep data cubes acquired with the DLP HSI match those captured by LCTF-based hyperspectral imagers, which, along with color tile calibration results, validates the DLP HSI prototype as an imaging spectrophotometer. Illuminating with only three complex broadband illuminations in the present invention "3 Shot" mode results in small data cubes with adequate spectral information to generate chemically-encoded images identical to the spectral sweep images at a much faster rate, i.e., 3 processed images per second. Typically, the wavelengths to be used depend on the tissue type due to the penetration of tissue depth. For example, in visible spectra, $HbO_2$, $Hb$, $HbCO_2$ can be measured. In near-infrared (NIR)

spectra, $HbO_2$, Hb, water and lipids can be measured. As shown in FIGS. 69A through 69C, the present invention can provide chemically encoded images. FIG. 69A shows an image of a human hand which has experienced a burn. FIG. 69B shows a hyperspectral image of the hand from FIG. 69A displaying chemically encoded data for relative contribution of oxyhemoglobin in the hand. Contrarily, FIG. 69C shows a hyperspectral image of the hand from FIG. 69A displaying chemically encoded data for relative contribution of water in the hand. Thus, it can be seen from these figures that the present invention is capable of displaying a variety of chemical encoding data.

A hyperspectral imaging system integrating DLP technology to illuminate the area of interest with band pass of light ranging over a spectral range from the visible to the near-infrared that is interfaced with a digital focal plane array for acquisitioning and storing a series of digital spectroscopic images (a hyperspectral data cube) that is analyzed using chemometric methods providing chemical information within the area of interest aiding the clinician in detecting, diagnosing and monitoring disease. Clinicians could also monitor patients with this technology for determining the best pharmacological therapy and maximize favorable patient outcomes. The present invention utilizes DLP technology with a focal plane array and chemometric deconvolution for visualizing the biochemical levels within a human non-invasively for clinical and surgical applications. The present invention can also be illuminated with spectrum of light.

Figure 70:
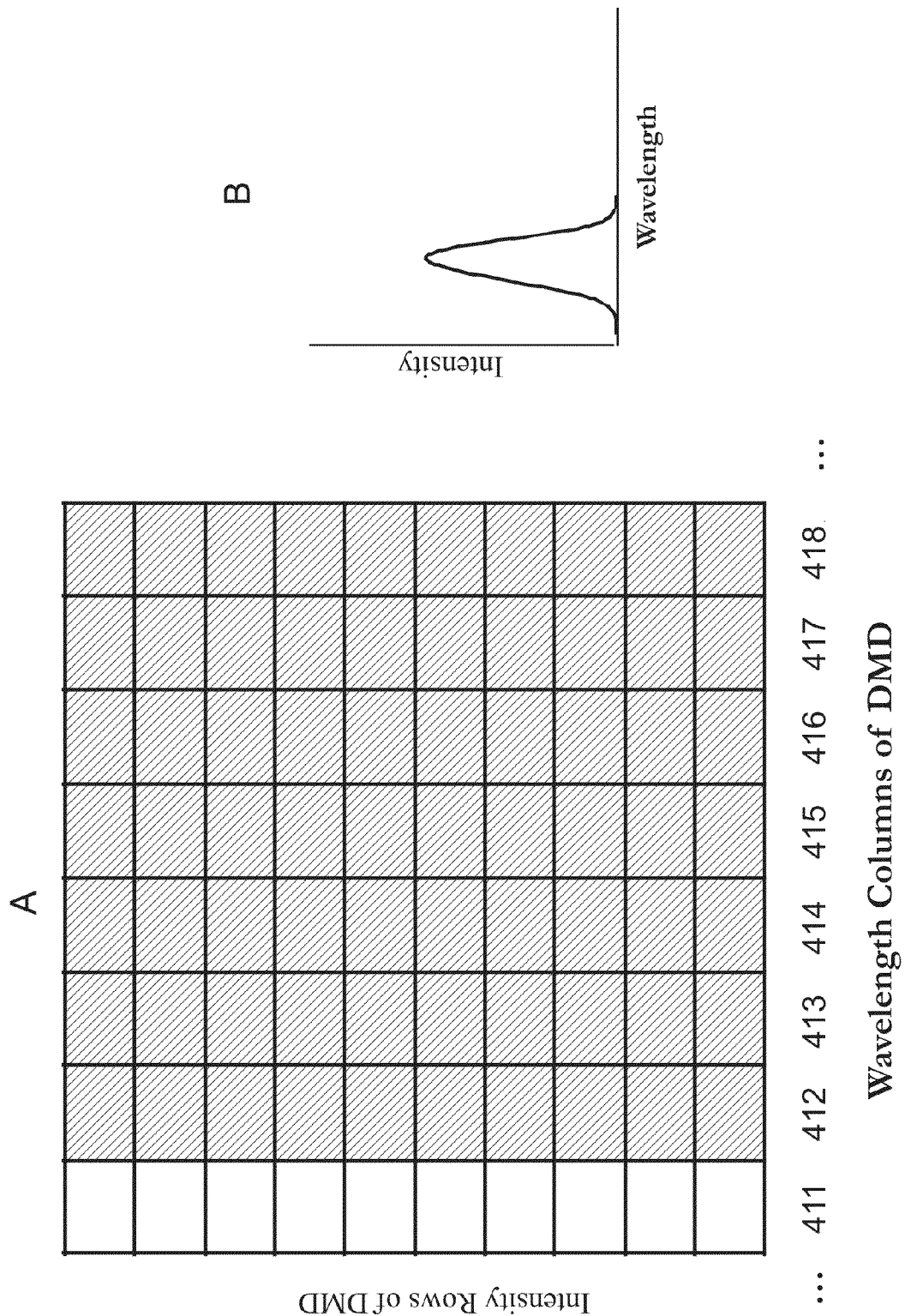
FIG. 70A is an representation of a portion of a digital micromirror device showing a single column of micromirrors in an "on" position.
FIG. 70B is a representation of an illumination spectrum produced by the digital micromirror device of FIG. 70A.
Figure 71:
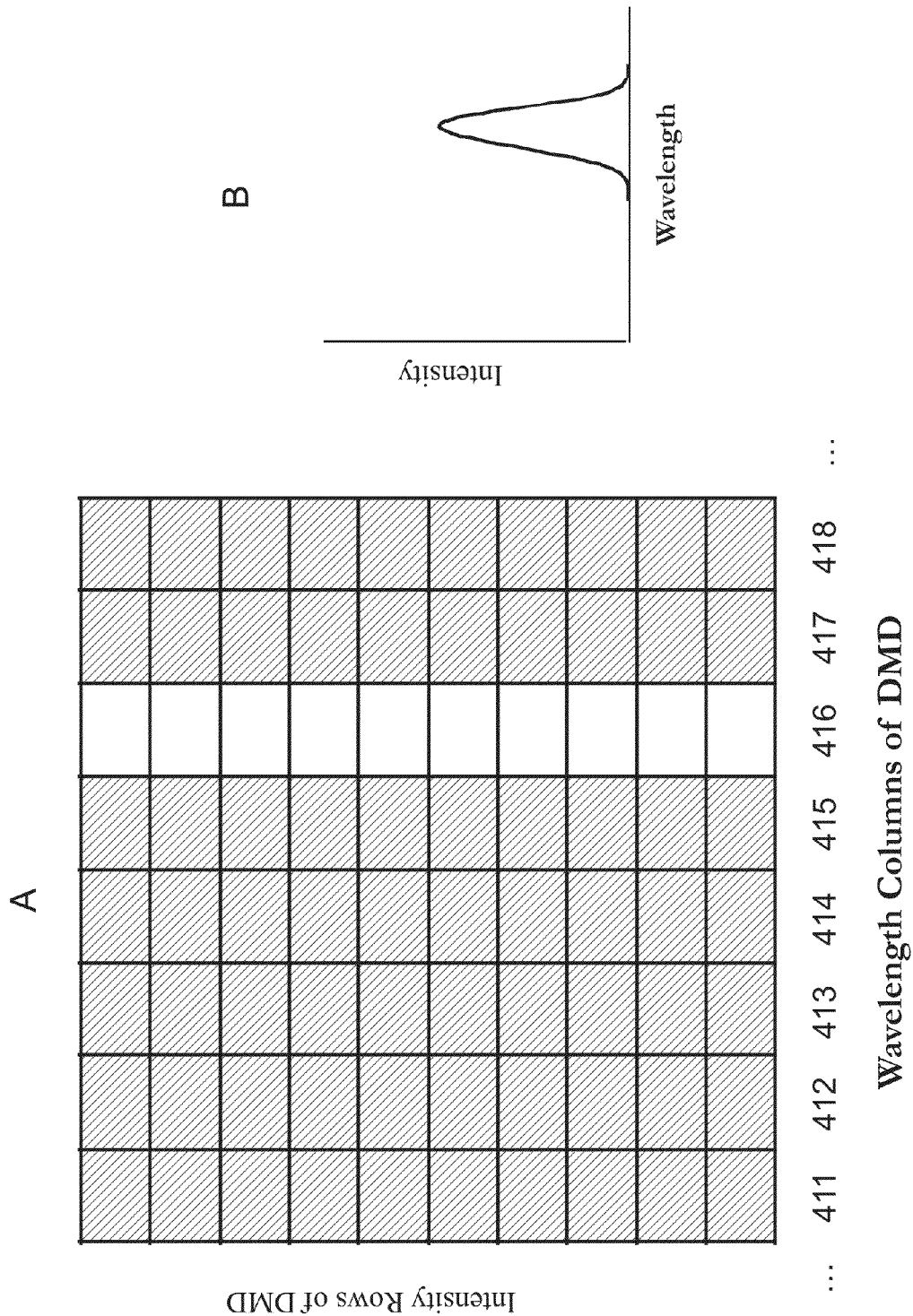
FIG. 71A is an representation of a portion of a digital micromirror device showing a single column of micromirrors in an "on" position.
FIG. 71B is a representation of an illumination spectrum produced by the digital micromirror device of FIG. 71A.
Figure 72:
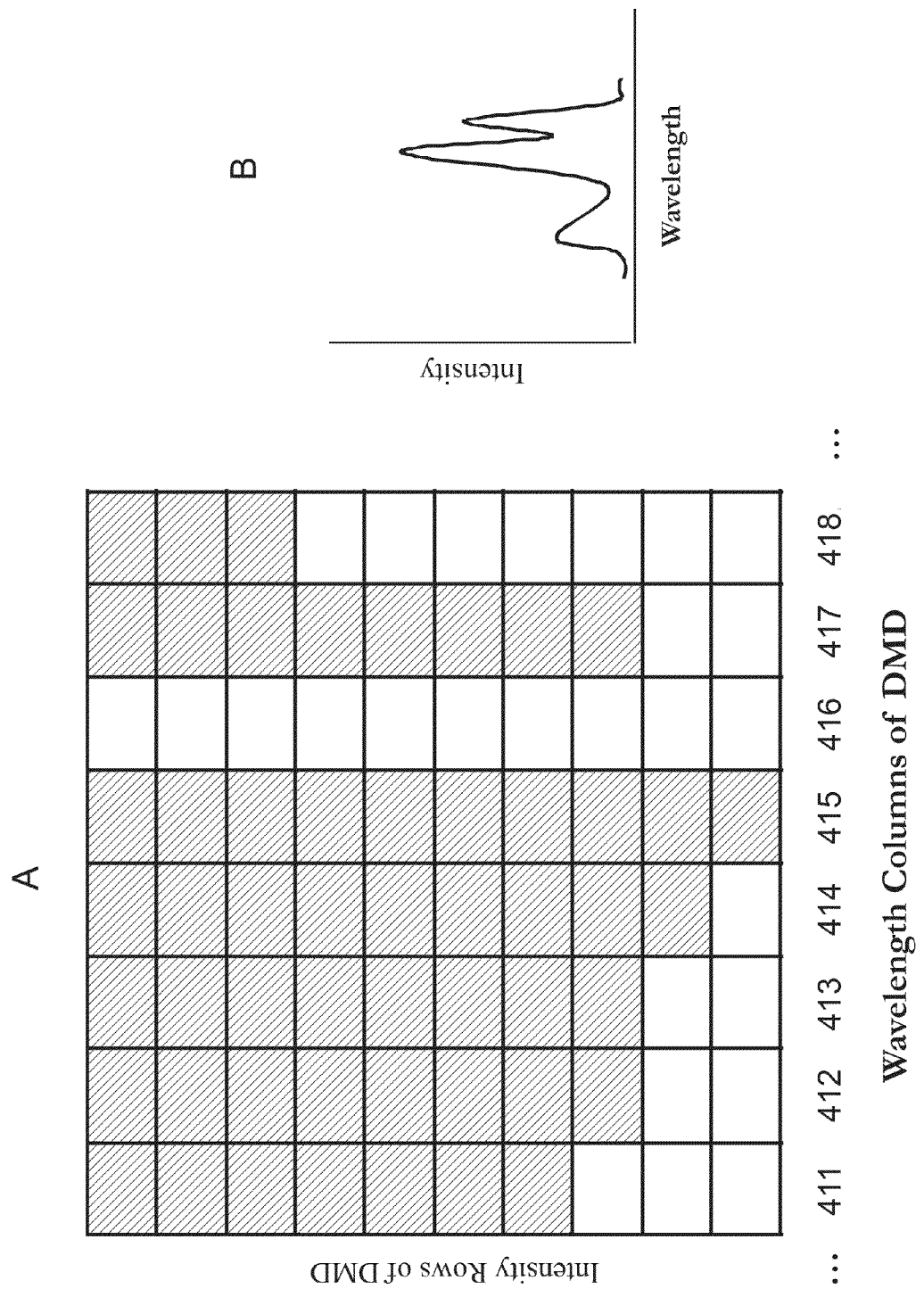
FIG. 72A is an representation of a portion of a digital micromirror device showing a plurality of columns of micromirrors in an "on" position where respective columns have different numbers of micromirrors in an "on" position; and, FIG. 72B is a representation of a complex illumination spectrum produced by the digital micromirror device of FIG. 72A.

As shown in FIG. 70A, a single column 411 of mirrors may be positioned in an "on" position while the remaining columns are positioned in an "off" position. The resulting spectrum is shown in FIG. 70B. Similarly, as shown in FIG. 71A, a single column 416 of mirrors may be positioned in an "on" position while the remaining columns are positioned in an "off" position. The resulting spectrum is shown in FIG. 71B. It is apparent to one of ordinary skill in the art that the selection of individual columns of mirrors can control the output spectrum of the present invention, and by varying the selected column, such spectrum can be shifted within the range of the present invention, i.e., the difference of the positions of the spectrum in FIGS. 70B and 71B. Furthermore, unlike all other known devices, the present invention can also provide complex spectra for illuminating a target. For example, as shown in FIG. 72A, various columns of mirrors 411, 412, 413, 414, 416, 417 and 418 can be positioned in an "on" position while column 415 is positioned in an "off" position thereby resulting in a complex spectrum. Moreover, a different number of mirrors within a particular column can be positioned in an "on" position thereby providing a different intensity of a particular wavelength of light. Thus, the complex spectrum created by the mirror positioned depicted in FIG. 72A is shown in FIG. 72B.

The DLP® hyperspectral imaging and chemometric deconvolution can be applied to all products that use light, for example, the fields of clinical endoscopy, clinical chemistry, microscopy, surgical microscopy, drug discovery, microarray scanners and microplate readers.

It should be appreciated that software included in some embodiments of the present invention can perform a variety of functions. For example, the software can provide a user interface through which a user can control all aspects of illumination, measurement and analysis. Thus, the software can provide full control of all hardware devices. Moreover, the software can perform mathematical functions based on internally programmed or embedded functions or can call math functions from outside software, e.g., MatLab.

It should also be appreciated that the present invention can be used to compare hyperspectral images of a target of interest, e.g., a patient's kidney, with images of know targets to evaluate the condition of the target of interest. For example, a hyperspectral image of a kidney can be obtained with the present invention and then compared against a library of kidney images including but limited to normal kidneys, ischemic kidneys, cancer containing kidneys, etc. Such comparison allows a medical professional to evaluate the condition/state of a target by comparison to an image library of similar targets in various conditions. Thus, a protocol for repairing/healing the target can be easily determined based on the closest match from the image library.

It should be appreciated that the range of usable wavelengths for the present invention is limited when using currently available digital micromirror devices, i.e., the physical size of each respective mirror element and the materials and coatings used on the front surface windows which protect the DMD limit the range of wavelengths. For example, the size of the mirrors limits what wavelengths will properly reflect from their surfaces, while the window materials and coatings limit what wavelengths of light can pass therethrough. The present invention, as claimed, is not limited by such DMD characteristics and therefore as new DMDs become available, they will be directly applicable to the present invention.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A hyperspectral imaging system having an optical path, said system comprising:
    an illumination source configured to output a light beam, said light beam illuminating a target;
    a dispersing element arranged in said optical path and configured to separate said light beam into a plurality of wavelengths;
    a spatial light modulator configured to tune said plurality of wavelengths into a spectrum;
    an optical device comprising a detector and configured to collect said spectrum reflected from said target and arranged in said optical path; and,
    a processor operatively connected to and configured to control at least one of: said illumination source; said dispersing element; said spatial light modulator; said optical device; and, said detector, said processor further configured to output a hyperspectral image of said target,
    wherein said dispersing element is arranged between said illumination source and said spatial light modulator, said spatial light modulator is arranged to transmit said spectrum to said target and said optical device is arranged in said optical path after said target,
    wherein said detector comprises a plurality of pixels and said processor further comprises a deconvolution algorithm configured to normalize said spectrum at each of said plurality of pixels prior to processing said hyperspectral image.

2. The hyperspectral imaging system according to claim 1 wherein said illumination source is an optically tunable radiation source is selected from the group consisting of: a supercontinuum laser and a light emitting diode.

3. The hyperspectral imaging system according to claim 1 wherein said illumination source is configured to produce said light beam comprising said plurality of wavelengths ranging from 250 nm to 2,500 nm.

4. The hyperspectral imaging system according to claim 1, wherein said target is a fluorescent target.

5. The hyperspectral imaging system according to claim 4, wherein said fluorescent target comprises a natural fluorescence of a tissue or a fluid.

6. The hyperspectral imaging system according to claim 4, wherein said fluorescent target comprises a natural fluorescence, a fluorescent dye, a fluorescence resonance energy donor, a fluorescence resonance energy acceptor, a fluorescence quencher or combinations thereof.

7. The hyperspectral imaging system according to claim 4, wherein said fluorescent target comprises a fluorescence molecule selected from the group consisting of: indocyanine green; 5-carboxyfluorescein (5-FAM); 6-carboxyfluorescein (6-FAM); fluorescein-5-isothiocyanate (FITC); 2'7'-dimethoxy-4'5'-dichloro-6-carboxyfluorescein (JOE); rhodamine and rhodamine derivatives such as N,N,N',N'-tetramethyl-6-carboxyrhodamine (TAMRA); 6-carboxyrhodamine (R6G); tetramethyl-indocarbocyanine (Cy3); tetramethyl-benzindo carbocyanine (Cy3.5); tetramethyl-indodicarbocyanine (Cy5); tetramethyl-indotricarbocyanine (Cy7); 6-carboxy-X-rhodamine (ROX); hexachloro fluorescein (HEX); tetrachloro fluorescein TET; R-Phycoerythrin; 4-(4'-dimethylaminophenylazo) benzoic acid (DABCYL); 5-(2'-aminoethyl)aminonaphthalene-1-sulfonic acid (EDANS); and, combinations thereof.

8. The hyperspectral imaging system according to claim 1, wherein said target comprises a structure selected from the group consisting of: a tissue in a bloodstream; a tissue in a lymphatic system; a tissue in a bodily secretion; a tissue in a biopsy; a skin tissue; a tissue of a blood vessel; a retinal tissue; a tissue imaged by laparoscopy; a tissue imaged by endoscopy; a central nervous system tissue; a bodily fluid; an organ; and, combinations thereof.

9. The hyperspectral imaging system according to claim 1, wherein said dispersing element is selected from the group consisting of: a grating; a prism; a tunable filters; an electro-mechanical optical filter wheel; an acousto-optical tunable filter; a liquid-crystal tunable filter; a digital micromirror device; an electro-optical filter; a holographic filter; and, combinations thereof.

10. The hyperspectral imaging system according to claim 1, wherein said spatial light modulator comprises a digital micromirror device.

11. The hyperspectral imaging system according to claim 1, wherein said spectrum comprises a narrow bandwidth of wavelengths of said light beam.

12. The hyperspectral imaging system according to claim 1, wherein said spectrum comprises a complex composition of wavelengths of said light beam and respective portions of said complex composition each comprise an intensity.

13. The hyperspectral imaging system according to claim 1, wherein said optical device comprises a camera.

14. The hyperspectral imaging system according to claim 1, wherein said detector is selected from the group consisting of: a spectrometer; a two-dimensional array detector; a multi-array detector; an on-chip amplification CCD camera; a back-illuminated CCD camera; a liquid nitrogen cooled focal plane array camera; a photomultiplier tube; a focal plane array; a CMOS array and, combination thereof.

15. The hyperspectral imaging system according to claim 1, wherein said processor is configured to perform at least one of: tune said spatial light modulator; trigger said detector for collection of a series of spectroscopic images formatted as a hyperspectral image cube; and, process said hyperspectral image cube for visualization.

16. The hyperspectral imaging system according to claim 1, wherein said processor comprises an image data acquisition software configured to perform at least one of: tune said spatial light modulator; trigger said detector for collection of a series of spectroscopic images formatted as a hyperspectral image cube; and, process said hyperspectral image cube for visualization, said processor further comprises a converter to digitize said hyperspectral image cube, wherein said processor is connect to a display.

17. The hyperspectral imaging system according to claim 1, wherein said processor further comprises:
    a computer comprising an image data processing software configured to process digital signals;
    a digital signal processor comprising an algorithm configured for chemometric analysis; and,
    an algorithm library configured for visualizing chemistry on and within said target for detection, monitoring and diagnosis.

18. The hyperspectral imaging system according to claim 1, wherein said processor is arranged to communicate with a database comprising a library of spectra of fluorescent targets, a library of spectra of absorbent targets, a library of spectra of reflective targets, a library of spectra of organs, a library of spectra of tissues, a library of spectra of physiological substances or combinations thereof.

19. The hyperspectral imaging system according to claim 1, wherein said processor is configured to process said hyperspectral image at a video rate.

20. The hyperspectral imaging system according to claim 1, wherein said processor is configured to form said hyperspectral image in less than 1.0 second.

21. The hyperspectral imaging system according to claim 20, wherein said processor is configured to form said hyperspectral image in approximately 0.33 second.

22. The hyperspectral imaging system according to claim 1 further comprising illumination optics selected from the group consisting of: a lens; a microscope; a dissection microscope; a surgical microscope; a slit lamp; an endoscope; a laparoscope; a colonoscope; funduscope; broncialscope and, combinations thereof.

23. The hyperspectral imaging system according to claim 1, wherein said hyperspectral imaging system is configured for non-invasive real-time in vivo or in vitro analysis of said target.

24. The hyperspectral imaging system according to claim 1 further comprising collimating optics configured to transmit said light beam from said dispersing element to said spatial light modulator as a collimated light beam.

25. The hyperspectral imaging system according to claim 1 further comprising beam shaping optics configured to transmit said light beam from said spatial light modulator to said target so that said light beam substantially illuminations all of said target.

26. The hyperspectral imaging system according to claim 1, wherein said hyperspectral image comprises chemically encoded data.

27. The hyperspectral imaging system according to claim 26, wherein said chemically encoded data is determined by comparing said spectrum reflected from said target to a known reflected spectrum, by comparing said spectrum reflected from said target to a previously obtained spectrum reflected from said target, or combinations thereof.

28. The hyperspectral imaging system according to claim 1, wherein said target comprises a biomarker configured to absorb, reflect or fluoresce in response to said spectrum.

29. The hyperspectral imaging system according to claim 28, wherein said biomarker comprises a naturally occurring substance within said target, a substance introduced into said target or combinations thereof.

30. The hyperspectral imaging system according to claim 28, wherein said biomarker comprises water, oxyhemoglobin, deoxyhemoglobin, carboxyhemoglobin, lipid, bilirubin, cholesterol, collagen, glucose, central nervous system fluid proteins, saliva proteins, semen or combinations thereof.

* * * * *